(12) United States Patent
Miyamoto et al.

(10) Patent No.: US 7,838,243 B2
(45) Date of Patent: Nov. 23, 2010

(54) PROTEIN FORMING COMPLEX WITH C-JUN PROTEIN, NUCLEIC ACID ENCODING THE SAME AND METHOD OF USING THE SAME

(75) Inventors: Etsuko Miyamoto, Yokohama (JP); Kenichi Horisawa, Yokohama (JP); Hiroshi Yanagawa, Yokohama (JP)

(73) Assignee: Keio University, Tokyo (JP)

( * ) Notice: Subject to any disclaimer, the term of this patent is extended or adjusted under 35 U.S.C. 154(b) by 412 days.

(21) Appl. No.: 10/579,802

(22) PCT Filed: Nov. 19, 2004

(86) PCT No.: PCT/JP2004/017306

§ 371 (c)(1),
(2), (4) Date: May 18, 2006

(87) PCT Pub. No.: WO2005/061706

PCT Pub. Date: Jul. 7, 2005

(65) Prior Publication Data

US 2007/0003534 A1   Jan. 4, 2007

(30) Foreign Application Priority Data

Nov. 19, 2003   (JP) ............................. 2003-389676

(51) Int. Cl.
*G01N 33/53* (2006.01)
*C12Q 1/68* (2006.01)
(52) U.S. Cl. ........................................... 435/7.1; 435/6
(58) Field of Classification Search ...................... None
See application file for complete search history.

(56) References Cited

U.S. PATENT DOCUMENTS

| 6,228,994 B1 | 5/2001 | Yanagawa et al. |
| 2002/0176987 A1 | 11/2002 | Yadav et al. |

FOREIGN PATENT DOCUMENTS

| JP | 11-322781 | 11/1999 |
| WO | 95/11922 A1 | 5/1995 |
| WO | 98/16636 A1 | 4/1998 |
| WO | 02/46395 A1 | 6/2002 |
| WO | 02/48347 | 6/2002 |
| WO | 03/048363 | 6/2003 |

OTHER PUBLICATIONS

Accession No. K01347. 1993.*
Lopez-Egido et al. Menin's Interaction with Glial Fibrillary Acidic Protein and Vimentin Suggests a Role for the Intermediate Filament Network in Regulating Menin Activity. Exp. Cell Res. 278: 175-183, 2002.*
K. Horisawa et al., "In vitro selection of Jun-associated proteins using mRNA display", Nucleic Acids Research, vol. 32, No. 21, pp. 1-10, 2004.
E. Miyamoto-Sato et al., "Highly stable and efficient mRNA templates for mRNA-protein fusions and C-terminally labeled proteins", Nucleic Acids Research, vol. 31, No. 15, pp. 1-9, 2003.
T. Ito et al., "Identification of SWI-SNF Complex Subunit BAF60a as a Determinant of the Transactivation Potential of Fos/Jun Dimers", The Journal of Biological Chemistry, vol. 276, No. 4, pp. 2852-2857, Jan. 26, 2001.
Y. Chinenov et al., "Close encounters of many kinds: Fos-Jun interaction that mediate transcription regulatory specificity", Oncogene, vol. 20, pp. 2438-2452, 2001.
N. Nemoto et al., "In vitro virus: Bonding of mRNA bearing puromycin at the 3'-terminal end to the C-terminal end of its encoded protein on the ribosome in vitro", FEBS Letters, vol. 414, pp. 405-408, 1997.
R. W. Roberts et al., "RNA-peptide fusions for the in vitro selection of peptides and proteins", Proc. Natl. Acad. Sci., vol. 94, pp. 12297-12302, Nov. 1997.
Saegusa, A., "Japan boosts proteomics and cell biology . . . " *Nature*, vol. 401, p. 313 (1999).
Dalton, R. et al., "Can researchers find recipe for proteins and chips?", *Nature*, vol. 402, pp. 718-719 (1999).
Miyamoto, E. et al., "Analyses of protein-protein interactions and gene networks by in vitro virus method", *Series Genome Science of Post-sequencing 3, Proteomics*, pp. 136 to 145 ( 2000). (Partial English Translation.).
Miyamoto, E. et al., "Applications of puromycin for evolutionary molecular engineering of proteins and analysis of gene networks", *Protein, Nucleic Acid and Enzyme*, vol. 46, No. 2, pp. 138 to 147 (2001). (Partial English Translation.).
Xiong, Y. et al., "p21 is a universal inhibitor of cyclin kinases", *Nature*, vol. 366, pp. 701-704 (1993).
Kaelin Jr., W. et al., "Identification of Cellular Proteins That Can Interact Specifically with the T/E1A-Binding Region of the Retinoblastoma Gene Product", *Cell*, vol. 64, pp. 521-532 (1991).
Rigaut, G. et al., "A generic protein purification method for protein complex characterization and proteome exploration", *Nature Biotechnology*, vol. 17, pp. 1030 to 1032 (1999).
Fields, S. et al., "A novel genetic system to detect protein-protein interactions", *Nature*, vol. 340, pp. 245-246 (1989).
Miyamoto-Sato, E., et al., "Construction of virus-type molecules in evolutionary molecular engineering", *Viva Origino*, vol. 25, p. 35 (1997). (Partial English Translation.).
Doi, N. et al., "STABLE: protein-DNA fusion system for screening of combinatorial protein libraries in vitro", *FEBS Letters*, vol. 457, pp. 227-230 (1999).
Smith, G., "Filamentous Fusion Phage: Novel Expression Vectors that Display Cloned Antigens on the Virion Surface", *Science*, vol. 228, No. 4705, pp. 1315-1317 (1985).

(Continued)

*Primary Examiner*—Michele K Joike
(74) *Attorney, Agent, or Firm*—Wenderoth, Lind & Ponack, L.L.P.

(57) ABSTRACT

Comprehensive analysis of transcription control factor complexes in a mouse brain cDNA library with c-Jun as a bait by using the cotranslation selection and screening of in vitro virus (IVV) and the C-terminal labeling method are conducted, thereby to provide known and unknown proteins which are unknown to form a complex with the c-Jun protein, whereby proteins that interact with c-Jun, nucleic acids encoding them and inhibitors utilizing them as well as methods for detecting an interaction and screening methods are provided.

2 Claims, 11 Drawing Sheets

OTHER PUBLICATIONS

Mattheakis, L. et al., "An in vitro polysome display system for identifying ligands from very large peptide libraries", *Proc. Natl. Acad. Sci.*, vol. 91, pp. 9022 to 9026 (1994).

Bohmann, D. et al., "Human Proto-Oncogene c-jun Encodes a DNA Binding Protein with Structural and Functional Properties of Transcription Factor AP-1" *Science,* vol. 238, No. 4832, pp. 1386-1392 (1987).

Hilberg, F. et al., "c-Jun is essential for normal mouse development and hepatogenesis", *Nature,* vol. 365, pp. 179-181 (1993).

Notice of Reason for Rejection from the Japanese Patent Office issued Sep. 7, 2010 in corresponding Japanese Patent Application No. 2005-516432.

E. Bengal et al., "Functional Antagonism between c-Jun and MyoD Proteins: A Direct Physical Association," *Cell*, vol. 68, pp. 507-519, Feb. 7, 1992.

H. Yang-Yen et al., "Transcriptional Interference between c-Jun and the Glucocorticoid Receptor: Mutual Inhibitor of DNA Binding Due to Direct Protein-Protein Interaction," *Cell*, vol. 62, pp. 1205-1215, Sep. 21, 1990.

* cited by examiner

| Amino acid SEQ ID NO. | Name of protein/gene, accession No. | leu zipper | Nucleic acid SEQ ID NO. | Number of clones | Alternate symbols & alias |
|---|---|---|---|---|---|
| 1-69 | Mus musculus similar to small nuclear RNA activating complex, polypeptide 5, 19kDa; small nuclear RNA activating complex, polypeptide 5, 19kD [Homo sapiens] (LOC330959), mRNA,XM_284503 | O | Refer to List 1 of Example 1 | 76 | SNAPc5, SNAP19 |
| 70-87 | Mus musculus kinesin family member 5C (Kif5c), mRNA, NM_008449 | O | 200(70), 201(71), 202(72), 203(73), 204(74), 205(75), 206(76), 207(77), 208(78), 209(79), 210(80), 211(81), 212(82), 213(83), 214(84), 215(85), 216(86), 217(87) | 19 | KINN, NKHC, NKHC2, NKHC-2 |
| 88-94 | Mus musculus kinesin family member 5A (Kif5a), mRNA, NM_008447 | O | 218(88), 219(89), 220(90), 221(91), 222(92), 223(93), 224(94) | 6 | Kns, Kif5 |
| 95-99 | Mus musculus eukaryotic translation elongation factor 1 delta (guanine nucleotide exchange protein) (Eef1d), mRNA, NM_023240 | O | 225(95), 226(96), 227(97), 228(98), 229(99) | 5 | |
| 100-104 | Mus musculus neurofilament 3, medium (Nef3), mRNA, NM_008691 | x | 230(100), 231(101), 232(102), 233(103), 234(104) | 4 | Nfm, NF-M, NF160 |
| 105-108 | Jip-c3.1 | O | 235(105), 236(106), 237(107), 238(108) | 3 | 4732436F15Rik(XM_143418) |
| 109-111 | Jip-c1 | O | 239(109), 240(110), 241(111) | 2 | expressed sequence AU022327 (XM_135706) |
| 112-113 | Mus musculus APC-binding protein EB2 mRNA, partial cds, U51204 | x | 242(112), 243(113) | 1 | Mapre3 (XM_131982) |
| 114-115 | Mus musculus chondroitin sulfate proteoglycan 6 (Cspg6), mRNA, NM_007790 | O | 244(114), 245(115) | 1 | HCAP, SMC3, SmcD(AF047601), Mmip1(Y15128), Bamacan(BC036330) |
| 116-117 | Mus musculus mitogen-activated protein kinase 8 interacting protein 3 (Mapk8ip3), mRNA, NM_013931 | O | 246(116), 247(117) | 1 | Jip3(AF178637), Syd2(AF262046), JSAP1(AB043125), JSAP1a, JSAP1b, JSAP1c, JSAP1d, D17Wsu15e |
| 118-119 | Jip-c3.2 | O | 248(118), 249(119) | 1 | 1200008A14Rik(NM_028915) |
| 120-121 | Mouse glial fibrillary acidic protein (GFAP) mRNA, K01347 | x | 250(120), 251(121) | 1 | |
| 122-123 | Jip-c8 | O | 252(122), 253(123) | 1 | B130050I23Rik(NM_153536) |
| 124-125 | Mus musculus kinesin family member 5B (Kif5b), mRNA, NM_008448 | x | 254(124), 255(125) | 1 | Khc |

Fig. 1

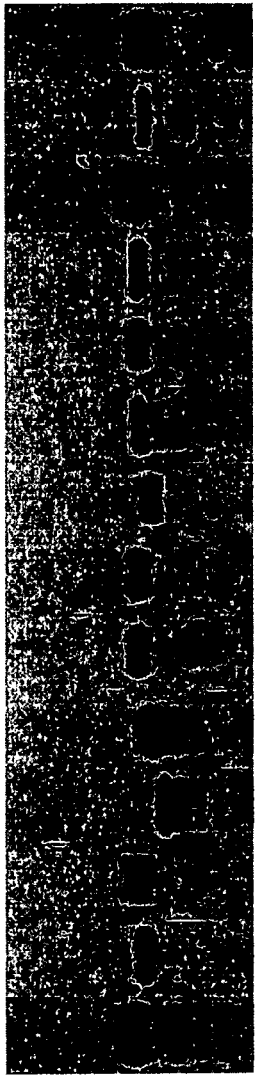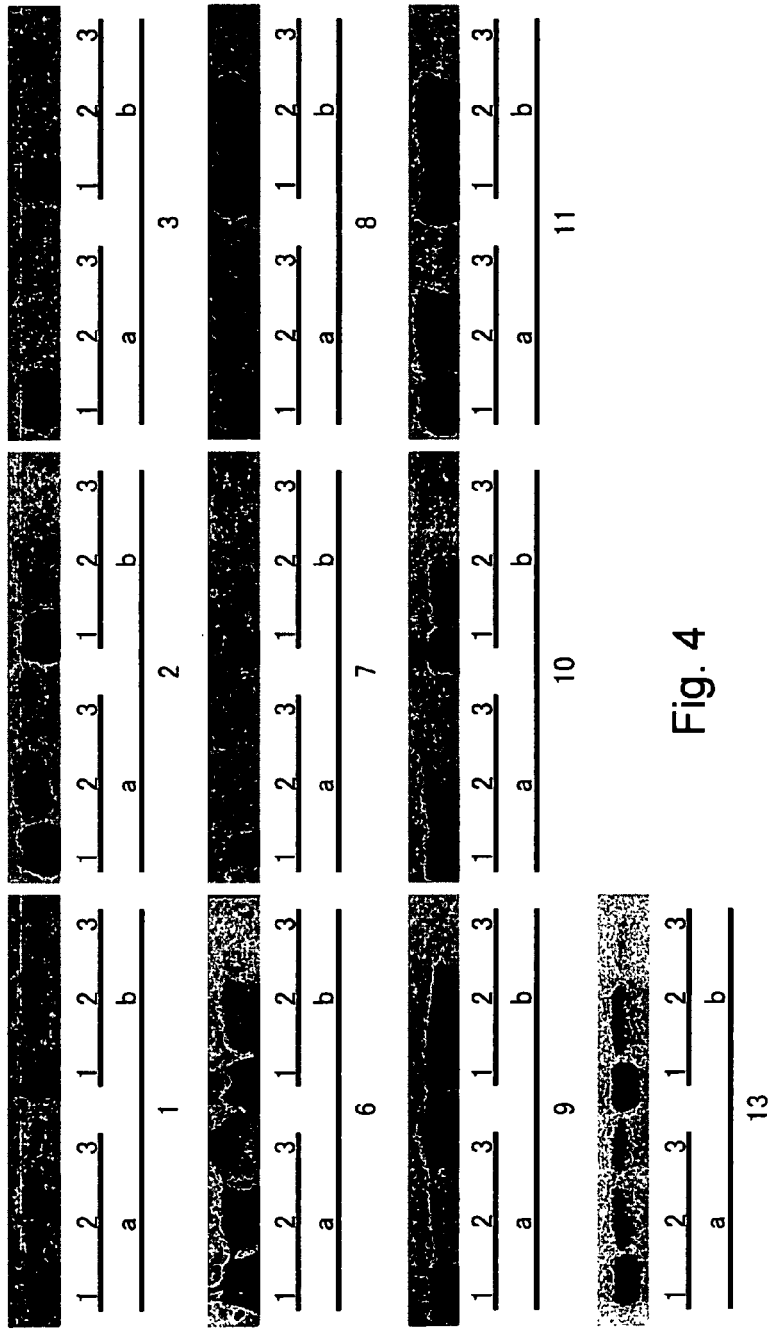
Fig. 4

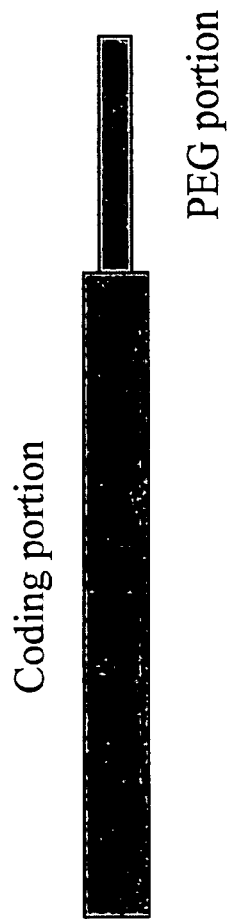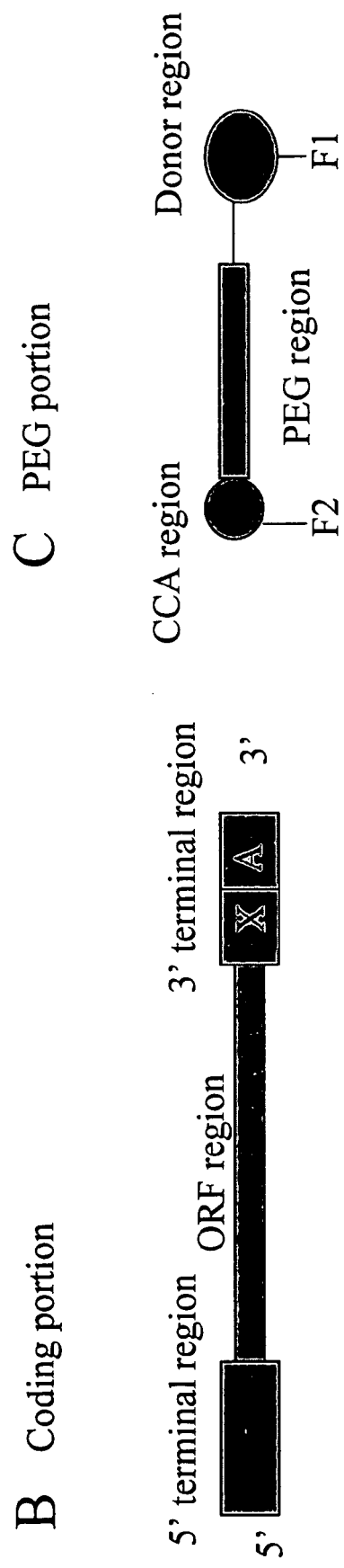
Fig. 7

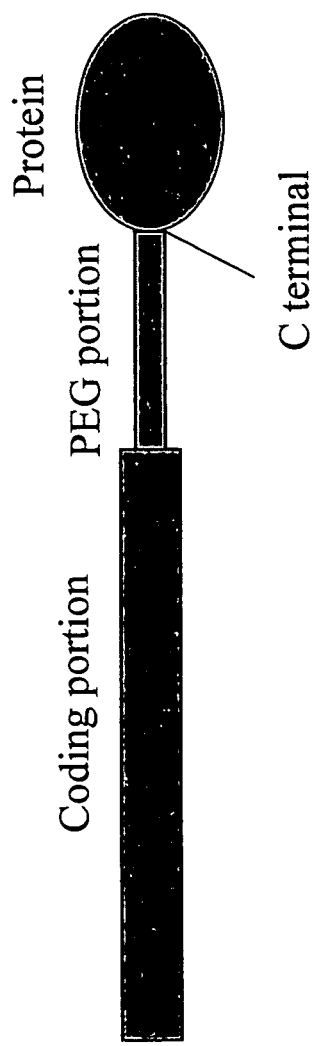
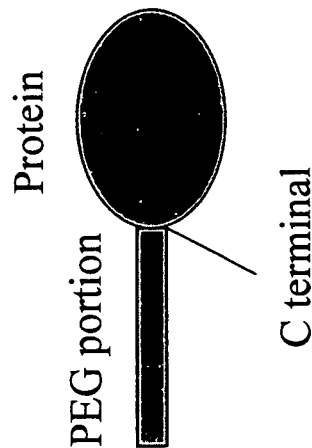
Fig. 8

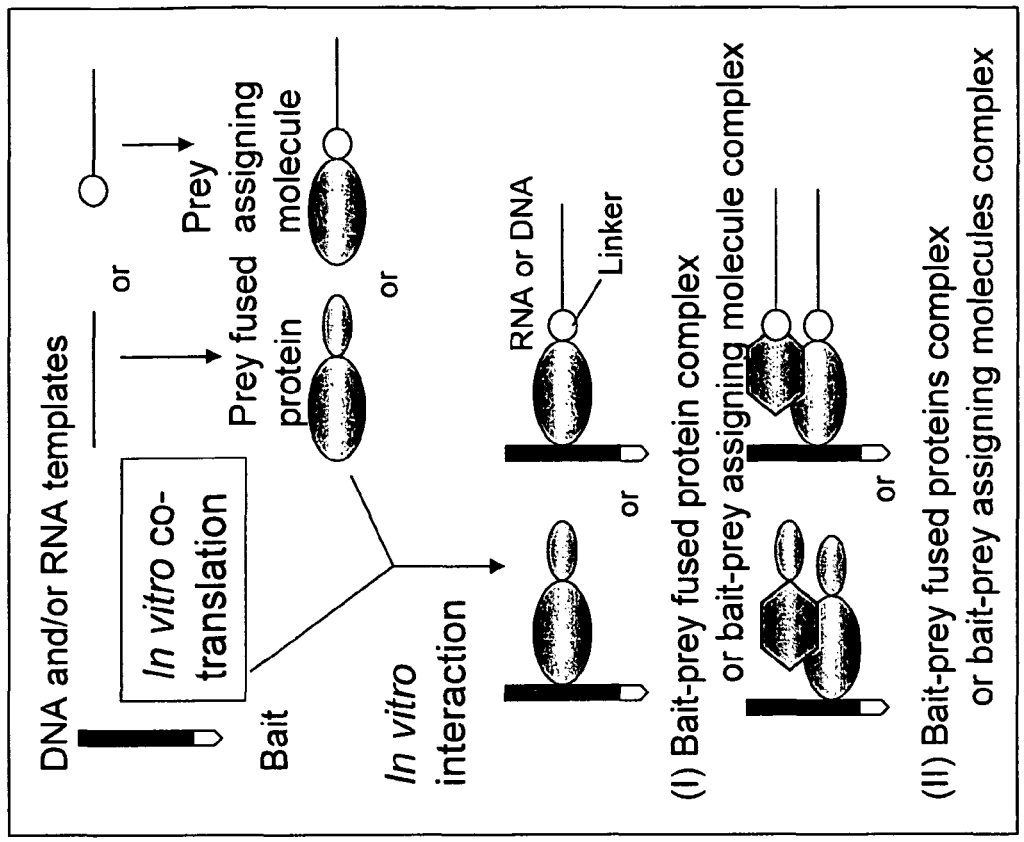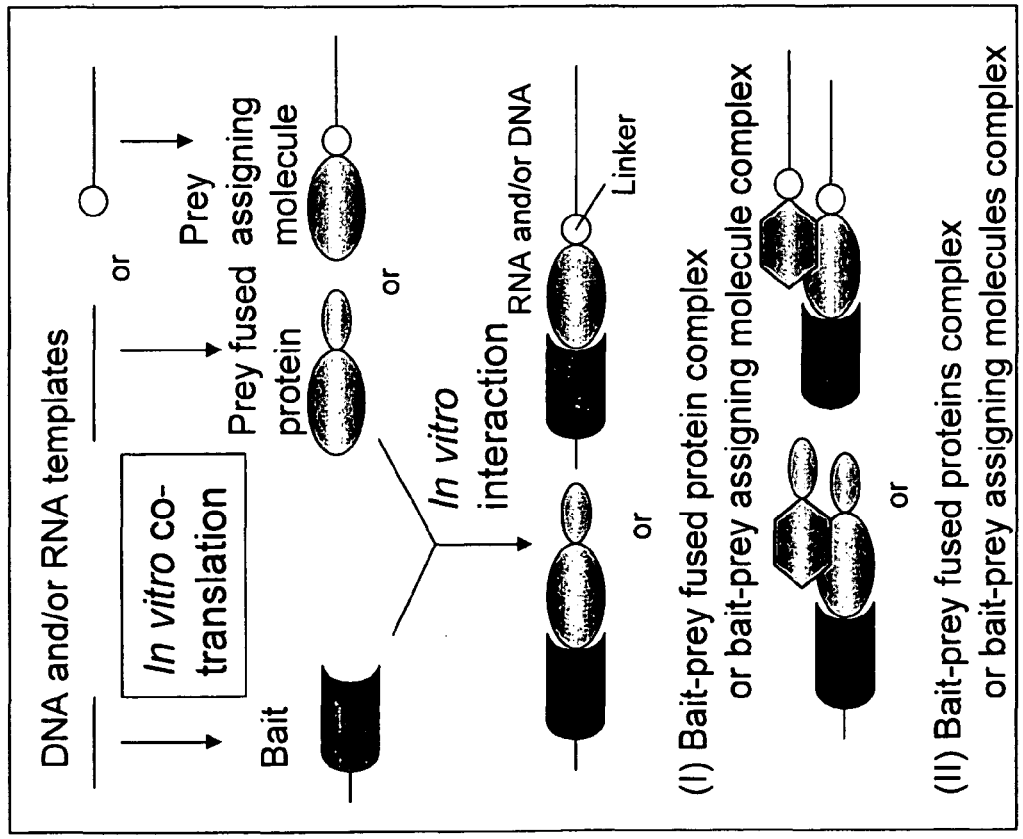
Fig. 9

SEQUENCE LISTING

<160> NUMBER OF SEQ ID NOS: 299

<210> SEQ ID NO 1
<211> LENGTH: 102
<212> TYPE: PRT
<213> ORGANISM: Mus musculus

<400> SEQUENCE: 1

Met Leu Ser Arg Leu Gln Glu Leu Arg Lys Glu Glu Thr Leu Leu
1               5                   10                  15

Arg Leu Lys Ala Ala Leu His Asp Gln Leu Asn Arg Leu Lys Val Glu
                20                  25                  30

Glu Leu Ala Leu Gln Ser Met Ile Asn Ser Arg Gly Arg Thr Glu Thr
            35                  40                  45

Leu Ser Ser Gln Pro Ala Pro Glu Gln Leu Cys Asp Met Ser Leu His
    50                  55                  60

Val Asp Asn Glu Val Thr Ile Asn Gln Thr Thr Leu Lys Leu Ser Thr
65                  70                  75                  80

Arg Ser Pro Met Glu Glu Glu Glu Glu Glu Glu Glu Glu Glu Glu Glu
                85                  90                  95

Glu Glu Glu Ser Asp Ser
            100

<210> SEQ ID NO 2
<211> LENGTH: 86
<212> TYPE: PRT
<213> ORGANISM: Mus musculus

<400> SEQUENCE: 2

Val Glu Gly Ser Ala Leu Arg Lys Trp Lys Gly Met Leu Ser Arg Leu
1               5                   10                  15

Gln Glu Leu Arg Lys Glu Glu Glu Thr Leu Leu Arg Leu Lys Ala Ala
                20                  25                  30

Leu His Asp Gln Leu Asn Arg Leu Lys Val Glu Glu Leu Ala Leu Gln
            35                  40                  45

Ser Val Ile Asn Ser Arg Gly Arg Thr Glu Thr Leu Ser Ser Gln Pro
    50                  55                  60

Ala Pro Glu Gln Leu Cys Asp Met Ser Leu His Val Asp His Glu Val
65                  70                  75                  80

Thr Ile Asn Gln Thr Thr
                85

<210> SEQ ID NO 3
<211> LENGTH: 84
<212> TYPE: PRT
<213> ORGANISM: Mus musculus

<400> SEQUENCE: 3

Ser Ala Leu Arg Lys Trp Lys Gly Met Leu Ser Arg Leu Gln Glu Leu
1               5                   10                  15

Arg Lys Glu Glu Glu Thr Gln Leu Arg Leu Lys Ala Ala Leu His Asp
                20                  25                  30

Gln Leu Asn Arg Leu Lys Val Glu Glu Leu Ala Leu Gln Ser Met Ile
            35                  40                  45

Asn Ser Arg Gly Arg Thr Glu Thr Leu Ser Ser Gln Pro Ala Pro Glu
    50                  55                  60

Gln Leu Cys Asp Met Ser Leu His Val Asp His Glu Val Thr Ile Asn
65                  70                  75                  80

Gln Thr Thr Leu

<210> SEQ ID NO 4
<211> LENGTH: 83
<212> TYPE: PRT
<213> ORGANISM: Mus musculus

<400> SEQUENCE: 4

Ser Ala Leu Arg Lys Trp Lys Gly Met Leu Ser Arg Leu Gln Glu Leu
1               5                   10                  15

Arg Lys Glu Glu Glu Thr Gln Leu Arg Leu Lys Ala Ala Leu His Asp
            20                  25                  30

Gln Leu Asn Arg Leu Lys Val Glu Leu Ala Leu Gln Ser Met Ile
        35                  40                  45

Asn Ser Arg Gly Arg Thr Glu Thr Leu Ser Ser Gln Pro Ala Pro Glu
    50                  55                  60

Gln Leu Cys Asp Met Ser Leu His Val Asp Asn Glu Val Thr Ile Asn
65                  70                  75                  80

Gln Lys Leu

<210> SEQ ID NO 5
<211> LENGTH: 83
<212> TYPE: PRT
<213> ORGANISM: Mus musculus

<400> SEQUENCE: 5

Ser Ala Leu Arg Lys Trp Lys Gly Met Leu Ser Arg Leu Gln Glu Leu
1               5                   10                  15

Arg Lys Glu Glu Glu Thr Gln Leu His Leu Lys Ala Ala Leu His Asp
            20                  25                  30

Gln Leu Asn Arg Leu Lys Val Glu Leu Ala Leu Gln Ser Met Ile
        35                  40                  45

Asn Ser Arg Gly Arg Thr Glu Thr Leu Ser Ser Gln Pro Ala Pro Glu
    50                  55                  60

Gln Leu Cys Asp Met Ser Leu His Val Asp Asn Glu Val Thr Ile Asn
65                  70                  75                  80

Gln Lys Leu

<210> SEQ ID NO 6
<211> LENGTH: 83
<212> TYPE: PRT
<213> ORGANISM: Mus musculus

<400> SEQUENCE: 6

Ser Ala Leu Arg Lys Trp Lys Gly Val Leu Ser Arg Leu Gln Glu Leu
1               5                   10                  15

Arg Lys Glu Glu Glu Thr Leu Leu Arg Leu Lys Ala Ala Leu His Asp
            20                  25                  30

Gln Leu Asn Arg Leu Lys Val Glu Leu Ala Leu Gln Ser Met Ile
        35                  40                  45

Asn Ser Arg Gly Arg Thr Glu Thr Leu Ser Ser Gln Pro Ala Pro Glu
    50                  55                  60

Gln Leu Cys Asp Met Ser Leu His Val Asp His Glu Val Thr Ile Asn
65                  70                  75                  80

Gln Ser Lys

<210> SEQ ID NO 7
<211> LENGTH: 65
<212> TYPE: PRT
<213> ORGANISM: Mus musculus

<400> SEQUENCE: 7

Ser Ala Leu Arg Lys Trp Lys Gly Met Leu Ser Arg Leu Gln Glu Leu
1               5                   10                  15

Arg Lys Glu Glu Glu Thr Gln Leu Arg Leu Lys Ala Ala Leu His Asp
            20                  25                  30

Gln Leu Asn Arg Leu Lys Val Glu Glu Leu Ala Leu Gln Ser Met Ile
        35                  40                  45

Asn Ser Arg Arg Arg Thr Glu Thr Leu Ser Ser Gln Pro Ala Pro Glu
50                  55                  60

Ser
65

<210> SEQ ID NO 8
<211> LENGTH: 75
<212> TYPE: PRT
<213> ORGANISM: Mus musculus

<400> SEQUENCE: 8

Ala Leu Arg Lys Trp Lys Gly Met Leu Ser Arg Leu Gln Glu Leu Arg
1               5                   10                  15

Lys Glu Glu Glu Thr Leu Leu Arg Leu Lys Ala Ala Leu His Asp Gln
            20                  25                  30

Leu Asn Arg Leu Lys Val Glu Glu Leu Ala Leu Gln Ser Met Ile Asn
        35                  40                  45

Ser Arg Gly Arg Thr Glu Thr Leu Ser Ser Gln Pro Ala Pro Glu Gln
50                  55                  60

Leu Cys Asp Met Ser Leu His Val Asp Asn Glu
65                  70                  75

<210> SEQ ID NO 9
<211> LENGTH: 95
<212> TYPE: PRT
<213> ORGANISM: Mus musculus

<400> SEQUENCE: 9

Leu Arg Lys Trp Lys Gly Met Leu Ser Arg Leu Gln Glu Leu Arg Lys
1               5                   10                  15

Glu Glu Glu Thr Leu Leu Arg Gln Lys Ala Ala Leu His Asp Gln Leu
            20                  25                  30

Asn Arg Leu Lys Val Glu Glu Leu Pro Leu Gln Ser Met Ile Asn Ser
        35                  40                  45

Arg Gly Arg Thr Glu Thr Leu Ser Ser Gln Pro Ala Pro Glu Gln Leu
50                  55                  60

Cys Asp Met Ser Leu His Val Asp Asn Glu Val Thr Ile Asn Gln Thr
65                  70                  75                  80

Thr Leu Lys Leu Ser Thr Arg Ser Pro Met Glu Glu Lys Glu Glu
                85                  90                  95

<210> SEQ ID NO 10
<211> LENGTH: 82
<212> TYPE: PRT
<213> ORGANISM: Mus musculus

```
<400> SEQUENCE: 10

Pro Arg Lys Trp Lys Gly Met Leu Ser Arg Leu Gln Glu Leu Arg Lys
1               5                   10                  15

Glu Glu Glu Thr Leu Leu Arg Leu Lys Ala Ala Leu His Asp Gln Leu
            20                  25                  30

Asn Arg Leu Lys Val Glu Glu Leu Ala Leu Gln Ser Met Ile Asn Ser
        35                  40                  45

Arg Gly Arg Thr Glu Thr Leu Ser Ser Gln Pro Ala Pro Glu Gln Leu
    50                  55                  60

Cys Asp Met Ser Leu His Val Asp Asn Glu Val Thr Ile Asn Gln Thr
65                  70                  75                  80

Thr Arg

<210> SEQ ID NO 11
<211> LENGTH: 82
<212> TYPE: PRT
<213> ORGANISM: Mus musculus

<400> SEQUENCE: 11

Leu Arg Lys Trp Lys Gly Met Leu Ser Arg Leu Gln Glu Leu Arg Lys
1               5                   10                  15

Glu Glu Glu Thr Leu Leu Arg Leu Lys Ala Ala Leu His Asp Gln Leu
            20                  25                  30

Asn Arg Leu Lys Val Glu Glu Leu Ala Leu Gln Ser Met Ile Asn Ser
        35                  40                  45

Arg Gly Arg Thr Glu Thr Leu Ser Phe Gln Pro Ala Pro Glu Gln Leu
    50                  55                  60

Cys Asp Met Ser Leu His Val Asp Asn Glu Val Thr Ile Asn Gln Thr
65                  70                  75                  80

Thr Arg

<210> SEQ ID NO 12
<211> LENGTH: 61
<212> TYPE: PRT
<213> ORGANISM: Mus musculus

<400> SEQUENCE: 12

Leu Arg Lys Trp Lys Gly Met Leu Ser Arg Leu Gln Glu Leu Arg Lys
1               5                   10                  15

Glu Glu Glu Thr Leu Leu Arg Leu Lys Ala Ala Leu His Asp Gln Leu
            20                  25                  30

Asn Arg Leu Lys Val Glu Glu Leu Ala Leu Gln Ser Met Ile Asn Ser
        35                  40                  45

Arg Gly Arg Thr Glu Thr Leu Ser Ser Gln Pro Ala Arg
    50                  55                  60

<210> SEQ ID NO 13
<211> LENGTH: 53
<212> TYPE: PRT
<213> ORGANISM: Mus musculus

<400> SEQUENCE: 13

Leu Arg Lys Trp Lys Gly Met Leu Ser Arg Leu Arg Glu Leu Arg Lys
1               5                   10                  15

Glu Glu Glu Thr Leu Leu Arg Leu Lys Ala Ala Leu His Asp Gln Leu
            20                  25                  30

Asn Arg Leu Lys Val Glu Glu Leu Ala Leu Gln Ser Met Ile Asn Ser
```

```
                35                  40                  45
Arg Gly Arg Thr Glu
         50

<210> SEQ ID NO 14
<211> LENGTH: 51
<212> TYPE: PRT
<213> ORGANISM: Mus musculus

<400> SEQUENCE: 14

Leu Arg Lys Trp Lys Gly Met Leu Ser Arg Leu Gln Gly Leu Arg Lys
1               5                   10                  15

Glu Glu Glu Thr Leu Leu Arg Leu Lys Ala Ala Leu His Asp Gln Leu
                20                  25                  30

Asn Arg Leu Lys Val Glu Glu Leu Ala Leu Gln Ser Met Ile Asn Ser
            35                  40                  45

Arg Gly Lys
         50

<210> SEQ ID NO 15
<211> LENGTH: 86
<212> TYPE: PRT
<213> ORGANISM: Mus musculus

<400> SEQUENCE: 15

Leu Arg Lys Trp Lys Gly Met Leu Ser Arg Leu Gln Glu Leu Arg Lys
1               5                   10                  15

Glu Glu Glu Thr Leu Leu Arg Leu Lys Ala Ala Leu His Asp Gln Leu
                20                  25                  30

Asn Arg Leu Lys Val Glu Glu Leu Ala Leu Gln Ser Met Ile Asn Ser
            35                  40                  45

Arg Gly Arg Thr Glu Thr Leu Ser Ser Gln Pro Ala Pro Glu Gln Leu
         50                  55                  60

Cys Asp Met Tyr Leu His Val Asp Asn Glu Val Thr Ile Asn Gln Thr
65                  70                  75                  80

Thr Leu Lys Leu Ser Thr
                85

<210> SEQ ID NO 16
<211> LENGTH: 82
<212> TYPE: PRT
<213> ORGANISM: Mus musculus

<400> SEQUENCE: 16

Leu Arg Lys Trp Lys Gly Met Leu Ser Arg Leu Gln Glu Leu Arg Lys
1               5                   10                  15

Glu Glu Glu Thr Leu Leu Arg Leu Lys Ala Ala Leu His Asp Gln Leu
                20                  25                  30

Asn Arg Leu Lys Val Glu Glu Leu Ala Leu Gln Ser Met Ile Asn Ser
            35                  40                  45

Arg Gly Arg Thr Glu Thr Leu Ser Ser Gln Pro Ala Pro Glu Gln Leu
         50                  55                  60

Cys Asp Met Ser Leu His Val Asp Asn Glu Val Thr Ile Asn Gln Thr
65                  70                  75                  80

Ser Thr

<210> SEQ ID NO 17
<211> LENGTH: 95
```

<212> TYPE: PRT
<213> ORGANISM: Mus musculus

<400> SEQUENCE: 17

Leu Arg Lys Trp Lys Gly Met Leu Ser Arg Gln Gln Glu Pro Arg Lys
1               5                   10                  15

Glu Glu Glu Thr Leu Leu Arg Leu Lys Ala Ala Leu Arg Asp Gln Leu
            20                  25                  30

Asn Arg Leu Lys Val Glu Glu Leu Ala Leu Gln Ser Met Ile Asn Ser
        35                  40                  45

Arg Gly Arg Thr Glu Thr Leu Ser Ser Gln Pro Ala Pro Glu Gln Leu
    50                  55                  60

Cys Asp Met Ser Leu His Val Asp Asn Glu Val Thr Ile Asn Gln Thr
65                  70                  75                  80

Thr Leu Lys Leu Ser Thr Arg Ser Pro Met Glu Glu Glu Val
                85                  90                  95

<210> SEQ ID NO 18
<211> LENGTH: 95
<212> TYPE: PRT
<213> ORGANISM: Mus musculus

<400> SEQUENCE: 18

Leu Arg Lys Trp Lys Gly Met Leu Ser Arg Leu Gln Glu Leu Arg Lys
1               5                   10                  15

Glu Glu Glu Thr Leu Leu Arg Leu Lys Ala Ala Leu His Asp Gln Leu
            20                  25                  30

Asn Arg Leu Lys Val Glu Glu Leu Ala Leu Gln Ser Met Ile Asn Ser
        35                  40                  45

Arg Gly Arg Thr Glu Thr Leu Ser Ser Gln Pro Ala Pro Glu Gln Leu
    50                  55                  60

Cys Asp Met Ser Leu His Val Asp Asn Glu Val Thr Ile Asn Gln Thr
65                  70                  75                  80

Thr Leu Lys Leu Ser Thr Arg Ser Pro Met Glu Glu Glu Gly Arg
                85                  90                  95

<210> SEQ ID NO 19
<211> LENGTH: 82
<212> TYPE: PRT
<213> ORGANISM: Mus musculus

<400> SEQUENCE: 19

Leu Arg Lys Trp Lys Gly Met Leu Ser Arg Leu Gln Glu Leu Arg Lys
1               5                   10                  15

Glu Glu Glu Thr Leu Leu Arg Leu Lys Ala Ala Leu His Asp Gln Leu
            20                  25                  30

Asn Arg Leu Lys Val Glu Glu Leu Ala Leu Gln Ser Met Ile Asn Ser
        35                  40                  45

Arg Gly Arg Thr Glu Thr Leu Ser Ser Gln Pro Ala Pro Glu Gln Leu
    50                  55                  60

Cys Asp Met Ser Leu His Val Asp Asn Glu Val Thr Ile Asn Gln Thr
65                  70                  75                  80

Thr Leu

<210> SEQ ID NO 20
<211> LENGTH: 82
<212> TYPE: PRT
<213> ORGANISM: Mus musculus

<400> SEQUENCE: 20

Leu Arg Lys Trp Lys Gly Met Leu Ser Arg Leu Gln Glu Leu Arg Lys
1               5                   10                  15

Glu Glu Glu Thr Leu Leu Arg Leu Arg Ala Ala Leu His Asp Gln Leu
            20                  25                  30

Asn Arg Leu Lys Val Glu Glu Leu Ala Leu Gln Ser Met Ile Asn Ser
        35                  40                  45

Arg Gly Arg Thr Glu Thr Pro Ser Ser Gln Pro Ala Pro Glu Gln Leu
    50                  55                  60

Cys Asp Met Ser Leu His Val Asp Asn Glu Val Thr Ile Asn Gln Thr
65                  70                  75                  80

Thr Leu

<210> SEQ ID NO 21
<211> LENGTH: 81
<212> TYPE: PRT
<213> ORGANISM: Mus musculus

<400> SEQUENCE: 21

Leu Arg Lys Trp Lys Gly Met Leu Ser Arg Leu Gln Glu Leu Arg Lys
1               5                   10                  15

Glu Glu Glu Thr Leu Leu Arg Leu Lys Ala Ala Leu His Asp Gln Leu
            20                  25                  30

Asn Arg Leu Lys Val Glu Glu Leu Ala Leu Gln Ser Met Ile Asn Ser
        35                  40                  45

Arg Gly Arg Thr Glu Thr Leu Ser Ser Gln Pro Ala Pro Glu Gln Leu
    50                  55                  60

Cys Asp Met Ser Leu His Val Asp Asn Glu Val Thr Ile Asn Gln Thr
65                  70                  75                  80

Thr

<210> SEQ ID NO 22
<211> LENGTH: 82
<212> TYPE: PRT
<213> ORGANISM: Mus musculus

<400> SEQUENCE: 22

Leu Arg Lys Trp Lys Gly Met Leu Ser Arg Leu Gln Glu Leu Arg Lys
1               5                   10                  15

Glu Glu Glu Thr Leu Leu Arg Leu Lys Ala Ala Leu His Asp Gln Leu
            20                  25                  30

Asn Arg Leu Lys Val Glu Glu Leu Ala Leu Gln Ser Met Ile Asn Ser
        35                  40                  45

Arg Gly Arg Thr Glu Thr Leu Ser Ser Gln Pro Ala Pro Glu Gln Leu
    50                  55                  60

Cys Asp Met Ser Leu His Val Asp Asn Lys Val Thr Ile Asn Gln Thr
65                  70                  75                  80

Thr Pro

<210> SEQ ID NO 23
<211> LENGTH: 82
<212> TYPE: PRT
<213> ORGANISM: Mus musculus

<400> SEQUENCE: 23

Leu Arg Lys Trp Lys Gly Met Leu Ser Arg Leu Gln Glu Leu Arg Lys

```
                 1               5                  10                 15
Glu Glu Glu Thr Leu Leu Arg Leu Asn Ala Ala Leu His Asp Gln Leu
                20                  25                  30

Asn Arg Leu Lys Val Glu Glu Leu Ala Leu Gln Ser Met Ile Asn Ser
            35                  40                  45

Arg Gly Arg Thr Glu Thr Leu Ser Ser Gln Pro Ala Pro Glu Gln Leu
        50                  55                  60

Cys Asp Met Ser Leu His Val Asp Asn Glu Val Thr Ile Asn Gln Thr
65                  70                  75                  80

Thr Leu

<210> SEQ ID NO 24
<211> LENGTH: 82
<212> TYPE: PRT
<213> ORGANISM: Mus musculus

<400> SEQUENCE: 24

Leu Arg Lys Trp Lys Gly Met Leu Ser Arg Leu Gln Glu Leu Arg Asn
1               5                   10                  15

Glu Glu Glu Thr Leu Leu Arg Leu Lys Ala Ala Leu His Asp Gln Leu
                20                  25                  30

Asn Arg Leu Lys Val Glu Glu Leu Ala Leu Gln Ser Met Ile Asn Ser
            35                  40                  45

Arg Gly Arg Thr Glu Thr Leu Ser Ser Gln Pro Ala Pro Glu Gln Leu
        50                  55                  60

Cys Asp Met Ser Leu His Val Asp Asn Glu Val Thr Ile Asn Gln Thr
65                  70                  75                  80

Thr Leu

<210> SEQ ID NO 25
<211> LENGTH: 82
<212> TYPE: PRT
<213> ORGANISM: Mus musculus

<400> SEQUENCE: 25

Leu Arg Lys Trp Lys Gly Met Leu Ser Gln Leu Gln Glu Leu Arg Lys
1               5                   10                  15

Glu Glu Glu Thr Leu Leu Arg Leu Lys Ala Ala Leu His Asp Gln Leu
                20                  25                  30

Asn Arg Leu Lys Val Glu Glu Leu Ala Leu Gln Ser Met Ile Asn Ser
            35                  40                  45

Arg Gly Arg Thr Glu Thr Leu Ser Ser Gln Pro Val Pro Glu Gln Leu
        50                  55                  60

Cys Asp Met Ser Leu His Val Asp Asn Glu Val Thr Ile Asn Gln Thr
65                  70                  75                  80

Thr Leu

<210> SEQ ID NO 26
<211> LENGTH: 82
<212> TYPE: PRT
<213> ORGANISM: Mus musculus

<400> SEQUENCE: 26

Leu Arg Lys Trp Lys Gly Val Leu Ser Arg Leu Gln Glu Leu Arg Lys
1               5                   10                  15

Glu Glu Glu Thr Leu Leu Arg Leu Lys Ala Ala Leu His Asp Gln Leu
                20                  25                  30
```

-continued

```
Asn Arg Leu Lys Val Glu Glu Leu Ala Leu Gln Ser Met Ile Asn Ser
        35                  40                  45
Arg Gly Arg Thr Glu Thr Leu Ser Ser Gln Pro Ala Pro Glu Gln Leu
    50                  55                  60
Cys Asp Met Ser Leu His Val Asp Ser Glu Val Thr Ile Asn Gln Thr
65                  70                  75                  80
His Lys

<210> SEQ ID NO 27
<211> LENGTH: 82
<212> TYPE: PRT
<213> ORGANISM: Mus musculus

<400> SEQUENCE: 27

Leu Arg Lys Trp Lys Gly Met Leu Ser Arg Leu Gln Glu Leu Arg Lys
1               5                   10                  15
Glu Glu Glu Thr Leu Leu Arg Leu Lys Ala Ala Leu His Asp Gln Leu
            20                  25                  30
Asn Arg Leu Lys Val Glu Glu Leu Ala Leu Gln Ser Met Ile Asn Ser
        35                  40                  45
Arg Gly Arg Thr Glu Thr Leu Ser Ser Gln Pro Ala Pro Glu Gln Leu
    50                  55                  60
Cys Asp Met Ser Leu His Val Asp Asn Glu Val Thr Ile Asn Gln Thr
65                  70                  75                  80
His Lys

<210> SEQ ID NO 28
<211> LENGTH: 63
<212> TYPE: PRT
<213> ORGANISM: Mus musculus

<400> SEQUENCE: 28

Leu Arg Lys Trp Lys Gly Met Leu Ser Arg Leu Gln Glu Leu Arg Lys
1               5                   10                  15
Glu Glu Glu Thr Leu Leu Arg Leu Lys Ala Ala Leu His Asp Gln Leu
            20                  25                  30
Asn Arg Leu Lys Val Glu Glu Leu Ala Leu Gln Ser Met Ile Asn Ser
        35                  40                  45
Arg Gly Arg Thr Glu Thr Leu Ser Ser Gln Pro Ala Pro Glu Ser
    50                  55                  60

<210> SEQ ID NO 29
<211> LENGTH: 63
<212> TYPE: PRT
<213> ORGANISM: Mus musculus

<400> SEQUENCE: 29

Leu Arg Lys Trp Lys Gly Met Leu Ser Arg Leu Gln Glu Leu Arg Lys
1               5                   10                  15
Glu Glu Glu Thr Leu Leu Arg Leu Asn Ala Ala Leu His Asp Gln Leu
            20                  25                  30
Asn Arg Leu Lys Val Glu Glu Leu Ala Leu Gln Ser Met Ile Asn Ser
        35                  40                  45
Arg Gly Arg Thr Glu Thr Leu Ser Ser Gln Pro Ala Pro Glu Ser
    50                  55                  60

<210> SEQ ID NO 30
```

```
<211> LENGTH: 60
<212> TYPE: PRT
<213> ORGANISM: Mus musculus

<400> SEQUENCE: 30

Gln Arg Lys Trp Lys Gly Met Leu Ser Arg Leu Gln Glu Leu Arg Lys
1               5                   10                  15

Glu Glu Glu Thr Leu Leu Arg Leu Lys Ala Ala Leu His Asp Gln Leu
            20                  25                  30

Asn Arg Leu Lys Val Glu Glu Leu Ala Leu Gln Ser Met Ile Asn Ser
        35                  40                  45

Arg Gly Arg Thr Glu Thr Leu Ser Ser Gln Pro Ala
    50                  55                  60

<210> SEQ ID NO 31
<211> LENGTH: 81
<212> TYPE: PRT
<213> ORGANISM: Mus musculus

<400> SEQUENCE: 31

Arg Glu Trp Lys Gly Met Leu Ser Arg Leu Gln Glu Leu Arg Lys Glu
1               5                   10                  15

Glu Glu Thr Leu Leu Arg Leu Lys Ala Ala Leu His Asp Gln Leu Asn
            20                  25                  30

Arg Leu Lys Val Glu Glu Leu Ala Leu Gln Ser Met Ile Asn Ser Arg
        35                  40                  45

Gly Arg Thr Glu Thr Leu Ser Ser Gln Pro Ala Pro Glu Gln Leu Cys
    50                  55                  60

Asp Met Ser Leu His Val Asp Asn Glu Val Thr Ile Asn Gln Thr His
65                  70                  75                  80

Ser

<210> SEQ ID NO 32
<211> LENGTH: 48
<212> TYPE: PRT
<213> ORGANISM: Mus musculus

<400> SEQUENCE: 32

Phe Leu Val Asn Glu Gly Trp Ser Gln Leu Ala Ala Met His Cys Val
1               5                   10                  15

Met Leu Pro Asp Leu Leu Gly Leu Glu Arg Phe Arg Pro Pro Leu Leu
            20                  25                  30

Glu Met Leu Ala Arg Arg Trp Gln Asp Arg Cys Leu Glu Val Arg Glu
        35                  40                  45

<210> SEQ ID NO 33
<211> LENGTH: 50
<212> TYPE: PRT
<213> ORGANISM: Mus musculus

<400> SEQUENCE: 33

Arg Lys Trp Lys Gly Met Leu Ser Arg Leu Gln Glu Leu Arg Lys Glu
1               5                   10                  15

Glu Glu Thr Leu Leu Arg Leu Lys Ala Ala Leu His Asp Gln Leu Asn
            20                  25                  30

Arg Leu Lys Val Glu Glu Leu Ala Leu Gln Ser Met Ile Asn Ser Arg
        35                  40                  45

Gly Arg
    50
```

<210> SEQ ID NO 34
<211> LENGTH: 81
<212> TYPE: PRT
<213> ORGANISM: Mus musculus

<400> SEQUENCE: 34

Arg Lys Trp Lys Gly Met Leu Ser Arg Leu Gln Glu Leu Arg Lys Glu
1               5                   10                  15
Glu Glu Thr Leu Leu Arg Leu Lys Ala Ala Leu His Asp Gln Leu Asn
            20                  25                  30
Arg Leu Lys Val Glu Glu Leu Ala Leu Gln Ser Met Ile Asn Ser Arg
        35                  40                  45
Gly Arg Thr Glu Thr Leu Ser Ser Gln Pro Ala Pro Glu Gln Leu Cys
    50                  55                  60
Asp Met Ser Leu His Val Asp His Glu Val Thr Ile Asn Gln Thr Thr
65                  70                  75                  80
Leu

<210> SEQ ID NO 35
<211> LENGTH: 81
<212> TYPE: PRT
<213> ORGANISM: Mus musculus

<400> SEQUENCE: 35

Arg Lys Trp Lys Gly Met Leu Ser Arg Leu Gln Glu Leu Arg Lys Glu
1               5                   10                  15
Glu Glu Thr Leu Leu Arg Leu Lys Ala Ala Leu His Asp Gln Leu Asn
            20                  25                  30
Arg Leu Lys Val Glu Glu Leu Ala Leu Gln Ser Met Ile Asn Ser Arg
        35                  40                  45
Gly Arg Thr Glu Thr Leu Ser Ser Gln Pro Ala Pro Glu Gln Leu Cys
    50                  55                  60
Asp Met Ser Leu His Val Asp Asn Glu Val Thr Ile Asn Gln Thr Thr
65                  70                  75                  80
Pro

<210> SEQ ID NO 36
<211> LENGTH: 81
<212> TYPE: PRT
<213> ORGANISM: Mus musculus

<400> SEQUENCE: 36

Arg Lys Trp Lys Gly Met Leu Ser Gln Leu Gln Glu Leu Arg Lys Glu
1               5                   10                  15
Glu Glu Thr Leu Leu Arg Leu Lys Ala Ala Leu His Asp Gln Leu Asn
            20                  25                  30
Arg Leu Lys Val Glu Glu Leu Ala Leu Gln Ser Met Ile Asn Ser Arg
        35                  40                  45
Gly Arg Thr Glu Thr Leu Ser Ser Gln Pro Ala Pro Glu Gln Leu Cys
    50                  55                  60
Asp Met Ser Leu His Val Asp Asn Glu Val Thr Ile Asn Gln Thr Thr
65                  70                  75                  80
Pro

<210> SEQ ID NO 37
<211> LENGTH: 81

```
<212> TYPE: PRT
<213> ORGANISM: Mus musculus

<400> SEQUENCE: 37

Arg Lys Trp Lys Gly Met Leu Ser Arg Leu Gln Glu Leu Arg Met Glu
1               5                   10                  15

Glu Glu Thr Leu Leu Arg Leu Lys Ala Ala Leu His Asp Gln Leu Asn
                20                  25                  30

Leu Leu Lys Val Glu Glu Leu Ala Leu Gln Ser Met Ile Asn Ser Arg
            35                  40                  45

Gly Arg Thr Glu Thr Leu Ser Ser Gln Pro Ala Pro Glu Gln Leu Cys
    50                  55                  60

Asp Met Ser Leu His Val Asp Asn Glu Val Thr Ile Asn Leu Thr Thr
65                  70                  75                  80

Pro

<210> SEQ ID NO 38
<211> LENGTH: 81
<212> TYPE: PRT
<213> ORGANISM: Mus musculus

<400> SEQUENCE: 38

Arg Lys Trp Lys Gly Met Leu Ser Arg Leu Gln Glu Leu Arg Lys Glu
1               5                   10                  15

Glu Glu Thr Leu Leu Arg Leu Asn Ala Ala Leu His Asp Gln Leu Asn
                20                  25                  30

Arg Leu Lys Val Glu Glu Leu Ala Leu Gln Ser Met Ile Asn Ser Arg
            35                  40                  45

Gly Arg Thr Glu Thr Leu Ser Ser Gln Pro Ala Pro Glu Gln Leu Cys
    50                  55                  60

Asp Met Ser Leu His Val Asp Asn Glu Val Thr Ile Asn Gln Thr Thr
65                  70                  75                  80

Pro

<210> SEQ ID NO 39
<211> LENGTH: 81
<212> TYPE: PRT
<213> ORGANISM: Mus musculus

<400> SEQUENCE: 39

Arg Lys Trp Lys Gly Met Leu Ser Arg Leu Gln Glu Leu Arg Lys Glu
1               5                   10                  15

Glu Glu Thr Leu Leu Arg Leu Lys Ala Ala Leu His Asp Gln Leu Asn
                20                  25                  30

Arg Leu Lys Val Glu Glu Leu Ala Leu Gln Ser Met Ile Asn Ser Arg
            35                  40                  45

Gly Arg Ala Glu Thr Leu Ser Ser Gln Pro Ala Pro Glu Gln Leu Cys
    50                  55                  60

Asp Met Ser Leu His Val Asp Asn Glu Val Thr Ile Asn Gln Thr Thr
65                  70                  75                  80

Pro

<210> SEQ ID NO 40
<211> LENGTH: 81
<212> TYPE: PRT
<213> ORGANISM: Mus musculus

<400> SEQUENCE: 40
```

-continued

```
Arg Lys Trp Lys Gly Met Leu Ser Arg Leu Gln Glu Leu Arg Lys Glu
1               5                   10                  15

Glu Glu Thr Leu Leu Arg Leu Lys Ala Ala Leu His Asp Gln Leu Asn
            20                  25                  30

Arg Leu Lys Val Glu Glu Leu Ala Leu Gln Ser Met Ile Asn Ser Arg
        35                  40                  45

Gly Arg Thr Glu Thr Leu Ser Ser Gln Pro Thr Pro Glu Gln Leu Cys
    50                  55                  60

Asp Met Ser Leu His Val Asp Asn Glu Val Thr Ile Asn Gln Thr Thr
65                  70                  75                  80

Thr

<210> SEQ ID NO 41
<211> LENGTH: 81
<212> TYPE: PRT
<213> ORGANISM: Mus musculus

<400> SEQUENCE: 41

Arg Lys Trp Lys Gly Met Leu Ser Arg Leu Gln Glu Leu Arg Lys Glu
1               5                   10                  15

Glu Glu Thr Leu Leu Arg Leu Lys Ala Ala Leu His Asp Gln Leu Asn
            20                  25                  30

Arg Leu Lys Val Glu Glu Leu Ala Leu Gln Ser Met Ile Asn Ser Arg
        35                  40                  45

Gly Arg Thr Glu Thr Leu Ser Ser Gln Pro Ala Pro Glu Gln Leu Cys
    50                  55                  60

Asp Met Ser Leu His Val Asp Asn Glu Val Thr Ile Asn Gln Thr Lys
65                  70                  75                  80

Leu

<210> SEQ ID NO 42
<211> LENGTH: 81
<212> TYPE: PRT
<213> ORGANISM: Mus musculus

<400> SEQUENCE: 42

Arg Lys Trp Lys Gly Met Leu Ser Arg Leu Gln Glu Leu Arg Lys Glu
1               5                   10                  15

Glu Glu Thr Leu Leu Arg Leu Lys Ala Ala Leu His Asp Gln Leu Asn
            20                  25                  30

Arg Leu Lys Val Glu Glu Leu Ala Leu Gln Ser Met Ile Asn Ser Arg
        35                  40                  45

Gly Arg Thr Glu Thr Leu Ser Ser Gln Pro Ala Pro Glu Gln Leu Cys
    50                  55                  60

Asp Met Ser Leu His Val Asp Asn Glu Val Thr Ile Asn Gln Thr Thr
65                  70                  75                  80

Gln

<210> SEQ ID NO 43
<211> LENGTH: 81
<212> TYPE: PRT
<213> ORGANISM: Mus musculus

<400> SEQUENCE: 43

Arg Lys Trp Lys Gly Met Leu Ser Arg Leu Gln Glu Leu Arg Lys Glu
1               5                   10                  15
```

```
Glu Glu Thr Leu Leu Arg Leu Lys Ala Ala Leu His Asp Gln Leu Asn
            20                  25                  30

Arg Leu Lys Val Glu Glu Leu Ala Leu Gln Ser Met Ile Asn Ser Arg
        35                  40                  45

Gly Arg Thr Glu Thr Leu Ser Ser Gln Pro Ala Pro Glu Gln Leu Cys
    50                  55                  60

Asp Met Ser Leu His Val Asp Asn Glu Val Thr Ile Asn Gln Thr Arg
65                  70                  75                  80

Pro

<210> SEQ ID NO 44
<211> LENGTH: 81
<212> TYPE: PRT
<213> ORGANISM: Mus musculus

<400> SEQUENCE: 44

Arg Lys Trp Glu Gly Met Leu Ser Arg Leu Gln Glu Leu Arg Lys Glu
1               5                   10                  15

Glu Glu Thr Leu Leu Arg Leu Lys Ala Ala Leu His Asp Gln Leu Asn
            20                  25                  30

Arg Leu Lys Val Glu Glu Leu Ala Leu Gln Ser Met Ile Asn Ser Arg
        35                  40                  45

Gly Arg Thr Glu Thr Leu Ser Ser Gln Pro Ala Pro Glu Gln Leu Cys
    50                  55                  60

Asp Met Ser Leu His Val Asp Asn Glu Val Thr Ile Asn Gln Thr Arg
65                  70                  75                  80

Pro

<210> SEQ ID NO 45
<211> LENGTH: 81
<212> TYPE: PRT
<213> ORGANISM: Mus musculus

<400> SEQUENCE: 45

Arg Lys Trp Lys Gly Thr Leu Ser Arg Leu Gln Asp Leu Arg Lys Glu
1               5                   10                  15

Glu Glu Thr Leu Leu Arg Leu Lys Ala Ala Leu His Asp Gln Leu Asn
            20                  25                  30

Arg Leu Lys Val Glu Glu Leu Ala Leu Gln Ser Met Ile Asn Ser Arg
        35                  40                  45

Gly Arg Thr Glu Thr Leu Ser Ser Gln Pro Ala Pro Glu Gln Leu Cys
    50                  55                  60

Asp Val Ser Leu His Val Asp Asn Glu Val Thr Ile Asn Gln Thr Arg
65                  70                  75                  80

Pro

<210> SEQ ID NO 46
<211> LENGTH: 49
<212> TYPE: PRT
<213> ORGANISM: Mus musculus

<400> SEQUENCE: 46

Lys Trp Lys Gly Met Leu Ser Arg Leu Lys Glu Leu Arg Lys Glu Glu
1               5                   10                  15

Glu Thr Leu Leu Arg Leu Lys Ala Ala Leu His Asp Gln Leu Asn Arg
            20                  25                  30

Leu Lys Val Glu Glu Leu Ala Leu Gln Ser Met Ile Asn Ser Arg Gly
```

35                  40                  45
Arg

<210> SEQ ID NO 47
<211> LENGTH: 79
<212> TYPE: PRT
<213> ORGANISM: Mus musculus

<400> SEQUENCE: 47

Trp Lys Gly Met Leu Ser Arg Leu Gln Glu Leu Arg Lys Glu Glu Glu
1               5                   10                  15

Thr Leu Leu Arg Leu Lys Ala Ala Leu His Asp Gln Leu Asn Arg Leu
            20                  25                  30

Lys Val Glu Glu Leu Ala Leu Gln Ser Met Ile Asn Ser Arg Gly Arg
        35                  40                  45

Thr Glu Thr Leu Ser Ser Gln Pro Ala Pro Glu Gln Leu Cys Asp Met
    50                  55                  60

Ser Leu His Val Asp Asn Glu Val Thr Ile Asn Gln Thr Thr Leu
65                  70                  75

<210> SEQ ID NO 48
<211> LENGTH: 79
<212> TYPE: PRT
<213> ORGANISM: Mus musculus

<400> SEQUENCE: 48

Trp Lys Gly Met Leu Ser Arg Leu Gln Glu Leu Arg Lys Glu Glu Glu
1               5                   10                  15

Ala Leu Leu Arg Leu Lys Ala Ala Leu His Asp Gln Leu Asn Arg Leu
            20                  25                  30

Lys Val Glu Glu Leu Ala Leu Gln Ser Met Ile Asn Ser Arg Gly Arg
        35                  40                  45

Thr Glu Thr Leu Ser Ser Gln Pro Ala Pro Glu Gln Leu Cys Asp Met
    50                  55                  60

Ser Leu His Val Asp Asn Glu Val Thr Ile Asn Gln Thr Thr Leu
65                  70                  75

<210> SEQ ID NO 49
<211> LENGTH: 47
<212> TYPE: PRT
<213> ORGANISM: Mus musculus

<400> SEQUENCE: 49

Lys Gly Met Leu Ser Arg Leu Gln Glu Leu Arg Lys Glu Glu Glu Thr
1               5                   10                  15

Leu Leu Arg Leu Lys Ala Ala Leu His Asp Gln Leu Asn Arg Leu Lys
            20                  25                  30

Val Lys Glu Leu Ala Leu Gln Ser Met Ile Asn Ser Arg Gly Arg
        35                  40                  45

<210> SEQ ID NO 50
<211> LENGTH: 90
<212> TYPE: PRT
<213> ORGANISM: Mus musculus

<400> SEQUENCE: 50

Gly Met Leu Ser Arg Leu Gln Glu Leu Arg Lys Glu Glu Glu Thr Leu
1               5                   10                  15

Leu Arg Leu Lys Ala Ala Leu His Asp Gln Leu Asn Arg Leu Lys Val

-continued

```
                    20                  25                  30
Glu Glu Leu Ala Leu Gln Ser Met Ile Asn Ser Arg Gly Arg Thr Glu
         35                  40                  45

Thr Leu Ser Ser Gln Pro Ala Pro Glu Gln Leu Cys Asp Met Ser Leu
 50                  55                  60

His Val Asp Asn Glu Val Thr Ile Asn Gln Thr Thr Leu Lys Leu Ser
65                  70                  75                  80

Thr Arg Ser Pro Met Glu Glu Glu Gly
                 85                  90

<210> SEQ ID NO 51
<211> LENGTH: 77
<212> TYPE: PRT
<213> ORGANISM: Mus musculus

<400> SEQUENCE: 51

Gly Met Leu Ser Arg Leu Gln Glu Leu Arg Lys Glu Glu Glu Thr Leu
1               5                   10                  15

Leu Arg Leu Lys Ala Ala Leu His Asp Gln Leu Asn Arg Leu Lys Val
                20                  25                  30

Glu Glu Leu Ala Leu Gln Ser Met Ile Asn Ser Arg Gly Arg Thr Glu
         35                  40                  45

Ala Leu Ser Ser Gln Pro Ala Pro Glu Gln Leu Cys Asp Thr Ser Leu
 50                  55                  60

His Val Asp Asn Glu Val Thr Ile Asn Gln Thr Thr Leu
65                  70                  75

<210> SEQ ID NO 52
<211> LENGTH: 77
<212> TYPE: PRT
<213> ORGANISM: Mus musculus

<400> SEQUENCE: 52

Gly Met Leu Ser Arg Leu Gln Glu Leu Arg Lys Glu Glu Glu Thr Leu
1               5                   10                  15

Leu Arg Leu Lys Ala Ala Leu His Asp Gln Leu Asn Arg Leu Lys Val
                20                  25                  30

Glu Glu Leu Ala Leu Gln Ser Met Ile Asn Ser Arg Gly Arg Thr Glu
         35                  40                  45

Thr Leu Ser Ser Gln Pro Ala Pro Glu Gln Leu Cys Asp Met Ser Leu
 50                  55                  60

His Val Asp Asn Glu Val Thr Ile Asn Gln Thr His Ser
65                  70                  75

<210> SEQ ID NO 53
<211> LENGTH: 77
<212> TYPE: PRT
<213> ORGANISM: Mus musculus

<400> SEQUENCE: 53

Gly Met Leu Ser Arg Leu Gln Glu Leu Arg Lys Glu Glu Glu Thr Leu
1               5                   10                  15

Leu Arg Leu Lys Ala Ala Leu His Asp Gln Leu Asn Arg Leu Lys Val
                20                  25                  30

Glu Glu Leu Ala Leu Gln Ser Met Ile Asn Ser Arg Gly Arg Thr Glu
         35                  40                  45

Thr Leu Ser Ser Gln Pro Ala Pro Glu Gln Leu Cys Asp Met Ser Leu
 50                  55                  60
```

```
His Val Asp Asn Glu Val Ala Ile Asn Gln Thr Thr Pro
65                  70                  75

<210> SEQ ID NO 54
<211> LENGTH: 77
<212> TYPE: PRT
<213> ORGANISM: Mus musculus

<400> SEQUENCE: 54

Gly Met Leu Ser Arg Leu Gln Glu Leu Arg Lys Glu Glu Thr Leu
1               5                   10                  15

Leu Arg Leu Lys Ala Ala Leu His Asp Gln Leu Asn Arg Leu Lys Val
                20                  25                  30

Glu Glu Leu Ala Leu Gln Ser Met Ile Asn Ser Arg Gly Arg Thr Glu
            35                  40                  45

Thr Leu Ser Ser Gln Pro Ala Pro Glu Gln Leu Cys Asp Met Ser Leu
        50                  55                  60

His Val Asp Asn Glu Val Thr Ile Asn Gln Thr Thr Pro
65                  70                  75

<210> SEQ ID NO 55
<211> LENGTH: 76
<212> TYPE: PRT
<213> ORGANISM: Mus musculus

<400> SEQUENCE: 55

Gly Met Leu Ser Arg Leu Gln Glu Leu Arg Lys Glu Glu Thr Leu
1               5                   10                  15

Leu Arg Leu Lys Ala Ala Leu His Asp Gln Leu Asn Arg Leu Lys Val
                20                  25                  30

Glu Glu Leu Ala Leu Gln Ser Met Ile Asn Ser Arg Glu Arg Thr Glu
            35                  40                  45

Thr Leu Ser Ser Arg Pro Ala Pro Glu Gln Leu Cys Asp Met Ser Leu
        50                  55                  60

His Val Asp Asn Glu Val Thr Ile Asn Gln Thr Thr
65                  70                  75

<210> SEQ ID NO 56
<211> LENGTH: 76
<212> TYPE: PRT
<213> ORGANISM: Mus musculus

<400> SEQUENCE: 56

Gly Met Leu Ser Arg Leu Gln Glu Leu Arg Lys Glu Glu Thr Leu
1               5                   10                  15

Leu Arg Leu Lys Ala Ala Leu His Asp Gln Leu Asn Arg Leu Lys Val
                20                  25                  30

Glu Glu Leu Ala Leu Gln Ser Met Ile Asn Ser Arg Gly Arg Thr Glu
            35                  40                  45

Thr Leu Ser Ser Gln Pro Ala Pro Glu Gln Leu Cys Asp Met Ser Leu
        50                  55                  60

His Val Asp Asn Glu Val Thr Ile Asp Gln Gly Ala
65                  70                  75

<210> SEQ ID NO 57
<211> LENGTH: 74
<212> TYPE: PRT
<213> ORGANISM: Mus musculus
```

```
<400> SEQUENCE: 57

Gly Met Leu Ser Arg Leu Gln Glu Leu Arg Lys Glu Glu Glu Thr Leu
1               5                   10                  15

Leu Arg Leu Lys Ala Ala Leu His Asn Gln Leu Asn Arg Leu Lys Val
            20                  25                  30

Glu Glu Leu Ala Leu Gln Ser Met Ile Asn Ser Arg Gly Arg Thr Glu
        35                  40                  45

Thr Leu Ser Ser Gln Pro Ala Pro Glu Gln Leu Cys Asp Met Ser Leu
    50                  55                  60

His Val Asp Asn Glu Val Thr Ile Asn Gln
65                  70

<210> SEQ ID NO 58
<211> LENGTH: 69
<212> TYPE: PRT
<213> ORGANISM: Mus musculus

<400> SEQUENCE: 58

Gly Met Leu Ser Arg Leu Gln Glu Leu Arg Lys Glu Glu Glu Thr Leu
1               5                   10                  15

Leu Arg Leu Lys Ala Ala Leu His Asp Gln Leu Asn Arg Leu Lys Val
            20                  25                  30

Glu Glu Leu Ala Leu Gln Ser Met Ile Asn Ser Arg Gly Arg Thr Glu
        35                  40                  45

Thr Leu Ser Ser Gln Pro Ala Pro Glu Gln Leu Cys Asp Met Ser Leu
    50                  55                  60

His Val Asp His Glu
65

<210> SEQ ID NO 59
<211> LENGTH: 69
<212> TYPE: PRT
<213> ORGANISM: Mus musculus

<400> SEQUENCE: 59

Gly Met Leu Ser Arg Leu Gln Glu Leu Arg Lys Glu Glu Glu Thr Leu
1               5                   10                  15

Leu Arg Leu Lys Ala Ala Leu His Asp Gln Leu Asn Arg Leu Lys Val
            20                  25                  30

Glu Glu Leu Ala Leu Gln Ser Met Ile Asn Ser Arg Gly Arg Thr Glu
        35                  40                  45

Thr Leu Ser Ser Gln Pro Ala Pro Glu Gln Leu Cys Asp Met Ser Leu
    50                  55                  60

His Val Asp Ile Glu
65

<210> SEQ ID NO 60
<211> LENGTH: 67
<212> TYPE: PRT
<213> ORGANISM: Mus musculus

<400> SEQUENCE: 60

Gly Met Leu Ser Arg Leu Gln Glu Leu Arg Lys Glu Glu Glu Thr Leu
1               5                   10                  15

Leu Arg Leu Lys Ala Ala Leu His Asp Gln Leu Asn Arg Leu Lys Val
            20                  25                  30

Glu Glu Leu Ala Leu Gln Ser Met Ile Asn Ser Arg Gly Arg Thr Glu
        35                  40                  45
```

```
Thr Leu Ser Ser Gln Pro Ala Pro Glu Gln Leu Cys Asp Thr Ser Leu
        50                  55                  60

His Val Thr
 65
```

<210> SEQ ID NO 61
<211> LENGTH: 46
<212> TYPE: PRT
<213> ORGANISM: Mus musculus

<400> SEQUENCE: 61

```
Gly Met Leu Ser Arg Leu Gln Glu Leu Arg Lys Glu Glu Glu Thr Leu
 1               5                  10                  15

Leu Arg Leu Lys Ala Ala Leu His Asp Gln Leu Asn Arg Leu Lys Val
            20                  25                  30

Glu Glu Leu Ala Leu Gln Ser Met Ile Asn Ser Arg Gly Arg
        35                  40                  45
```

<210> SEQ ID NO 62
<211> LENGTH: 46
<212> TYPE: PRT
<213> ORGANISM: Mus musculus

<400> SEQUENCE: 62

```
Arg Met Leu Ser Gln Leu Gln Glu Leu Arg Lys Glu Glu Glu Thr Leu
 1               5                  10                  15

Leu Arg Leu Lys Ala Thr Leu His Asp Gln Leu Asn Arg Leu Lys Val
            20                  25                  30

Glu Glu Leu Ala Leu Gln Ser Met Ile Asn Ser Arg Gly Lys
        35                  40                  45
```

<210> SEQ ID NO 63
<211> LENGTH: 75
<212> TYPE: PRT
<213> ORGANISM: Mus musculus

<400> SEQUENCE: 63

```
Leu Ser Arg Leu Gln Glu Leu Arg Lys Glu Glu Glu Thr Leu Leu Arg
 1               5                  10                  15

Leu Lys Ala Ala Leu His Asp Gln Leu Asn Arg Leu Lys Val Glu Glu
            20                  25                  30

Leu Ala Leu Gln Ser Met Ile Asn Ser Arg Gly Arg Thr Glu Thr Leu
        35                  40                  45

Ser Ser Gln Pro Ala Pro Glu Gln Leu Cys Asp Met Ser Leu His Val
    50                  55                  60

Asp Asn Glu Val Thr Ile Asn Gln Thr Thr Leu
 65                  70                  75
```

<210> SEQ ID NO 64
<211> LENGTH: 69
<212> TYPE: PRT
<213> ORGANISM: Mus musculus

<400> SEQUENCE: 64

```
Leu Ser Arg Leu Gln Glu Leu Arg Lys Glu Glu Glu Thr Leu Leu Arg
 1               5                  10                  15

Leu Lys Ala Ala Leu His Asp Gln Leu Asn Arg Leu Lys Val Glu Glu
            20                  25                  30

Leu Ala Leu Gln Ser Met Ile Asn Ser Arg Gly Arg Thr Glu Thr Leu
```

-continued

```
                35                  40                  45

Ser Ser Gln Pro Ala Pro Glu Gln Leu Cys Asp Met Ser Leu His Val
    50                  55                  60

Asp Asn Glu Ala Thr
65

<210> SEQ ID NO 65
<211> LENGTH: 66
<212> TYPE: PRT
<213> ORGANISM: Mus musculus

<400> SEQUENCE: 65

Arg Leu Gln Glu Leu Arg Lys Glu Glu Glu Thr Leu Leu Arg Leu Lys
1               5                   10                  15

Ala Ala Leu His Asp Gln Leu Asn Arg Leu Lys Val Glu Glu Leu Ala
                20                  25                  30

Leu Gln Ser Met Ile Asn Ser Arg Gly Arg Thr Glu Thr Leu Ser Ser
            35                  40                  45

Gln Pro Ala Pro Glu Gln Leu Cys Asp Met Ser Leu His Val Asp Asn
    50                  55                  60

Glu Val
65

<210> SEQ ID NO 66
<211> LENGTH: 61
<212> TYPE: PRT
<213> ORGANISM: Mus musculus

<400> SEQUENCE: 66

Arg Leu Arg Glu Leu Arg Lys Glu Glu Lys Thr Leu Leu Arg Leu Lys
1               5                   10                  15

Ala Ala Leu His Asp Gln Leu Asn Arg Leu Lys Val Glu Glu Leu Ala
                20                  25                  30

Leu Gln Ser Met Ile Asn Ser Arg Gly Arg Thr Glu Thr Leu Ser Ser
            35                  40                  45

Gln Pro Ala Pro Glu Gln Cys Pro Tyr Met Leu Thr Thr
    50                  55                  60

<210> SEQ ID NO 67
<211> LENGTH: 61
<212> TYPE: PRT
<213> ORGANISM: Mus musculus

<400> SEQUENCE: 67

Arg Leu Gln Glu Leu Arg Lys Glu Glu Glu Thr Leu Leu Arg Leu Lys
1               5                   10                  15

Ala Ala Leu His Asp Gln Leu Asn Arg Leu Lys Val Glu Glu Leu Ala
                20                  25                  30

Leu Gln Ser Met Ile Asn Ser Arg Gly Arg Thr Glu Thr Leu Ser Ser
            35                  40                  45

Gln Pro Ala Pro Gly Gln Cys Pro Tyr Met Leu Thr Thr
    50                  55                  60

<210> SEQ ID NO 68
<211> LENGTH: 61
<212> TYPE: PRT
<213> ORGANISM: Mus musculus

<400> SEQUENCE: 68
```

```
Arg Leu Gln Glu Leu Arg Lys Glu Glu Glu Thr Gln Leu Arg Leu Lys
1               5                   10                  15

Ala Ala Leu His Asp Gln Leu Asn Arg Leu Lys Val Glu Glu Leu Ala
                20                  25                  30

Leu Gln Ser Met Ile Asn Ser Arg Gly Arg Thr Glu Thr Leu Ser Ser
            35                  40                  45

Gln Pro Ala Pro Glu Gln Cys Pro Tyr Met Leu Thr Thr
    50                  55                  60
```

<210> SEQ ID NO 69
<211> LENGTH: 40
<212> TYPE: PRT
<213> ORGANISM: Mus musculus

<400> SEQUENCE: 69

```
Arg Leu Gln Glu Leu Arg Lys Glu Glu Glu Thr Leu Leu Arg Leu Lys
1               5                   10                  15

Ala Ala Leu His Asp Gln Leu Asn Arg Leu Lys Val Glu Glu Leu Ala
                20                  25                  30

Leu Gln Ser Met Ile Asn Ser Arg
            35                  40
```

<210> SEQ ID NO 70
<211> LENGTH: 956
<212> TYPE: PRT
<213> ORGANISM: Mus musculus

<400> SEQUENCE: 70

```
Met Ala Asp Pro Ala Glu Cys Ser Ile Lys Val Met Cys Arg Phe Arg
1               5                   10                  15

Pro Leu Asn Glu Ala Glu Ile Leu Arg Gly Asp Lys Phe Ile Pro Lys
                20                  25                  30

Phe Lys Gly Glu Glu Thr Val Val Ile Gly Gln Gly Lys Pro Tyr Val
            35                  40                  45

Phe Asp Arg Val Leu Pro Pro Asn Thr Thr Gln Glu Gln Val Tyr Asn
    50                  55                  60

Ala Cys Ala Lys Gln Ile Val Lys Asp Val Leu Glu Gly Tyr Asn Gly
65                  70                  75                  80

Thr Ile Phe Ala Tyr Gly Gln Thr Ser Ser Gly Lys Thr His Thr Met
                85                  90                  95

Glu Gly Lys Leu His Asp Pro Gln Leu Met Gly Ile Ile Pro Arg Ile
            100                 105                 110

Ala His Asp Ile Phe Asp His Ile Tyr Ser Met Asp Glu Asn Leu Glu
        115                 120                 125

Phe His Ile Lys Val Ser Tyr Phe Glu Ile Tyr Leu Asp Lys Ile Arg
    130                 135                 140

Asp Leu Leu Asp Val Ser Lys Thr Asn Leu Ala Val His Glu Asp Lys
145                 150                 155                 160

Asn Arg Val Pro Tyr Val Lys Gly Cys Thr Glu Arg Phe Val Ser Ser
                165                 170                 175

Pro Glu Glu Val Met Asp Val Ile Asp Glu Gly Lys Ala Asn Arg His
            180                 185                 190

Val Ala Val Thr Asn Met Asn Glu His Ser Ser Arg Ser His Ser Ile
        195                 200                 205

Phe Leu Ile Asn Ile Lys Gln Glu Asn Val Glu Thr Glu Lys Lys Leu
    210                 215                 220
```

-continued

```
Ser Gly Lys Leu Tyr Leu Val Asp Leu Ala Gly Ser Glu Lys Val Ser
225                 230                 235                 240

Lys Thr Gly Ala Glu Gly Ala Val Leu Asp Glu Ala Lys Asn Ile Asn
            245                 250                 255

Lys Ser Leu Ser Ala Leu Gly Asn Val Ile Ser Ala Leu Ala Glu Gly
        260                 265                 270

Thr Lys Thr His Val Pro Tyr Arg Asp Ser Lys Met Thr Arg Ile Leu
    275                 280                 285

Gln Asp Ser Leu Gly Gly Asn Cys Arg Thr Thr Ile Val Ile Cys Cys
290                 295                 300

Ser Pro Ser Val Phe Asn Glu Ala Glu Thr Lys Ser Thr Leu Met Phe
305                 310                 315                 320

Gly Gln Arg Ala Lys Thr Ile Lys Asn Thr Val Ser Val Asn Leu Glu
            325                 330                 335

Leu Thr Ala Glu Glu Trp Lys Lys Lys Tyr Glu Lys Glu Lys Glu Lys
            340                 345                 350

Asn Lys Ala Leu Lys Ser Val Leu Gln His Leu Glu Met Glu Leu Asn
        355                 360                 365

Arg Trp Arg Asn Gly Glu Ala Val Pro Glu Asp Glu Gln Ile Ser Ala
370                 375                 380

Lys Asp His Lys Ser Leu Glu Pro Cys Asp Asn Thr Pro Ile Ile Asp
385                 390                 395                 400

Asn Ile Thr Pro Val Val Asp Gly Ile Ser Ala Glu Lys Glu Lys Tyr
            405                 410                 415

Asp Glu Glu Ile Thr Ser Leu Tyr Arg Gln Leu Asp Asp Lys Asp Asp
            420                 425                 430

Glu Ile Asn Gln Gln Ser Gln Leu Ala Glu Lys Leu Lys Gln Gln Met
        435                 440                 445

Leu Asp Gln Asp Glu Leu Leu Ala Ser Thr Arg Arg Asp Tyr Glu Lys
    450                 455                 460

Ile Gln Glu Glu Leu Thr Arg Leu Gln Ile Glu Asn Glu Ala Ala Lys
465                 470                 475                 480

Asp Glu Val Lys Glu Val Leu Gln Ala Leu Glu Glu Leu Ala Val Asn
            485                 490                 495

Tyr Asp Gln Lys Ser Gln Glu Val Glu Asp Lys Thr Arg Ala Asn Glu
            500                 505                 510

Gln Leu Thr Asp Glu Leu Ala Gln Lys Thr Thr Thr Leu Thr Thr Thr
        515                 520                 525

Gln Arg Glu Leu Ser Gln Leu Gln Glu Leu Ser Asn His Gln Lys Lys
    530                 535                 540

Arg Ala Thr Glu Ile Leu Asn Leu Leu Leu Lys Asp Leu Gly Glu Ile
545                 550                 555                 560

Gly Gly Ile Ile Gly Thr Asn Asp Val Lys Thr Leu Ala Asp Val Asn
            565                 570                 575

Gly Val Ile Glu Glu Phe Thr Met Ala Arg Leu Tyr Ile Ser Lys
            580                 585                 590

Met Lys Ser Glu Val Lys Ser Leu Val Asn Arg Ser Lys Gln Leu Glu
        595                 600                 605

Ser Ala Gln Met Asp Ser Asn Arg Lys Met Asn Ala Ser Glu Arg Glu
    610                 615                 620

Leu Ala Ala Cys Gln Leu Leu Ile Ser Gln His Glu Ala Lys Ile Lys
625                 630                 635                 640

Ser Leu Thr Asp Tyr Met Gln Asn Met Glu Gln Lys Arg Arg Gln Leu
```

```
                     645                 650                 655
Glu Glu Ser Gln Asp Ser Leu Ser Glu Leu Ala Lys Leu Arg Ala
            660                 665                 670
Gln Glu Lys Met His Glu Val Ser Phe Gln Asp Lys Glu Lys Glu His
        675                 680                 685
Leu Thr Arg Leu Gln Asp Ala Glu Glu Val Lys Lys Ala Leu Glu Gln
    690                 695                 700
Gln Met Glu Ser His Arg Glu Ala His Gln Lys Gln Leu Ser Arg Leu
705                 710                 715                 720
Arg Asp Glu Ile Glu Glu Lys Gln Arg Ile Ile Asp Glu Ile Arg Asp
                725                 730                 735
Leu Asn Gln Lys Leu Gln Leu Glu Gln Glu Arg Leu Ser Ser Asp Tyr
            740                 745                 750
Asn Lys Leu Lys Ile Glu Asp Gln Glu Arg Glu Val Lys Leu Glu Lys
        755                 760                 765
Leu Leu Leu Asn Asp Lys Arg Glu Gln Ala Arg Glu Asp Leu Lys
    770                 775                 780
Gly Leu Glu Glu Thr Val Ser Ile Glu Leu Gln Thr Leu His Asn Leu
785                 790                 795                 800
Arg Lys Leu Phe Val Gln Asp Leu Thr Thr Arg Val Lys Lys Ser Val
                805                 810                 815
Glu Leu Asp Ser Asp Gly Gly Ser Ala Ala Gln Lys Gln Lys
            820                 825                 830
Ile Ser Phe Leu Glu Asn Asn Leu Glu Gln Leu Thr Lys Val His Lys
        835                 840                 845
Gln Leu Val Arg Asp Asn Ala Asp Leu Arg Cys Glu Leu Pro Lys Leu
    850                 855                 860
Glu Lys Arg Leu Arg Ala Thr Ala Glu Arg Val Lys Ala Leu Glu Ser
865                 870                 875                 880
Ala Leu Lys Glu Ala Lys Glu Asn Ala Met Arg Asp Arg Lys Arg Tyr
                885                 890                 895
Gln Gln Glu Val Asp Arg Ile Lys Glu Ala Val Arg Ala Lys Asn Met
            900                 905                 910
Ala Arg Arg Ala His Ser Ala Gln Ile Ala Lys Pro Ile Arg Pro Gly
        915                 920                 925
His Tyr Pro Ala Ser Ser Pro Thr Ala Val His Ala Val Arg Gly Gly
    930                 935                 940
Gly Gly Gly Ser Ser Asn Ser Thr His Tyr Gln Lys
945                 950                 955

<210> SEQ ID NO 71
<211> LENGTH: 61
<212> TYPE: PRT
<213> ORGANISM: Mus musculus

<400> SEQUENCE: 71

Gly Ser Ala Ala Gln Lys Gln Lys Ile Ser Phe Leu Glu Asn Asn Leu
1               5                   10                  15
Glu Gln Leu Thr Lys Val His Lys Gln Leu Val Arg Asp Asn Ala Asp
            20                  25                  30
Leu Arg Cys Glu Leu Pro Lys Leu Glu Lys Arg Leu Arg Ala Thr Ala
        35                  40                  45
Glu Arg Val Lys Ala Leu Glu Ser Ala Leu Lys Glu Ala
    50                  55                  60
```

```
<210> SEQ ID NO 72
<211> LENGTH: 61
<212> TYPE: PRT
<213> ORGANISM: Mus musculus

<400> SEQUENCE: 72

Gly Ser Ala Ala Gln Lys Gln Lys Ile Ser Phe Leu Glu Asn Asn Leu
1               5                   10                  15

Glu Gln Leu Thr Lys Val His Lys Gln Pro Val Arg Asp Asn Ala Asp
            20                  25                  30

Leu Arg Cys Glu Leu Pro Lys Leu Glu Lys Arg Leu Arg Ala Thr Ala
        35                  40                  45

Glu Arg Val Lys Ala Leu Glu Ser Ala Leu Lys Glu Ala
    50                  55                  60

<210> SEQ ID NO 73
<211> LENGTH: 61
<212> TYPE: PRT
<213> ORGANISM: Mus musculus

<400> SEQUENCE: 73

Gly Ser Ala Ala Gln Lys Gln Lys Ile Ser Phe Leu Glu Asn Asn Leu
1               5                   10                  15

Glu Gln Leu Thr Lys Val His Lys Gln Leu Val Arg Asp Asn Ala Asp
            20                  25                  30

Leu Arg Cys Glu Leu Pro Lys Leu Glu Lys Arg Leu Arg Ala Thr Ala
        35                  40                  45

Lys Arg Val Lys Ala Leu Glu Ser Ala Leu Lys Asp Ala
    50                  55                  60

<210> SEQ ID NO 74
<211> LENGTH: 64
<212> TYPE: PRT
<213> ORGANISM: Mus musculus

<400> SEQUENCE: 74

Gly Ser Ala Ala Gln Lys Gln Lys Ile Ser Phe Leu Glu Asn Asn Leu
1               5                   10                  15

Glu Gln Leu Thr Lys Val His Lys Gln Leu Val Arg Asp Asn Ala Asp
            20                  25                  30

Leu Arg Cys Glu Leu Pro Lys Leu Glu Lys Arg Leu Arg Ala Thr Ala
        35                  40                  45

Lys Arg Val Lys Ala Leu Val Ser Ala Leu Lys Glu Ala Lys Glu Arg
    50                  55                  60

<210> SEQ ID NO 75
<211> LENGTH: 64
<212> TYPE: PRT
<213> ORGANISM: Mus musculus

<400> SEQUENCE: 75

Gly Ser Ala Ala Gln Lys Gln Lys Ile Ser Phe Leu Glu Asn Asn Leu
1               5                   10                  15

Glu Gln Leu Thr Lys Val His Lys Gln Leu Val Arg Asp Asn Ala Asp
            20                  25                  30

Leu Arg Cys Glu Leu Pro Lys Leu Glu Lys Arg Leu Arg Ala Thr Ala
        35                  40                  45

Glu Arg Val Met Ala Leu Glu Ser Ala Leu Lys Glu Ala Lys Glu Arg
    50                  55                  60
```

```
<210> SEQ ID NO 76
<211> LENGTH: 64
<212> TYPE: PRT
<213> ORGANISM: Mus musculus

<400> SEQUENCE: 76

Gly Ser Ala Ala Gln Lys Gln Lys Ile Ser Leu Leu Glu Asn Asn Leu
1               5                   10                  15

Glu Gln Leu Thr Lys Val His Lys Gln Leu Val Arg Asp Asn Ala Asp
                20                  25                  30

Leu Arg Cys Glu Leu Pro Lys Leu Glu Lys Arg Leu Arg Ala Thr Ala
            35                  40                  45

Glu Arg Val Lys Ala Leu Glu Ser Ala Leu Lys Glu Ala Lys Glu Arg
        50                  55                  60

<210> SEQ ID NO 77
<211> LENGTH: 64
<212> TYPE: PRT
<213> ORGANISM: Mus musculus

<400> SEQUENCE: 77

Gly Ser Ala Ala Gln Lys Gln Lys Ile Ser Phe Leu Glu Asn His Leu
1               5                   10                  15

Glu Gln Leu Thr Lys Val His Lys Leu Leu Val Arg Asp Asn Ala Asp
                20                  25                  30

Leu Arg Cys Glu Leu Pro Lys Leu Glu Lys Arg Leu Arg Ala Thr Ala
            35                  40                  45

Glu Arg Val Lys Ala Leu Glu Ser Ala Leu Lys Glu Ala Lys Glu Arg
        50                  55                  60

<210> SEQ ID NO 78
<211> LENGTH: 54
<212> TYPE: PRT
<213> ORGANISM: Mus musculus

<400> SEQUENCE: 78

Leu Glu Gln Leu Thr Lys Val His Lys Gln Leu Val Arg Asp Asn Ala
1               5                   10                  15

Asp Leu Arg Cys Glu Leu Pro Lys Leu Glu Lys Arg Leu Arg Ala Thr
                20                  25                  30

Ala Glu Arg Val Lys Ala Leu Glu Ser Ala Leu Lys Glu Ala Lys Glu
            35                  40                  45

Asn Ala Met Arg Asp Arg
        50

<210> SEQ ID NO 79
<211> LENGTH: 54
<212> TYPE: PRT
<213> ORGANISM: Mus musculus

<400> SEQUENCE: 79

Leu Glu Gln Leu Thr Arg Val His Lys Gln Leu Val Arg Asp Asn Ala
1               5                   10                  15

Asp Leu Arg Tyr Glu Leu His Lys Leu Glu Lys Arg Leu Arg Ala Thr
                20                  25                  30

Ala Glu Arg Val Lys Ala Leu Glu Ser Ala Leu Lys Glu Ala Lys Glu
            35                  40                  45

Asn Ala Met Arg Asp Arg
```

```
<210> SEQ ID NO 80
<211> LENGTH: 54
<212> TYPE: PRT
<213> ORGANISM: Mus musculus

<400> SEQUENCE: 80

Leu Glu Gln Leu Thr Lys Val His Lys Gln Leu Val Arg Asp Asn Ala
1               5                   10                  15

Asp Leu Arg Cys Glu Leu Pro Lys Leu Glu Lys Arg Leu Arg Ala Thr
            20                  25                  30

Ala Lys Arg Val Lys Ala Leu Glu Ser Ala Leu Lys Glu Ala Lys Glu
        35                  40                  45

Asn Ala Met Arg Asp Arg
    50

<210> SEQ ID NO 81
<211> LENGTH: 54
<212> TYPE: PRT
<213> ORGANISM: Mus musculus

<400> SEQUENCE: 81

Leu Glu Gln Leu Thr Lys Val His Lys Gln Leu Val Gln Asp Asn Ala
1               5                   10                  15

Asp Leu Arg Cys Glu Leu Pro Lys Leu Glu Lys Arg Leu Arg Ala Thr
            20                  25                  30

Ala Glu Arg Val Lys Ala Leu Glu Ser Ala Leu Lys Glu Ala Lys Glu
        35                  40                  45

Asn Ala Met Arg Asp Arg
    50

<210> SEQ ID NO 82
<211> LENGTH: 61
<212> TYPE: PRT
<213> ORGANISM: Mus musculus

<400> SEQUENCE: 82

Ser Phe Leu Asp Asn Leu Glu Gln Leu Thr Lys Val His Lys Gln
1               5                   10                  15

Leu Val Arg Asp Asn Ala Asp Leu Arg Cys Glu Leu Pro Arg Leu Glu
            20                  25                  30

Lys Met Leu Arg Ala Thr Ala Glu Arg Val Lys Ala Leu Glu Ser Ala
        35                  40                  45

Leu Lys Glu Ala Lys Glu Asn Ala Met Ser Asp Ala Lys
    50                  55                  60

<210> SEQ ID NO 83
<211> LENGTH: 54
<212> TYPE: PRT
<213> ORGANISM: Mus musculus

<400> SEQUENCE: 83

Leu Glu Gln Leu Thr Lys Val His Lys Gln Leu Val Arg Asp Asn Ala
1               5                   10                  15

Asp Leu Arg Cys Glu Leu Pro Lys Leu Glu Lys Arg Leu Arg Ala Thr
            20                  25                  30

Ala Lys Arg Val Lys Ala Leu Glu Ser Ala Leu Lys Glu Ala Lys Glu
        35                  40                  45
```

```
Asn Ala Met Arg Asp Arg
    50

<210> SEQ ID NO 84
<211> LENGTH: 49
<212> TYPE: PRT
<213> ORGANISM: Mus musculus

<400> SEQUENCE: 84

Ala Lys Thr Ile Lys Asn Thr Val Ser Val Asn Leu Glu Leu Thr Ala
1               5                   10                  15

Glu Glu Trp Lys Lys Glu Tyr Glu Lys Glu Lys Glu Lys Asn Lys Ala
            20                  25                  30

Leu Lys Ser Val Leu Gln His Leu Glu Met Glu Leu Asn Arg Trp Arg
        35                  40                  45

Glu

<210> SEQ ID NO 85
<211> LENGTH: 51
<212> TYPE: PRT
<213> ORGANISM: Mus musculus

<400> SEQUENCE: 85

Gln Arg Ala Lys Thr Ile Asn Asn Thr Val Ser Val Asn Leu Glu Leu
1               5                   10                  15

Thr Ala Glu Glu Trp Lys Lys Arg Tyr Glu Lys Glu Lys Glu Lys Asn
            20                  25                  30

Lys Ala Leu Lys Ser Val Leu Gln His Leu Glu Met Glu Leu Asn Arg
        35                  40                  45

Trp Arg Arg
    50

<210> SEQ ID NO 86
<211> LENGTH: 48
<212> TYPE: PRT
<213> ORGANISM: Mus musculus

<400> SEQUENCE: 86

Gln Arg Ala Lys Ala Ile Lys Asn Thr Val Ser Val Asn Leu Glu Leu
1               5                   10                  15

Thr Ala Glu Glu Trp Lys Lys Lys Tyr Glu Lys Glu Lys Glu Lys Asn
            20                  25                  30

Lys Ala Leu Lys Asn Val Leu Gln His Leu Glu Met Glu Leu Asn Arg
        35                  40                  45

<210> SEQ ID NO 87
<211> LENGTH: 70
<212> TYPE: PRT
<213> ORGANISM: Mus musculus

<400> SEQUENCE: 87

Cys Cys Ser Pro Ser Val Phe Asn Glu Ala Glu Thr Lys Ser Thr Leu
1               5                   10                  15

Met Phe Gly Gln Arg Ala Lys Thr Ile Lys Asn Thr Val Ser Val Asn
            20                  25                  30

Leu Glu Leu Thr Ala Glu Glu Trp Lys Lys Lys Tyr Glu Lys Glu Lys
        35                  40                  45

Glu Lys Asn Lys Ala Leu Lys Ser Val Leu Gln His Leu Glu Met Glu
    50                  55                  60
```

```
Leu Asn Arg Trp Arg Asn
 65                  70

<210> SEQ ID NO 88
<211> LENGTH: 1027
<212> TYPE: PRT
<213> ORGANISM: Mus musculus

<400> SEQUENCE: 88

Met Ala Glu Thr Asn Glu Cys Ser Ile Lys Val Leu Cys Arg Phe
 1               5                  10                  15

Arg Pro Leu Asn Gln Ala Glu Ile Leu Arg Gly Asp Lys Phe Ile Pro
                20                  25                  30

Ile Phe Gln Gly Asp Asp Ser Val Ile Gly Gly Lys Pro Tyr Val
            35                  40                  45

Phe Asp Arg Val Phe Pro Pro Asn Thr Thr Gln Glu Gln Val Tyr His
 50                  55                  60

Ala Cys Ala Met Gln Ile Val Lys Asp Val Leu Ala Gly Tyr Asn Gly
 65                  70                  75                  80

Thr Ile Phe Ala Tyr Gly Gln Thr Ser Ser Gly Lys Thr His Thr Met
                85                  90                  95

Glu Gly Lys Leu His Asp Pro Gln Leu Met Gly Ile Ile Pro Arg Ile
                100                 105                 110

Ala Arg Asp Ile Phe Asn His Ile Tyr Ser Met Asp Glu Asn Leu Glu
                115                 120                 125

Phe His Ile Lys Val Ser Tyr Phe Glu Ile Tyr Leu Asp Lys Ile Arg
        130                 135                 140

Asp Leu Leu Asp Val Thr Lys Thr Asn Leu Ser Val His Glu Asp Lys
145                 150                 155                 160

Asn Arg Val Pro Phe Val Lys Gly Cys Thr Glu Arg Phe Val Ser Ser
                165                 170                 175

Pro Glu Glu Ile Leu Asp Val Ile Asp Glu Gly Lys Ser Asn Arg His
                180                 185                 190

Val Ala Val Thr Asn Met Asn Glu His Ser Ser Arg Ser His Ser Ile
                195                 200                 205

Phe Leu Ile Asn Ile Lys Gln Glu Asn Val Glu Thr Glu Gln Lys Leu
        210                 215                 220

Ser Gly Lys Leu Tyr Leu Val Asp Leu Ala Gly Ser Glu Lys Val Ser
225                 230                 235                 240

Lys Thr Gly Ala Glu Gly Ala Val Leu Asp Glu Ala Lys Asn Ile Asn
                245                 250                 255

Lys Ser Leu Ser Ala Leu Gly Asn Val Ile Ser Ala Leu Ala Glu Gly
                260                 265                 270

Thr Lys Ser Tyr Val Pro Tyr Arg Asp Thr Lys Met Thr Arg Ile Leu
                275                 280                 285

Gln Asp Ser Leu Gly Gly Asn Cys Arg Thr Thr Met Phe Ile Cys Cys
        290                 295                 300

Ser Pro Ser Ser Tyr Asn Asp Ala Glu Thr Lys Ser Thr Leu Met Phe
305                 310                 315                 320

Gly Gln Arg Ala Lys Thr Ile Lys Asn Thr Ala Ser Val Asn Leu Glu
                325                 330                 335

Leu Thr Ala Glu Gln Trp Lys Lys Lys Tyr Glu Lys Glu Lys Glu Lys
                340                 345                 350

Thr Lys Ala Gln Lys Glu Thr Ile Ala Asn Val Glu Ala Glu Leu Ser
                355                 360                 365
```

-continued

```
Arg Trp Arg Asn Gly Glu Asn Val Pro Glu Thr Glu Arg Leu Ala Gly
    370                 375                 380

Glu Asp Ser Ala Leu Gly Ala Glu Leu Cys Glu Glu Thr Pro Val Asn
385                 390                 395                 400

Asp Asn Ser Ser Ile Val Arg Ile Ala Pro Glu Arg Gln Lys
                405                 410                 415

Tyr Glu Glu Ile Arg Arg Leu Tyr Lys Gln Leu Asp Asp Lys Asp
            420                 425                 430

Asp Glu Ile Asn Gln Gln Ser Gln Leu Ile Glu Lys Leu Lys Gln Gln
                435                 440                 445

Met Leu Asp Gln Glu Glu Leu Leu Val Ser Thr Arg Gly Asp Asn Glu
    450                 455                 460

Lys Val Gln Arg Glu Leu Ser His Leu Gln Ser Glu Asn Asp Ala Ala
465                 470                 475                 480

Lys Asp Glu Val Lys Glu Val Leu Gln Ala Leu Glu Glu Leu Ala Val
                485                 490                 495

Asn Tyr Asp Gln Lys Ser Gln Glu Val Glu Glu Lys Ser Gln Gln Asn
                500                 505                 510

Gln Leu Leu Val Asp Glu Leu Ser Gln Lys Val Ala Thr Met Leu Ser
            515                 520                 525

Leu Glu Ser Glu Leu Gln Arg Leu Gln Glu Val Ser Gly His Gln Arg
    530                 535                 540

Lys Arg Ile Ala Glu Val Leu Asn Gly Leu Met Arg Asp Leu Ser Glu
545                 550                 555                 560

Phe Ser Val Ile Val Gly Asn Gly Glu Ile Lys Leu Pro Val Glu Ile
                565                 570                 575

Ser Gly Ala Ile Glu Glu Glu Phe Thr Val Ala Arg Leu Tyr Ile Ser
                580                 585                 590

Lys Ile Lys Ser Glu Val Lys Ser Val Val Lys Arg Cys Arg Gln Leu
    595                 600                 605

Glu Asn Leu Gln Val Glu Cys His Arg Lys Met Glu Val Thr Gly Arg
    610                 615                 620

Glu Leu Ser Ser Cys Gln Leu Leu Ile Ser Gln His Glu Ala Lys Ile
625                 630                 635                 640

Arg Ser Leu Thr Glu Tyr Met Gln Thr Val Glu Leu Lys Lys Arg His
                645                 650                 655

Leu Glu Glu Ser Tyr Asp Ser Leu Ser Asp Glu Leu Ala Arg Leu Gln
                660                 665                 670

Ala His Glu Thr Val His Glu Val Ala Leu Lys Asp Lys Glu Pro Asp
    675                 680                 685

Thr Gln Asp Ala Glu Glu Val Lys Lys Ala Leu Glu Leu Gln Met Glu
    690                 695                 700

Asn His Arg Glu Ala His His Arg Gln Leu Ala Arg Leu Arg Asp Glu
705                 710                 715                 720

Ile Asn Glu Lys Gln Lys Thr Ile Asp Glu Leu Lys Asp Leu Asn Gln
                725                 730                 735

Lys Leu Gln Leu Glu Leu Glu Lys Leu Gln Ala Asp Tyr Glu Arg Leu
                740                 745                 750

Lys Asn Glu Asn Glu Lys Ser Ala Lys Leu Gln Glu Leu Thr Phe
                755                 760                 765

Leu Tyr Glu Arg His Glu Gln Ser Lys Gln Asp Leu Lys Gly Leu Glu
    770                 775                 780
```

```
Glu Thr Val Ala Arg Glu Leu Gln Thr Leu His Asn Leu Arg Lys Leu
785                 790                 795                 800

Phe Val Gln Asp Val Thr Thr Arg Val Lys Lys Ser Ala Glu Met Glu
            805                 810                 815

Pro Glu Asp Ser Gly Gly Ile His Ser Gln Lys Gln Lys Ile Ser Phe
            820                 825                 830

Leu Glu Asn Asn Leu Glu Gln Leu Thr Lys Val His Lys Gln Leu Val
            835                 840                 845

Arg Asp Asn Ala Asp Leu Arg Cys Glu Leu Pro Lys Leu Glu Lys Arg
850                 855                 860

Leu Arg Ala Thr Ala Glu Arg Val Lys Ala Leu Glu Gly Ala Leu Lys
865                 870                 875                 880

Glu Ala Lys Glu Gly Ala Met Lys Asp Lys Arg Arg Tyr Gln Gln Glu
                885                 890                 895

Val Asp Arg Ile Lys Glu Ala Val Arg Tyr Lys Ser Ser Gly Lys Arg
            900                 905                 910

Gly His Ser Ala Gln Ile Ala Lys Pro Val Arg Pro Gly His Tyr Pro
        915                 920                 925

Ala Ser Ser Pro Thr Asn Pro Tyr Gly Thr Arg Ser Pro Glu Cys Ile
    930                 935                 940

Ser Tyr Thr Asn Asn Leu Phe Gln Asn Tyr Gln Asn Leu His Leu Gln
945                 950                 955                 960

Ala Ala Pro Ser Ser Thr Ser Asp Met Tyr Phe Ala Ser Ser Gly Arg
                965                 970                 975

Thr Ser Val Ala Pro Leu Ala Ser Tyr Gln Lys Ala Asn Met Asp Asn
            980                 985                 990

Gly Asn Ala Thr Asp Ile Asn Asp  Asn Arg Ser Asp Leu  Pro Cys Gly
        995                 1000                 1005

Tyr Glu  Ala Glu Asp Gln Ala  Lys Leu Phe Pro Leu  His Gln Glu
   1010                1015                 1020

Thr Ala  Ala Ser
   1025

<210> SEQ ID NO 89
<211> LENGTH: 52
<212> TYPE: PRT
<213> ORGANISM: Mus musculus

<400> SEQUENCE: 89

Ile Ser Phe Leu Lys Asn Asn Leu Glu Arg Leu Thr Lys Val His Lys
1               5                   10                  15

Gln Leu Val Arg Asp Asn Ala Asp Leu Arg Cys Glu Leu Pro Lys Leu
            20                  25                  30

Glu Lys Arg Leu Arg Ala Thr Ala Glu Arg Val Lys Ala Leu Glu Gly
        35                  40                  45

Ala Leu Lys Gly
    50

<210> SEQ ID NO 90
<211> LENGTH: 59
<212> TYPE: PRT
<213> ORGANISM: Mus musculus

<400> SEQUENCE: 90

Gln Lys Gln Lys Ile Ser Phe Leu Glu Asp Asn Leu Glu Gln Leu Thr
1               5                   10                  15
```

```
Lys Val His Lys Gln Leu Val Arg Asp Asn Ala Asp Leu Arg Cys Glu
         20                  25                  30

Leu Pro Lys Leu Glu Lys Arg Leu Arg Ala Thr Ala Glu Arg Val Lys
         35                  40                  45

Ala Leu Glu Gly Ala Leu Lys Glu Gly Lys Glu
         50                  55

<210> SEQ ID NO 91
<211> LENGTH: 62
<212> TYPE: PRT
<213> ORGANISM: Mus musculus

<400> SEQUENCE: 91

His Ser Gln Lys Gln Lys Ile Ser Phe Leu Glu Asn Asn Leu Glu Gln
1               5                   10                  15

Leu Thr Lys Val His Lys Gln Leu Val Arg Asp Asn Ala Asp Leu Arg
             20                  25                  30

Cys Glu Leu Pro Lys Leu Glu Lys Gln Leu Arg Ala Thr Ala Glu Arg
         35                  40                  45

Val Lys Ala Leu Glu Gly Thr Leu Lys Glu Ala Lys Glu Gly
         50                  55                  60

<210> SEQ ID NO 92
<211> LENGTH: 62
<212> TYPE: PRT
<213> ORGANISM: Mus musculus

<400> SEQUENCE: 92

Arg Ile Pro Ser Phe Leu Glu Asn Asn Leu Glu Gln Leu Thr Lys Val
1               5                   10                  15

His Lys Gln Leu Val Arg Asp Asn Ala Asp Leu Arg Cys Glu Leu Pro
             20                  25                  30

Lys Leu Glu Lys Arg Leu Arg Ala Thr Ala Glu Arg Val Lys Ala Leu
         35                  40                  45

Glu Gly Ala Leu Lys Glu Ala Lys Glu Gly Ala Met Lys Asp
         50                  55                  60

<210> SEQ ID NO 93
<211> LENGTH: 59
<212> TYPE: PRT
<213> ORGANISM: Mus musculus

<400> SEQUENCE: 93

Ser Phe Leu Glu Asn Asn Leu Glu Gln Leu Thr Lys Val His Lys Gln
1               5                   10                  15

Leu Val Arg Asp Asn Ala Asp Leu Arg Cys Glu Leu Pro Lys Leu Glu
             20                  25                  30

Lys Arg Leu Arg Ala Thr Ala Glu Arg Val Lys Ala Leu Glu Gly Ala
         35                  40                  45

Leu Lys Glu Ala Lys Glu Gly Ala Met Lys Asp
         50                  55

<210> SEQ ID NO 94
<211> LENGTH: 12
<212> TYPE: PRT
<213> ORGANISM: Mus musculus

<400> SEQUENCE: 94

Gln Lys Tyr Glu Glu Glu Ile Arg Arg Leu Tyr Lys
1               5                   10
```

<210> SEQ ID NO 95
<211> LENGTH: 281
<212> TYPE: PRT
<213> ORGANISM: Mus musculus

<400> SEQUENCE: 95

Met Ala Thr Asn Phe Leu Ala His Glu Lys Ile Trp Phe Asp Lys Phe
1               5                   10                  15

Lys Tyr Asp Asp Ala Glu Arg Arg Phe Tyr Glu Gln Met Asn Gly Pro
            20                  25                  30

Val Thr Ser Gly Ser Arg Gln Glu Asn Gly Ala Ser Val Ile Leu Arg
        35                  40                  45

Asp Ile Ala Arg Ala Arg Glu Asn Ile Gln Lys Ser Leu Ala Gly Ser
    50                  55                  60

Ser Gly Pro Gly Ala Ser Ser Gly Pro Gly Gly Asp His Ser Glu Leu
65                  70                  75                  80

Ile Val Arg Ile Thr Ser Leu Glu Val Glu Asn Gln Asn Leu Arg Gly
                85                  90                  95

Val Val Gln Asp Leu Gln Gln Ala Ile Ser Lys Leu Glu Ala Arg Leu
            100                 105                 110

Ser Ser Leu Glu Lys Ser Ser Pro Thr Pro Arg Ala Thr Ala Pro Gln
        115                 120                 125

Thr Gln His Val Ser Pro Met Arg Gln Val Glu Pro Pro Thr Lys Lys
    130                 135                 140

Gly Ala Thr Pro Ala Glu Asp Asp Glu Asp Lys Asp Ile Asp Leu Phe
145                 150                 155                 160

Gly Ser Asp Glu Glu Glu Asp Lys Glu Ala Ala Arg Leu Arg Glu
                165                 170                 175

Glu Arg Leu Arg Gln Tyr Ala Glu Lys Lys Ala Lys Lys Pro Thr Leu
            180                 185                 190

Val Ala Lys Ser Ser Ile Leu Leu Asp Val Lys Pro Trp Asp Asp Glu
        195                 200                 205

Thr Asp Met Ala Gln Leu Glu Thr Cys Val Arg Ser Ile Gln Leu Asp
    210                 215                 220

Gly Leu Val Trp Gly Ala Ser Lys Leu Val Pro Val Gly Tyr Gly Ile
225                 230                 235                 240

Arg Lys Leu Gln Ile Gln Cys Val Val Glu Asp Asp Lys Val Gly Thr
                245                 250                 255

Asp Leu Leu Glu Glu Glu Ile Thr Lys Phe Glu Glu His Val Gln Ser
            260                 265                 270

Val Asp Ile Ala Ala Phe Asp Lys Ile
        275                 280

<210> SEQ ID NO 96
<211> LENGTH: 73
<212> TYPE: PRT
<213> ORGANISM: Mus musculus

<400> SEQUENCE: 96

Glu Leu Ile Val Arg Ile Thr Ser Leu Glu Val Glu Asn Gln Asn Leu
1               5                   10                  15

Arg Gly Val Val Gln Asp Leu Gln Gln Ala Ile Ser Lys Leu Glu Ala
            20                  25                  30

Arg Leu Ser Ser Leu Glu Lys Ser Ser Pro Thr Pro Arg Ala Thr Ala
        35                  40                  45

```
Pro Gln Thr Gln His Val Ser Pro Met Arg Gln Val Glu Pro Pro Thr
        50                  55                  60

Lys Lys Gly Ala Thr Pro Ala Glu Val
 65                  70
```

<210> SEQ ID NO 97
<211> LENGTH: 66
<212> TYPE: PRT
<213> ORGANISM: Mus musculus

<400> SEQUENCE: 97

```
Ile Thr Ser Leu Glu Val Glu Asn Gln Asn Leu Arg Gly Val Val Gln
 1               5                   10                  15

Asp Leu Gln Gln Ala Ile Ser Lys Leu Glu Ala Arg Leu Ser Ser Leu
                20                  25                  30

Glu Lys Ser Ser Pro Thr Pro Arg Ala Thr Thr Pro Gln Thr Gln His
            35                  40                  45

Val Ser Pro Met Arg Gln Val Glu Pro Pro Thr Lys Lys Gly Ala Thr
        50                  55                  60

Pro Ala
 65
```

<210> SEQ ID NO 98
<211> LENGTH: 89
<212> TYPE: PRT
<213> ORGANISM: Mus musculus
<220> FEATURE:
<221> NAME/KEY: UNSURE
<222> LOCATION: (57)

<400> SEQUENCE: 98

```
Asp His Ser Glu Leu Ile Val Arg Ile Thr Ser Leu Glu Val Glu Asn
 1               5                   10                  15

Gln Asn Leu Arg Gly Val Val Gln Asp Leu Gln Gln Ala Ile Ser Lys
                20                  25                  30

Leu Glu Ala Arg Leu Ser Ser Leu Glu Lys Ser Ser Pro Thr Pro Arg
            35                  40                  45

Ala Thr Ala Pro Gln Thr Gln His Xaa Phe Pro Leu Arg Gln Val Glu
        50                  55                  60

Pro Pro Thr Lys Lys Gly Ala Thr Pro Ala Glu Asp Asp Glu Asp Lys
 65                  70                  75                  80

Asp Ile Asp Leu Phe Gly Arg Asn Glu
                85
```

<210> SEQ ID NO 99
<211> LENGTH: 118
<212> TYPE: PRT
<213> ORGANISM: Mus musculus

<400> SEQUENCE: 99

```
Glu Gln Met Asn Gly Pro Val Thr Ser Ser Arg Gln Glu Asn Gly
 1               5                   10                  15

Ala Ser Val Ile Leu Arg Asp Ile Ala Arg Pro Arg Glu Asn Ile Gln
                20                  25                  30

Lys Ser Leu Ala Gly Ser Ser Gly Pro Gly Ala Ser Gly Pro Gly
            35                  40                  45

Gly Asp His Ser Glu Leu Ile Val Arg Ile Thr Ser Leu Glu Val Glu
        50                  55                  60
```

```
Asn Gln Asn Leu Arg Gly Val Val Gln Asp Leu Gln Gln Ala Ile Ser
 65                  70                  75                  80

Lys Leu Glu Ala Arg Leu Ser Ser Leu Glu Lys Ser Ser Pro Thr Pro
                 85                  90                  95

Arg Ala Thr Ala Pro Gln Thr Gln His Val Ser Pro Leu Arg Gln Val
            100                 105                 110

Glu Pro Pro Thr Lys Arg
            115

<210> SEQ ID NO 100
<211> LENGTH: 849
<212> TYPE: PRT
<213> ORGANISM: Mus musculus

<400> SEQUENCE: 100

Met Ser Tyr Thr Leu Asp Ser Leu Gly Asn Pro Ser Ala Tyr Arg Arg
  1               5                  10                  15

Val Pro Thr Glu Thr Arg Ser Ser Phe Ser Arg Val Ser Gly Ser Pro
                 20                  25                  30

Ser Ser Gly Phe Arg Ser Gln Ser Trp Ser Arg Gly Ser Pro Ser Thr
             35                  40                  45

Val Ser Ser Tyr Thr Arg Ser Ala Val Ala Pro Arg Leu Ala Tyr
 50                  55                  60

Ser Ser Ala Met Leu Ser Ser Ala Glu Ser Ser Leu Asp Phe Ser Gln
 65                  70                  75                  80

Ser Ser Ser Leu Leu Asn Gly Gly Ser Gly Gly Asp Tyr Lys Leu Ser
                 85                  90                  95

Arg Ser Asn Glu Lys Glu Gln Leu Gln Gly Leu Asn Asp Arg Phe Ala
            100                 105                 110

Gly Tyr Ile Glu Lys Val His Tyr Leu Glu Gln Gln Asn Lys Glu Ile
        115                 120                 125

Glu Ala Glu Ile Gln Ala Leu Arg Gln Lys Gln Ala Ser His Ala Gln
130                 135                 140

Leu Gly Asp Ala Tyr Asp Gln Glu Ile Arg Glu Leu Arg Ala Thr Leu
145                 150                 155                 160

Glu Met Val Asn His Glu Lys Ala Gln Val Gln Leu Asp Ser Asp His
                165                 170                 175

Leu Glu Glu Asp Ile His Arg Leu Lys Glu Arg Phe Glu Glu Ala
            180                 185                 190

Arg Leu Arg Asp Asp Thr Glu Ala Ala Ile Arg Ala Leu Arg Lys Asp
        195                 200                 205

Ile Glu Glu Ser Ser Met Val Lys Val Glu Leu Asp Lys Lys Val Gln
210                 215                 220

Ser Leu Gln Asp Glu Val Ala Phe Leu Arg Arg Asn His Glu Glu Glu
225                 230                 235                 240

Val Ala Asp Leu Leu Ala Gln Ile Gln Ala Ser His Ile Thr Val Glu
                245                 250                 255

Arg Lys Asp Tyr Leu Lys Thr Asp Ile Ser Thr Ala Leu Lys Glu Ile
            260                 265                 270

Arg Ser Gln Leu Glu Cys His Ser Asp Gln Asn Met His Gln Ala Glu
        275                 280                 285

Glu Trp Phe Lys Cys Arg Tyr Ala Lys Leu Thr Glu Ala Ala Glu Gln
290                 295                 300

Asn Lys Glu Ala Ile Arg Ser Ala Lys Glu Glu Ile Ala Glu Tyr Arg
305                 310                 315                 320
```

```
Arg Gln Leu Gln Ser Lys Ser Ile Glu Leu Glu Ser Val Arg Gly Thr
                325                 330                 335
Lys Glu Ser Leu Glu Arg Gln Leu Ser Asp Ile Glu Glu Arg His Asn
            340                 345                 350
His Asp Leu Ser Ser Tyr Gln Asp Thr Ile Gln Gln Leu Glu Asn Glu
        355                 360                 365
Leu Arg Gly Thr Lys Trp Glu Met Ala Arg His Leu Arg Glu Tyr Gln
    370                 375                 380
Asp Leu Leu Asn Val Lys Met Ala Leu Asp Ile Glu Ile Ala Ala Tyr
385                 390                 395                 400
Arg Lys Leu Leu Glu Gly Glu Thr Arg Phe Ser Thr Phe Ser Gly
                405                 410                 415
Ser Ile Thr Gly Pro Leu Tyr Thr His Arg Gln Pro Ser Val Thr Ile
                420                 425                 430
Ser Ser Lys Ile Gln Lys Thr Lys Val Glu Ala Pro Lys Leu Lys Val
            435                 440                 445
Gln His Lys Phe Val Glu Ile Ile Glu Glu Thr Lys Val Glu Asp
        450                 455                 460
Glu Lys Ser Glu Met Glu Glu Thr Leu Thr Ala Ile Ala Glu Glu Leu
465                 470                 475                 480
Ala Ala Ser Ala Lys Glu Glu Lys Glu Ala Glu Lys Glu Glu
                485                 490                 495
Glu Pro Glu Ala Glu Lys Ser Pro Val Lys Ser Pro Glu Ala Lys Glu
            500                 505                 510
Glu Glu Glu Glu Gly Glu Lys Glu Glu Glu Glu Gly Gln Glu Glu
                515                 520                 525
Glu Glu Glu Asp Glu Gly Val Lys Ser Asp Gln Ala Glu Glu Gly
                530                 535                 540
Gly Ser Glu Lys Glu Gly Ser Ser Glu Lys Asp Glu Gly Glu Gln Glu
545                 550                 555                 560
Glu Glu Glu Gly Glu Thr Glu Ala Glu Gly Glu Gly Glu Glu Ala Glu
                565                 570                 575
Ala Lys Glu Glu Lys Lys Ile Glu Gly Lys Val Glu Glu Val Ala Val
                580                 585                 590
Lys Glu Glu Ile Lys Val Glu Lys Pro Glu Lys Ala Lys Ser Pro Met
                595                 600                 605
Pro Lys Ser Pro Val Glu Glu Val Lys Pro Lys Pro Glu Ala Lys Ala
            610                 615                 620
Gly Lys Gly Glu Gln Lys Glu Glu Lys Val Glu Glu Lys Lys
625                 630                 635                 640
Glu Val Thr Lys Glu Ser Pro Lys Glu Glu Lys Val Glu Lys Lys Glu
                645                 650                 655
Glu Lys Pro Lys Asp Val Ala Asp Lys Lys Ala Glu Ser Pro Val
            660                 665                 670
Lys Glu Lys Ala Val Glu Glu Val Ile Thr Ile Ser Lys Ser Val Lys
                675                 680                 685
Val Ser Leu Glu Lys Asp Thr Lys Glu Glu Lys Pro Gln Pro Gln Glu
            690                 695                 700
Lys Val Lys Glu Lys Ala Glu Glu Gly Gly Ser Glu Glu Gly
705                 710                 715                 720
Ser Asp Arg Ser Pro Gln Glu Ser Lys Lys Glu Asp Ile Ala Ile Asn
            725                 730                 735
```

```
Gly Glu Val Glu Gly Lys Glu Glu Gln Glu Thr Gln Glu Lys
            740                 745                 750
Gly Ser Gly Arg Glu Glu Lys Gly Val Val Thr Asn Gly Leu Asp
    755                 760                 765
Val Ser Pro Ala Glu Glu Lys Lys Gly Glu Asp Ser Ser Asp Asp Lys
    770                 775                 780
Val Val Val Thr Lys Lys Val Glu Lys Ile Thr Ser Glu Gly Gly Asp
785                 790                 795                 800
Gly Ala Thr Lys Tyr Ile Thr Lys Ser Val Thr Val Thr Gln Lys Val
                805                 810                 815
Glu Glu His Glu Glu Thr Phe Glu Glu Lys Leu Val Ser Thr Lys Lys
            820                 825                 830
Val Glu Lys Val Thr Ser His Ala Ile Val Lys Glu Val Thr Gln Gly
            835                 840                 845
Asp

<210> SEQ ID NO 101
<211> LENGTH: 50
<212> TYPE: PRT
<213> ORGANISM: Mus musculus

<400> SEQUENCE: 101

Ser Tyr Gln Asp Thr Ile Gln Gln Leu Glu Asn Glu Leu Arg Gly Thr
1               5                   10                  15
Lys Trp Glu Met Ala Arg His Leu Arg Glu Tyr Gln Asp Leu Leu Asn
            20                  25                  30
Val Lys Met Ala Leu Asp Ile Glu Ile Ala Ala Tyr Arg Arg Leu Leu
        35                  40                  45
Glu Gly
    50

<210> SEQ ID NO 102
<211> LENGTH: 55
<212> TYPE: PRT
<213> ORGANISM: Mus musculus

<400> SEQUENCE: 102

His Asp Leu Ser Ser Tyr Gln Asp Thr Ile Gln Gln Leu Glu Asn Glu
1               5                   10                  15
Leu Arg Gly Thr Lys Trp Glu Met Ala Arg His Leu Arg Glu Tyr Gln
            20                  25                  30
Asp Leu Leu Asn Val Lys Met Ala Leu Asp Ile Glu Ile Ala Ala Tyr
        35                  40                  45
Arg Lys Leu Leu Glu Gly Glu
    50                  55

<210> SEQ ID NO 103
<211> LENGTH: 53
<212> TYPE: PRT
<213> ORGANISM: Mus musculus

<400> SEQUENCE: 103

Leu Ser Ser Tyr Gln Asp Thr Ile Gln Gln Leu Glu Asn Glu Leu Arg
1               5                   10                  15
Gly Thr Lys Trp Glu Met Ala Arg His Leu Arg Glu Tyr Gln Asp Leu
            20                  25                  30
Leu Asn Val Lys Met Ala Leu Asp Ile Glu Ile Ala Ala Tyr Arg Lys
        35                  40                  45
```

```
Leu Leu Glu Gly Gly
    50

<210> SEQ ID NO 104
<211> LENGTH: 38
<212> TYPE: PRT
<213> ORGANISM: Mus musculus

<400> SEQUENCE: 104

Leu Arg Gly Thr Lys Trp Glu Met Ala Arg His Leu Arg Glu Tyr Gln
1               5                   10                  15

Asp Leu Leu Asn Val Lys Met Ala Leu Asp Ile Glu Ile Ala Ala Tyr
            20                  25                  30

Arg Lys Leu Leu Glu Gly
        35

<210> SEQ ID NO 105
<211> LENGTH: 996
<212> TYPE: PRT
<213> ORGANISM: Mus musculus

<400> SEQUENCE: 105

Met Lys Arg Ile Phe Ser Cys Ser Ser Gln Val Ala Val Glu Lys
1               5                   10                  15

Trp Asn Arg Arg Asp Gln Lys Leu Leu Glu Ala Val Gln Arg Gly Asp
            20                  25                  30

Val Gly Arg Val Ala Ala Leu Ala Ser Arg Lys Ser Ala Arg Pro Thr
        35                  40                  45

Lys Leu Asp Ser Asn Gly Gln Ser Pro Phe His Leu Ala Ala Ser Lys
50                  55                  60

Gly Leu Thr Glu Cys Leu Thr Ile Leu Leu Ala Asn Gly Ala Asp Ile
65                  70                  75                  80

Asn Ser Lys Asn Glu Asp Gly Ser Thr Ala Leu His Leu Ala Thr Ile
                85                  90                  95

Ser Cys Gln Pro Gln Cys Val Lys Val Leu Leu Gln His Gly Ala Asn
            100                 105                 110

Glu Asp Ala Val Asp Ala Glu Asn Arg Ser Pro Leu His Trp Ala Ala
        115                 120                 125

Ser Ser Gly Cys Ala Ser Ser Val Leu Leu Leu Cys Asp His Glu Ala
    130                 135                 140

Phe Leu Asp Val Leu Asp Asn Asp Gly Arg Thr Pro Leu Met Ile Ala
145                 150                 155                 160

Ser Leu Gly Gly His Ala Ala Ile Cys Ser Gln Leu Leu Gln Arg Gly
                165                 170                 175

Ala Arg Val Asn Val Thr Asp Lys Asp Asp Lys Ser Ala Leu Ile Leu
            180                 185                 190

Ala Cys Glu Lys Gly Ser Ala Glu Val Ala Glu Leu Leu Leu Ser His
        195                 200                 205

Gly Ala Asp Ala Gly Ala Val Asp Ser Leu Gly His Asn Ala Leu His
    210                 215                 220

Tyr Ala Leu Arg Thr Gln Asp Lys Glu Leu Trp Arg Leu Leu Gln Gln
225                 230                 235                 240

Ala Leu Asn Arg Arg Arg Gly Gly His Gly Leu Val Gln His Pro
                245                 250                 255

Asp His Pro Ser Gln Ala Ser Ser Cys Glu Pro Arg Val Gly Ser Pro
            260                 265                 270
```

```
Pro Lys Asn Ser Arg Lys Val Glu Pro Glu Glu Gln Glu Glu
        275                 280                 285
Gly Glu Glu Arg Cys Ser Glu Trp Arg Trp Lys Phe Glu Glu
    290                 295                 300
Gln Arg Lys Val His Gln Leu Glu Gln Glu Leu Val Arg Lys Thr Asp
305                 310                 315                 320
Glu Cys Lys Ala His Ala Ala Ala Phe Ser Ser Leu Glu Glu Gln Ile
                325                 330                 335
Arg Glu Gln Ala Gln Glu Leu Gly His Leu Leu Val Gln Glu Pro Gly
                340                 345                 350
Ala Pro Gly Asn Gln Gly Pro Gly Leu Arg Pro Glu Gly Asp Gly Met
                355                 360                 365
Glu Glu Gly Cys Pro Leu Asn Leu Leu Ala Glu Arg Ile Gln Glu Leu
        370                 375                 380
Lys Lys Gln Gln Lys Ala Leu Ala Thr Ile Asn Pro Thr Leu Val Pro
385                 390                 395                 400
Lys Arg Ala Glu Glu Leu Ala Pro Ala Glu Ile His His Glu Val His
                405                 410                 415
Arg Lys Ser Gln Pro Glu Gln Gly Leu Pro Gln Gly Pro Ser Ser Glu
                420                 425                 430
Thr Thr Gly Lys Ala Thr Gly Gln Gln Pro Asn Thr Asn Gly Gly Gln
        435                 440                 445
Asn Leu Gly Leu Gln Asn Thr Glu Gln Val Cys Ala Gly Gln Lys Glu
        450                 455                 460
Arg Thr Pro Ala Pro Gly Thr Glu Thr Ala Gly Thr Val Gly Glu Pro
465                 470                 475                 480
Val Gly Ile Ala Met Asn Gln Leu Leu Leu Gln Leu Arg Glu Glu Leu
                485                 490                 495
Ala Ala Val Trp Arg Glu Lys Asp Ala Ala Arg Gly Ala Leu Ser Arg
                500                 505                 510
Pro Val Leu Glu Gly Ala Leu Gly Thr Pro Arg Ala Glu Ala Ala Ala
        515                 520                 525
Ala Ala Trp Glu Lys Met Glu Ala Arg Leu Glu Arg Val Leu Val Arg
        530                 535                 540
Leu Asp Gly Ala Lys Met Gly Leu His Val Lys Pro Glu Val Pro Val
545                 550                 555                 560
Gln Gly Ser Arg Asp Gly Ala Pro Lys Ala Val Pro Gly Cys Ser Lys
                565                 570                 575
Glu Gln Glu Glu Lys Lys Ala Leu Gly Thr Arg Gly Glu Pro Leu Gly
                580                 585                 590
Ala Pro Gly Lys Glu Gln Ala Leu Gly Gly Leu Ala Lys Gly Gln
                595                 600                 605
Leu Glu Lys Glu Val Ser Ala Leu Arg Leu Ser Asn Ser Asn Leu Leu
        610                 615                 620
Glu Glu Leu Gly Glu Leu Gly Arg Glu Arg Gln Arg Leu Gln Gly Glu
625                 630                 635                 640
Leu Gln Ser Leu Thr Gln Arg Leu His Arg Glu Phe Val Pro Lys Pro
                645                 650                 655
Glu Ala Gln Val Gln Leu Gln Gln Leu Arg Arg Ser Val Gly Met Leu
                660                 665                 670
Thr Glu Glu Leu Ala Met Glu Lys Glu Ala Thr Asp Lys Leu Arg Arg
        675                 680                 685
```

```
Leu Leu Ala Ser Gln Thr Ser Gly Leu Gln Gly Leu Trp Lys Cys Leu
    690                 695                 700
Pro Pro Asp Leu Val Gly Lys Gly Asn Thr Gln Ser Thr Ala Ala Glu
705                 710                 715                 720
Pro Leu Glu Glu Leu Gln Ala Cys Ile Ser Thr Leu Val Asp Arg His
                725                 730                 735
Leu Glu Ala Gln Arg Val Leu Ala Arg Leu Glu Glu Glu Asn Gln Gln
            740                 745                 750
Leu Arg Gly Ser Leu Ala Pro Cys Gly Glu Pro Glu Ala Ser Leu Lys
        755                 760                 765
Val Thr Ala Ser Pro Gln Val Ala Leu Glu Glu Asp Leu Gly Met
    770                 775                 780
Leu Glu Glu Glu Leu Arg Ala Val Gln Ala Thr Met Ser Gly Lys Ser
785                 790                 795                 800
Gln Glu Ile Cys Lys Leu Lys Gln Leu Leu Tyr Gln Ala Thr Glu Glu
                805                 810                 815
Val Ala Glu Leu Arg Ala Arg Glu Ala Ala Ser Leu Arg Gln His Glu
            820                 825                 830
Lys Thr Arg Gly Ser Leu Val Ala Gln Ala Gln Ala Trp Gly Gln Glu
        835                 840                 845
Leu Lys Val Val Leu Glu Lys Tyr Asn Thr Ala Cys Arg Glu Met Thr
    850                 855                 860
Arg Leu Arg Asp Thr Val Ala Glu Glu Arg Arg Ser Glu Asp Leu
865                 870                 875                 880
Ala Ala Arg Ala Ala Glu Glu Arg Gln Ala Gly Glu Met Arg Gly
                885                 890                 895
Arg Ser Glu Gln Phe Glu Lys Thr Ala Glu Leu Leu Lys Glu Lys Thr
            900                 905                 910
Asn His Leu Ile Gly Ala Cys Arg Asp Lys Glu Ala Lys Ile Lys Glu
        915                 920                 925
Leu Leu Lys Lys Leu Glu Gln Leu Ser Glu Glu Val Leu Glu Val Arg
    930                 935                 940
Gly Glu Asn Ala His Leu Ala Leu Gln Leu Gln Asp Ser Gln Lys Asn
945                 950                 955                 960
His Glu Glu Ile Ile Ser Thr Tyr Arg Ser His Leu Leu Asn Ala Ala
                965                 970                 975
Arg Gly Tyr Met Glu Gln Asp Val Tyr Asn Ile Leu Leu Arg Ile Leu
            980                 985                 990
Ser Met Gln Glu
        995

<210> SEQ ID NO 106
<211> LENGTH: 68
<212> TYPE: PRT
<213> ORGANISM: Mus musculus

<400> SEQUENCE: 106

Gly Leu Ala Lys Gly Gln Leu Glu Lys Glu Val Ser Ala Leu Arg Leu
1               5                   10                  15
Ser Asn Ser Asn Leu Leu Glu Glu Leu Gly Glu Leu Gly Arg Glu Arg
            20                  25                  30
Gln Arg Leu Gln Gly Glu Leu Gln Ser Leu Thr Gln Arg Leu His Arg
        35                  40                  45
Glu Phe Val Pro Lys Pro Glu Ala Gln Val Gln Leu Gln Gln Leu Arg
    50                  55                  60
```

```
Arg Ser Val Arg
 65

<210> SEQ ID NO 107
<211> LENGTH: 68
<212> TYPE: PRT
<213> ORGANISM: Mus musculus

<400> SEQUENCE: 107

Gly Leu Ala Lys Gly Gln Leu Glu Lys Glu Val Ser Ala Leu Arg Leu
 1               5                  10                  15

Ser Asn Ser Asn Leu Leu Glu Glu Leu Gly Glu Leu Gly Arg Glu Arg
            20                  25                  30

Gln Arg Leu Gln Gly Glu Leu Gln Ser Leu Thr Gln Arg Leu His Arg
        35                  40                  45

Glu Phe Val Pro Lys Pro Glu Ala Gln Val Gln Leu Gln Gln Leu Arg
    50                  55                  60

Arg Ser Met Arg
 65

<210> SEQ ID NO 108
<211> LENGTH: 68
<212> TYPE: PRT
<213> ORGANISM: Mus musculus

<400> SEQUENCE: 108

Gly Leu Ala Lys Gly Gln Leu Glu Lys Glu Val Ser Ala Leu Gly Leu
 1               5                  10                  15

Ser Asn Ser Asn Leu Leu Glu Glu Leu Gly Glu Leu Gly Arg Glu Arg
            20                  25                  30

Gln Arg Leu Gln Gly Glu Leu Gln Ser Leu Thr Gln Arg Leu His Arg
        35                  40                  45

Glu Phe Val Pro Lys Pro Glu Ala Gln Val Leu Gln Gln Leu Arg
    50                  55                  60

Arg Ser Val Met
 65

<210> SEQ ID NO 109
<211> LENGTH: 450
<212> TYPE: PRT
<213> ORGANISM: Mus musculus

<400> SEQUENCE: 109

Met Met Asp Val Ser Arg Thr Gln Thr Ala Val Ser Ile Val Glu Glu
 1               5                  10                  15

Asp Leu Lys Leu Leu Gln Leu Lys Leu Arg Ala Ser Met Ser Thr Lys
            20                  25                  30

Cys Asn Leu Glu Asp Gln Ile Lys Lys Leu Glu Asp Asp Arg Ser Ser
        35                  40                  45

Leu Gln Thr Ala Lys Ala Gly Leu Glu Asp Glu Cys Lys Thr Leu Arg
    50                  55                  60

Gln Lys Val Glu Ile Leu Asn Glu Leu Tyr Gln Gln Lys Glu Met Ala
 65                  70                  75                  80

Leu Gln Lys Lys Leu Ser Gln Glu Glu Tyr Glu Arg Gln Asp Arg Glu
                85                  90                  95

Gln Arg Leu Thr Ala Ala Asp Glu Lys Val Val Leu Ala Ala Glu Glu
            100                 105                 110
```

```
Val Lys Thr Tyr Lys Arg Arg Ile Glu Glu Met Glu Glu Leu Gln
        115                 120                 125

Lys Thr Glu Arg Ser Phe Lys Asn Gln Ile Ala Ala His Glu Lys Lys
    130                 135                 140

Ala His Asp Asn Trp Leu Lys Ala Arg Ala Glu Arg Ala Met Ala
145                 150                 155                 160

Glu Glu Lys Arg Glu Ala Ala Asn Leu Arg His Lys Leu Leu Glu Met
                165                 170                 175

Thr Gln Lys Met Ala Met Arg Gln Asp Glu Pro Val Ile Val Lys Pro
        180                 185                 190

Met Pro Gly Arg Pro Asn Thr Gln Asn Pro Pro Arg Arg Gly Leu Leu
        195                 200                 205

Ser Gln Asn Gly Ser Phe Gly Pro Ser Pro Val Ser Gly Glu Cys
    210                 215                 220

Ser Pro Pro Leu Pro Ala Glu Pro Pro Gly Arg Pro Leu Ser Ala Thr
225                 230                 235                 240

Leu Ser Arg Arg Asp Thr Pro Arg Ser Glu Phe Gly Ser Leu Asp Arg
                245                 250                 255

His Leu Pro Arg Pro Arg Trp Pro Ser Glu Ala Ser Gly Lys His Ser
                260                 265                 270

Ala Ser Asp Pro Gly Pro Ala Pro Val Val Asn Ser Ser Arg Ser
    275                 280                 285

Ser Ser Pro Ala Lys Ala Val Asp Glu Gly Lys Val Asn Met Ala Pro
    290                 295                 300

Lys Gly Pro Pro Pro Phe Pro Gly Val Pro Leu Met Gly Gly Pro Val
305                 310                 315                 320

Pro Pro Pro Ile Arg Tyr Gly Pro Pro Gln Leu Cys Gly Pro
                325                 330                 335

Phe Gly Pro Arg Pro Leu Pro Pro Phe Val Pro Gly Met His Pro
                340                 345                 350

Pro Leu Gly Val Arg Glu Tyr Ala Pro Gly Val Leu Pro Gly Lys Arg
        355                 360                 365

Asp Leu Pro Leu Asp Pro Arg Glu Phe Leu Pro Gly His Thr Pro Phe
        370                 375                 380

Arg Pro Pro Gly Ser Leu Gly Pro Arg Glu Phe Phe Ile Pro Gly Thr
385                 390                 395                 400

Arg Leu Pro Pro Pro Thr His Gly Pro Gln Glu Tyr Pro Pro Pro
                405                 410                 415

Pro Ala Val Arg Asp Ser Leu Pro Ser Gly Pro Arg Glu Glu Ala Lys
                420                 425                 430

Pro Ala Ser Pro Ser Ser Val Gln Asp Arg Ser Gln Ala Ser Lys Pro
        435                 440                 445

Thr Pro
    450

<210> SEQ ID NO 110
<211> LENGTH: 58
<212> TYPE: PRT
<213> ORGANISM: Mus musculus

<400> SEQUENCE: 110

Leu Leu Gln Leu Lys Leu Arg Ala Ser Met Ser Thr Lys Cys Asn Leu
1               5                   10                  15

Glu Asn Gln Ile Lys Lys Leu Glu Asp Asp Arg Ser Ser Leu Gln Thr
            20                  25                  30
```

```
Ala Lys Ala Gly Leu Glu Asp Glu Cys Lys Thr Leu Arg Gln Lys Val
        35                  40                  45

Glu Ile Leu Asn Glu Leu Tyr Leu Gln Thr
        50                  55

<210> SEQ ID NO 111
<211> LENGTH: 44
<212> TYPE: PRT
<213> ORGANISM: Mus musculus

<400> SEQUENCE: 111

Leu Glu Asp Gln Ile Lys Lys Leu Glu Asp Asp Arg Ser Ser Leu Gln
1               5                   10                  15

Thr Ala Lys Ala Gly Leu Glu Asp Glu Cys Lys Thr Leu Arg Gln Lys
            20                  25                  30

Val Glu Ile Leu Asn Glu Leu Tyr Gln Gln Ser Arg
        35                  40

<210> SEQ ID NO 112
<211> LENGTH: 225
<212> TYPE: PRT
<213> ORGANISM: Mus musculus

<400> SEQUENCE: 112

His Leu Arg Lys Val Lys Phe Gln Ala Lys Leu Glu His Glu Tyr Ile
1               5                   10                  15

His Asn Phe Lys Val Leu Gln Ala Ala Phe Lys Lys Met Gly Val Asp
            20                  25                  30

Lys Ile Ile Pro Val Glu Lys Leu Val Lys Gly Lys Phe Gln Asp Asn
        35                  40                  45

Phe Glu Phe Ile Gln Trp Phe Lys Lys Phe Phe Asp Ala Asn Tyr Asp
    50                  55                  60

Gly Lys Asp Tyr Asn Pro Leu Leu Ala Arg Gln Gly Gln Asp Val Ala
65                  70                  75                  80

Pro Pro Pro Asn Pro Gly Asp Gln Ile Phe Asn Lys Ser Lys Lys Leu
                85                  90                  95

Ile Gly Thr Ala Val Pro Gln Arg Thr Ser Pro Thr Gly Pro Lys Asn
            100                 105                 110

Met Gln Thr Ser Gly Arg Leu Ser Asn Val Ala Pro Pro Cys Ile Leu
        115                 120                 125

Arg Lys Asn Pro Pro Ser Ala Arg Asn Gly Gly His Glu Ala Asp Ala
    130                 135                 140

Gln Ile Leu Glu Leu Asn Gln Gln Leu Leu Asp Leu Lys Leu Thr Val
145                 150                 155                 160

Asp Gly Leu Glu Lys Glu Arg Asp Phe Tyr Phe Ser Lys Leu Arg Asp
                165                 170                 175

Ile Glu Leu Ile Cys Gln Glu His Glu Ser Glu Asn Ser Pro Val Ile
            180                 185                 190

Ser Gly Ile Ile Gly Ile Leu Tyr Ala Thr Glu Glu Gly Phe Ala Pro
        195                 200                 205

Pro Glu Asp Asp Glu Ile Glu Glu His Gln Gln Glu Asp Gln Asp Glu
    210                 215                 220

Tyr
225

<210> SEQ ID NO 113
```

```
<211> LENGTH: 86
<212> TYPE: PRT
<213> ORGANISM: Mus musculus

<400> SEQUENCE: 113

Arg Asn Gly Gly His Glu Ala Asp Ala Gln Ile Leu Glu Leu Asn Gln
1               5                   10                  15

Gln Leu Leu Asp Leu Lys Leu Thr Val Asp Gly Leu Glu Arg Glu Arg
            20                  25                  30

Asp Phe Tyr Phe Ser Lys Leu Arg Asp Ile Glu Leu Ile Cys Gln Glu
        35                  40                  45

His Glu Ser Glu Asn Ser Pro Val Ile Ser Gly Ile Ile Gly Ile Leu
    50                  55                  60

Tyr Ala Thr Glu Glu Gly Phe Ala Pro Pro Glu Asp Glu Ile Glu
65                  70                  75                  80

Glu His Gln Gln Glu Glu
                85

<210> SEQ ID NO 114
<211> LENGTH: 485
<212> TYPE: PRT
<213> ORGANISM: Mus musculus

<400> SEQUENCE: 114

Met Asn Asn Phe Glu Cys Glu Pro Ala Phe Tyr Thr Cys Val Glu Val
1               5                   10                  15

Thr Ala Gly Asn Arg Leu Phe Tyr His Ile Val Asp Ser Asp Glu Val
            20                  25                  30

Ser Thr Lys Ile Leu Met Glu Phe Asn Lys Met Asn Leu Pro Gly Glu
        35                  40                  45

Val Thr Phe Leu Pro Leu Asn Lys Leu Asp Val Arg Asp Thr Ala Tyr
    50                  55                  60

Pro Glu Thr Asn Asp Ala Ile Pro Met Ile Ser Lys Leu Arg Tyr Asn
65                  70                  75                  80

Pro Arg Phe Asp Lys Ala Phe Lys His Val Phe Gly Lys Thr Leu Ile
            85                  90                  95

Cys Arg Ser Met Glu Val Ser Thr Gln Leu Ala Arg Ala Phe Thr Met
            100                 105                 110

Asp Cys Ile Thr Leu Glu Gly Asp Gln Val Ser His Arg Gly Ala Leu
        115                 120                 125

Thr Gly Gly Tyr Tyr Asp Thr Arg Lys Ser Arg Leu Glu Leu Gln Lys
    130                 135                 140

Asp Val Arg Lys Ala Glu Glu Glu Leu Gly Glu Leu Glu Ala Lys Leu
145                 150                 155                 160

Asn Glu Asn Leu Arg Arg Asn Ile Glu Arg Ile Asn Asn Glu Ile Asp
            165                 170                 175

Gln Leu Met Asn Gln Met Gln Ile Glu Thr Gln Arg Lys Phe
        180                 185                 190

Lys Ala Ser Arg Asp Ser Ile Leu Ser Glu Met Lys Met Leu Lys Glu
    195                 200                 205

Lys Arg Gln Gln Ser Glu Lys Thr Phe Met Pro Lys Gln Arg Ser Leu
210                 215                 220

Gln Ser Leu Glu Ala Ser Leu His Ala Met Glu Ser Thr Arg Glu Ser
225                 230                 235                 240

Leu Lys Ala Glu Leu Gly Thr Asp Leu Leu Ser Gln Leu Ser Leu Glu
            245                 250                 255
```

```
Asp Gln Lys Arg Val Asp Ala Leu Asn Asp Glu Ile Arg Gln Leu Gln
            260                 265                 270

Gln Glu Asn Arg Gln Leu Leu Asn Glu Arg Ile Lys Leu Glu Gly Ile
        275                 280                 285

Ile Thr Arg Val Glu Thr Tyr Leu Asn Glu Asn Leu Arg Lys Arg Leu
    290                 295                 300

Asp Gln Val Glu Gln Glu Leu Asn Glu Leu Arg Glu Thr Glu Gly Gly
305                 310                 315                 320

Thr Val Leu Thr Ala Thr Thr Ser Glu Leu Glu Ala Ile Asn Lys Arg
                325                 330                 335

Val Lys Asp Thr Met Ala Arg Ser Glu Asp Leu Asp Asn Ser Ile Asp
            340                 345                 350

Lys Thr Glu Ala Gly Ile Lys Glu Leu Gln Lys Ser Met Glu Arg Trp
        355                 360                 365

Lys Asn Met Glu Lys Glu His Met Asp Ala Ile Asn His Asp Thr Lys
    370                 375                 380

Glu Leu Glu Lys Met Thr Asn Arg Gln Gly Met Leu Leu Lys Lys Lys
385                 390                 395                 400

Glu Glu Cys Met Lys Lys Ile Arg Glu Leu Gly Ser Leu Pro Gln Glu
                405                 410                 415

Ala Phe Glu Lys Tyr Gln Thr Leu Ser Leu Lys Gln Leu Phe Arg Lys
            420                 425                 430

Leu Glu Gln Cys Asn Thr Glu Leu Lys Lys Tyr Ser His Val Asn Lys
        435                 440                 445

Lys Ala Leu Asp Gln Phe Val Asn Phe Ser Glu Gln Lys Glu Arg Leu
    450                 455                 460

Ile Lys Arg Gln Glu Glu Leu Asp Arg Gly Tyr Lys Ser Ile Met Glu
465                 470                 475                 480

Leu Met Lys Cys Thr
                485

<210> SEQ ID NO 115
<211> LENGTH: 73
<212> TYPE: PRT
<213> ORGANISM: Mus musculus

<400> SEQUENCE: 115

Gln Lys Arg Val Asp Ala Leu Asn Asp Glu Ile Arg Gln Leu Gln Gln
1               5                   10                  15

Glu Asn Arg Gln Leu Leu Asn Glu Arg Ile Lys Leu Glu Gly Ile Ile
            20                  25                  30

Thr Arg Val Glu Thr Tyr Leu Asn Glu Asn Leu Arg Lys Arg Leu Asp
        35                  40                  45

Gln Val Glu Gln Glu Leu Asn Glu Leu Arg Glu Thr Glu Gly Gly Thr
    50                  55                  60

Val Leu Thr Ala Thr Thr Ser Glu Lys
65                  70

<210> SEQ ID NO 116
<211> LENGTH: 1337
<212> TYPE: PRT
<213> ORGANISM: Mus musculus

<400> SEQUENCE: 116

Met Met Glu Ile Gln Met Asp Glu Gly Gly Gly Val Val Val Tyr Gln
1               5                   10                  15
```

```
Asp Asp Tyr Cys Ser Gly Ser Val Met Ser Glu Arg Val Ser Gly Leu
            20                  25                  30

Ala Gly Ser Ile Tyr Arg Glu Phe Glu Arg Leu Ile His Cys Tyr Asp
            35                  40                  45

Glu Glu Val Val Lys Glu Leu Met Pro Leu Val Val Asn Val Leu Glu
            50                  55                  60

Asn Leu Asp Ser Val Leu Ser Glu Asn Gln His Glu Val Glu Leu
 65                  70                  75                  80

Glu Leu Leu Arg Glu Asp Asn Glu Gln Leu Leu Thr Gln Tyr Glu Arg
                 85                  90                  95

Glu Lys Ala Leu Arg Lys Gln Ala Glu Lys Phe Ile Glu Phe Glu
                100                 105                 110

Asp Ala Leu Glu Gln Glu Lys Lys Glu Leu Gln Ile Gln Val Glu His
            115                 120                 125

Tyr Glu Phe Gln Thr Arg Gln Leu Glu Leu Lys Ala Lys Asn Tyr Ala
            130                 135                 140

Asp Gln Ile Ser Arg Leu Glu Glu Arg Glu Ser Glu Met Lys Lys Glu
145                 150                 155                 160

Tyr Asn Ala Leu His Gln Arg His Thr Glu Met Ile Gln Thr Tyr Val
                165                 170                 175

Glu His Ile Glu Arg Ser Lys Met Gln Gln Val Gly Gly Ser Gly Gln
            180                 185                 190

Thr Glu Ser Ser Leu Pro Gly Arg Ser Arg Lys Glu Arg Pro Thr Ser
            195                 200                 205

Leu Asn Val Phe Pro Leu Ala Asp Gly Met Val Arg Ala Gln Met Gly
            210                 215                 220

Gly Lys Leu Val Pro Ala Gly Asp His Trp His Leu Ser Asp Leu Gly
225                 230                 235                 240

Gln Leu Gln Ser Ser Ser Tyr Gln Cys Pro Asn Asp Glu Met Ser
                245                 250                 255

Glu Ser Gly Gln Ser Ser Ala Ala Ala Thr Pro Ser Thr Thr Gly Thr
            260                 265                 270

Lys Ser Asn Thr Pro Thr Ser Ser Val Pro Ser Ala Ala Val Thr Pro
            275                 280                 285

Leu Asn Glu Ser Leu Gln Pro Leu Gly Asp Tyr Val Ser Val Thr Lys
            290                 295                 300

Asn Asn Lys Gln Ala Arg Glu Lys Arg Asn Ser Arg Asn Met Glu Val
305                 310                 315                 320

Gln Val Thr Gln Glu Met Arg Asn Val Ser Ile Gly Met Gly Ser Ser
                325                 330                 335

Asp Glu Trp Ser Asp Val Gln Asp Ile Ile Asp Ser Thr Pro Glu Leu
            340                 345                 350

Asp Val Cys Pro Glu Thr Arg Leu Glu Arg Thr Gly Ser Ser Pro Thr
            355                 360                 365

Gln Gly Ile Val Asn Lys Ala Leu Gly Ile Asn Thr Asp Ser Leu Tyr
            370                 375                 380

His Glu Leu Ser Thr Ala Gly Ser Glu Val Ile Gly Asp Val Asp Glu
385                 390                 395                 400

Gly Ala Asp Leu Leu Gly Glu Phe Ser Val Arg Asp Asp Phe Phe Gly
                405                 410                 415

Met Gly Lys Glu Val Gly Asn Leu Leu Leu Glu Asn Ser Gln Leu Leu
            420                 425                 430
```

-continued

```
Glu Thr Lys Asn Ala Leu Asn Val Val Lys Asn Asp Leu Ile Ala Lys
    435                 440                 445

Val Asp Gln Leu Ser Gly Gln Glu Val Leu Lys Gly Glu Leu Glu
    450                 455                 460

Ala Ala Lys Gln Ala Lys Val Lys Leu Glu Asn Arg Ile Lys Glu Leu
465                 470                 475                 480

Glu Glu Glu Leu Lys Arg Val Lys Ser Glu Ala Val Thr Ala Arg Arg
                485                 490                 495

Glu Pro Arg Glu Glu Val Glu Asp Val Ser Ser Tyr Leu Cys Thr Glu
                500                 505                 510

Leu Asp Lys Ile Pro Met Ala Gln Arg Arg Arg Phe Thr Arg Val Glu
    515                 520                 525

Met Ala Arg Val Leu Met Glu Arg Asn Gln Tyr Lys Glu Arg Leu Met
    530                 535                 540

Glu Leu Gln Glu Ala Val Arg Trp Thr Glu Met Ile Arg Ala Ser Arg
545                 550                 555                 560

Glu His Pro Ser Val Gln Lys Lys Lys Ser Thr Ile Trp Gln Phe
                565                 570                 575

Phe Ser Arg Leu Phe Ser Ser Ser Ser Pro Pro Ala Lys Arg
                580                 585                 590

Ser Tyr Pro Ser Val Asn Ile His Tyr Lys Ser Pro Thr Ala Ala Gly
                595                 600                 605

Phe Ser Gln Arg Arg Ser His Ala Leu Cys Gln Ile Ser Ala Gly Ser
                610                 615                 620

Arg Pro Leu Glu Phe Phe Pro Asp Asp Cys Thr Ser Ser Ala Arg
625                 630                 635                 640

Arg Glu Gln Lys Arg Glu Gln Tyr Arg Gln Val Arg Glu His Val Arg
                645                 650                 655

Asn Asp Asp Gly Arg Leu Gln Ala Cys Gly Trp Ser Leu Pro Ala Lys
                660                 665                 670

Tyr Lys Gln Leu Ser Pro Asn Gly Gly Gln Glu Asp Thr Arg Met Lys
                675                 680                 685

Asn Val Pro Val Pro Val Tyr Cys Arg Pro Leu Val Glu Lys Asp Pro
    690                 695                 700

Ser Thr Lys Leu Trp Cys Ala Ala Gly Val Asn Leu Ser Gly Trp Lys
705                 710                 715                 720

Pro His Glu Glu Asp Ser Ser Asn Gly Pro Lys Pro Val Pro Gly Arg
                725                 730                 735

Asp Pro Leu Thr Cys Asp Arg Glu Gly Glu Gly Pro Lys Ser Thr
                740                 745                 750

His Pro Ser Pro Glu Lys Lys Lys Ala Lys Glu Thr Pro Glu Ala Asp
                755                 760                 765

Ala Thr Ser Ser Arg Val Trp Ile Leu Thr Ser Thr Leu Thr Thr Ser
    770                 775                 780

Lys Val Val Ile Ile Asp Ala Asn Gln Pro Gly Thr Ile Val Asp Gln
785                 790                 795                 800

Phe Thr Val Cys Asn Ala His Val Leu Cys Ile Ser Ser Ile Pro Ala
                805                 810                 815

Ala Ser Asp Ser Asp Tyr Pro Pro Gly Glu Met Phe Leu Asp Ser Asp
                820                 825                 830

Val Asn Pro Glu Asp Ser Gly Ala Asp Gly Val Leu Ala Gly Ile Thr
                835                 840                 845

Leu Val Gly Cys Ala Thr Arg Cys Asn Val Pro Arg Ser Asn Cys Ser
```

-continued

```
            850             855             860
Ser Arg Gly Asp Thr Pro Val Leu Asp Lys Gly Gln Gly Asp Val Ala
865                     870              875                 880

Thr Thr Ala Asn Gly Lys Val Asn Pro Ser Gln Ser Thr Glu Glu Ala
                885                 890                 895

Thr Glu Ala Thr Glu Val Pro Asp Pro Gly Pro Ser Glu Ser Glu Ala
                900                 905                 910

Thr Thr Val Arg Pro Gly Pro Leu Thr Glu His Val Phe Thr Asp Pro
                915                 920                 925

Ala Pro Thr Pro Ser Ser Thr Gln Pro Ala Ser Glu Asn Gly Ser
930                 935                 940

Glu Ser Asn Gly Thr Ile Val Gln Pro Gln Val Glu Pro Ser Gly Glu
945                 950                 955                 960

Leu Ser Thr Thr Thr Ser Ser Ala Ala Pro Thr Met Trp Leu Gly Ala
                965                 970                 975

Gln Asn Gly Trp Leu Tyr Val His Ser Ala Val Ala Asn Trp Lys Lys
                980                 985                 990

Cys Leu His Ser Ile Lys Leu Lys Asp Ser Val Leu Ser Leu Val His
            995                 1000                1005

Val Lys Gly Arg Val Leu Ala Leu Ala Asp Gly Thr Leu Ala
        1010                1015                1020

Ile Phe His Arg Gly Glu Gly Gln Trp Asp Leu Ser Asn Tyr
        1025                1030                1035

His Leu Met Asp Leu Gly His Pro His His Ser Ile Arg Cys Met
        1040                1045                1050

Ala Val Val Asn Asp Arg Val Trp Cys Gly Tyr Lys Asn Lys Val
        1055                1060                1065

His Val Ile Gln Pro Lys Thr Met Gln Ile Glu Lys Ser Phe Asp
        1070                1075                1080

Ala His Pro Arg Arg Glu Ser Gln Val Arg Gln Leu Ala Trp Ile
        1085                1090                1095

Gly Asp Gly Val Trp Val Ser Ile Arg Leu Asp Ser Thr Leu Arg
        1100                1105                1110

Leu Tyr His Ala His Thr His Gln His Leu Gln Asp Val Asp Ile
        1115                1120                1125

Glu Pro Tyr Val Ser Lys Met Leu Gly Thr Gly Lys Leu Gly Phe
        1130                1135                1140

Ser Phe Val Arg Ile Thr Ala Leu Leu Ile Ala Gly Asn Arg Leu
        1145                1150                1155

Trp Val Gly Thr Gly Asn Gly Val Val Ile Ser Ile Pro Leu Thr
        1160                1165                1170

Glu Thr Val Val Leu His Arg Gly Gln Leu Leu Gly Leu Arg Ala
        1175                1180                1185

Asn Lys Thr Ser Pro Thr Ser Gly Glu Gly Thr Arg Pro Gly Gly
        1190                1195                1200

Ile Ile His Val Tyr Gly Asp Asp Ser Ser Asp Lys Ala Ala Ser
        1205                1210                1215

Ser Phe Ile Pro Tyr Cys Ser Met Ala Gln Ala Gln Leu Cys Phe
        1220                1225                1230

His Gly His Arg Asp Ala Val Lys Phe Phe Val Ser Val Pro Gly
        1235                1240                1245

Asn Val Leu Ala Thr Leu Asn Gly Ser Val Leu Asp Ser Pro Ser
        1250                1255                1260
```

Glu Gly Pro Gly Pro Ala Ala Pro Ala Ala Asp Ala Glu Gly Gln
        1265                1270                1275

Lys Leu Lys Asn Ala Leu Val Leu Ser Gly Gly Glu Gly Tyr Ile
        1280                1285                1290

Asp Phe Arg Ile Gly Asp Gly Glu Asp Asp Glu Thr Glu Glu Cys
        1295                1300                1305

Ala Gly Asp Val Asn Gln Thr Lys Pro Ser Leu Ser Lys Ala Glu
        1310                1315                1320

Arg Ser His Ile Ile Val Trp Gln Val Ser Tyr Thr Pro Glu
        1325                1330                1335

<210> SEQ ID NO 117
<211> LENGTH: 71
<212> TYPE: PRT
<213> ORGANISM: Mus musculus

<400> SEQUENCE: 117

Glu Thr Lys Asn Ala Leu Asn Val Val Lys Asn Asp Leu Ile Ala Lys
1               5                   10                  15

Val Asp Gln Leu Ser Gly Glu Gln Glu Val Leu Lys Gly Glu Leu Glu
            20                  25                  30

Ala Ala Lys Gln Ala Lys Val Lys Leu Glu Asn Arg Ile Lys Glu Leu
        35                  40                  45

Glu Lys Glu Leu Lys Arg Val Lys Ser Glu Ala Val Thr Ala Arg Arg
    50                  55                  60

Glu Pro Arg Glu Glu Val Asp
65                  70

<210> SEQ ID NO 118
<211> LENGTH: 993
<212> TYPE: PRT
<213> ORGANISM: Mus musculus

<400> SEQUENCE: 118

Met Glu Ala Ala Val Cys Ser Glu Ile Glu Arg Glu Asp Gly Asp Ser
1               5                   10                  15

Ser Cys Gly Asp Val Cys Phe Met Asp Lys Gly Leu His Ser Ile Ser
            20                  25                  30

Glu Leu Ser Leu Asp Ser Ser Ile His Ala Ile Asn Leu His Cys Asn
        35                  40                  45

Asn Ile Ser Lys Ile Ser Ser Ile Asp His Ile Trp Asn Leu Arg His
    50                  55                  60

Leu Asp Leu Ser Ser Asn Gln Ile Ser Gln Ile Glu Gly Leu Asn Thr
65                  70                  75                  80

Leu Thr Lys Leu Cys Thr Leu Asn Leu Ser Cys Asn Leu Ile Thr Arg
                85                  90                  95

Val Glu Gly Leu Glu Ala Leu Val Asn Leu Thr Lys Leu Asn Leu Ser
            100                 105                 110

Tyr Asn His Ile Asn Asp Leu Ser Gly Leu Met Pro Leu His Gly Leu
        115                 120                 125

Lys Tyr Lys Leu Arg Tyr Ile Asp Leu His Ser Asn Tyr Ile Asp Ser
    130                 135                 140

Ile His His Leu Leu Gln Cys Thr Val Gly Leu His Phe Leu Thr Asn
145                 150                 155                 160

Leu Ile Leu Glu Lys Asp Gly Glu Gly Asn Pro Ile Cys Leu Ile Pro
                165                 170                 175

```
Gly Tyr Arg Ala Ile Ile Leu Gln Thr Leu Pro Gln Leu Arg Ile Leu
            180                 185                 190

Asp Cys Lys Asn Ile Phe Gly Glu Pro Val Ser Leu Glu Glu Ile Asn
            195                 200                 205

Ser Ser His Leu Gln Cys Leu Glu Gly Leu Leu Asp Asn Leu Val Ser
            210                 215                 220

Ser Asp Ser Pro Leu Asn Ile Ser Glu Asp Glu Val Asn Asp Asp Val
225                 230                 235                 240

Ser Ala Pro Pro Met Asp Val Leu Pro Ser Leu Lys Glu Phe Lys Ser
            245                 250                 255

Thr Pro Glu Asp Asn Val Leu Ala Ser Leu Leu Ser Val Cys Pro Ser
            260                 265                 270

Ser Glu Pro Glu Lys Ile Asn Gln Glu Asn Asp Phe Gln Asn Glu Val
            275                 280                 285

Lys Leu Gln Lys Leu Asp Asp Gln Ile Leu Gln Leu Leu Asn Glu Thr
            290                 295                 300

Asn Asn Ser Leu Ile Asp Asn Val Pro Glu Lys Asp Leu Arg Pro Lys
305                 310                 315                 320

Arg Asp Thr Asp Ile Thr Ser Glu Ser Asp Tyr Gly Asn Arg Arg Glu
            325                 330                 335

Cys Ser Arg Lys Val Pro Arg Arg Thr Lys Ile Pro Tyr Tyr Ser Arg
            340                 345                 350

Thr Ile Gln Thr Ile Lys His His Asn Lys Asn Asn Gly Ala Phe Val
            355                 360                 365

Ser Cys Asn Arg Lys Met Arg Gln Pro Tyr Leu Arg Asp Leu Tyr Val
            370                 375                 380

Arg Ser Ser Leu Val Asn Cys Asn Asn Leu Arg Asp Leu Asp Glu Gln
385                 390                 395                 400

Lys Thr Gly Val Ile Lys Val Asp Lys Asn Phe Ser Asp Asn Ser Thr
            405                 410                 415

Tyr Arg Ser Leu Val Glu Gln Leu Asp Gln Glu Arg Glu Met Arg Trp
            420                 425                 430

Lys Ala Glu Gln Thr Glu Lys Lys Leu Met Asp Tyr Ile Asp Glu Leu
            435                 440                 445

His Lys Gln Ala Asp Glu Lys Lys Asp Val His Ser Gln Ala Leu Ile
            450                 455                 460

Thr Thr Asp Arg Leu Lys Asp Ala Ile Phe Lys Glu Arg His Cys Lys
465                 470                 475                 480

Ala Gln Leu Glu Ile Ile Val His Arg Leu Gln Asn Glu Val Lys Lys
            485                 490                 495

Leu Thr Ile Glu Leu Met Lys Ala Arg Asp Gln Gln Glu Asp His Ile
            500                 505                 510

Arg His Leu Arg Thr Leu Glu Arg Ala Leu Glu Lys Met Glu Lys Gln
            515                 520                 525

Lys Ala Gln Gln Gln Ala Ala Gln Ile Arg Leu Ile Gln Glu Val Glu
            530                 535                 540

Leu Lys Ala Ser Ala Ala Asp Arg Glu Ile Asn Leu Leu Arg Thr Ser
545                 550                 555                 560

Leu His Gln Glu Lys Gln Gln Val Gln Leu His Glu Leu Leu Ala
            565                 570                 575

Leu Lys Glu Gln Glu His Arg Gln Glu Ile Glu Thr Arg Gln Phe Phe
            580                 585                 590
```

```
Thr Asp Ala Glu Phe Gln Asp Ala Leu Thr Lys Arg Leu Cys Lys Glu
        595                 600                 605

Glu Arg Lys His Glu Gln Glu Val Lys Glu Tyr Gln Glu Lys Ile Asp
610                 615                 620

Ile Leu Asn Gln Gln Tyr Leu Asp Leu Glu Asn Glu Phe Arg Ile Ala
625                 630                 635                 640

Leu Thr Val Glu Ala Arg Arg Phe Lys Asp Val Gln Asp Gly Phe Glu
            645                 650                 655

Asp Val Ala Thr Glu Leu Ala Lys Ser Lys His Ala Leu Ile Trp Ala
            660                 665                 670

Gln Arg Lys Glu Asn Glu Ser Ser Leu Ile Lys Asp Leu Thr Cys
        675                 680                 685

Met Val Lys Glu Gln Lys Thr Lys Leu Ser Glu Val Cys Lys Leu Lys
    690                 695                 700

Gln Glu Ala Ala Ala Asn Leu Gln Asn Gln Ile Asn Thr Leu Glu Ile
705                 710                 715                 720

Leu Ile Glu Asp Asp Lys Gln Lys Ser Ile Gln Ile Glu Leu Leu Lys
                725                 730                 735

His Glu Lys Thr Gln Leu Ile Ser Glu Leu Ala Ala Lys Glu Ser Leu
            740                 745                 750

Ile Tyr Gly Leu Arg Thr Glu Arg Lys Val Trp Gly Gln Glu Leu Ala
        755                 760                 765

Cys Gln Ser Ser Thr Leu Ser Gln Ser Arg Gly Lys Leu Glu Ala Gln
    770                 775                 780

Ile Glu Ser Leu Cys Arg Glu Asn Glu Ser Leu Arg Lys Ser His Glu
785                 790                 795                 800

Ser Asp Cys Asp Ala Leu Arg Ile Lys Cys Lys Ile Ile Glu Asp Gln
                805                 810                 815

Asn Glu Thr Ile Arg Lys Leu Lys Asp Ser Leu Gln Glu Lys Asp Gly
            820                 825                 830

Gln Ile Lys Leu Leu Gln Glu Gln Ile Ala Leu Ile Glu Lys Cys Ser
        835                 840                 845

Gln Glu Gln Leu Asn Glu Lys Ser Pro Gln Leu Asp Ser Ile Val Glu
    850                 855                 860

Lys Leu Glu Arg His Asn Glu Arg Lys Glu Lys Leu Lys Gln Gln Leu
865                 870                 875                 880

Lys Ala Lys Glu Leu Glu Leu Glu Glu Ile Arg Lys Ala Tyr Ser Thr
                885                 890                 895

Leu Asn Lys Lys Trp His Asp Lys Gly Glu Leu Leu Ser His Leu Glu
            900                 905                 910

Met Gln Val Lys Glu Val Lys Glu Lys Phe Glu Asp Lys Glu Arg Lys
        915                 920                 925

Leu Lys Ala Glu Arg Asp Lys Ser Leu Glu Leu Gln Lys Asp Ala Met
    930                 935                 940

Glu Lys Leu Gln Asn Met Asp Asp Ala Phe Arg Arg Gln Val Asp Glu
945                 950                 955                 960

Ile Val Glu Ala His Gln Ala Glu Ile Met Gln Leu Ala Asn Glu Lys
                965                 970                 975

Gln Lys Tyr Ile Asp Cys Ala Asn Leu Lys Gly Asp Tyr Ala Arg Gly
            980                 985                 990

Asp

<210> SEQ ID NO 119
```

```
<211> LENGTH: 52
<212> TYPE: PRT
<213> ORGANISM: Mus musculus

<400> SEQUENCE: 119

His Ser Gln Ala Leu Ile Thr Thr Asp Arg Leu Lys Asp Ala Ile Phe
1               5                   10                  15

Lys Glu Arg His Cys Lys Ala Gln Leu Glu Ile Ile Val His Arg Leu
            20                  25                  30

Gln Asn Glu Val Lys Lys Leu Thr Ile Glu Leu Met Lys Ala Arg Asp
        35                  40                  45

Gln Gln Glu Asp
    50

<210> SEQ ID NO 120
<211> LENGTH: 403
<212> TYPE: PRT
<213> ORGANISM: Mus musculus

<400> SEQUENCE: 120

Leu Gly Thr Met Pro Arg Phe Ser Leu Ser Arg Met Thr Pro Pro Leu
1               5                   10                  15

Pro Ala Arg Val Asp Phe Ser Leu Ala Gly Ala Leu Asn Ala Gly Phe
            20                  25                  30

Lys Glu Thr Arg Ala Ser Glu Arg Ala Glu Met Met Glu Leu Asn Asp
        35                  40                  45

Arg Phe Ala Ser Tyr Ile Glu Lys Val Arg Phe Leu Glu Gln Gln Asn
    50                  55                  60

Lys Ala Leu Ala Ala Glu Leu Asn Gln Leu Arg Ala Lys Glu Pro Thr
65                  70                  75                  80

Lys Leu Ala Asp Val Tyr Gln Ala Glu Leu Arg Glu Leu Arg Leu Arg
                85                  90                  95

Leu Asp Gln Leu Thr Ala Asn Ser Ala Arg Leu Glu Val Glu Arg Asp
            100                 105                 110

Asn Phe Ala Gln Asp Leu Gly Thr Leu Arg Gln Lys Leu Gln Asp Glu
        115                 120                 125

Thr Asn Leu Arg Leu Glu Ala Glu Asn Asn Leu Ala Ala Tyr Arg Gln
    130                 135                 140

Glu Ala His Glu Ala Thr Leu Ala Arg Val Asp Leu Glu Arg Lys Val
145                 150                 155                 160

Glu Ser Leu Glu Glu Glu Ile Gln Phe Leu Arg Lys Ile Tyr Glu Glu
                165                 170                 175

Glu Val Arg Asp Leu Arg Glu Gln Leu Ala Gln Gln Val His Val
            180                 185                 190

Glu Met Asp Val Ala Lys Pro Asp Leu Thr Ala Ala Leu Arg Glu Ile
        195                 200                 205

Arg Thr Gln Tyr Glu Ala Val Ala Thr Ser Asn Met Gln Glu Thr Glu
    210                 215                 220

Glu Trp Tyr Arg Ser Lys Phe Ala Asp Leu Thr Asp Ala Ala Ser Arg
225                 230                 235                 240

Asn Ala Glu Leu Leu Arg Gln Ala Lys His Glu Ala Asn Asp Tyr Arg
                245                 250                 255

Arg Gln Leu Gln Ala Leu Thr Cys Asp Leu Glu Ser Leu Arg Gly Thr
            260                 265                 270

Asn Glu Ser Leu Glu Arg Gln Met Arg Glu Gln Glu Glu Arg His Ala
        275                 280                 285
```

```
Arg Glu Ser Ala Ser Tyr Gln Glu Ala Leu Ala Arg Leu Glu Glu
        290                 295                 300

Gly Gln Ser Leu Lys Glu Met Ala Arg His Leu Gln Glu Tyr Gln
305                 310                 315                 320

Asp Leu Leu Asn Val Lys Leu Ala Leu Asp Ile Glu Ile Ala Thr Tyr
                325                 330                 335

Arg Lys Leu Leu Glu Gly Glu Asn Arg Ile Thr Ile Pro Val Gln
                340                 345                 350

Thr Phe Ser Asn Leu Gln Ile Arg Glu Thr Ser Leu Asp Thr Lys Ser
        355                 360                 365

Val Ser Glu Gly His Leu Lys Arg Asn Ile Val Lys Thr Val Glu
        370                 375                 380

Met Arg Asp Gly Glu Val Ile Lys Asp Ser Lys Gln Glu His Lys Asp
385                 390                 395                 400

Val Val Met

<210> SEQ ID NO 121
<211> LENGTH: 45
<212> TYPE: PRT
<213> ORGANISM: Mus musculus

<400> SEQUENCE: 121

Leu Ala Arg Leu Glu Glu Gly Arg Ser Leu Lys Glu Glu Met Ala
1               5                   10                  15

Arg His Leu Gln Glu Tyr Gln Asp Leu Leu Asn Val Lys Leu Ala Leu
                20                  25                  30

Asp Ile Glu Ile Ala Thr Tyr Arg Lys Leu Leu Glu Gly
            35                  40                  45

<210> SEQ ID NO 122
<211> LENGTH: 451
<212> TYPE: PRT
<213> ORGANISM: Mus musculus

<400> SEQUENCE: 122

Met Ala Ser Pro Thr Leu Ser Pro Asp Ser Ser Gln Glu Ala Leu
1               5                   10                  15

Ser Ala Pro Thr Cys Ser Pro Thr Ser Asp Ser Glu Asn Leu Ser Pro
                20                  25                  30

Asp Glu Leu Glu Leu Leu Ala Lys Leu Glu Glu Gln Asn Arg Leu Leu
                35                  40                  45

Glu Ala Asp Ser Lys Ser Met Arg Ser Met Asn Gly Ser Arg Arg Asn
50                  55                  60

Ser Gly Ser Ser Leu Val Ser Ser Ser Ala Ser Ser Asn Leu Ser
65                  70                  75                  80

His Leu Glu Glu Asp Thr Trp Ile Leu Trp Gly Arg Ile Ala Asn Glu
                85                  90                  95

Trp Glu Glu Trp Arg Arg Arg Lys Glu Lys Leu Leu Lys Glu Leu Ile
                100                 105                 110

Arg Lys Gly Ile Pro His His Phe Arg Ala Ile Val Trp Gln Leu Leu
            115                 120                 125

Cys Ser Ala Thr Asp Met Pro Val Lys Asn Gln Tyr Ser Glu Leu Leu
130                 135                 140

Lys Met Ser Ser Pro Cys Glu Lys Leu Ile Arg Arg Asp Ile Ala Arg
145                 150                 155                 160
```

Thr Tyr Pro Glu His Glu Phe Lys Gly Gln Asp Ser Leu Gly Gln
            165                 170                 175

Glu Val Leu Phe Asn Val Met Lys Ala Tyr Ser Leu Val Asp Arg Glu
            180                 185                 190

Val Gly Tyr Cys Gln Gly Ser Ala Phe Ile Val Gly Leu Leu Leu Met
            195                 200                 205

Gln Met Pro Glu Glu Ala Phe Cys Val Phe Val Arg Leu Met Gln
210                 215                 220

Glu Tyr Arg Leu Arg Glu Leu Phe Lys Pro Ser Met Ala Glu Leu Gly
225                 230                 235                 240

Leu Cys Ile Tyr Gln Phe Glu Tyr Met Leu Gln Glu Gln Leu Pro Asp
            245                 250                 255

Leu Asn Thr His Phe Arg Ser Gln Ser Phe His Thr Ser Met Tyr Ala
            260                 265                 270

Ser Ser Trp Phe Leu Thr Leu Phe Leu Thr Thr Phe Pro Leu Pro Val
            275                 280                 285

Ala Thr Arg Val Phe Asp Ile Phe Met Tyr Glu Gly Leu Glu Ile Val
            290                 295                 300

Phe Arg Val Gly Leu Ala Leu Leu Gln Val Asn Gln Thr Glu Leu Met
305                 310                 315                 320

Gln Leu Asp Met Glu Gly Met Ser Gln Tyr Phe Gln Arg Val Ile Pro
            325                 330                 335

His Gln Phe Asp Ser Cys Pro Asp Lys Leu Val Leu Lys Ala Tyr Gln
            340                 345                 350

Val Lys Tyr Asn Pro Lys Lys Met Lys Arg Leu Glu Lys Glu Tyr Ala
            355                 360                 365

Ala Met Lys Ser Lys Glu Met Glu Glu Gln Ile Glu Ile Lys Arg Leu
            370                 375                 380

Arg Thr Glu Asn Arg Leu Leu Lys Gln Arg Ile Glu Thr Leu Glu Lys
385                 390                 395                 400

Gly Gln Val Thr Arg Ala Gln Glu Ala Glu Glu Asn Tyr Val Ile Lys
            405                 410                 415

Arg Glu Leu Ala Val Val Arg Gln Gln Cys Ser Ser Thr Ala Glu Asp
            420                 425                 430

Leu Gln Lys Ala Gln Ser Thr Ile Arg Gln Leu Gln Glu Gln Val
            435                 440                 445

Pro Gly Gly
    450

<210> SEQ ID NO 123
<211> LENGTH: 104
<212> TYPE: PRT
<213> ORGANISM: Mus musculus

<400> SEQUENCE: 123

Ala Leu Leu Gln Val Asn Gln Thr Glu Leu Met Gln Leu Asp Met Glu
1               5                   10                  15

Gly Met Ser Gln Tyr Phe Gln Arg Val Ile Pro His Gln Phe Asp Ser
            20                  25                  30

Cys Pro Asp Lys Leu Val Leu Lys Ala Tyr Gln Val Lys Tyr Asn Pro
            35                  40                  45

Lys Lys Met Lys Arg Leu Glu Lys Glu Tyr Ala Ala Met Lys Ser Lys
        50                  55                  60

Glu Met Glu Glu Gln Ile Glu Ile Lys Arg Leu Arg Thr Glu Asn Arg
65                  70                  75                  80

```
Leu Leu Lys Gln Arg Ile Gly Thr Leu Glu Lys Glu Ser Ala Ala Leu
                85                  90                  95

Ala Asp Arg Leu Ile Gln Gly Ala
            100
```

<210> SEQ ID NO 124
<211> LENGTH: 963
<212> TYPE: PRT
<213> ORGANISM: Mus musculus

<400> SEQUENCE: 124

```
Met Ala Asp Pro Ala Glu Cys Asn Ile Lys Val Met Cys Arg Phe Arg
1               5                   10                  15

Pro Leu Asn Glu Ser Glu Val Asn Arg Gly Asp Lys Tyr Val Ala Lys
                20                  25                  30

Phe Gln Gly Glu Asp Thr Val Val Ile Ala Ser Lys Pro Tyr Ala Phe
            35                  40                  45

Asp Arg Val Phe Gln Ser Ser Thr Ser Gln Glu Gln Val Tyr Asn Asp
50                  55                  60

Cys Ala Lys Lys Ile Val Lys Asp Val Leu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
```

-continued

```
            340                 345                 350
Thr Leu Arg Asn Thr Ile Gln Trp Leu Glu Asn Glu Leu Asn Arg Trp
            355                 360                 365
Arg Asn Gly Glu Thr Val Pro Ile Asp Glu Gln Phe Asp Lys Glu Lys
            370                 375                 380
Ala Asn Leu Glu Ala Phe Thr Ala Asp Lys Asp Ile Ala Ile Thr Ser
385                 390                 395                 400
Asp Lys Gly Ala Ala Val Gly Met Ala Gly Ser Phe Thr Asp Ala
                405                 410                 415
Glu Arg Arg Lys Cys Glu Glu Leu Ala Lys Leu Tyr Lys Gln Leu
            420                 425                 430
Asp Asp Lys Asp Glu Ile Asn Gln Gln Ser Gln Leu Val Glu Lys
            435                 440                 445
Leu Lys Thr Gln Met Leu Asp Gln Glu Glu Leu Leu Ala Ser Thr Arg
    450                 455                 460
Arg Asp Gln Asp Asn Met Gln Ala Glu Leu Asn Arg Leu Gln Ala Glu
465                 470                 475                 480
Asn Asp Ala Ser Lys Glu Glu Val Lys Glu Val Leu Gln Ala Leu Glu
                485                 490                 495
Glu Leu Ala Val Asn Tyr Asp Gln Lys Ser Gln Glu Val Glu Asp Lys
            500                 505                 510
Thr Lys Glu Tyr Glu Leu Leu Thr Asp Glu Phe Asn Gln Lys Ser Ala
    515                 520                 525
Thr Leu Ala Ser Ile Asp Ala Glu Leu Gln Lys Leu Lys Glu Met Thr
    530                 535                 540
Asn His Gln Lys Lys Arg Ala Ala Glu Met Met Ala Ser Leu Leu Lys
545                 550                 555                 560
Asp Leu Ala Glu Ile Gly Ile Ala Val Gly Asn Asn Asp Val Lys Gln
                565                 570                 575
Pro Glu Gly Thr Gly Met Ile Asp Glu Glu Phe Thr Val Ala Arg Leu
            580                 585                 590
Tyr Ile Ser Lys Met Lys Ser Glu Val Lys Thr Met Val Lys Arg Cys
    595                 600                 605
Lys Gln Leu Glu Ser Thr Gln Thr Glu Ser Asn Lys Lys Met Glu Glu
    610                 615                 620
Asn Glu Lys Glu Leu Ala Ala Cys Gln Leu Arg Ile Ser Gln His Glu
625                 630                 635                 640
Ala Lys Ile Lys Ser Leu Thr Glu Tyr Leu Gln Asn Asp Glu Gln Lys
                645                 650                 655
Lys Arg Gln Leu Glu Glu Ser Leu Asp Ser Leu Gly Glu Glu Leu Val
            660                 665                 670
Gln Leu Arg Ala Gln Glu Lys Val His Glu Met Glu Lys Glu His Leu
    675                 680                 685
Asn Lys Val Gln Thr Ala Asn Glu Val Lys Gln Ala Val Glu Gln Gln
    690                 695                 700
Ile Gln Ser His Arg Glu Thr His Gln Lys Gln Ile Ser Ser Leu Arg
705                 710                 715                 720
Asp Glu Val Glu Ala Lys Glu Lys Leu Ile Thr Asp Leu Gln Asp Gln
                725                 730                 735
Asn Gln Lys Met Val Leu Glu Thr Glu Arg Leu Arg Val Glu His Glu
            740                 745                 750
Arg Leu Lys Ala Thr Asp Gln Glu Lys Ser Arg Lys Leu His Glu Leu
    755                 760                 765
```

```
Thr Val Met Gln Asp Arg Arg Glu Gln Ala Arg Gln Asp Leu Lys Gly
    770                 775                 780
Leu Glu Glu Thr Val Ala Lys Glu Leu Gln Thr Leu His Asn Leu Arg
785                 790                 795                 800
Lys Leu Phe Val Gln Asp Leu Ala Thr Arg Val Lys Lys Ser Ala Glu
                805                 810                 815
Val Asp Ser Asp Thr Gly Gly Ser Ala Ala Gln Lys Gln Lys Ile
            820                 825                 830
Ser Phe Leu Glu Asn Asn Leu Glu Gln Leu Thr Lys Val His Lys Gln
        835                 840                 845
Leu Val Arg Asp Asn Ala Asp Leu Arg Cys Glu Leu Pro Lys Leu Glu
    850                 855                 860
Phe Arg Leu Arg Ala Thr Ala Glu Arg Val Lys Ala Leu Glu Ser Ala
865                 870                 875                 880
Leu Lys Glu Ala Lys Glu Asn Ala Ser Arg Asp Arg Lys Arg Tyr Gln
                885                 890                 895
Gln Glu Val Asp Arg Ile Lys Glu Ala Val Arg Ser Lys Asn Met Ala
            900                 905                 910
Arg Arg Gly His Ser Ala Gln Ile Ala Lys Pro Ile Arg Pro Gly Gln
        915                 920                 925
His Pro Ala Ala Ser Pro Thr His Pro Gly Thr Val Arg Gly Gly Gly
    930                 935                 940
Ser Phe Val Gln Asn Asn Gln Pro Val Gly Leu Arg Gly Gly Gly Gly
945                 950                 955                 960
Lys Gln Ser

<210> SEQ ID NO 125
<211> LENGTH: 45
<212> TYPE: PRT
<213> ORGANISM: Mus musculus

<400> SEQUENCE: 125

Val Cys Val Asn Val Glu Leu Thr Ala Glu Gln Trp Lys Lys Lys Tyr
1               5                   10                  15
Glu Lys Glu Lys Glu Lys Asn Lys Thr Leu Arg Asn Thr Ile Gln Trp
            20                  25                  30
Leu Glu Asn Glu Leu Asn Arg Trp Arg Asn Arg Glu Thr
        35                  40                  45

<210> SEQ ID NO 126
<211> LENGTH: 306
<212> TYPE: DNA
<213> ORGANISM: Mus musculus

<400> SEQUENCE: 126
atgttgagtc gactgcagga gctccgcaag gaggaggaaa ccctgctgcg tctaaaggcg      60
gctctacacg accaactgaa ccgcctcaag gttgaagaat tagcccttca atccatgata     120
aattctcgag gaaggaccga gacactgtct tctcagcctg cacctgaaca gttatgtgat     180
atgtccctac atgtagacaa cgaagtgaca ataaatcaga ctacactgaa gctgagcaca     240
aggagcccta tggaagaaga ggaggaggaa gaggaggagg agaggagga ggaagaatct     300 gattcg                                                                306

<210> SEQ ID NO 127
<211> LENGTH: 260
```

```
<212> TYPE: DNA
<213> ORGANISM: Mus musculus

<400> SEQUENCE: 127
gtagaaggca gcgccctaag gaagtggaag gggatgttga gtcgactgca ggagctccgc        60
aaggaggagg aaaccctgct gcgtctaaag gcggctctac acgaccaact gaaccgcctc       120
aaggttgaag aattagccct tcaatccgtg ataaattctc gaggaaggac cgagacactg       180
tcttctcagc ctgcacctga acagttatgt gatatgtccc tacatgtaga ccacgaagtg       240
acaataaatc agacgactga                                                   260

<210> SEQ ID NO 128
<211> LENGTH: 252
<212> TYPE: DNA
<213> ORGANISM: Mus musculus

<400> SEQUENCE: 128
agcgccctaa ggaagtggaa gggatgttg agtcgactgc aggagctccg caaggaggag         60
gaaacccagc tgcgtctaaa ggcggctcta cacgaccaac tgaaccgcct caaggttgaa       120
gaattagccc ttcaatccat gataaattct cgaggaagga ccgagacact gtcttctcag       180
cctgcacctg aacagttatg tgatatgtcc ctacatgtag accacgaagt gacaataaat       240
cagactacac tg                                                           252

<210> SEQ ID NO 129
<211> LENGTH: 250
<212> TYPE: DNA
<213> ORGANISM: Mus musculus

<400> SEQUENCE: 129
agcgccctaa ggaagtggaa gggatgttg agtcgactgc aggagctccg caaggaggag         60
gaaacccagc tgcgtctaaa ggcggctcta cacgaccaac tgaaccgcct caaggttgaa       120
gaattagccc ttcaatccat gataaattct cgaggaagga ccgagacact gtcttctcag       180
cctgcacctg aacagttatg tgatatgtcc ctacatgtag acaacgaagt gacaataaat       240
cagaaattgg                                                              250

<210> SEQ ID NO 130
<211> LENGTH: 249
<212> TYPE: DNA
<213> ORGANISM: Mus musculus

<400> SEQUENCE: 130
agcgccctaa ggaagtggaa gggatgttg agtcgactgc aggagctccg caaggaggag         60
gaaacccagc tgcatctaaa ggcggctcta cacgaccaac tgaaccgcct caaggttgaa       120
gaattagccc ttcaatccat gataaattct cgaggaagga ccgagacact gtcttctcag       180
cctgcacctg aacagttatg tgatatgtcc ctacatgtag acaacgaagt aacaataaat       240
cagaaattg                                                               249

<210> SEQ ID NO 131
<211> LENGTH: 249
<212> TYPE: DNA
<213> ORGANISM: Mus musculus

<400> SEQUENCE: 131
agcgccctaa ggaagtggaa ggggtgttg agtcgactgc aggagctccg caaggaggag         60
```

```
gaaaccctgc tgcgtctaaa ggcggctcta cacgaccaac tgaaccgcct caaggttgaa      120
gaattagccc ttcaatccat gataaattct cgaggaagga ccgagacact gtcttctcag      180
cctgcacctg aacagttatg tgatatgtcc ctacatgtag accacgaagt gacaataaat      240
cagagcaaa                                                              249

<210> SEQ ID NO 132
<211> LENGTH: 195
<212> TYPE: DNA
<213> ORGANISM: Mus musculus

<400> SEQUENCE: 132
agcgccctaa ggaagtggaa ggggatgttg agtcgactgc aggagctccg caaggaggag       60
gaaacccagc tgcgtctaaa ggcggctcta cacgaccaac tgaaccgcct caaggttgaa      120
gaattagccc ttcaatccat gataaattct cgaagaagga ccgagacact gtcttctcag      180
cctgcacctg aatca                                                       195

<210> SEQ ID NO 133
<211> LENGTH: 227
<212> TYPE: DNA
<213> ORGANISM: Mus musculus

<400> SEQUENCE: 133
gccctaagga agtggaaggg gatgttgagt cgactgcagg agctccgcaa ggaggaggaa       60
accctgctgc gtctaaaggc ggctctacac gaccaactga accgcctcaa ggttgaagaa      120
ttagcccttc aatccatgat aaattctcga ggaaggaccg agacactgtc ttctcagcct      180
gcacctgaac agttatgtga tatgtcccta catgtagaca cgaacg                     227

<210> SEQ ID NO 134
<211> LENGTH: 289
<212> TYPE: DNA
<213> ORGANISM: Mus musculus

<400> SEQUENCE: 134
ccctaaggaa gtggaagggg atgttgagtc gactgcagga gctccgcaag gaggaggaaa       60
ccctgctgcg tcaaaaggcg gctctacacg accaactgaa ccgcctcaag gttgaagaat      120
taccccttca atccatgata aattctcgag gaaggaccga gacactgtct tctcagcctg      180
cacctgaaca gttatgtgat atgtccctac atgtagacaa cgaagtgaca ataaatcaga      240
ctacactgaa gctgagcaca aggagcccta tggaagaaaa ggaggagga                  289

<210> SEQ ID NO 135
<211> LENGTH: 248
<212> TYPE: DNA
<213> ORGANISM: Mus musculus

<400> SEQUENCE: 135
ccccaaggaa gtggaagggc atgttgagtc gactgcagga gctccgcaag gaggaggaaa       60
ccctgctgcg tctaaaggcg gctctacacg accagctgaa ccgcctcaag gttgaagaat      120
tagcccttca atccatgata aattctcgag gaaggaccga gacactgtct tctcagcctg      180
cacctgaaca gttatgtgat atgtccctac atgtagacaa cgaagtgaca ataaatcaga      240
ctacacgg                                                               248

<210> SEQ ID NO 136
<211> LENGTH: 248
```

```
<212> TYPE: DNA
<213> ORGANISM: Mus musculus

<400> SEQUENCE: 136
ccctaaggaa gtggaagggc atgttgagtc gactgcagga gctccgcaag gaggaggaaa      60
ccctgctgcg tttaaaggcg gctctacacg accaactgaa ccgcctcaag gttgaagaat     120
tagcccttca atccatgata aattcccgag gaaggaccga gacactgtct tttcagcctg     180
cacctgaaca gttatgtgat atgtccctac atgtagacaa cgaagtgaca ataaatcaga     240
ctacacgg                                                              248

<210> SEQ ID NO 137
<211> LENGTH: 185
<212> TYPE: DNA
<213> ORGANISM: Mus musculus

<400> SEQUENCE: 137
ccctaaggaa gtggaagggg atgttgagtc gactgcagga gctccgcaag gaggaggaaa      60
ccctgctgcg tctaaaggcg gctctacacg accaactgaa ccgcctcaag gttgaagaat     120
tagcccttca atccatgata aattctcgag gaaggaccga gacactgtct tctcagcctg     180
cacga                                                                 185

<210> SEQ ID NO 138
<211> LENGTH: 161
<212> TYPE: DNA
<213> ORGANISM: Mus musculus

<400> SEQUENCE: 138
ccctaaggaa gtggaagggg atgttgagtc gactgcgaga gctccgcaag gaggaggaaa      60
ccctgctgcg tctaaaggcg gctctacacg accaactgaa ccgcctcaag gttgaagaat     120
tagcccttca atccatgata aattctcgag gaaggaccga g                         161

<210> SEQ ID NO 139
<211> LENGTH: 155
<212> TYPE: DNA
<213> ORGANISM: Mus musculus

<400> SEQUENCE: 139
ccctaaggaa gtggaagggg atgttgagtc gactgcaggg gctccgcaag gaggaggaaa      60
ccctgctgcg tctaaaggcg gctctacacg accaactgaa ccgcctcaag gttgaagaat     120
tagcccttca atccatgata aattctcgag gaaag                                155

<210> SEQ ID NO 140
<211> LENGTH: 261
<212> TYPE: DNA
<213> ORGANISM: Mus musculus

<400> SEQUENCE: 140
cctaaggaag tggaagggga tgttgagtcg actgcaggag ctccgcaagg aggaggaaac      60
cctgctgcgt ctaaaggcgg ctctacacga ccaactgaac cgcctcaagg ttgaagaatt     120
agcccttcaa tccatgataa attctcgagg aaggaccgag acactgtctt ctcagcctgc     180
acctgaacag ttatgtgata tgtacctaca tgtagacaac gaagtgacaa taaatcagac     240
tacactgaag ctgagcacaa a                                               261

<210> SEQ ID NO 141
```

<211> LENGTH: 249
<212> TYPE: DNA
<213> ORGANISM: Mus musculus

<400> SEQUENCE: 141
cctaaggaag tggaagggga tgttgagtcg actgcaggag ctccgcaagg aggaggaaac      60
cctgctgcgt ctaaaggcgg ctctacacga ccaactgaac cgcctcaagg ttgaagaatt     120
agcccttcaa tccatgataa attctcgagg aaggaccgag acactgtctt ctcagcctgc     180
acctgaacag ttatgtgata tgtccctaca tgtagacaac gaagtgacaa taaatcagac     240
tagcactaa                                                             249

<210> SEQ ID NO 142
<211> LENGTH: 285
<212> TYPE: DNA
<213> ORGANISM: Mus musculus

<400> SEQUENCE: 142
ctaaggaagt ggaaggggat gttgagtcga cagcaggagc ccgcaagga ggaggaaacc      60 ctgctgcgtc taaggcggc tctacgcgac caactgaacc gcctcaaggt tgaagaatta     120
gcccttcaat ccatgataaa ttctcgagga aggaccgaga cactgtcttc tcagcctgca     180
cctgaacagt tatgtgatat gtccctacat gtagacaacg aagtgacaat aaaccagact     240
acactgaagc tgagcacaag gagccctatg aagaagagg aggta                     285

<210> SEQ ID NO 143
<211> LENGTH: 285
<212> TYPE: DNA
<213> ORGANISM: Mus musculus

<400> SEQUENCE: 143
ctaaggaagt ggaaggggat gttgagtcga ctgcaggaac tccgcaagga ggaggaaacc      60
ctgctgcgtc taaggcggc tctacacgac caactgaacc gcctcaaggt tgaagaatta     120
gcccttcaat ccatgataaa ttctcgagga aggaccgaga cactgtcttc tcagcctgca     180
cctgaacagt tatgtgatat gtccctacat gtagacaacg aagtgacaat aaatcagact     240
acactgaagc tgagcacaag gagccctatg aagaagaag gaagg                      285

<210> SEQ ID NO 144
<211> LENGTH: 248
<212> TYPE: DNA
<213> ORGANISM: Mus musculus

<400> SEQUENCE: 144
ctaaggaagt ggaagggcat gttgagtcga ctgcaggagc tccgcaagga ggaggaaacc      60
ctgctgcgtc taaggcggc tctacacgac caactgaacc gcctcaaggt tgaagaatta     120
gcccttcaat ccatgataaa ttctcgagga aggaccgaga cactgtcttc tcagcctgca     180
cctgaacagt tatgtgatat gtccctacat gtagacaacg aagtgacaat aaatcagacg     240
acactgaa                                                              248

<210> SEQ ID NO 145
<211> LENGTH: 248
<212> TYPE: DNA
<213> ORGANISM: Mus musculus

<400> SEQUENCE: 145
ctaaggaagt ggaagggcat gttgagtcga ctgcaggagc tccgcaagga ggaggaaacc      60
ctgctgcgtc taagggcggc tctacacgac caactgaacc gcctcaaggt tgaagaatta    120
gcccttcaat ccatgataaa ttctcgagga aggaccgaga caccgtcttc tcagcctgca    180
cctgaacagt tatgtgatat gtccctacat gtagacaacg aagtgacaat aaatcagacg    240
acactgaa                                                              248

<210> SEQ ID NO 146
<211> LENGTH: 245
<212> TYPE: DNA
<213> ORGANISM: Mus musculus

<400> SEQUENCE: 146
ctaaggaagt ggaagggat gttgagtcga ctgcaggagc tccgcaagga ggaggaaacc     60
ctgctgcgtc taaggcggc tctacacgac caactgaacc gcctcaaggt tgaagaatta    120
gcccttcaat ccatgataaa ttctcgagga aggaccgaga cactgtcttc tcagcctgca    180
cctgaacagt tatgtgatat gtccctacat gtagacaacg aagtgacaat aaatcagaca    240
acaag                                                                 245

<210> SEQ ID NO 147
<211> LENGTH: 246
<212> TYPE: DNA
<213> ORGANISM: Mus musculus

<400> SEQUENCE: 147
ctaaggaagt ggaagggcat gttgagtcga ctgcaggagc tccgcaagga ggaggaaacc    60
ctgctgcgtc taaggcggc tctacacgac caactgaacc gcctcaaggt tgaagaatta    120
gcccttcaat ccatgataaa ttctcgagga aggaccgaga cactgtcttc tcagcctgca    180
cctgaacagt tatgtgatat gtccctacat gtagacaacg aagtgacaat aaatcagact    240
acacga                                                                246

<210> SEQ ID NO 148
<211> LENGTH: 246
<212> TYPE: DNA
<213> ORGANISM: Mus musculus

<400> SEQUENCE: 148
ctaaggaagt ggaagggat gctgagtcga ctgcaggagc tccgcaagga ggaggaaacc     60
ctgctgcgtc taaggcggc tctacacgac caactgaacc gcctcaaggt tgaagaatta    120
gcccttcaat ccatgataaa ttctcgagga aggaccgaga cactgtcttc tcagcctgca    180
cctgaacagt tatgtgatat gtccctacat gtagacaaca aagtgacaat aaatcagacg    240
acaccg                                                                246

<210> SEQ ID NO 149
<211> LENGTH: 246
<212> TYPE: DNA
<213> ORGANISM: Mus musculus

<400> SEQUENCE: 149
ctaaggaagt ggaagggcat gttgagtcga ctgcaggagc tccgcaagga ggaggaaacc    60
ctgctgcgtc taaatgcggc tctacacgac caactgaacc gcctcaaggt tgaagaatta    120
gcccttcaat ccatgataaa ttctcgagga aggaccgaga cactgtcttc tcagcctgca    180
cctgaacagt tatgtgatat gtccctacat gtagacaacg aagtgacaat aaatcagacg    240

-continued acactg 246

<210> SEQ ID NO 150
<211> LENGTH: 246
<212> TYPE: DNA
<213> ORGANISM: Mus musculus

<400> SEQUENCE: 150
ctaaggaagt ggaaggggat gttgagtcga ctgcaggagc tccgcaatga ggaggaaacc     60
ctgctgcgtc taaaggcggc tctacacgac caactgaacc gcctcaaggt tgaagaatta    120
gcccttcaat ccatgataaa ttctcgagga aggaccgaga cactgtcttc tcagcctgca    180
cctgaacagt tatgtgatat gtccctacat gtagacaacg aagtgacaat aaatcagact    240
acactg    246

<210> SEQ ID NO 151
<211> LENGTH: 246
<212> TYPE: DNA
<213> ORGANISM: Mus musculus

<400> SEQUENCE: 151
ctaaggaagt ggaaggggat gttgagtcaa ctgcaggagc tccgcaagga ggaggaaacc     60
ctgctgcgtc taaaggcggc tctacacgac caactgaacc gcctcaaggt tgaagaatta    120
gcccttcaat ccatgataaa ttctcgagga aggaccgaga cactgtcttc tcagcctgta    180
cctgaacagt tatgtgatat gtccctacat gtagacaacg aagtgacaat aaatcagact    240
acactg    246

<210> SEQ ID NO 152
<211> LENGTH: 246
<212> TYPE: DNA
<213> ORGANISM: Mus musculus

<400> SEQUENCE: 152
ctaaggaagt ggaaggggt gttgagtcga ctgcaggagc tccgcaagga ggaggaaacc     60
ctgctgcgtc taaaggcggc tctacacgac caactgaacc gcctcaaggt tgaagaatta    120
gcccttcaat ccatgataaa ttctcgagga aggaccgaga cactgtcttc tcagcctgca    180
cctgaacagt tatgtgatat gtccctacat gtagacagcg aagtgacaat aaatcagact    240
cacaaa    246

<210> SEQ ID NO 153
<211> LENGTH: 246
<212> TYPE: DNA
<213> ORGANISM: Mus musculus

<400> SEQUENCE: 153
ctaaggaagt ggaaggggat gttgagtcga ctgcaggagc tccgcaagga ggaggaaacc     60
ctgctgcgtc taaaggcggc tctacacgac caactgaacc gcctcaaggt tgaagaatta    120
gcccttcaat ccatgataaa ttctcgagga aggaccgaga cactgtcttc tcagcctgca    180
cctgaacagt tatgtgatat gtccctacat gtagacaacg aagtgacaat aaatcagact    240
cacaaa    246

<210> SEQ ID NO 154
<211> LENGTH: 189
<212> TYPE: DNA
<213> ORGANISM: Mus musculus

<400> SEQUENCE: 154

```
ctaaggaagt ggaaggggat gttgagtcga ctgcaggagc tccgcaagga ggaggaaacc      60
ctgctgcgtc taaaggcggc tctacacgac caactgaacc gcctcaaggt tgaagaatta    120
gcccttcaat ccatgataaa ttctcgagga aggaccgaga cactgtcttc tcagcctgca    180
cctgaatca                                                            189
```

<210> SEQ ID NO 155
<211> LENGTH: 189
<212> TYPE: DNA
<213> ORGANISM: Mus musculus

<400> SEQUENCE: 155

```
ctaaggaagt ggaaggggat gttgagtcga ctgcaggagc tccgcaagga ggaggaaacc      60
ctgctgcgtc taaatgcggc tctacacgac caactgaacc gcctcaaggt tgaagaatta    120
gcccttcaat ccatgataaa ttctcgagga aggaccgaga cactgtcttc tcagcctgca    180
cctgaatca                                                            189
```

<210> SEQ ID NO 156
<211> LENGTH: 180
<212> TYPE: DNA
<213> ORGANISM: Mus musculus

<400> SEQUENCE: 156

```
caaaggaagt ggaaggggat gttgagccga ctgcaggagc tccgcaagga ggaggaaacc      60
ctgctgcgtc taaaggcggc tctacacgac caactgaacc gcctcaaggt tgaagaatta    120
gcccttcaat ccatgataaa ttctcgagga aggaccgaga cactgtcttc tcagcctgca    180
```

<210> SEQ ID NO 157
<211> LENGTH: 245
<212> TYPE: DNA
<213> ORGANISM: Mus musculus

<400> SEQUENCE: 157

```
taagggagtg aaggggatg ttgagtcgac tgcaggagct ccgcaaggag gaggaaaccc      60
tgctgcgtct aaaggcggct ctacacgacc aactgaaccg cctcaaggtt gaagaattag    120
cccttcaatc catgataaat tctcgaggaa ggaccgagac actgtcttct cagcctgcac    180
ctgaacagtt atgtgatatg tccctacatg tagacaacga agtgacaata aatcagacac    240
actcg                                                                245
```

<210> SEQ ID NO 158
<211> LENGTH: 147
<212> TYPE: DNA
<213> ORGANISM: Mus musculus

<400> SEQUENCE: 158

```
gtttcttagt aaatgaaggc tggagccagt tagccgccat gcactgtgtt atgttgcctg      60
acctgctggg gctggagaga ttcaggcctc ctctcctgga gatgctagct cgaagatggc    120
aggaccgatg cttggaggtg agagagg                                        147
```

<210> SEQ ID NO 159
<211> LENGTH: 152
<212> TYPE: DNA
<213> ORGANISM: Mus musculus

<400> SEQUENCE: 159

```
taaggaagtg aaggggatg ctgagtcgac tgcaggagct ccgcaaggag gaggaaaccc    60
tgctgcgtct aaaggcggct ctacacgacc aactgaaccg cctcaaggtt gaagaattag   120
cccttcaatc catgataaat tctcgaggaa gg                                 152
```

<210> SEQ ID NO 160
<211> LENGTH: 243
<212> TYPE: DNA
<213> ORGANISM: Mus musculus

<400> SEQUENCE: 160

```
aggaagtgga aggggatgtt gagtcgactg caggagctcc gcaaggagga ggaaaccctg    60
ctgcgtctaa aggcggctct acacgaccaa ctgaaccgcc tcaaggttga agaattagcc   120
cttcaatcca tgataaattc tcgaggaagg accgagacac tgtcttctca gcctgcacct   180
gaacagttat gtgatatgtc cctacatgta gacaacgaag tgacaataaa tcagactaca   240
ctg                                                                 243
```

<210> SEQ ID NO 161
<211> LENGTH: 243
<212> TYPE: DNA
<213> ORGANISM: Mus musculus

<400> SEQUENCE: 161

```
aggaagtgga aggggatgtt gagtcgactg caggagctcc gcaaggagga agaaaccctg    60
ctgcgtctaa aggcggctct acacgaccaa ctgaaccgcc tcaaggttga agaattagcc   120
cttcaatcca tgataaattc tcgaggaagg accgagacac tgtcttctca gcctgcacct   180
gaacagttat gtgatatgtc cctacatgta gaccacgaag tgacaataaa tcagactaca   240
ctg                                                                 243
```

<210> SEQ ID NO 162
<211> LENGTH: 243
<212> TYPE: DNA
<213> ORGANISM: Mus musculus

<400> SEQUENCE: 162

```
aggaagtgga aggggatgtt gagtcgactg caggagctcc gcaaggagga ggaaaccctg    60
ctgcgtctaa aggcggctct acacgaccaa ctgaaccgcc tcaaggttga agaattagcc   120
cttcaatcca tgataaattc tcgaggaagg accgagacac tgtcttctca gcctgcacct   180
gaacagttat gtgatatgtc cctacatgta gacaacgaag tgacaataaa ccagacgaca   240
ccg                                                                 243
```

<210> SEQ ID NO 163
<211> LENGTH: 243
<212> TYPE: DNA
<213> ORGANISM: Mus musculus

<400> SEQUENCE: 163

```
aggaagtgga aggggatgtt gagtcaactg caggagctcc gcaaggagga ggaaaccctg    60
ctgcgtctaa aggctgctct acacgaccaa ctgaaccgcc tcaaggttga agaattagcc   120
cttcaatcca tgataaattc tcgaggaagg accgagacac tgtcttctca gcctgcacct   180
gaacagttat gtgatatgtc cctacatgta gacaacgaag tgacaataaa tcagacgaca   240
ccg                                                                 243
```

<210> SEQ ID NO 164
<211> LENGTH: 243
<212> TYPE: DNA
<213> ORGANISM: Mus musculus

<400> SEQUENCE: 164
aggaagtgga agggatgtt gagtcgactg caggagctcc gcatggagga ggaaaccctg    60
ctgcgtctaa aggcggctct acacgaccaa ctgaacctcc tcaaggttga agaattagcc   120
cttcaatcca tgataaattc tcgaggaagg accgagacac tgtcttctca gcctgcacct   180
gaacagttat gtgatatgtc cctacatgta gacaacgaag tgacaataaa tctgacgaca   240
ccg                                                                 243

<210> SEQ ID NO 165
<211> LENGTH: 243
<212> TYPE: DNA
<213> ORGANISM: Mus musculus

<400> SEQUENCE: 165
aggaagtgga agggatgtt gagtcgactg caggagctcc gcaaggagga ggaaaccctg    60
ctgcgtctaa atgcggctct acacgaccaa ctgaaccgcc tcaaggtcga agaattagcc   120
cttcaatcca tgataaattc tcgaggaagg accgagacac tgtcttctca gcctgcacct   180
gaacagttat gtgatatgtc cctacatgta gacaacgaag tgacaataaa tcagacgaca   240
ccg                                                                 243

<210> SEQ ID NO 166
<211> LENGTH: 243
<212> TYPE: DNA
<213> ORGANISM: Mus musculus

<400> SEQUENCE: 166
aggaagtgga agggatgtt gagtcgactg caggagctcc gcaaggagga ggaaaccctg    60
ctgcgtctaa aggcggctct acacgaccaa ctgaaccgcc tcaaggttga agaattagcc   120
cttcaatcca tgataaattc tcgaggaagg gccgagacac tgtcttctca gcctgcacct   180
gaacagttat gtgatatgtc cctacatgta gacaacgaag tgacaataaa tcagacgaca   240
ccg                                                                 243

<210> SEQ ID NO 167
<211> LENGTH: 245
<212> TYPE: DNA
<213> ORGANISM: Mus musculus

<400> SEQUENCE: 167
aggaagtgga agggatgtt gagtcgactg caggagctcc gcaaggagga ggaaaccctg    60
ctgcgtctaa aggcggctct acacgaccaa ctgaaccgcc tcaaggttga agaattagcc   120
cttcaatcca tgataaattc tcgaggaagg accgagacac tgtcttctca gcctacacct   180
gaacagttat gtgatatgtc cctacatgta gacaacgaag tgacaataaa tcagactaca   240
accaa                                                               245

<210> SEQ ID NO 168
<211> LENGTH: 243
<212> TYPE: DNA
<213> ORGANISM: Mus musculus

<400> SEQUENCE: 168

```
aggaagtgga aggggatgtt gagtcgactg caggagctcc gcaaggagga ggaaaccctg      60
ctgcgtctaa aggcggctct acacgaccaa ctgaaccgcc tcaaggttga agaattagcc     120
cttcaatcca tgataaattc tcgaggaagg accgagacac tgtcttctca gcctgcacct     180
gaacagttat gtgatatgtc cctacatgta gacaacgaag tgacaataaa tcagactaaa     240
ctg                                                                   243
```

<210> SEQ ID NO 169
<211> LENGTH: 245
<212> TYPE: DNA
<213> ORGANISM: Mus musculus

<400> SEQUENCE: 169

```
aggaagtgga aggggatgtt gagtcgactg caggagctcc gcaaggagga ggaaaccctg      60
ctgcgtctaa aggcggctct acacgaccaa ctgaaccgcc tcaaggttga agaattagcc     120
cttcaatcca tgataaattc tcgaggaagg accgagacac tgtcctctca gcctgcacct     180
gaacagttat gtgatatgtc cctacatgta gacaacgaag tgacaataaa tcagactaca     240
caagg                                                                 245
```

<210> SEQ ID NO 170
<211> LENGTH: 243
<212> TYPE: DNA
<213> ORGANISM: Mus musculus

<400> SEQUENCE: 170

```
aggaagtgga aggggatgtt gagtcgactg caggagctcc gcaaggagga ggaaaccctg      60
ctgcgtctaa aggcggctct acacgaccaa ctgaaccgcc tcaaggttga agaattagcc     120
cttcaatcca tgataaattc tcgaggaagg accgagacac tgtcttctca gcctgcacct     180
gaacagttat gtgatatgtc cctacatgta gacaacgaag tgacaataaa tcagactaga     240
cca                                                                   243
```

<210> SEQ ID NO 171
<211> LENGTH: 243
<212> TYPE: DNA
<213> ORGANISM: Mus musculus

<400> SEQUENCE: 171

```
aggaagtgga aggggatgtt gagtcgactg caggagctcc gcaaggagga ggaaaccctg      60
ctgcgtctaa aggcggctct acacgaccaa ctgaaccgcc tcaaggttga agaattagcc     120
cttcaatcca tgataaattc tcgaggaagg accgagacac tgtcttctca gcctgcacct     180
gaacagttat gtgatatgtc cctgcatgta gacaacgaag tgacaataaa tcagactaga     240
cca                                                                   243
```

<210> SEQ ID NO 172
<211> LENGTH: 243
<212> TYPE: DNA
<213> ORGANISM: Mus musculus

<400> SEQUENCE: 172

```
aggaagtggg aggggatgtt gagtcgactg caggagctcc gcaaggagga ggaaaccctg      60
ctgcgtctaa aggcggctct acacgaccaa ctgaaccgcc tcaaggttga agaattagcc     120
cttcaatcca tgataaattc tcgaggaagg accgagacac tgtcttctca gcctgcacct     180
```

```
gaacagttat gtgatatgtc cctacatgta gacaacgaag tgacaataaa tcagactaga    240
cca                                                                  243

<210> SEQ ID NO 173
<211> LENGTH: 243
<212> TYPE: DNA
<213> ORGANISM: Mus musculus

<400> SEQUENCE: 173
aggaagtgga aggggacgtt gagtcgactg caggacctcc gcaaggagga agaaaccctg    60
ctgcgtctaa aggcggctct acacgaccaa ctgaaccgcc tcaaggttga agaattagcc   120
cttcaatcca tgataaattc tcgaggaagg accgagacac tgtcttctca gcctgcacct   180
gaacagttat gtgatgtgtc cctacatgta gacaacgaag tgacaataaa tcagactaga   240
cca                                                                  243

<210> SEQ ID NO 174
<211> LENGTH: 149
<212> TYPE: DNA
<213> ORGANISM: Mus musculus

<400> SEQUENCE: 174
ggaagtggaa ggggatgttg agtcgactga aggagctccg caaggaggag aaaccctgc    60 tgcgtctaaa ggcggctcta cacgaccaac tgaaccgcct caaggttgaa gaattagccc   120
ttcaatccat gataaattct agaggaagg                                     149

<210> SEQ ID NO 175
<211> LENGTH: 237
<212> TYPE: DNA
<213> ORGANISM: Mus musculus

<400> SEQUENCE: 175
tggaagggga tgttgagtcg actgcaggag ctccgcaagg aggaggaaac cctgctgcgt    60
ctaaaggcgg ctctacacga ccaactgaac cgcctcaagg ttgaagaatt agcccttcaa   120
tccatgataa attctcgagg aaggaccgag acactgtctt ctcagcctgc acctgaacag   180
ttatgtgata tgtccctaca gtagacaac gaagtgacaa taaatcagac tacactg       237

<210> SEQ ID NO 176
<211> LENGTH: 237
<212> TYPE: DNA
<213> ORGANISM: Mus musculus

<400> SEQUENCE: 176
tggaagggga tgttgagtcg actgcaggag ctccgcaagg aagaggaagc cctgctgcgt    60
ctaaaggcgg ctctacacga ccaactgaac cgcctcaagg ttgaagaatt agcccttcaa   120
tccatgataa attctcgagg aaggaccgag acactgtctt ctcagccagc acctgaacag   180
ttatgtgata tgtccctaca gtagacaac gaagtgacaa taaatcagac tacactg       237

<210> SEQ ID NO 177
<211> LENGTH: 143
<212> TYPE: DNA
<213> ORGANISM: Mus musculus

<400> SEQUENCE: 177
ggaaggggat gttgagtcga ctgcaggagc tccgcaagga ggaggaaacc ctgctgcgtc    60
```

```
taaaggcggc tctacacgac caactgaacc gcctcaaggt taaagaatta gcccttcaat    120
ccatgataaa ttctcgggga agg                                            143

<210> SEQ ID NO 178
<211> LENGTH: 270
<212> TYPE: DNA
<213> ORGANISM: Mus musculus

<400> SEQUENCE: 178
gggatgttga gtcgactgca ggagctccgc aaggaggagg aaaccctgct gcgtctaaag     60
gcggctctac acgaccaact gaaccgcctc aaggttgaag aattagccct tcaatccatg    120
ataaattctc gaggaaggac cgagacactg tcttctcagc ctgcacctga acagttatgt    180
gatatgtccc tacatgtaga caacgaagtg acaataaatc agactacact gaagctgagc    240
acaaggagcc ctatggaaga agaggagggg                                     270

<210> SEQ ID NO 179
<211> LENGTH: 231
<212> TYPE: DNA
<213> ORGANISM: Mus musculus

<400> SEQUENCE: 179
gggatgttga gtcgactgca ggagctccgc aaggaggagg aaaccctgct gcgtctaaag     60
gcggctctac acgaccaact gaaccgcctc aaggttgaag aattagccct tcaatccatg    120
ataaattctc gaggaaggac cgaggcactg tcttctcagc ctgcacctga acagttatgt    180
gatacgtccc tacatgtaga caacgaagtg acaataaatc agactacact a              231

<210> SEQ ID NO 180
<211> LENGTH: 231
<212> TYPE: DNA
<213> ORGANISM: Mus musculus

<400> SEQUENCE: 180
gggatgttga gtcgactgca ggagctccgc aaggaggagg aaaccctgct gcgtctaaag     60
gcggctctac acgaccaact gaaccgcctc aaggttgaag aattagccct tcaatccatg    120
ataaattctc gaggaaggac cgagacactg tcttctcagc ctgcacctga acagttatgt    180
gatatgtccc tacatgtaga caacgaagtg acaataaatc agacacactc g              231

<210> SEQ ID NO 181
<211> LENGTH: 231
<212> TYPE: DNA
<213> ORGANISM: Mus musculus

<400> SEQUENCE: 181
gggatgttga gtcgactgca ggagctccgc aaggaggagg aaaccctgct gcgtctaaag     60
gcggctctac acgaccaact gaaccgcctc aaggttgaag aattagccct tcaatccatg    120
ataaattctc gaggaaggac cgagacactg tcttctcagc ctgcacctga acagttatgt    180
gatatgtccc tacatgtaga caacgaagtg gcaataaatc agactacgcc g              231

<210> SEQ ID NO 182
<211> LENGTH: 231
<212> TYPE: DNA
<213> ORGANISM: Mus musculus

<400> SEQUENCE: 182
gggatgttga gtcgactgca ggagctccgc aaggaggagg aaaccctgct gcgtctaaag     60
```
gcggctctac acgaccaact gaaccgcctc aaggttgaag aattagccct tcaatccatg    120
ataaattctc gaggaaggac cgagacactg tcttctcagc ctgcacctga acagttatgt    180
gatatgtccc tacatgtaga caacgaagtg acaataaatc agacgacacc g            231

<210> SEQ ID NO 183
<211> LENGTH: 229
<212> TYPE: DNA
<213> ORGANISM: Mus musculus

<400> SEQUENCE: 183
gggatgttga gtcgactgca ggagctccgc aaggaggagg aaaccctgct gcgtctaaag    60
gcggctctac acgaccaact gaaccgcctc aaggttgaag aattagccct tcaatccatg    120
ataaattctc gagaaaggac cgagacactg tcttctcggc ctgctcctga acagttatgt    180
gatatgtccc tacatgtaga caacgaagtg acaataaatc agacaactc                229

<210> SEQ ID NO 184
<211> LENGTH: 228
<212> TYPE: DNA
<213> ORGANISM: Mus musculus

<400> SEQUENCE: 184
gggatgttga gtcgactgca ggagctccgc aaggaggagg aaaccctgct gcgtctaaag    60
gcggctctac acgaccaact gaaccgcctc aaggttgaag aattagccct tcaatccatg    120
ataaattctc gaggaaggac cgagacactg tcttctcagc ctgcacctga acagttatgt    180
gatatgtccc tacatgtaga caacgaagtg acaatagatc agggagct                 228

<210> SEQ ID NO 185
<211> LENGTH: 224
<212> TYPE: DNA
<213> ORGANISM: Mus musculus

<400> SEQUENCE: 185
gggatgttga gtcgactgca ggagctccgc aaggaggagg aaaccctgct gcgtctaaag    60
gcggctctac acaaccaatt gaaccgcctc aaggttgaag aattagccct tcaatccatg    120
ataaattctc gaggaaggac cgagacactg tcttctcagc ctgcacctga acagttatgt    180
gatatgtccc tacatgtaga caacgaagtg acaataaatc agaa                     224

<210> SEQ ID NO 186
<211> LENGTH: 209
<212> TYPE: DNA
<213> ORGANISM: Mus musculus

<400> SEQUENCE: 186
gggatgttga gtcgactgca ggagctccgc aaggaggagg aaaccctgct gcgtctaaag    60
gcggctctac acgaccaact gaaccgcctc aaggttgaag aattagccct tcaatccatg    120
ataaattctc gaggaaggac cgagacactg tcttctcagc ctgcacctga acagttatgt    180
gatatgtccc tacatgtaga ccacgaacg                                      209

<210> SEQ ID NO 187
<211> LENGTH: 208
<212> TYPE: DNA
<213> ORGANISM: Mus musculus

<400> SEQUENCE: 187

```
gggatgttga gtcgactaca ggagctccgc aaggaggagg aaaccctgct gcgtctaaag    60
gcggctctac acgaccaact gaaccgcctc aaggttgaag aattagccct tcaatccatg   120
ataaattctc gaggaaggac cgagacactg tcttctcagc ctgcacctga acagttatgt   180
gatatgtccc tacatgtaga catcgaaa                                      208

<210> SEQ ID NO 188
<211> LENGTH: 203
<212> TYPE: DNA
<213> ORGANISM: Mus musculus

<400> SEQUENCE: 188
gggatgttga gtcgactgca ggagctccgc aaggaggagg aaaccctgct gcgtctaaag    60
gcggctctac acgaccaact gaaccgcctc aaggttgaag aattagccct tcaatccatg   120
ataaattctc gaggaaggac cgagacactg tcttctcagc ctgcacctga acagttatgt   180
gatacgtccc tacatgtaac aac                                           203

<210> SEQ ID NO 189
<211> LENGTH: 138
<212> TYPE: DNA
<213> ORGANISM: Mus musculus

<400> SEQUENCE: 189
gggatgttga gtcgactgca ggagctccgc aaggaggagg aaaccctgct gcgtctaaag    60
gcggctctac acgaccaact gaaccgcctc aaggttgaag aattagccct tcaatccatg   120
ataaattcta ggggaagg                                                 138

<210> SEQ ID NO 190
<211> LENGTH: 138
<212> TYPE: DNA
<213> ORGANISM: Mus musculus

<400> SEQUENCE: 190
gggatgttga gtcgactgca ggagctccgc aaggaggagg aaaccctgct gcgtctaaag    60
gcggctctac acgaccaact gaaccgcctc aaggttgaag aattagccct tcaatccatg   120
ataaattctc gaggaagg                                                 138

<210> SEQ ID NO 191
<211> LENGTH: 139
<212> TYPE: DNA
<213> ORGANISM: Mus musculus

<400> SEQUENCE: 191
caggatgttg agtcaactgc aggagctccg caaggaggag gaaaccctgc tgcgtctaaa    60
ggcgactcta cacgaccaac tgaaccgcct caaggttgaa gaattagccc ttcaatccat   120
gataaattct cgaggaaag                                                139

<210> SEQ ID NO 192
<211> LENGTH: 228
<212> TYPE: DNA
<213> ORGANISM: Mus musculus

<400> SEQUENCE: 192
gttgagtcga ctgcaggagc tccgcaagga ggaggaaacc ctgctgcgtc taaaggcggc    60
tctacacgac caactgaacc gcctcaaggt tgaagaatta gcccttcaat ccatgataaa   120
ttctcgagga aggaccgaga cactgtcttc tcagcctgca cctgaacagt tatgtgatat   180
```
gtccctacat gtagacaacg aagtgacaat aaatcagacg acactgaa          228

<210> SEQ ID NO 193
<211> LENGTH: 208
<212> TYPE: DNA
<213> ORGANISM: Mus musculus

<400> SEQUENCE: 193
gttgagtcga ctgcaggagc tccgcaagga ggaggaaacc ctgctgcgtc taaaggcggc    60
tctacacgac caactgaacc gcctcaaggt tgaagaatta gcccttcaat ccatgataaa   120
ttctcgagga aggaccgaga cactgtcttc tcagcctgca cctgaacagt tatgtgatat   180
gtccctacat gtagacaacg aagcgaca                                      208

<210> SEQ ID NO 194
<211> LENGTH: 208
<212> TYPE: DNA
<213> ORGANISM: Mus musculus

<400> SEQUENCE: 194
gttgagtcga ctgcaggagc tccgcaagga ggaggaaacc ctgctgcgtc taaaggcggc    60
tctacacgac caactgaatc gcctcaaggt tgaagaatta gcccttcaat ccatgataaa   120
ttctcgagga aggaccgaga cactgtcttc tcagcctgca cctgaacagt tatgtgatat   180
gtccctacat gtagacaacg aagcgaca                                      208

<210> SEQ ID NO 195
<211> LENGTH: 200
<212> TYPE: DNA
<213> ORGANISM: Mus musculus

<400> SEQUENCE: 195
cgactgcagg agctccgcaa ggaggaggaa accctgctgc gtctaaaggc ggctctacac    60
gaccaactga accgcctcaa ggttgaagaa ttagcccttc aatccatgat aaattctcga   120
ggaaggaccg agacactgtc ttctcagcct gcacctgaac agttatgtga tatgtcccta   180
catgtagaca acgaagtgac                                               200

<210> SEQ ID NO 196
<211> LENGTH: 183
<212> TYPE: DNA
<213> ORGANISM: Mus musculus

<400> SEQUENCE: 196
cgactgcggg agctccgcaa ggaggagaaa accctgctgc gtctaaaggc ggctctacac    60
gaccaactga accgcctcaa ggttgaagaa ttagcccttc aatccatgat aaattctcga   120
ggaaggaccg agacactgtc ttctcagcct gcacctgaac aatgtcccta catgttgaca   180
acg                                                                 183

<210> SEQ ID NO 197
<211> LENGTH: 183
<212> TYPE: DNA
<213> ORGANISM: Mus musculus

<400> SEQUENCE: 197
cgactgcagg agctccgcaa ggaggaggaa accctgctgc gtctaaaggc ggctctacac    60
gaccaactga accgcctcaa ggttgaagaa ttagcccttc aatccatgat aaattccga    120

```
ggaaggaccg agacactgtc ttctcagcct gcacctggac aatgtccta catgttgaca    180 acg                                                                 183

<210> SEQ ID NO 198
<211> LENGTH: 183
<212> TYPE: DNA
<213> ORGANISM: Mus musculus

<400> SEQUENCE: 198
cgactgcagg agctccgcaa ggaggaggaa acccagctgc gtctaaaggc ggctctacac    60
gaccaactga accgcctcaa ggttgaagaa ttagcccttc aatccatgat aaattctcga   120
ggaaggaccg agacactgtc ttctcagcct gcacctgaac aatgtccta catgttgaca   180 acg                                                                 183

<210> SEQ ID NO 199
<211> LENGTH: 120
<212> TYPE: DNA
<213> ORGANISM: Mus musculus

<400> SEQUENCE: 199
cgactgcagg agctccgcaa ggaggaggaa accctgctgc gtctaaaggc ggctctacac    60
gaccaactga accgcctcaa ggttgaagaa ttagcccttc aatccatgat aaattccagg   120

<210> SEQ ID NO 200
<211> LENGTH: 2868
<212> TYPE: DNA
<213> ORGANISM: Mus musculus

<400> SEQUENCE: 200
atggcggatc cagccgaatg cagcatcaaa gtgatgtgcc ggttccggcc cctcaacgaa    60
gcggagatcc tccgcgggga caaattcatc cccaaattca aggcgagga  acggtggtg   120 atcgggcaag ggaagccgta tgtctttgac cgagtgctgc cgcccaacac aacccaggag   180
caggtctaca atgcctgtgc aaagcagatt gtcaaagatg tccttgaggg ttataatgga   240
acaattttgg catatgggca gcttcatca ggaaaaactc ataccatgga ggggaagtta   300
catgatcctc agcttatggg tatcattcca aggattgcac atgatatttt tgatcacatc   360
tattccatgg acgagaacct ggagtttcat atcaaggttt cctattttga gatctacttg   420
gacaaaataa gggacttgct tgatgtgtcc aagaccaact tggcagttca tgaagacaaa   480
aacagagtcc cctatgtaaa ggggtgcacc gagaggtttt gtgtcaagcc ggaggaggtc   540
atggatgtga tcgatgaggg caaagcaaac cgacacgtgg ctgtgacaaa catgaacgaa   600
cacagctcta ggagtcacag tatcttcctg attaacatta gcaagagaa tgtggagact   660 gaaaaaaaac tcagcgggaa gctgtatttg gttgatttgg ctgggagtga aaaggtcagc   720
aaaaccggtg ccgagggagc tgttcttgat gaagctaaaa atatcaacaa gtctttgtct   780
gctcttggaa atgtgatttc tgccttggca gaagggacaa aaacacatgt accgtaccgg   840
gacagcaaga tgactcggat tctccaggac tctctgggtg ggaactgtag gaccaccatt   900
gtcatttgct gttctccttc agtcttcaat gaagccgaga ccaagtccac gctgatgttt   960
ggacagagag caaagaccat caagaataca gtctctgtga acttggaact aacagcagaa  1020
gagtggaaga agaaatatga aaagagaaa gagaagaaca aggccttgaa gagtgtcctc  1080
cagcatctgg agatggagct gaacaggtgg aggaacgggg aagctgtacc cgaggacgaa  1140
cagatcagcg ccaaggacca taagagccta gagccctgtg acaacacacc catcatagac  1200
```

```
aacatcacgc ctgttgtgga cggcatctct gccgagaagg agaagtatga cgaggagatc   1260
accagtttgt accgacagct cgatgataag gatgatgaaa ttaaccagca gagccagctg   1320
gctgaaaagc tgaagcaaca gatgttggat caggatgaac tcctggcttc acgagaagg   1380 gactatgaga agattcagga ggagctgaca cgcctccaga tcgaaaatga ggcagctaaa   1440
gacgaagtga agaagtcct ccaggccctg gaggagctgg ctgtcaatta cgaccagaag   1500
tcacaagaag tggaggacaa gaccagggcc aacgagcaac tgactgatga gctggcccag   1560
aaaacgacga cactgacaac cacccagcga gagctgagtc agctgcaaga gcttagtaac   1620
caccagaaaa agagggccac agagatcctg aacctgcttc tcaaggacct gggggagata   1680
ggcggaatta ttggcaccaa cgatgtgaag actctggcag atgtgaacgg ggtcattgag   1740
gaggagttca ccatggcacg cctgtacatt agcaagatga agtcggaggt caagtctctc   1800
gtgaaccgca gcaagcagct ggagagtgcc cagatggact ctaacaggaa gatgaacgcc   1860
agtgagcgcg agctggcagc gtgccagttg cttatctcac agcacgaagc caagatcaag   1920
tctctgacag actacatgca gaacatggaa cagaagaggc ggcagctgga agagtcccag   1980
gactccctca gcgaggaact ggccaagctc cgggcccagg aaaaaatgca cgaagtcagt   2040
ttccaagata aggaaaagga gcacctgacg aggctgcagg atgctgagga ggtgaagaaa   2100
gctctggagc agcagatgga gagccaccgg gaagcgcacc aaaagcagct gtccagactt   2160
cgcgatgaga ttgaggagaa gcagagaatc attgatgaga tccgggattt gaatcagaaa   2220
ctgcaactgg aacaggagag gctcagctct gattataaca agctgaaaat agaggaccag   2280
gagagagaag tgaaactgga gaagctccta ttgctcaatg acaaaaggga gcaagccagg   2340
gaggacctca agggactgga ggagactgtg tctatagaac tccagaccct tcataacctg   2400
cgcaaactct tcgtccagga tttgacaacc cgggtgaaaa agagtgtgga gctggacagc   2460
gacgatggag ggggcagcgc tgctcagaag cagaagatct ccttcctgga gaacaacctg   2520
gaacagctta ccaaggtgca caagcagctg gtccgggaca atgcagattt cgctgtgaa   2580 ctccccaagc tggagaagag gcttcgtgct accgcagaac gcgtcaaggc cttggagagt   2640
gcgctgaaag aggccaagga gaatgccatg agggaccgaa aacgctacca gcaggaagta   2700
gatcgcatca aggaggctgt gcgagccaag aacatggcca ggagggcaca ttcggctcag   2760
atcgccaagc ccatccgccc aggccattac ccagcatcat ctccgacagc tgtccatgcc   2820
gtccgaggag gaggaggtgg ctcttcaaac tctactcact accagaaa              2868
```

<210> SEQ ID NO 201
<211> LENGTH: 183
<212> TYPE: DNA
<213> ORGANISM: Mus musculus

<400> SEQUENCE: 201

```
ggcagcgctg ctcagaagca gaagatctcc ttcctggaga caacctggaa acagcttacc     60
aaggtgcaca agcagctggt ccgggacaat gcagatttgc gctgtgaact ccccaagctg    120
gagaagaggc ttcgtgctac cgcagaacgc gtcaaggcct tggagagtgc gctgaaagag    180
gcc                                                                  183
```

<210> SEQ ID NO 202
<211> LENGTH: 183
<212> TYPE: DNA
<213> ORGANISM: Mus musculus

```
<400> SEQUENCE: 202
ggcagcgctg ctcagaagca gaagatctcc ttcctggaga caacctggaa acagcttacc      60
aaggtgcaca agcagccggt ccgggacaat gcagatttgc gctgtgaact ccccaagctg     120
gagaagaggc ttcgtgctac cgcagaacgc gtcaaggcct tggagagtgc gctgaaagag     180
gcc                                                                    183

<210> SEQ ID NO 203
<211> LENGTH: 183
<212> TYPE: DNA
<213> ORGANISM: Mus musculus

<400> SEQUENCE: 203
ggcagcgctg ctcagaagca gaagatctcc ttcctggaga caacctggaa acagcttacc      60
aaggtgcaca agcagctggt ccgggacaat gcagatttgc gctgtgaact ccccaagctg     120
gagaagaggc ttcgtgctac cgcaaaacgc gtcaaggcct tggagagtgc gctgaaagat     180
gcc                                                                    183

<210> SEQ ID NO 204
<211> LENGTH: 192
<212> TYPE: DNA
<213> ORGANISM: Mus musculus

<400> SEQUENCE: 204
ggcagcgctg ctcagaagca gaagatctcc ttcctggaga caacctggaa acagcttacc      60
aaggtgcaca agcagctggt ccgggacaat gcagatttgc gctgtgaact ccccaagctg     120
gagaagaggc ttcgtgctac cgcaaaacgc gtcaaggcct tggtgagtgc gctgaaagag     180
gccaaggaga ga                                                          192

<210> SEQ ID NO 205
<211> LENGTH: 192
<212> TYPE: DNA
<213> ORGANISM: Mus musculus

<400> SEQUENCE: 205
ggcagcgctg ctcagaagca gaagatctcc ttcctggaga caacctggaa acagcttacc      60
aaggtgcaca agcagctggt ccgggacaat gcagatttgc gctgtgaact ccccaagctg     120
gagaagaggc ttcgtgctac cgcagaacgc gtcatggcct tggagagtgc gctgaaagag     180
gccaaggaga ga                                                          192

<210> SEQ ID NO 206
<211> LENGTH: 192
<212> TYPE: DNA
<213> ORGANISM: Mus musculus

<400> SEQUENCE: 206
ggcagcgctg ctcagaagca gaagatctcc ctcctggaga caacctggaa acagcttacc      60
aaggtgcaca agcagctggt ccgggacaat gcagatttgc gctgtgaact ccccaagctg     120
gagaagaggc ttcgtgctac cgcagaacgc gtcaaggcct tggagagtgc gctgaaagag     180
gccaaggaga ga                                                          192

<210> SEQ ID NO 207
<211> LENGTH: 192
<212> TYPE: DNA
<213> ORGANISM: Mus musculus
```

```
<400> SEQUENCE: 207
ggcagcgctg ctcagaagca gaagatctcc ttcctggaga accacctgga acagcttacc      60
aaggtgcaca agctgctggt ccgggacaat gcagatttgc gctgtgaact ccccaagctg     120
gagaagaggc ttcgtgctac cgcagaacgc gtcaaggcct tggagagtgc gctgaaagag     180
gccaaggaga ga                                                         192

<210> SEQ ID NO 208
<211> LENGTH: 162
<212> TYPE: DNA
<213> ORGANISM: Mus musculus

<400> SEQUENCE: 208
ctggaacagc ttaccaaggt gcacaagcag ctggtccggg acaatgcaga tttgcgctgt      60
gaactcccca gctggagaa gaggcttcgt gctaccgcag aacgcgtcaa ggccttggag     120
agtgcgctga agaggccaa ggagaatgcc atgagagaca ga                         162

<210> SEQ ID NO 209
<211> LENGTH: 162
<212> TYPE: DNA
<213> ORGANISM: Mus musculus

<400> SEQUENCE: 209
ctggaacagc ttaccagggt gcacaagcag ctggtccggg acaatgcaga tttgcgctat      60
gaactccaca gctggagaa gaggcttcgt gctaccgcag aacgcgtcaa ggccttggag     120
agtgcgctga agaggccaa ggagaatgcc atgagagaca ga                         162

<210> SEQ ID NO 210
<211> LENGTH: 162
<212> TYPE: DNA
<213> ORGANISM: Mus musculus

<400> SEQUENCE: 210
ctggaacagc ttaccaaggt gcacaagcag ctggtccggg acaatgcaga tttgcgctgt      60
gaactcccca gctggagaa gaggcttcgt gctaccgcaa aacgcgtcaa ggccttggag     120
agtgcgctga agaggccaa ggagaatgcc atgagagaca ga                         162

<210> SEQ ID NO 211
<211> LENGTH: 162
<212> TYPE: DNA
<213> ORGANISM: Mus musculus

<400> SEQUENCE: 211
ctggaacagc ttaccaaggt gcacaagcag ctggtccagg acaatgcaga tttgcgctgt      60
gaactcccca gctggagaa gaggcttcgt gctaccgcag aacgcgtcaa ggccttggag     120
agtgcgctga agaggccaa ggagaatgcc atgagagaca ga                         162

<210> SEQ ID NO 212
<211> LENGTH: 184
<212> TYPE: DNA
<213> ORGANISM: Mus musculus

<400> SEQUENCE: 212
ctccttcctg gataacaacc tggaacagct taccaaggtg cacaagcagc tggtccggga      60
caatgcagat ttgcgctgtg aactccccag gctggagaag atgcttcgtg ctaccgcaga     120
```

```
acgcgtcaag gccttggaga gtgcgctgaa agaggccaag gagaatgcca tgagtgacgc    180
gaaa                                                                 184

<210> SEQ ID NO 213
<211> LENGTH: 162
<212> TYPE: DNA
<213> ORGANISM: Mus musculus

<400> SEQUENCE: 213
ctggaacagc ttaccaaggt gcacaagcag ctggtccggg acaatgcaga tttgcgctgt    60
gaactcccca agctggagaa gaggcttcgt gctaccgcaa acgcgtcaa ggccttggag     120 agtgcgctga agaggccaa ggagaatgcc atgagagaca ga                       162

<210> SEQ ID NO 214
<211> LENGTH: 147
<212> TYPE: DNA
<213> ORGANISM: Mus musculus

<400> SEQUENCE: 214
gcaaagacca tcaagaatac agtctctgtg aacttggaac taacagcaga agagtggaag    60
aaagaatatg aaaagagaa agagaagaac aaggccttga agagtgtcct ccagcatctg    120
gagatggagc tgaacaggtg gagggag                                       147

<210> SEQ ID NO 215
<211> LENGTH: 153
<212> TYPE: DNA
<213> ORGANISM: Mus musculus

<400> SEQUENCE: 215
cagagagcaa agaccatcaa taatacagtc tctgtgaact tggaactaac agcagaagag    60
tggaaaaaga gatatgaaaa agagaaagag aagaacaagg ccttgaagag tgtcctccag   120
catctggaga tggagctgaa caggtggagg agg                                153

<210> SEQ ID NO 216
<211> LENGTH: 146
<212> TYPE: DNA
<213> ORGANISM: Mus musculus

<400> SEQUENCE: 216
cagagagcaa aggccatcaa gaatacagtc tctgtgaact tggaactaac agcagaagag    60
tggaagaaga aatatgaaaa agagaaagag aagaacaagg ccttgaagaa tgtcctccag   120
catctggaga tggagctgaa caggtg                                        146

<210> SEQ ID NO 217
<211> LENGTH: 210
<212> TYPE: DNA
<213> ORGANISM: Mus musculus

<400> SEQUENCE: 217
tgctgttccc cttcagtctt caatgaagcc gagaccaagt ccacgctgat gtttggacag    60
agagcaaaga ccatcaagaa tacagtctct gtgaacttgg aactaacagc agaagagtgg   120
aaaaagaaat atgaaaaaga gaaagagaag aacaaggcct tgaagagtgt cctccagcat   180
ctggagatgg agctgaacag gtggaggaat                                    210

<210> SEQ ID NO 218
<211> LENGTH: 3081
```

<212> TYPE: DNA
<213> ORGANISM: Mus musculus

<400> SEQUENCE: 218

```
atggcggaga ctaacaacga atgcagcatc aaggtgcttt gccgatttcg gccccctgaac      60
caggccgaga ttctgcgggg ggacaagttc atccccattt tccaagggga cgacagcgtc     120
attattgggg gaaagccata tgtctttgac cgcgtcttcc ccccaaacac cactcaggag     180
caggtttacc acgcctgtgc catgcagatc gtcaaagacg tccttgctgg ttacaatggc     240
acaatcttcg cttatggaca gacatcctca gggaaaacgc ataccatgga ggggaagctg     300
cacgaccctc agctgatggg catcattccc cggatcgctc gagacatctt caaccacatc     360
tactccatgg atgagaacct tgaattccac attaaggtat cttacttcga gatttacctg     420
gataagatcc gtgaccttttt ggatgtgacc aagacgaacc tgtccgtgca tgaggacaaa     480
aaccgggtgc cgtttgtcaa gggttgtacc gaacgctttg tgtccagccc agaggagatt     540
ctggatgtga tcgatgaggg gaagtccaac cgtcacgtag ctgtcaccaa catgaacgag     600
cacagttctc ggagccacag catcttcctc atcaacatca agcaggagaa cgtagagacc     660
gagcagaagc tcagcgggaa gctgtacctc gtggatctgg ccggaagcga aaggtcagc     720
aagacagggg cagagggagc cgttctggac gaggcaaaga atatcaacaa gtcgctgtcg     780
gccctgggga acgtgatctc tgcactggca gagggcacca aaagctacgt gccgtaccgc     840
gacacgaaaa tgacgaggat tctccaggac tctctgggag ggactgcag gactaccatg     900
ttcatctgct gctcgccgtc cagctacaat gacgcagaga ccaagtccac gctcatgttt     960
ggacagcggg cgaagaccat caagaacact gcctcagtga atctggagct gactgctgag    1020
cagtggaaga agaagtatga aggagaagaag gagaagacca aggcccagaa ggagacaatt    1080
gcgaacgtag aggctgagct tagccggtgg cgcaatggag agaatgtgcc tgagactgag    1140
cgcctggctg gagaggactc agctctggga gctgagctct gcgaggagac ccctgtgaat    1200
gacaactcat ccattgtggt acgcatcgca cctgaggaaa ggcagaaata tgaggaagag    1260
atccgccgtc tctacaagca gcttgatgac aaggatgatg agatcaacca gcagagccag    1320
ctcattgaga agctgaagca gcagatgctg gaccaggaag agctgctcgt gtccactcgg    1380
ggagacaacg agaaggtcca gcgggagctt agccacctgc agtccgagaa cgatgctgcg    1440
aaggacgagg tgaaggaagt gctgcaggcc ctagaggagc tggcggtcaa ctacgaccag    1500
aagtcccagg aggtggagga aagagccag cagaaccagc tgctggtgga cgagctgtcc    1560
cagaaagtgg ccaccatgct gtccctggag tccgagctac agcggctcca ggaggtcagt    1620
ggacaccagc gaaagcggat cgctgagtgt ctgaatgggc tgatgaggga cctgagtgag    1680
ttcagtgtca tcgtgggcaa cggcgagatt aagctgcccg tggagatcag tggggccatc    1740
gaggaggagt tcacggtggc ccggctctac atcagcaaga tcaagtcgga ggtgaagtcc    1800
gtggttaagc gatgtcggca gctggagaac ctccaggtgg agtgtcatcg caagatggag    1860
gtgaccggta gggagctgtc atcttgccaa ctgctcatct cacagcatga ggccaagatc    1920
cgttcactca cggagtacat gcagactgtg gagttgaaga acggcacct ggaagagtcc    1980
tacgactccc tgagcgatga gcttgccagg ctccaggcgc acgaaactgt acacgaggta    2040
gctctgaaag acaaggagcc agacacacag gacgcgggag gtgaagaa ggccctggaa    2100
ctacagatgg agaatcaccg tgaggcccat caccggcagc tggcccgcct ccgggatgag    2160
attaatgaga aacagaaaac cattgatgag ctgaaagacc tgaaccagaa gctccagtta    2220
```

```
gagctggaga agcttcaggc cgactatgag aggctgaaga atgaagagaa cgagaagagc    2280
gccaagctcc aggagctgac atttctgtat gagcgacatg agcagtccaa gcaggacctc    2340
aaggggctgg aggagacagt tgcccgtgaa ctccagaccc tccacaacct tcgcaagctg    2400
ttcgttcaag acgtcacgac tcgagtcaag aaaagtgcag aaatggagcc cgaggacagt    2460 gggggggattc attcccaaaa gcagaagatc tcctttcttg agaacaacct ggaacagctt    2520
acaaaggttc acaaacagct ggtacgtgac aatgcagatc tgcgttgtga gcttcctaaa    2580
ttggaaaaac gacttcgggc tacggctgag agagttaagg ccctgagggg tgcactgaag    2640
gaggccaagg agggcgctat gaaggacaag cgtagatacc agcaggaggt ggaccgcatc    2700
aaagaagccg tgcggtacaa gagctccggc aagcggggcc attctgccca gatcgctaag    2760
cctgtgaggc ctggccacta tcctgcctcc tcacccacca accccacgg cacccggagc    2820 cccgagtgta tcagctacac caacaacctc ttccagaact accagaacct gcacctgcag    2880
gctgcgccta gctccacttc agatatgtac tttgccagca gcggacgcac atctgttgcc    2940
cccttggctt cctaccagaa ggccaacatg acaatggaa atgccacaga tatcaacgac    3000
aacaggagtg acctgccgtg tggctatgag gctgaggacc aggccaagct tttccctctc    3060
caccaagaga cagcagccag c                                              3081

<210> SEQ ID NO 219
<211> LENGTH: 158
<212> TYPE: DNA
<213> ORGANISM: Mus musculus

<400> SEQUENCE: 219
atctcctttc ttaagaacaa cctggaacgg cttacaaaag ttcacaaaca gctggtacgt    60
gacaatgcag atctgcgttg tgagcttcct aaattggaaa acgacttcg ggctacggct    120 gagagagtta aggccctgga gggtgcacta aaaggagg                            158

<210> SEQ ID NO 220
<211> LENGTH: 177
<212> TYPE: DNA
<213> ORGANISM: Mus musculus

<400> SEQUENCE: 220
caaaagcaga agatctcctt tcttgaggac aacctggaac agcttacaaa ggttcacaaa    60
cagctggtac gtgacaatgc agatctgcgt tgtgagcttc ctaaattgga aaaacgactt    120
cgggctacgg ctgagagagt taaggccctg gagggtgcac tgaaggaggg caaggag       177

<210> SEQ ID NO 221
<211> LENGTH: 186
<212> TYPE: DNA
<213> ORGANISM: Mus musculus

<400> SEQUENCE: 221
cattcccaaa agcagaagat ctcctttctt gagaacaacc tggaacagct tacaaaggtt    60
cacaaacagc tggtacgtga caatgcagat ctgcgttgtg agcttcctaa attggaaaaa    120
caacttcggg ctacggctga gagagttaag gctctggagg gtacactgaa ggaggccaag    180
gagggg                                                               186

<210> SEQ ID NO 222
<211> LENGTH: 186
<212> TYPE: DNA
<213> ORGANISM: Mus musculus
```

<400> SEQUENCE: 222

```
cgaatcccct cctttcttga aaacaacctg gaacagctta caaaggttca caaacagctg      60
gtacgtgaca atgcagattt acgttgtgag cttcctaaat tggaaaaacg acttcgggct     120
acggctgaga gagttaaggc cctggagggt gcactgaagg aggccaagga gggcgctatg     180
aaggac                                                                186
```

<210> SEQ ID NO 223
<211> LENGTH: 180
<212> TYPE: DNA
<213> ORGANISM: Mus musculus

<400> SEQUENCE: 223

```
ctcctttctt gagaacaacc tggaacagct tacaaaggtt cacaaacagc tggtacgtga      60
caatgcagat ctgcgttgtg agcttcctaa attggaaaaa cgacttcggg ctacggctga     120
gagagttaag gccctggagg gtgcactgaa ggaggccaag gagggcgcta tgaaggacga     180
```

<210> SEQ ID NO 224
<211> LENGTH: 37
<212> TYPE: DNA
<213> ORGANISM: Mus musculus

<400> SEQUENCE: 224

```
cagaaatatg aggaagagat ccgccgtctc tacaagc                               37
```

<210> SEQ ID NO 225
<211> LENGTH: 843
<212> TYPE: DNA
<213> ORGANISM: Mus musculus

<400> SEQUENCE: 225

```
atggctacaa actttctagc gcatgagaag atctggtttg acaagtttaa atatgatgat      60
gcagaaagga gattctatga gcagatgaac gggcctgtga cctccggctc ccgccaggag     120
aatggtgcca gcgtgatcct ccgagacatt gcaagagcca gagagaacat ccagaaatcc     180
ttggctggaa gctcaggccc tggagcctcc agtggacctg gtggagacca cagtgagctc     240
attgtgagga ttaccagtct ggaagtggag aaccagaacc ttcgaggcgt ggtgcaagat     300
ttgcagcagg ccatttccaa gttggaggcc cggctgagct ctctagagaa gagttcacct     360
actccccgag ccacggcccc acagacccaa catgtctctc ctatgcgtca gtggagcccc     420
ccaaccaaga aaggagccac accagcagag gacgatgagg acaaggacat tgacctgttc     480
ggcagtgacg aggaggaaga agataaggag gctgcccgac tacgggagga gaggctacgc     540
cagtacgcag agaagaaggc caagaagccc acactggtgg ccaaatcctc catccttttg     600
gatgttaaac ctgggatga tgagactgac atggcccagc tagagacttg tgtgcgttcc     660
atccaattgg acgggctggt ttggggggcc tccaagcttg tgcctgttgg ctatggcatc     720
cggaagctgc agatccagtg tgtggtggag gatgacaaag tgggcaccga cttgctcgag     780
gaggagatca ccaaatttga ggagcatgtg cagagtgtcg acatcgcagc tttcgacaag     840
atc                                                                   843
```

<210> SEQ ID NO 226
<211> LENGTH: 219
<212> TYPE: DNA
<213> ORGANISM: Mus musculus

<400> SEQUENCE: 226

```
gagctcattg tgaggattac cagtctggaa gtggagaacc agaaccttcg aggcgtggtg      60
caagatttgc agcaggccat ttccaagttg gaggcccggc tgagctctct agagaagagt     120
tcacctactc cccgagccac ggccccacag acccaacatg tctctcctat gcgtcaagtg     180
gagcccccaa ccaagaaagg agccacacca gcagaggtg                            219
```

<210> SEQ ID NO 227
<211> LENGTH: 200
<212> TYPE: DNA
<213> ORGANISM: Mus musculus

<400> SEQUENCE: 227

```
attaccagtc tggaagtgga gaaccaaaac cttcgaggcg tggtgcaaga tttgcagcag      60
gccatttcca agttggaggc ccggctgagc tctctagaga gagttcacc tactccccga     120
gccacgaccc cacagaccca acatgtctct cctatgcgtc aagtggagcc cccaaccaag     180
aaaggagcca caccagcaga                                                 200
```

<210> SEQ ID NO 228
<211> LENGTH: 268
<212> TYPE: DNA
<213> ORGANISM: Mus musculus
<220> FEATURE:
<221> NAME/KEY: Unsure
<222> LOCATION: (172)

<400> SEQUENCE: 228

```
agaccacagt gagctcattg tgaggattac cagtctggaa gtggagaacc agaaccttcg      60
aggcgtggtg caagatttgc agcaggccat ttccaagttg gaggcccggc tgagctctct     120
agagaagagt tcacctactc cccgagccac ggccccacag acccaacatg tntttccttt     180
gcgtcaagtg gagcccccaa ccaagaaagg agccacacca gcagaggacg atgaggacaa     240
ggacattgac ctgttcggca gaaacgag                                        268
```

<210> SEQ ID NO 229
<211> LENGTH: 356
<212> TYPE: DNA
<213> ORGANISM: Mus musculus

<400> SEQUENCE: 229

```
gagcagatga cgggcctgt gacctccagc tcccgccagg agaatggtgc cagcgtgatc      60
ctccgagaca ttgcaagacc cagagagaac atccagaaat ccttggctgg aagctcaggc     120
cctggagcct ccagtggacc tggtggagac acagtgagc tcattgtgag gattaccagt     180
ctggaagtgg agaaccagaa ccttcgaggc gtggtgcaag atttgcagca ggccatttcc     240
aagttggagg cccggctgag ctctctagag aagagttcac ctactccccg agccacggcc     300
ccacagaccc aacatgtctc tcccctgcgt caagtggagc cccaaccaa gagagg         356
```

<210> SEQ ID NO 230
<211> LENGTH: 2547
<212> TYPE: DNA
<213> ORGANISM: Mus musculus

<400> SEQUENCE: 230

```
atgagctaca cgctggactc gctgggcaac ccgtccgcct accggcgcgt tccaaccgag      60
acccggtcca gcttcagccg cgtgagcggt tccccgtcca gcggcttccg ctcgcagtcc     120
```

```
tggtcccgcg gctcgcccag caccgtgtcc tcctcctaca cgcgcagcgc ggtcgccccg      180
cgtctcgcct acagctcggc tatgctcagc tcggccgaga gcagcctcga cttcagccag      240
tcctcgtcgc tgctcaacgg cggctccggc ggcgactaca aactgtcccg ctctaacgag      300
aaagagcagc tgcagggcct gaacgaccgc ttcgccggct acatcgagaa agtgcactac      360
ttggaacaac agaacaagga gatcgaagca gagatccagg cactgcggca gaagcaggcc      420
tcgcacgccc agctgggtga tgcttacgac caggagatcc gagagctgcg cgccaccctc      480
gagatggtga accacgagaa ggctcaagtg cagctggact ccgatcactt ggaggaagac      540
atccaccggc tcaaggagcg cttcgaggag gaggcgcggt tgcgggacga caccgaggct      600
gccattcgcg cgctgcgcaa agacatcgaa gagtcgtcga tggttaaggt ggagctggac      660
aagaaggtgc agtcgctgca ggatgaggtg gctttcctgc ggcgtaatca cgaagaggag      720
gtggccgacc tgctggctca gatccaggcg tcgcacatca cggtagagcg caaagattac      780
ctgaagacag acatctccac ggcgctgaag gagatccgct cccagctcga gtgtcactca      840
gaccagaaca tgcaccaggc cgaagagtgg ttcaaatgcc gctacgccaa gctcaccgag      900
gcggccgagc agaacaagga ggccattcgc tctgccaagg aagagatcgc cgagtaccgg      960
cgccagctgc agtccaagag catcgagctc gagtcggtgc gaggcactaa ggagtccctg     1020
gaacggcagc tcagcgacat cgaggagcgc acaaccacg acctcagcag ctaccaggac     1080
accatccagc agttggaaaa tgaacttcgg ggaaccaagt gggaaatggc tcgtcatttg     1140
cgagaatacc aggatctcct taacgtcaag atggccctgg acatcgagat cgccgcgtac     1200
aggaaactcc tagaggggga agagaccaga tttagcacat tttcaggaag catcaccggg     1260
cctctgtaca cacaccgaca gccctcagtc acaatatcca gtaagattca aagaccaaa     1320 gtcgaggccc ccaagctcaa ggtccaacac aaatttgtgg aggagatcat cgaagaaact     1380 aaagtgaag atgagaagtc agaaatggaa gaaaccctca cagccatcgc agaggagttg     1440
gcagcctccg ccaaagagga gaaggaagag gccgaagaaa aggaggagga accagaagcc     1500
gaaaagtctc ccgtgaagtc tcctgaggct aaggaagagg aggaggaagg ggaaaaggag     1560
gaagaagagg aaggccagga ggaagaagag gaggaagatg aaggtgtcaa gtcagaccag     1620
gcagaagagg ggggatctga gaaggaaggc tccagtgaaa aagatgaagg tgagcaggaa     1680
gaagaagaag gagaaaccga ggcagaaggt gaaggagagg aagcagaagc taaggaggaa     1740
aagaaaattg agggaaaggt tgaggaagtg gctgtcaagg aggaaatcaa ggtcgagaag     1800
cctgagaaag ccaaatcccc tatgcccaaa tcacccgtgg aagaagtaaa gccaaaacca     1860
gaggccaagg ccgggaaggg tgagcagaag gaggaagaga agttgaggga agagaagaag     1920
gaagtcacca aagaatcacc caaggaagag aaggtggaga aaaggagga gaagccaaaa     1980 gatgttgcag ataaaaagaa ggccgagtcc ccggtgaaag agaaggctgt ggaggaggtg     2040
atcaccatca gcaagtcggt aaaggtgagc ctggagaaag acaccaaaga ggagaagccg     2100
cagccgcagg agaaggtgaa ggagaaggca ggaggaggag ggggcagtga ggaggaaggg     2160
agtgaccgta gcccgcagga gtccaagaag gaagacatag ctatcaatgg ggaggtggaa     2220
ggaaaagagg aggaggagca ggaaaactca gagaagggca gtgggcggga ggaggagaaa     2280 gggggtggtca ctaatggctt agatgtgagc cctgcagagg agaagaaagg agaggatagc     2340
agtgatgata aagtggtggt caccaagaag gtagaaaaga tcaccagcga gggaggcgat     2400
ggtgctacca aatacatcac caaatctgta accgtcactc aaaaggttga agagcatgag     2460
gagacctttg aggagaagct ggtctcaact aaaaaggtag aaaaggtcac ttcacacgcc     2520
```

```
atagtcaagg aagtcaccca gggtgac                                         2547

<210> SEQ ID NO 231
<211> LENGTH: 150
<212> TYPE: DNA
<213> ORGANISM: Mus musculus

<400> SEQUENCE: 231
agctaccagg acaccatcca gcagttggaa atgaacttc ggggaaccaa gtgggaaatg      60
gctcgtcatt tgcgagaata ccaggatctc cttaacgtca agatggccct ggacatcgag    120
atcgccgcgt acaggagact cctagagggg                                     150

<210> SEQ ID NO 232
<211> LENGTH: 167
<212> TYPE: DNA
<213> ORGANISM: Mus musculus

<400> SEQUENCE: 232
cacgacctca gcagctacca ggacaccatc cagcagttgg aaaatgaact tcggggaacc     60
aagtgggaaa tggctcgtca tttgcgagaa taccaggatc tccttaacgt caagatggcc   120
ctggacatcg agatcgccgc gtacaggaaa ctcctagagg gggaatt                 167

<210> SEQ ID NO 233
<211> LENGTH: 159
<212> TYPE: DNA
<213> ORGANISM: Mus musculus

<400> SEQUENCE: 233
ctcagcagct accaggacac catccagcag ttggaaaatg aacttcgggg aaccaagtgg     60
gaaatggctc gtcatttgcg agaataccag gatctcctta acgtcaagat ggccctggac   120
atcgagatcg ccgcgtacag gaaactccta gagggaggt                          159

<210> SEQ ID NO 234
<211> LENGTH: 116
<212> TYPE: DNA
<213> ORGANISM: Mus musculus

<400> SEQUENCE: 234
cttcggggaa ccaagtggga atggctcgt catttgcgag aataccagga tctccttaac     60
gtcaagatgg ccctggacat cgagatcgcc gcgtacagga actcctaga ggggga        116

<210> SEQ ID NO 235
<211> LENGTH: 2988
<212> TYPE: DNA
<213> ORGANISM: Mus musculus

<400> SEQUENCE: 235
atgaagcgca tcttctcctg ctccagttca caagtggcgg tggagaaatg gaaccgacgt     60
gatcagaagc tgctggaggc ggtgcagcgg ggggacgtgg acgcgtggc tgccttggcc    120 tctaggaagt cagcccgacc caccaaaacta gactcaaatg ccagtcccc gttccatctg    180 gcagcctcca aaggcctgac agagtgtctg acaatactgc ttgcaaatgg ggctgatatc    240
aacagcaaga acgaggacgg aagcactgcc cttcatttgg ccaccatctc ctgtcagcca    300
cagtgtgtga aggtcttgct tcagcacggt gctaatgaag atgctgtgga tgcagaaaat    360
cgcagtccat tacactgggc agcctcctct ggctgcgcct caagtgtcct cctgctgtgt    420
```

```
gaccacgaag ccttcctgga cgtgctggat aatgatggac gcacacccct gatgattgca    480
tcgctgggtg gtcatgcagc tatctgctca cagctgttgc agagaggtgc ccgagttaat    540
gtcacagaca aggatgacaa atcagctttg atcctggcct gtgagaaagg cagcgctgag    600
gtggccgagc tgctcctgag ccatggagcg gacgctggag cggtggacag tttgggacac    660
aacgctcttc attatgcttt gcgtacacaa gacaaggagc tgtggaggct gttacagcag    720
gccctgaacc ggcggcggag aggcggtcat ggactggttc aacacccaga tcacccatct    780
caggcctctt catgtgagcc tcgggtggga tctcctccta agaactcacg gaaagtggag    840
cctgaggaag agcaggagga ggaggggggag agcggtgct cagaagagtg gaggtggaag    900
ttcgaggagg agcagaggaa agttcatcag ctggagcagg agctcgtgcg aaagacagat    960
gagtgcaagg ctcacgctgc agccttctca agcctagagg agcagattcg agagcaagcg   1020
caagaactag ccatctcct agtgcaagaa ccggagctc caggaaatca aggccctggt    1080
ctccggcctg agggagatgg tatggaggag ggttgtcccc tgaacctgct ggctgagcgg   1140
atccaagagc tgaagaagca gcagaaggca ctggctacaa taaacccaac attagttccc   1200
aagagagctg aagaattagc cccggctgag atccatcatg aagtacacag aaagtcccaa   1260
ccagagcagg ggctgcccca gggcccaagt tcagaaacca ccgggaaagc cacaggacag   1320
caaccaaaca ccaatggggg gcagaaccttc ggcctccaga acactgagca ggtgtgtgct   1380
ggccagaagg agaggacccc agctccaggg actgaaacag caggcacagt gggagaacca   1440
gtgggcatag ccatgaatca gctcctccta cagctaaggg aagagctggc tgcagtgtgg   1500
cgagaaaagg atgctgccag agggggcttg tcaagaccag ttctggaggg agccctgggg   1560
actcccagag ctgaggctgc agcagctgcc tgggaaaaga tggaagccag gcttgagagg   1620
gtgctggtaa ggttagatgg agcaaagatg ggactgcatg tgaaacctga ggtccctgtc   1680
caggggtcca gagacggagc cccgaaggca gtcccgggat gctctaaaga gcaggaagaa   1740
aagaaggctc ttggaaccag aggagagccc ttaggggccc ctggaaaaga acaggcctta   1800
ggaggaggcc tggcaaaggg acagctggag aaagaggtgt cagctttgag actgagcaat   1860
agcaacttgc tggaggaatt gggagagttg gggcgcgaga gacaacgctt gcagggagag   1920
ctgcagtcct tgacccagag gctacaccgg gagtttgtgc ccaagcccga ggcacaggtc   1980
cagctacagc agttgcggag gagcgtgggg atgttgacag aggaactggc catggagaag   2040
gaggccacag ataagctgcg caggctactg gcctcccaga ctagcggcct ccaaggactg   2100
tggaaatgcc tacccccaga cctcgtgggc aaggggaata cacagagtac agctgcagaa   2160
cccctggagg agctgcaggc ctgcatcagc accctggtgg ataggcacct tgaggctcaa   2220
cgggtgctgg ctcggttgga agaggaaaac cagcagctga gggggatcctt ggctccctgt   2280 ggggaaccag aggcctccct caaggttaca gcatccccgc aagtggccgc cctggaggaa   2340
gatctgggaa tgctagagga agagctacgg ccgtgcagg ccacgatgag tgggaagagc   2400
caggagattt gcaagctgaa acaactgctc taccaagcca cggaagaagt ggccgagctg   2460
agagctcggg aagcagccag cctgcgccag cacgagaaga cgcgaggctc gctggtggcc   2520
caggcacagg cttggggcca ggagctcaaa gtcgtgctgg agaagtacaa cacagcctgt   2580
cgggaaatga ctcgattgcg ggacactgtg gcggaggaac gtcgccgcag cgaggacctg   2640
gcggctaggg cggcggagca ggagcgccag gctggcgaga tgcgcgggcg ctcggagcag   2700
ttcgagaaaa ctgctgagct cctgaaagag aagacaaacc acctcatcgg ggcttgccgg   2760
gacaaggaag ccaagatcaa ggagttgctg aagaagctcg agcagctttc ggaagaagtt   2820
```

```
ctagaagtcc ggggcgagaa tgcccacctc gccctacagc tgcaggactc ccagaagaac    2880
cacgaagaga tcatctccac atacaggagt catctactga atgctgctcg gggctacatg    2940
gaacaagacg tctacaacat cctacttcga atcctcagca tgcaggag                 2988

<210> SEQ ID NO 236
<211> LENGTH: 204
<212> TYPE: DNA
<213> ORGANISM: Mus musculus

<400> SEQUENCE: 236
ggcctggcaa agggacagct ggagaaagag gtgtcagctt tgagactgag caatagcaac     60
ttgctggagg aatttgggaga gttggggcgc gagagacaac gcttgcaggg agagctgcag   120
tccttgaccc agaggctaca ccgggagttt gtgcccaagc ccgaggcaca ggtccagcta   180
cagcagttgc ggaggagcgt gagg                                           204

<210> SEQ ID NO 237
<211> LENGTH: 204
<212> TYPE: DNA
<213> ORGANISM: Mus musculus

<400> SEQUENCE: 237
ggcctggcaa agggacagct ggagaaagag gtgtcagctt tgagactgag caatagcaac     60
ttgctggagg aatttgggaga gttggggcgc gagagacaac gcttgcaggg agagctgcag   120
tccttgaccc agaggctaca ccgggagttt gtgcccaagc ccgaggcaca ggtccagcta   180
cagcagttgc ggaggagcat gagg                                           204

<210> SEQ ID NO 238
<211> LENGTH: 204
<212> TYPE: DNA
<213> ORGANISM: Mus musculus

<400> SEQUENCE: 238
ggcctggcaa agggacagct ggagaaagag gtgtcagctt tgggactgag caatagcaac     60
ttgctggagg aatttgggaga gttggggcgc gagagacaac gcttgcaggg agagctgcag   120
tccttgaccc agaggctaca ccgggagttt gtacccaagc ccgaggcaca ggtcctgcta   180
cagcagttgc ggaggagcgt gatg                                           204

<210> SEQ ID NO 239
<211> LENGTH: 1350
<212> TYPE: DNA
<213> ORGANISM: Mus musculus

<400> SEQUENCE: 239
atgatggacg tctctcggac acaaactgca gtctcaatag ttgaagagga tctaaaactt     60
ttacagctta agctaagagc atcgatgtcc actaaatgta acctggaaga ccaaatcaag   120
aaattagaag atgaccgcag ctcgctgcag actgctaaag ctgggttgga agacgagtgc   180
aaaactctga ggcagaaagt ggagatcctg aatgagctgt accagcagaa ggagatggcg   240
ctgcagaaga aactgagtca agaagagtat gagcggcaag acagagagca gaggctcacg   300
gcggccgatg agaaggtggt tctggctgca gaggaagtga aaacgtacaa gcggcgaatc   360
gaagaaatgg aagaagaatt acagaaaaca gaacgttcat ttaaaaacca gattgctgct   420
catgagaaga aagctcatga taattggctc aaagctcgtg ctgcagagag agccatggca   480
```

```
gaggagaaga gagaagctgc taacttaagg cacaaattac tggaaatgac tcaaaagatg    540
gcaatgaggc aagatgagcc cgtgattgta aagccgatgc aggaagacc  gaacacacag    600 aaccctcccc ggcgaggtct gctgagccag aatggctctt ttggcccatc ccctgtgagt    660
ggtggggaat gctcccctcc cctaccagca gagccgcctg ggagacctct ctctgccaca    720
ctcagtcgaa gagacactcc tagaagtgaa tttgggtcac tggacaggca tttacctcgc    780
cctcgatggc catcagaggc atctggcaaa cactctgctt ctgacccggg tcccgctcct    840
gtggtgaaca gcagctccag gagctcttct cccgctaagg ccgtggatga gggcaaggtt    900
aatatggctc ccaaagggcc gcctccattt ccaggggtgc ctctcatggg aggcccagtg    960
ccaccaccca tacgatatgg accacctccc cagctatgtg gtgggccttt tgggcctcgc   1020
ccacttcctc caccatttgt tccaggcatg catccaccac taggcgtaag agaatatgca   1080
ccaggtgttc tgcctgggaa acgggacctg cctcttgatc ctcgggaatt tttaccagga   1140
catacaccat ttagacctcc aggttcactc ggtccaagag agttctttat tcctggtacc   1200
cgattaccac ctccaaccca tggtcctcag gaatacccac caccaccacc tgctgtaaga   1260
gactcactgc cttcaggccc gagagaggaa gccaaacctg cctctccaag cagtgtccag   1320
gaccgctcac aggcttcaaa gcccaccccc                                     1350

<210> SEQ ID NO 240
<211> LENGTH: 174
<212> TYPE: DNA
<213> ORGANISM: Mus musculus

<400> SEQUENCE: 240
cttttacagc ttaagctaag agcatcgatg tccactaaat gtaacctgga aaaccaaatc     60
aagaaattag aagatgaccg cagctcgctg cagactgcta aagctgggtt ggaagacgag    120
tgcaaaactt tgaggcagaa agtggagatc ctgaatgagc tgtacctgca gacg          174

<210> SEQ ID NO 241
<211> LENGTH: 132
<212> TYPE: DNA
<213> ORGANISM: Mus musculus

<400> SEQUENCE: 241
ctggaagacc aaatcaagaa attagaagat gaccgcagct cgctgcagac tgctaaagct     60
gggttggaag acgagtgcaa aactctgagg cagaaagtgg atcctgaa tgagctgtac    120 cagcagagta ga                                                        132

<210> SEQ ID NO 242
<211> LENGTH: 675
<212> TYPE: DNA
<213> ORGANISM: Mus musculus

<400> SEQUENCE: 242
cacttgagga aggtcaagtt ccaggccaaa ctagaacacg agtacatcca acttcaag      60 gtgctgcaag cagcttttcaa gaagatgggt gttgacaaaa tcattcccgt agagaagtta   120
gtgaaaggaa aattccaaga taattttgag tttatacagt ggtttaagaa attctttgac   180
gcaaactatg atggaaagga ttacaaccct ctgctggcgc ggcagggcca ggacgtagca   240
ccacctccta acccaggtga tcagatcttc aacaaatcca agaaactcat tggcacagca   300
gttccgcaga ggacgtcccc cacaggcccc aagaacatgc agacctctgg acgactcagc   360
aacgtggctc cgccctgcat cctccggaag aatccccccct cagcccgaaa cggtggccat   420
```

```
gaggctgacg cccagatcct cgagcttaac cagcagctgc tggacttgaa gctgaccgta      480
gacgggcttg agaaagaacg agatttctat ttcagcaaat tgcgagacat cgagctgatc      540
tgccaggaac atgagagcga gaacagcccc gtcatctcgg gcatcattgg cattctctat      600
gccacggagg agggatttgc accccctgag gatgatgaga ttgaagaaca ccaacaggaa      660
gaccaggacg agtac                                                       675

<210> SEQ ID NO 243
<211> LENGTH: 258
<212> TYPE: DNA
<213> ORGANISM: Mus musculus

<400> SEQUENCE: 243
cgaaacggtg gccatgaggc tgacgcccag atcctcgagc ttaaccagca gctgctggac      60
ttgaagctga ccgtagacgg gcttgagaga gaacgagatt tctatttcag caaattgcga      120
gacatcgagc tgatctgcca ggaacatgag agcgagaaca gccccgtcat ctcgggcatc      180
attggcattc tctatgccac ggaggaggga tttgcacccc ctgaggatga tgagattgaa      240
gaacaccaac aggaagaa                                                    258

<210> SEQ ID NO 244
<211> LENGTH: 1455
<212> TYPE: DNA
<213> ORGANISM: Mus musculus

<400> SEQUENCE: 244
atgaataact ttgagtgtga accagctttc tatacttgtg tggaagtcac tgctggtaac      60
aggttatttt atcacattgt tgattcagat gaagtcagca cgaaaatttt aatggagttc      120
aataaaatga atcttcctgg agaggtgact ttcctgcctc ttaacaagtt agatgtgaga      180
gatactgcct atcctgaaac taacgatgct attcctatga tcagtaagct gaggtacaat      240
cccagatttg acaaagcttt caaacatgta tttggaaaga cactcatctg tcggagcatg      300
gaagtttcaa ctcagctggc ccgggccttc actatggact gtattacttt ggaaggtgat      360
caagtcagcc atcgaggtgc tctgactgga ggttattacg acacaagaaa gtctcgactt      420
gagttacaga aagacgttag aaggcagag gaggagctgg gtgagctgga ggctaagctc      480
aatgaaaacc tacgcaggaa cattgaaagg attaataatg aaattgacca gttgatgaac      540
caaatgcagc agatagagac ccaacaaaga aaatttaaag catccagaga tagcatatta      600
tcagagatga agatgctaaa agagaagaga cagcaatcag aaaagacctt catgccaaag      660
caacgtagct acaaagcttt ggaggcaagt ctgcatgcta tggagtccac cagagagtca      720
ctgaaagcgg agctagggac ggatttgctt tctcaactca gtctggaaga tcagaaaaga      780
gtcgacgctc tgaatgatga aatccgtcag ctgcagcagg aaaacagaca gctgctaaat      840
gaaagaatta aactagaagg cattattact cgagtagaga cttacctgaa tgagaatctg      900
aggaaacgct tggaccaagt agaacaggaa cttaatgaac tgagagagac agaaggtggt      960
actgttctta ctgccacaac atcagaactt gaagctatta taaaagagt aaagatact      1020 atggcaagat cagaagattt ggacaattcc attgacaaaa cagaagctgg aattaaagag      1080
ctccagaaaa gtatggagcg ctggaaaaat atggagaaag aacacatgga tgccataaat      1140
catgatacta agagctggaa gaagatgacc aaccggcaag gcatgctgtt gaagaagaag      1200
gaggagtgta tgaagaagat ccgggagctg gggtccctcc cccaggaagc gtttgagaag      1260
```

| | |
|---|---:|
| taccagacac tgagcctgaa gcagttgttt cgaaaactgg agcaatgcaa cacagagtta | 1320 |
| aagaagtaca gccacgtgaa caaaaaggct ctagatcagt ttgtgaattt ctctgagcag | 1380 |
| aaggaaaggc tgataaagcg gcaagaggaa ttggatagag gctacaaatc aatcatggaa | 1440 |
| ttgatgaaat gtact | 1455 |

<210> SEQ ID NO 245
<211> LENGTH: 219
<212> TYPE: DNA
<213> ORGANISM: Mus musculus

<400> SEQUENCE: 245

| | |
|---|---:|
| cagaaaagag tcgacgctct gaatgatgag atccgtcagc tgcagcagga aaacagacag | 60 |
| ctgctaaatg aaagaattaa actagaaggc attattactc gagtagagac ttacctgaat | 120 |
| gagaatctga ggaaacgctt ggaccaagta gaacaggaac ttaatgaact gagagagaca | 180 |
| gaaggtggta ctgttcttac tgccacaaca tcagaaaag | 219 |

<210> SEQ ID NO 246
<211> LENGTH: 4011
<212> TYPE: DNA
<213> ORGANISM: Mus musculus

<400> SEQUENCE: 246

| | |
|---|---:|
| atgatggaga tccagatgga cgagggagga ggtgtggtgg tgtaccaaga cgactactgc | 60 |
| tcgggctcgg tcatgtcgga gcgtgtgtcg ggcctggcgg gctccatcta ccgcgagttc | 120 |
| gagcgcctca ttcactgcta tgacgaggag gtggtcaagg agctcatgcc gctggtggtg | 180 |
| aacgtgctgg agaaccttga ctcggtgctg agcgagaacc aggagcacga ggtggagctg | 240 |
| gagctcctac gcgaggacaa cgagcagctg ctcacgcaat acgagcgcga aaggcgctg | 300 |
| cgcaaacagg ccgaggagaa attcatcgaa tttgaagatg ccttggaaca agagaagaaa | 360 |
| gaactccaga tccaggtaga acattatgag tttcagacac gccagctgga gctaaaggcc | 420 |
| aaaaactatg cagatcagat ttcccgactg gaggaacgag aatcggagat gaagaaggaa | 480 |
| tacaatgccc tgcaccagcg gcacacagag atgatccaga cctatgtgga acacattgaa | 540 |
| agatccaaga tgcagcaagt tgggggtagc ggccaaacag aaagcagcct gcccgggcgg | 600 |
| agcaggaagg agcgtcccac ctctctgaat gtcttccccc tggctgatgg catggtacgt | 660 |
| gcacagatgg ggggcaagct cgtgcctgcg ggggaccact ggcacctgag tgacctcggc | 720 |
| cagctacagt ccagctccag ctaccagtgt ccaaacgatg agatgtctga gtcaggccag | 780 |
| tcctcagcag ctgcaacacc cagtaccaca ggtaccaagt ccaacacacc cacgtcctcc | 840 |
| gtgccctcag cagcagtcac gccactcaac gagagcctac agccctgggg gactatgtc | 900 |
| agtgtcacaa agaacaacaa gcaggcccga gagaagcgca atagccgtaa catggaggtc | 960 |
| caggtcaccc aagagatgcg gaacgtcagt atcggcatgg gcagcagtga cgagtggtcc | 1020 |
| gatgttcagg acattatcga ctccaccccca gagctggatg tgtgtcctga acccgtctg | 1080 |
| gagcgcacag gaagcagccc aacccaggga attgtaaaca agctttgggg aatcaacact | 1140 |
| gactccttgt atcacgaact ctccacggcg ggatctgagg tcatcgggga tgtggacgag | 1200 |
| ggagctgatc tcctagggga gttttcagtg cgcgatgatt ttttggaat gggcaaagaa | 1260 |
| gtggggaacc tgctgctgga gaactcacag cttctagaga caaaaaatgc tttaaatgta | 1320 |
| gtgaagaatg acctcattgc taaggttgac caactgtcag gagaacagga ggtcctgaag | 1380 |
| ggtgagctgg aagcagccaa gcaagccaaa gtcaagctgg agaaccgaat caaagagctt | 1440 |

```
gaagaagaac tgaagagagt caagtcagag gcagtaactg cccgccgtga gcccagagaa    1500
gaggtggagg atgtaagcag ctatctctgt acagaattgg acaaaatccc catggcccag    1560
cgccgacgct tcacacgggt ggagatggcc cgagtgctca tggaacgcaa ccagtacaag    1620
gaacgcctca tggagctgca ggaggctgtg aggtggactg aaatgatcag agcatcaagg    1680
gaacacccat ctgtccagga gaagaagaag tccaccatct ggcagttctt tagtcgcctc    1740
ttcagctcct catctagccc ccctccggcc aaacgatcct acccatctgt gaacattcac    1800
tacaagtcac ccactgcagc tggctttagc cagcgtcgca gccatgcttt gtgccagatc    1860
tcagccggca gcaggcccct ggagttcttc cctgatgatg actgcacctc ttctgcccgg    1920
cgggagcaga agcgggagca gtaccgccag gttcgtgaac acgtgcgcaa tgatgacggg    1980
aggctgcagg cctgtgggtg gagcctgcct gccaagtaca agcagctgag ccccaatgga    2040
ggccaggaag acacccggat gaaaaatgtg cctgtccctg tgtactgtcg ccctctggtg    2100
gagaaggacc cttcgacaaa gctgtggtgt gctgctggtg tcaacctgag tgggtggaag    2160
ccacatgaag aggactctag caatggaccc aagcctgtac caggtcgaga ccctctgacc    2220
tgtgaccggg aaggagaagg cgaacccaag agcacacacc catcacctga aagaagaag     2280 gcaaaggaaa cccctgaggc agatgctacc tccagtcggg tatggatcct caccagcacc    2340
ctgacaacca gcaaggtggt gatcattgat gccaaccagc caggcacaat tgtggatcag    2400
ttcacagtct gcaatgccca cgtcctgtgt atctccagca ttcctgcggc cagtgacagt    2460
gactatcccc ctggggagat gttcctagac agtgatgtga accctgaaga ttcaggtgct    2520
gatggtgtgc tggctggcat caccctggtg gggtgtgcta cccgctgcaa tgttccacgt    2580
agcaactgtt cctcacgagg agacaccccca gtactggaca aggggcaggg ggatgtggcg    2640
accactgcca atgggaaggt caacccgtcc caatccacag aagaagccac agaagccaca    2700
gaggtgccag accctggtcc cagcgagtca gaagcaacga cagtccggcc cgggcctctc    2760
acagagcatg tctttactga cccagcaccc accccatcct ccagcaccca gcctgccagt    2820
gagaatgggt cagaatccaa tggcaccatt gtacagcctc aggtggagcc cagtggggaa    2880
ctctcaacaa caaccagtag cgctgcaccc actatgtggc taggagccca gaatggctgg    2940
ctctatgtgc attcagcggt agccaactgg aagaagtgtc tgcactccat caagctaaaa    3000
gactctgtgc tgagcctggt gcatgtcaaa ggccgagtgc tggtagctct tgcagatggg    3060
accctggcta tcttccatcg tggagaggat ggccagtggg acctgagcaa ctaccaccta    3120
atggacctgg gccacccaca ccactccatc cgctgcatgg ctgttgtgaa tgaccgagtt    3180
tggtgtggct acaagaacaa ggtgcatgtt atccagccca agacaatgca gattgagaaa    3240
tcatttgatg cccacccaag gcgggaaagc caggtacgtc agctggcctg gatcggtgat    3300
ggagtgtggg tctctattcg cttggattct acccttcggc tctaccatgc tcacacccac    3360
cagcacctgc aggatgtgga cattgagccc tatgttagca agatgctagg aaccggcaag    3420
ctgggcttct ccttcgtgcg catcacagcc ttactcattg caggcaaccg tctgtgggtg    3480
ggcactggca atgggggttgt catctccatc cccttgactg agactgtggt cctgcatcga    3540
ggccagctcc tagggctccg agccaacaag acatccccaa catctgggga ggggaccccgc   3600 ccaggggggca tcatccatgt gtatggggac gacagcagtg acaaggccgc cagtagtttc    3660
atcccctact gctccatggc acaggctcag cttttgcttcc atgggcaccg tgatgctgtc    3720
aaattctttg tctctgtgcc aggaaatgtg ctggccactc tcaatggcag tgtgctagac    3780
```

| | | |
|---|---|---|
| agcccatcag agggccctgg gcctgctgca cccgctgcag atgctgaggg ccagaagttg | 3840 | |
| aagaatgcac tggtgctgag tggtggtgaa ggttacattg acttccgtat cggagacgga | 3900 | |
| gaggatgatg aaactgagga atgtgccggg acgtgaacc agacaaagcc ctcgttgtcc | 3960 | |
| aaggctgagc gcagccacat catcgtgtgg caggtgtcct acacccctga g | 4011 | |

<210> SEQ ID NO 247
<211> LENGTH: 213
<212> TYPE: DNA
<213> ORGANISM: Mus musculus

<400> SEQUENCE: 247

| | |
|---|---|
| gagacaaaaa atgctttaaa tgtagtgaag aatgacctca ttgctaaggt tgaccaactg | 60 |
| tcaggagaac aggaggtcct gaagggtgag ctggaagcag ccaagcaagc caaagtcaag | 120 |
| ctggagaacc gaatcaaaga gcttgaaaaa gaactgaaga gagtcaagtc agaggcagta | 180 |
| actgcccgcc gtgagcccag agaagaagtg gat | 213 |

<210> SEQ ID NO 248
<211> LENGTH: 2979
<212> TYPE: DNA
<213> ORGANISM: Mus musculus

<400> SEQUENCE: 248

| | |
|---|---|
| atggaggcgg cggtgtgtag cgaaatcgaa cgggaggatg gcgacagcag ctgcggggat | 60 |
| gtgtgtttca tggacaaagg cctgcacagt atatcagagt tatctttaga ttcatccatt | 120 |
| catgccatca atttgcattg taataacatc tccaagatct catccattga ccacatttgg | 180 |
| aacctacgac atttagatct gtcatctaat caaataagtc aaattgaagg cctgaacaca | 240 |
| ctgacaaagc tatgcacttt aaatttgtcc tgcaatttga tcacaagagt ggaaggactt | 300 |
| gaagcactgg ttaatctgac taaactgaac ttgtcttata tcacataaa tgatcttagt | 360 |
| gggttgatgc cccttcatgg actaaagtat aaacttagat atattgacct ccatagtaat | 420 |
| tatatagata gcatccatca cttacttcag tgtacagtag gattgcactt cctaaccaat | 480 |
| cttattttag agaaagatgg agaaggtaat cctatctgcc ttataccagg gtaccgagca | 540 |
| atcattctcc agactttacc acaactgaga atcttagatt gcaagaatat atttggagag | 600 |
| ccagtaagct tggaagaaat aaaactcatcc catctacagt gcttagaagg acttttggat | 660 |
| aacttagttt cttctgattc cccctgaat ataagtgaag atgaggtcaa tgatgatgtg | 720 |
| tcagcaccac caatggatgt gttgccttct ttgaaggaat ttaaaagtac accagaagac | 780 |
| aatgttttag cctcactttt atctgtgtgt ccatcttctg aaccagaaaa aattaatcag | 840 |
| gaaaacgact tcagaatgga ggtgaaactt cagaaattag atgaccaaat cctacagctt | 900 |
| ctcaatgaaa ctaataattc cttaatagat aatgttcctg agaagacct cagaccaaaa | 960 |
| agagacacag atataacttc tgaaagtgac tatggaaaca agagagtg cagcagaaaa | 1020 |
| gttcccagga gaacaaaaat cccatattat tccagaacta ttcaaaccat taagcaccac | 1080 |
| aataaaaaca atggtgcttt tgtaagttgt aatcgtaaaa tgagacagcc ttaccttaga | 1140 |
| gatttatatg taagatcatc tttagtaaac tgtaataact tacgagactt agatgagcag | 1200 |
| aagactggcg taattaaagt agacaagaac ttctcggaca cagcaccta ccggtccctc | 1260 |
| gtggaacagt tagaccaaga gagagatg cggtggaaag ctgagcaaac ggaaaagaaa | 1320 |
| cttatggatt atatcgatga gctacataag caagcagatg agaaaaaaga tgttcacagc | 1380 |
| caggctctca ttaccacaga tagactaaag gatgctattt ttaaggagag acattgcaag | 1440 |

```
gctcaacttg aaattatagt tcacagactt caaaatgaag ttaaaaaact aactattgaa    1500
ttaatgaaag cgcgagatca acaggaagat cacatcagac acctgagaac cctggaaagg    1560
gcattggaaa aaatggagaa gcagaaagca cagcagcagg cggcacagat aagactgatc    1620
caagaggtgg agctcaaagc ctcagctgct gatcgagaaa taaacttact tcgaacttct    1680
cttcaccaag aaaagcagca agtgcaacaa cttcatgaac ttctggcgtt gaaagagcag    1740
gaacacaggc aagaaattga aactcggcag tttttcactg atgctgagtt ccaggatgca    1800
ttaactaaac gattatgcaa agaagaacga aaacatgagc aagaagtaaa agaataccaa    1860
gaaaaaattg atatattaaa ccagcagtat ttggacttag aaaatgagtt ccgtattgct    1920
ttaactgttg aagctagaag atttaaagat gttcaggatg ctttgaaga tgttgcgact    1980 gagttagcga agagtaaaca tgctcttatt tgggctcagc gtaaagaaaa tgagtcgtct    2040
tctttaatta aagatctgac atgtatggtg aaggaacaga agacaaagct ctccgaagtc    2100
tgcaaactga agcaggaagc agcagccaat ttacagaatc aaatcaacac tcttgaaatt    2160
ttgattgaag atgacaagca gaagagcatt caaatagaac ttctcaaaca tgaaaaaacc    2220
cagctgattt ctgagctggc agccaaagag tcactgattt atggcttacg gactgagaga    2280
aaagtatggg gacaggaact ggcatgtcag agctcgacac tatcccagag tcgtgggaaa    2340
ttagaagccc agattgaaag tttatgcaga gaaaatgaat ctctgagaaa aagccatgaa    2400
agtgactgtg atgcattgag aataaagtgc aagatcattg aagaccaaaa tgaaaccatc    2460
cggaaactaa aagacagttt acaagaaaaa gatgggcaaa tcaaattgct acaagaacag    2520
atcgctctca tcgaaaagtg ttctcaagag caacttaatg aaaagtctcc acaactagat    2580
tctatagttg agaaactaga gagacacaat gagagaaagg aaaaattaaa gcaacagttg    2640
aaagcaaagg aattagaact tgaagaaatc agaaaagctt acagcacact aaataagaaa    2700
tggcatgata aaggagaact actctctcat cttgaaatgc aagtaaaaga agtaaaagaa    2760
aaatttgaag acaaggaaag gaaactgaaa gcagagagag acaaaagtct tgagctacaa    2820
aaggatgcaa tggaaaagct tcagaacatg gatgatgcct ttagaagaca agtggatgag    2880
attgtggaag cgcaccaagc tgaaataatg cagctagcaa atgagaagca gaagtatatt    2940
gactgtgcaa atttaaaggg tgactatgcg cgtggcgac                           2979

<210> SEQ ID NO 249
<211> LENGTH: 156
<212> TYPE: DNA
<213> ORGANISM: Mus musculus

<400> SEQUENCE: 249
cacagtcagg ctctcattac cacagataga ctaaaggatg ctatttttaa ggagagacat      60
tgcaaggctc aacttgaaat tatagttcac agacttcaaa atgaagttaa aaaactaact     120
attgaattaa tgaaagcgcg agatcaacag gaagat                                156

<210> SEQ ID NO 250
<211> LENGTH: 1209
<212> TYPE: DNA
<213> ORGANISM: Mus musculus

<400> SEQUENCE: 250
ctgggtacca tgccacgttt ctccttgtct cgaatgactc ctccactccc tgccagggtg      60
gacttctccc tggccggggc gctcaatgct ggcttcaagg agacacgggc gagcgagcgt     120
```

```
gcagagatga tggagctcaa tgaccgcttt gctagctaca tcgagaaggt ccgcttcctg      180
gaacagcaaa acaaggcgct ggcagctgaa ctgaaccagc ttcgagccaa ggagcccacc      240
aaactggctg atgtctacca ggcggagctt cgggagctgc ggctgcggct ggaccagctt      300
acggccaaca gtgcccggct ggaggtggag agggacaact ttgcacagga cctcggcacc      360
ctgaggcaga agctccaaga tgaaaccaac ctgaggctgg aggcagagaa caacctggct      420
gcgtatagac aggaggcaca tgaagccacc ctggctcgtg tggatttgga gagaaaggtt      480
gaatcgctgg aggaggagat ccagttctta aggaagatct atgaggagga agttcgagat      540
ctccgggagc agctggccca acagcaggtc cacgtgagta tggatgtggc caagccagac      600
ctcacagcgg ccctgagaga gattcgcact caatacgagg cagtggccac cagtaacatg      660
caagagacag aggagtggta tcggtctaag tttgcagacc tcacagacgc tgcgtcccgc      720
aacgcagagc tcctccgcca agccaaacac gaagctaacg actatcgccg ccaactgcag      780
gccttgacct gcgatctgga gtccctccgc ggcacgaacg agtccctaga gcggcaaatg      840
cgcgaacagg aagagcgcca tgcgcgggag tcggccagtt accaggaggc acttgctcgg      900
ctggaggagg agggccaaag cctcaaggag gagatggccc gccacctgca ggagtaccag      960
gatctactca acgttaagct agccctggac atcgagatcg ccacctacag gaaattgctg     1020
gagggcgaag aaaaccgcat caccattcct gtacagactt tctccaacct ccagatccga     1080
gaaaccagcc tggacaccaa atccgtgtca aaggccacct caagaggaa catcgtggta     1140 aagactgtgg agatgcggga tggtgaggtc attaaggact cgaagcagga gcacaaggac     1200
gtggtgatg                                                              1209

<210> SEQ ID NO 251
<211> LENGTH: 135
<212> TYPE: DNA
<213> ORGANISM: Mus musculus

<400> SEQUENCE: 251
cttgctcggc tggaggagga gggccgaagc ctcaaggagg agatggcccg ccacctgcag       60
gagtaccagg atctactcaa cgttaagcta gccctggaca tcgagatcgc cacctacagg      120
aaattgctgg agggg                                                       135

<210> SEQ ID NO 252
<211> LENGTH: 1353
<212> TYPE: DNA
<213> ORGANISM: Mus musculus

<400> SEQUENCE: 252
atggcaagcc ccactctgag cccggactcc tcatctcaag aggccctgtc agcacccacc       60
tgctccccaa cctctgactc cgagaatctc agcccagatg agctagaact actggccaag      120
ctcgaggagc agaaccggct cctggaagcc gactccaagt ccatgcgctc catgaatggc      180
tcccggagga acagtggctc ctcactggta tccagctcct cagcctcctc caacctgagc      240
cacctggagg aggacacgtg gattctctgg ggccgaattg ccaacgagtg ggaggagtgg      300
cggcgcagga aggaaaaact actcaaggag ctgatccgga agggcatccc acaccacttt      360
cgggccatcg tctggcagct cctgtgcagt gccacagata tgcccgtcaa aaaccagtac      420
tctgagctcc tcaagatgtc ctccccatgt gagaaactca tcaggaggga tattgcccgc      480
acctacccag agcatgaatt cttcaaaggc caggacagcc tgggcaggaa gtcctcttc      540 aatgtcatga aggcatactc cctggttgat cgggaggtgg gctactgcca gggcagtgcc      600
```

| | |
|---|---|
| ttcattgtgg gcttactcct catgcagatg cctgaggaag aggccttctg tgtattcgtg | 660 |
| cgactgatgc aggagtaccg gctacgggag ctcttcaagc ccagcatggc cgagctggga | 720 |
| ctctgtatct accagtttga atacatgcta caggagcagc ttccggacct gaatacccac | 780 |
| ttccgctcac agagcttcca cacgtccatg tatgcatcgt cctggttcct tacgcttttc | 840 |
| cttaccacct tcccctgcc tgttgccacc cgggtctttg atatctttat gtatgaggga | 900 |
| ctggagattg tgttccgagt aggccttgcc ctgctgcaag tgaaccagac agagttgatg | 960 |
| caactggaca tggagggcat gtcccagtac ttccagagag tcatccccca ccagtttgac | 1020 |
| agctgcccag acaagctggt cctcaaggct tatcaggtca gtacaacccc taaaaagatg | 1080 |
| aagaggctgg agaaggagta cgcagctatg aagagtaaag atgtgaggga gcagatcgag | 1140 |
| atcaaaaggc ttcgaacaga gaaccggctg ctcaaacagc ggattgagac cctagagaag | 1200 |
| gggcaggtga cacgggcaca ggaggctgag gagaactatg tcatcaaacg ggagttggca | 1260 |
| gtagtgagac aacagtgtag ctcgactgca gaggaccttc agaaagcaca gagtaccatt | 1320 |
| cggcagttgc aagaacagca ggtacccggc ggt | 1353 |

<210> SEQ ID NO 253
<211> LENGTH: 312
<212> TYPE: DNA
<213> ORGANISM: Mus musculus

<400> SEQUENCE: 253

| | |
|---|---|
| gccctgctgc aagtgaacca gacagagttg atgcaactgg acatggaggg catgtcccag | 60 |
| tacttccaga gagtcatccc ccaccagttt gacagctgcc cagacaagct ggtcctcaag | 120 |
| gcttatcagg tcaagtacaa ccctaaaaag atgaagaggc tggagaagga gtacgcagct | 180 |
| atgaagagta aagagatgga ggagcagatc gagatcaaaa ggcttcgaac agagaaccgg | 240 |
| ctgctcaaac agcggattgg gaccctagag aaggagagcg cggccttggc tgataggtta | 300 |
| atccaggggg ca | 312 |

<210> SEQ ID NO 254
<211> LENGTH: 2889
<212> TYPE: DNA
<213> ORGANISM: Mus musculus

<400> SEQUENCE: 254

| | |
|---|---|
| atggcggacc cggcggagtg caacatcaaa gtgatgtgtc gcttcagacc tctcaacgaa | 60 |
| tctgaagtga accgcggcga taagtacgtc gccaaattcc agggagaaga cacggtcgtg | 120 |
| atcgcgtcca gcctttatgc atttgatcgg gtgttccagt caagcacatc tcaagagcaa | 180 |
| gtgtataatg actgtgcaaa gaagattgtt aaagatgtac ttgaaggata taatggaaca | 240 |
| atatttgcat atggacaaac atcctctggg aagacccaca cgatggaggg taaacttcat | 300 |
| gatccagaag gcatgggaat tattccaaga atagtgcaag atattttaa ttatatttac | 360 |
| tccatggatg aaaatttgga atttcatatt aaggtttcat attttgaaat atatttggat | 420 |
| aagataaggg acttgttaga tgtttcaaag actaacccttt cagtccatga agacaaaaac | 480 |
| cgtgttccct atgtaaaggg gtgcacagaa cgtttcgtgt gtagtccaga tgaagtcatg | 540 |
| gataccatag atgaagggaa atccaacaga catgtcgcag ttacaaatat gaatgaacat | 600 |
| agctctagga gtcacagcat atttcttatt aatgtaaaac aagagaatac acaaacggaa | 660 |
| caaaagctga gtggaaaact ttatctggtt gatttagctg gtagtgaaaa ggttagtaaa | 720 |

-continued

```
actggagctg aaggtgctgt gctggatgaa gctaaaaaca tcaacaagtc actttctgct    780
cttggaaatg ttatttctgc tttggctgag ggtagtacat atgttccata tcgagatagt    840
aaaatgacaa gaatccttca agattcatta ggtggcaact gtagaaccac tattgtaatt    900
tgctgctctc catcatcata caatgagtct gaaacaaaat ctacactctt atttggccaa    960
agggccaaaa caattaagaa cacagtctgt gtcaatgtag agttaactgc ggagcagtgg   1020
aaaaagaagt atgaaaaaga aaggaaaaa ataaaactc tacggaacac tattcagtgg    1080
ctggaaaacg agctaaaccg ttggcgtaac ggggagacag tgcctattga tgagcagttt   1140
gacaaagaga agctaatttt ggaagccttc acagcggata agatattgc tattaccagt    1200 gataaaggag ctgctgcagt cggaatggct ggtagttttta ccgatgctga agaagaaag   1260 tgtgaagaag aacttgctaa attgtataaa caacttgatg acaaggatga agagattaac   1320
caacaaagcc aattggtaga gaaattgaag acacaaatgc tggatcagga gagcttctg    1380 gcatcaacca gaagggatca agataatatg caagctgaac tgaatcgcct ccaagcagaa   1440
aatgatgctt ctaaagaaga agtcaaagaa gttttacagg ccttagagga actggctgtt   1500
aattatgatc agaagtctca ggaagttgaa gacaaaacaa aggaatatga attgcttact   1560
gatgaattca atcaaaaatc tgcaacttta gcaagtattg atgctgagct tcagaagctg   1620
aaggaaatga ccaaccacca gaagaaacga gcagctgaaa tgatggcatc attattaaaa   1680
gaccttgcag aaataggaat tgctgtgggg aataacgatg tgaagcaacc agaaggaact   1740
ggtatgatga tgaagagtt tactgttgca agactctaca ttagcaaaat gaatcagaa    1800 gtaaagacca tggtgaaacg ctgcaaacag ctagaaagca cacagactga gagcaacaaa   1860
aaaatggaag aaaatgagaa agagttagca gcatgccagc ttcggatctc caacatgaa    1920 gccaaaatca agtcactgac tgagtacctt cagaatgatg aacaaaagaa gaggcagctg   1980
gaggagtctc ttgattccct tggtgaggag ctagtccaac tccgagcaca agagaaagtc   2040
catgaaatgg aaaagagca cttgaacaag gttcagactg caaatgaagt caagcaagct   2100
gttgagcagc agatccagag tcacagagaa acccaccaaa aacaaatcag tagtttgcga   2160
gatgaagtgg aggcaaagga aaagctaatc actgacctcc aagaccaaaa ccagaagatg   2220
gtgttggaga cggaacggct aagggtggag catgagaggc tgaaggctac agaccaagag   2280
aagagcagga agctgcacga gctcacggtt atgcaagaca gacgagaaca agcaagacaa   2340
gacttgaagg gttttgagga gaccgtggca aaagaacttc agactttaca caacctgcgt   2400 aagctcttg ttcaggactt ggctaccagg gtgaaaaaga gcgccgaggt cgactctgac   2460
gacactggcg gcagtgctgc acagaagcag aaaatctcct tccttgaaaa caaccttgaa   2520
cagctcacca aagtgcacaa gcagttggta cgcgataatg cagatcttcg ctgtgaactt   2580
cctaagttag agtttcggct tagagctact gcagaaagag tgaaagcttt ggagtcagcc   2640
ctgaaagaag ccaaagaaaa tgcatctcga gaccgtaaac gctatcagca agaagtagac   2700
cggataaagg aagcagtcag gtcaaagaac atggccagaa ggggacattc tgcccagatt   2760
gcaaagccga tccgtcctgg acagcatcca gcggcctcgc caactcaccc gggcacagtt   2820
cgtggaggag gctcatttgt tcagaacaac cagccagtgg ggcttcgtgg tggtggaggc   2880
aagcagtcg                                                          2889
```

<210> SEQ ID NO 255
<211> LENGTH: 135
<212> TYPE: DNA
<213> ORGANISM: Mus musculus

<400> SEQUENCE: 255

```
gtctgtgtca atgtagagtt aactgcggag cagtggaaaa agaagtatga aaaagaaaag    60
gaaaaaaata aaactctacg gaacactatt cagtggctgg aaaacgagct aaaccgttgg   120
cgtaacaggg agacg                                                   135
```

<210> SEQ ID NO 256
<211> LENGTH: 5346
<212> TYPE: DNA
<213> ORGANISM: Artificial Sequence
<220> FEATURE:
<223> OTHER INFORMATION: vector CMV-FosCBPzz

<400> SEQUENCE: 256

```
atgcattagt tattaatagt aatcaattac gggtcatta gttcatagcc catatatgga     60
gttccgcgtt acataactta cggtaaatgg cccgcctggc tgaccgccca acgacccccg   120
cccattgacg tcaataatga cgtatgttcc catagtaacg ccaatagga ctttccattg    180 acgtcaatgg gtggagtatt tacggtaaac tgcccacttg gcagtacatc aagtgtatca   240
tatgccaagt acgcccccta ttgacgtcaa tgacggtaaa tggcccgcct ggcattatgc   300
ccagtacatg accttatggg actttcctac ttggcagtac atctacgtat tagtcatcgc   360
tattaccatg gtgatgcggt tttggcagta catcaatggg cgtggatagc ggtttgactc   420
acggggattt ccaagtctcc accccattga cgtcaatggg agtttgtttt ggcaccaaaa   480
tcaacgggac tttccaaaat gtcgtaacaa ctccgcccca ttgacgcaaa tgggcggtag   540
gcgtgtacgg tgggaggtct atataagcag agctggttta gtgaaccgtc agatccgcta   600
gcgattacgc caagctcgaa attaaccctc actaaaggga caaaagctg gagctccacc   660 gcggtggcgg ccgctctagc ccgggcggat cacgatcccg cgaaattaat acgactcact   720
ataggggaat tgtgagcgga taacaattcc cctctagaaa taattttgtt taactttaag   780
aaggagatat accatggcta gcatgactgg tggacagcaa atgggtcgcg gatccccggt   840
ctacgccaac ctcagcaact tcaacccggg tgcgctgagc agcggcggtg gggcgccctc   900
ctatggcgcg gccgggctgg cctttcctc gcagccgcag cagcagcagc agccgcctca   960
gccgccgcac cacttgcccc aacagatccc ggtgcagcac ccgcggctgc aagccctgaa  1020
ggaagagccg cagaccgtgc cggagatgcc gggagagacg ccgcccctgt ccctatcga  1080 catggagtct caggagcgga tcaaggcaga gaggaagcgc atgaggaacc gcattgccgc  1140
ctccaagtgc cggaaaagga agctggagcg gatcgctcgg ctagaggaaa agtgaaaac  1200 cttgaaagcg caaaactccg agctggcatc acggccaac atgctcaggg aacaggtggc  1260
acagcttaag cagaaagtca tgaaccacgt tctcgagctc aagagaagat ggaaaaagaa  1320
tttcatagcc gtctcagcag ccaaccgctt aagaaaatc tcatcctccg ggcacttgg   1380 atcagattat gatattccaa ctactgctag cgagaatttg tattttcagg gtggtaccaa  1440
aaccgcggct cttgcgcaac acgatgaagc cgtagacaac aaattcaaca agaacaaca   1500 aaacgcgttc tatgagatct acatttacc taacttaaac gaagaacaac gaaacgcctt  1560
catccaaagt ttaaaagatg acccaagcca aagcgctaac ctttagcag aagctaaaaa   1620 gctaaatgat gctcaggcgc cgaaagtaga caacaaattc aacaagaac aacaaaacgc   1680 gttctatgag atcttacatt tacctaactt aaacgaagaa caacgaaacg ccttcatcca   1740
aagtttaaaa gatgacccaa gccaaagcgc taaccttta gcagaagcta aaaagctaaa   1800
```

```
tgatgctcag gcgccgaaag tagacgcgaa ttctagctct gtaccccatc accatcacca    1860
tcactaagtc gacttcgatc gcccttccca acagttgcgc agcctgaatg gcgaatggag    1920
atccaatttt taagtgtata atgtgttaaa ctactgattc taattgtttg tgtattttag    1980
attcacagtc ccaaggctca tttcaggccc ctcagtcctc acagtctgtt catgatcata    2040
atcagccata ccacatttgt agaggtttta cttgctttaa aaacctccc acacctcccc    2100 ctgaacctga aacataaaat gaatgcaatt gttgttgtta acttgtttat tgcagcttat    2160
aatggttaca aataaagcaa tagcatcaca aatttcacaa ataaagcatt tttttcactg    2220
cattctagtt gtggttttgtc caaactcatc aatgtatctt aacgcgtaaa ttgtaagcgt    2280
taatattttg ttaaaattcg cgttaaattt ttgttaaatc agctcatttt ttaaccaata    2340
ggccgaaatc ggcaaaatcc cttataaatc aaaagaatag accgagatag ggttgagtgt    2400
tgttccagtt tggaacaaga gtccactatt aaagaacgtg gactccaacg tcaaagggcg    2460
aaaaaccgtc tatcagggcg atgggccact acgtgaacca tcaccctaat caagtttttt    2520
ggggtcgagg tgccgtaaag cactaaatcg gaaccctaaa gggagccccc gatttagagc    2580
ttgacgggga agccggcga acgtggcgag aaggaaggg aagaaagcga aggagcggg    2640 cgctagggcg ctggcaagtg tagcggtcac gctgcgcgta accaccacac ccgccgcgct    2700
taatgcgccg ctacagggcg cgtcaggtgg cacttttcgg ggaaatgtgc gcggaacccc    2760
tatttgttta ttttttctaaa tacattcaaa tatgtatccg ctcatgagac aataaccctg    2820
ataaatgctt caataatatt gaaaaaggaa gaatcctgag gcggaaagaa ccagctgtgg    2880
aatgtgtgtc agttagggtg tggaaagtcc ccaggctccc cagcaggcag aagtatgcaa    2940
agcatgcatc tcaattagtc agcaaccagg tgtggaaagt ccccaggctc cccagcaggc    3000
agaagtatgc aaagcatgca tctcaattag tcagcaacca tagtcccgcc cctaactccg    3060
cccatcccgc ccctaactcc gcccagttcc gcccattctc cgccccatgg ctgactaatt    3120 tttttttattt atgcagaggc cgaggccgcc tcggcctctg agctattcca gaagtagtga    3180
ggaggctttt ttggaggcct aggcttttgc aaagatcgat caagagacag gatgaggatc    3240
gtttcgcatg attgaacaag atggattgca cgcaggttct ccggccgctt gggtggagag    3300
gctattcggc tatgactggg cacaacagac aatcggctgc tctgatgccg ccgtgttccg    3360
gctgtcagcg caggggcgcc cggttctttt tgtcaagacc gacctgtccg gtgccctgaa    3420
tgaactgcaa gacgaggcag cgcggctatc gtggctggcc acgacgggcg ttccttgcgc    3480
agctgtgctc gacgttgtca ctgaagcggg aagggactgg ctgctattgg gcgaagtgcc    3540
ggggcaggat ctcctgtcat ctcaccttgc tcctgccgag aaagtatcca tcatggctga    3600
tgcaatgcgg cggctgcata cgcttgatcc ggctacctgc ccattcgacc accaagcgaa    3660
acatcgcatc gagcgagcac gtactcggat ggaagccggt cttgtcgatc aggatgatct    3720
ggacgaagaa catcaggggc tcgcgccagc cgaactgttc gccaggctca aggcgagcat    3780
gcccgacggc gaggatctcg tcgtgaccca tggcgatgcc tgcttgccga atatcatggt    3840
ggaaaatggc cgcttttctg gattcatcga ctgtggccgg ctgggtgtgg cggaccgcta    3900
tcaggacata gcgttggcta cccgtgatat tgctgaagaa cttggcggcg aatgggctga    3960
ccgcttcctc gtgctttacg gtatcgccgc tcccgattcg cagcgcatcg ccttctatcg    4020
ccttcttgac gagttcttct gagcgggact ctggggttcg aaatgaccga ccaagcgacg    4080
cccaacctgc catcacgaga tttcgattcc accgccgcct tctatgaaag gttgggcttc    4140
ggaatcgttt tccgggacgc cggctggatg atcctccagc gcggggatct catgctggag    4200
```

-continued

```
ttcttcgccc accctagggg gaggctaact gaaacacgga aggagacaat accggaagga    4260
acccgcgcta tgacggcaat aaaaagacag aataaaacgc acggtgttgg gtcgtttgtt    4320
cataaacgcg gggttcggtc ccagggctgg cactctgtcg ataccccacc gagacccat     4380 tggggccaat acgcccgcgt tcttcctttt tccccacccc accccccaag ttcgggtgaa    4440
ggcccagggc tcgcagccaa cgtcggggcg gcaggccctg ccatagcctc aggttactca    4500
tatatacttt agattgattt aaaacttcat ttttaattta aaaggatcta ggtgaagatc    4560 cttttttgata atctcatgac caaaatccct taacgtgagt tttcgttcca ctgagcgtca    4620
gaccccgtag aaaagatcaa aggatcttct tgagatcctt ttttctgcg cgtaatctgc     4680 tgcttgcaaa caaaaaaacc accgctacca gcggtggttt gtttgccgga tcaagagcta    4740
ccaactcttt ttccgaaggt aactggcttc agcagagcgc agataccaaa tactgtcctt    4800
ctagtgtagc cgtagttagg ccaccacttc aagaactctg tagcaccgcc tacatacctc    4860
gctctgctaa tcctgttacc agtggctgct gccagtggcg ataagtcgtg tcttaccggg    4920
ttggactcaa gacgatagtt accggataag gcgcagcggt cgggctgaac ggggggttcg    4980
tgcacacagc ccagcttgga gcgaacgacc tacaccgaac tgagatacct acagcgtgag    5040
ctatgagaaa gcgccacgct tcccgaaggg agaaaggcgg acaggtatcc ggtaagcggc    5100
agggtcggaa caggagagcg cacgagggag cttccagggg gaaacgcctg gtatctttat    5160
agtcctgtcg ggtttcgcca cctctgactt gagcgtcgat ttttgtgatg ctcgtcaggg    5220
gggcggagcc tatggaaaaa cgccagcaac gcggcctttt tacggttcct ggccttttgc    5280
tggccttttg ctcacatgtt ctttcctgcg ttatcccctg attctgtgga taaccgtatt    5340
accgcc                                                                5346
```

<210> SEQ ID NO 257
<211> LENGTH: 70
<212> TYPE: DNA
<213> ORGANISM: Artificial Sequence
<220> FEATURE:
<223> OTHER INFORMATION: PCR primer 5'SP6(O29)T7-FosCBPzz

<400> SEQUENCE: 257

```
gaatttaggt gacactatag aacaacaaca acaacaaaca acaacaaaat ggctagcatg    60
actggtggac                                                            70
```

<210> SEQ ID NO 258
<211> LENGTH: 20
<212> TYPE: DNA
<213> ORGANISM: Artificial Sequence
<220> FEATURE:
<223> OTHER INFORMATION: PCR primer 3'FosCBPzz

<400> SEQUENCE: 258

```
ggatctccat tcgccattca                                                 20
```

<210> SEQ ID NO 259
<211> LENGTH: 89
<212> TYPE: DNA
<213> ORGANISM: Artificial Sequence
<220> FEATURE:
<223> OTHER INFORMATION: DNA beit template DNA-Fos/Jun

<400> SEQUENCE: 259

```
cgactctgac ggcagtttac gtgactcatg agtcatgact catgagtcat gactcatgag    60
```
tcacgttaga acgcggctac aattaatac									89

<210> SEQ ID NO 260
<211> LENGTH: 21
<212> TYPE: DNA
<213> ORGANISM: Artificial Sequence
<220> FEATURE:
<223> OTHER INFORMATION: PCR primer 5'DNA

<400> SEQUENCE: 260
cgactctgac ggcagtttac g									21

<210> SEQ ID NO 261
<211> LENGTH: 26
<212> TYPE: DNA
<213> ORGANISM: Artificial Sequence
<220> FEATURE:
<223> OTHER INFORMATION: PCR primer 3'DNA

<400> SEQUENCE: 261
gtattaattg tagccgcgtt ctaacg									26

<210> SEQ ID NO 262
<211> LENGTH: 67
<212> TYPE: DNA
<213> ORGANISM: Artificial Sequence
<220> FEATURE:
<223> OTHER INFORMATION: main chain of adaptor

<400> SEQUENCE: 262
gaacaacaac aacaacaaac aacaacaaaa tgactggtgg acagcaaatg ggtgcggccg		60 cgaattc										67

<210> SEQ ID NO 263
<211> LENGTH: 68
<212> TYPE: DNA
<213> ORGANISM: Artificial Sequence
<220> FEATURE:
<223> OTHER INFORMATION: main chain of adaptor

<400> SEQUENCE: 263
gaacaacaac aacaacaaac aacaacaaaa tggctagcat gactggtgga cagcaaatgg		60 cgaattcc										68

<210> SEQ ID NO 264
<211> LENGTH: 32
<212> TYPE: DNA
<213> ORGANISM: Artificial Sequence
<220> FEATURE:
<223> OTHER INFORMATION: random primer for reverse transcription
<220> FEATURE:
<221> NAME/KEY: misc_feature
<222> LOCATION: (24)..(32)
<223> OTHER INFORMATION: n = a, g, c or t

<400> SEQUENCE: 264
tcatcgtcct tgtagtcaag cttnnnnnnn nn							32

<210> SEQ ID NO 265
<211> LENGTH: 58
<212> TYPE: DNA
<213> ORGANISM: Artificial Sequence
<220> FEATURE:
<223> OTHER INFORMATION: PCR 5' primer (O29)

<400> SEQUENCE: 265
ggaagatcta tttaggtgac actatagaac aacaacaaca acaaacaaca acaaaatg      58

<210> SEQ ID NO 266
<211> LENGTH: 36
<212> TYPE: DNA
<213> ORGANISM: Artificial Sequence
<220> FEATURE:
<223> OTHER INFORMATION: PCR 3' primer

<400> SEQUENCE: 266 tttttttct tgtcgtcatc gtccttgtag tcaagc                               36

<210> SEQ ID NO 267
<211> LENGTH: 3851
<212> TYPE: DNA
<213> ORGANISM: Artificial Sequence
<220> FEATURE:
<223> OTHER INFORMATION: pDrive vector

<400> SEQUENCE: 267
gcgcccaata cgcaaaccgc ctctccccgc gcgttggccg attcattaat gcagctggca    60
cgacaggttt cccgactgga aagcgggcag tgagcgcaac gcaattaatg tgagttagct   120
cactcattag gcaccccagg ctttacactt tatgcttccg gctcgtatgt tgtgtggaat   180
tgtgagcgga taacaatttc acacaggaaa cagctatgac catgattacg ccaagctcta   240
atacgactca ctatagggaa agctcggtac cacgcatgct gcagacgcgt tacgtatcgg   300
atccagaatt cgtgatatct gaattcgtcg acaagcttct cgagcctagg ctagctctag   360
accacacgtg tggggcccg agctcgcggc cgctgtattc tatagtgtca cctaaatggc    420
cgcacaattc actggccgtc gttttacaac gtcgtgactg ggaaaaccct ggcgttaccc   480
aacttaatcg ccttgcagca catcccccct tcgccagctg gcgtaatagc gaagaggccc   540
gcaccgatcg cccttcccaa cagttgcgca gcctgaatgg cgaatggaaa ttgtaagcgt   600
taatattttg ttaaaattcg cgttaaattt ttgttaaatc agctcatttt ttaaccaata   660
ggccgaaatc ggcaaaatcc cttataaatc aaaagaatag accgagatag ggttgagtgt   720
tgttccagtt tggaacaaga gtccactatt aaagaacgtg gactccaacg tcaaagggcg   780
aaaaaccgtc tatcagggcg atggcccact acgtgaacca tcaccctaat caagtttttt   840
ggggtcgagg tgccgtaaag cactaaatcg gaaccctaaa gggagccccc gatttagagc   900
ttgacgggga agccggcga acgtggcgag aaaggaaggg aagaaagcga aaggagcggg   960
cgctagggcg ctggcaagtg tagcggtcac gctgcgcgta accaccacac ccgccgcgct  1020
taatgcgccg ctacagggcg cgtcaggtgg cactttttcgg ggaaatgtgc gcggaacccc  1080
tatttgttta ttttttctaaa tacattcaaa tatgtatccg ctcatgagac aataaccctg  1140
ataaatgctt caataatatt gaaaaaggaa gagtatgagt attcaacatt tccgtgtcgc  1200
ccttattccc ttttttgcgg cattttgcct tcctgttttt gctcacccag aaacgctggt  1260
gaaagtaaaa gatgctgaag atcagttggg tgcacgagtg ggttacatcg aactggatct  1320
caacagcggt aagatccttg agagttttcg ccccgaagaa cgttttccaa tgatgagcac  1380
ttttaaagtt ctgctatgtg gcgcggtatt atcccgtatt gacgccgggc aagagcaact  1440
cggtcgccgc atacactatt ctcagaatga cttggttgag tactcaccag tcacagaaaa  1500
gcatcttacg gatggcatga cagtaagaga attatgcagt gctgccataa ccatgagtga  1560
taacactgcg gccaacttac ttctgacaac gatcggagga ccgaaggagc taaccgcttt  1620

-continued

```
tttgcacaac atgggggatc atgtaactcg ccttgatcgt tgggaaccgg agctgaatga    1680
agccatacca aacgacgagc gtgacaccac gatgcctgta gcaatggcaa caacgttgcg    1740
caaactatta actggcgaac tacttactct agcttcccgg caacaattaa tagactggat    1800
ggaggcggat aaagttgcag gaccacttct gcgctcggcc cttccggctg ctggtttat    1860 tgctgataaa tctggagccg tgagcgtgg gtctcgcggt atcattgcag cactggggcc    1920
agatggtaag ccctcccgta tcgtagttat ctacacgacg gggagtcagg caactatgga    1980
tgaacgaaat agacagatcg ctgagatagg tgcctcactg attaagcatt ggtaactgtc    2040
agaccaagtt tactcatata tactttagat tgatttaaaa cttcattttt aatttaaaag    2100
gatctaggtg aagatccttt ttgataatct catgaacaat aaaactgtct gcttacataa    2160
acagtaatac aaggggtgtt atgagccata ttcaacggga aacgtcttgc tctaggccgc    2220
gattaaattc caacatggat gctgatttat atgggtataa atgggctcgc gataatgtcg    2280
ggcaatcagg tgcgacaatc tatcgattgt atgggaagcc cgatgcgcca gagttgtttc    2340
tgaaacatgg caaaggtagc gttgccaatg atgttacaga tgagatggtc agactaaact    2400
ggctgacgga atttatgcct cttccgacca tcaagcattt tatccgtact cctgatgatg    2460
catggttact caccactgcg atccccggga aaacagcatt ccaggtatta gaagaatatc    2520
ctgattcagg tgaaaatatt gttgatgcgc tggcagtgtt cctgcgccgg ttgcattcga    2580
ttcctgtttg taattgtcct tttaacagcg atcgcgtatt tcgtctcgct caggcgcaat    2640
cacgaatgaa taacggtttg gttgatgcga gtgattttga tgacgagcgt aatggctggc    2700
ctgttgaaca agtctggaaa gaaatgcata acttttgccc attctcaccg gattcagtcg    2760
tcactcatgg tgatttctca cttgataacc ttatttttga cgaggggaaa ttaataggtt    2820
gtattgatgt tggacgagtc ggaatcgcag accgatacca ggatcttgcc atcctatgga    2880
actgcctcgg tgagttttct ccttcattac agaaacggct ttttcaaaaa tatggtattg    2940
ataatcctga tatgaataaa ttgcagtttc atttgatgct cgatgagttt ttctaagaat    3000
taattcatga ccaaaatccc ttaacgtgag ttttcgttcc actgagcgtc agaccccgta    3060
gaaaagatca aaggatcttc ttgagatcct ttttttctgc gcgtaatctg ctgcttgcaa    3120
acaaaaaaac caccgctacc agcggtggtt tgtttgccgg atcaagagct accaactctt    3180
tttccgaagg taactggctt cagcagagcg cagataccaa atactgtcct tctagtgtag    3240
ccgtagttag gccaccactt caagaactct gtagcaccgc ctacatacct cgctctgcta    3300
atcctgttac cagtggctgc tgccagtggc gataagtcgt gtcttaccgg gttggactca    3360
agacgatagt taccggataa ggcgcagcgg tcgggctgaa cggggggttc gtgcacacag    3420
cccagcttgg agcgaacgac ctacaccgaa ctgagatacc tacagcgtga gctatgagaa    3480
agcgccacgc ttcccgaagg gagaaaggcg gacaggtatc cggtaagcgg cagggtcgga    3540
acaggagagc gcacgaggga gcttccaggg ggaaacgcct ggtatcttta tagtcctgtc    3600
gggtttcgcc acctctgact tgagcgtcga ttttgtgat gctcgtcagg ggggcggagc    3660
ctatggaaaa acgccagcaa cgcggccttt ttacggttcc tggccttttg ctggcctttt    3720
gctcacatgt tctttcctgc gttatcccct gattctgtgg ataaccgtat taccgccttt    3780
gagtgagctg ataccgctcg ccgcagccga acgaccgagc gcagcgagtc agtgagcgag    3840
gaagcggaag a                                                        3851
```

<210> SEQ ID NO 268
<211> LENGTH: 58

<212> TYPE: DNA
<213> ORGANISM: Artificial Sequence
<220> FEATURE:
<223> OTHER INFORMATION: primer 5'F3

<400> SEQUENCE: 268
ggaagatcta tttaggtgac actatagaac aacaacaaca acaaacaaca acaaaatg      58

<210> SEQ ID NO 269
<211> LENGTH: 27
<212> TYPE: DNA
<213> ORGANISM: Artificial Sequence
<220> FEATURE:
<223> OTHER INFORMATION: primer 3'R3

<400> SEQUENCE: 269
ttttttttct cgagcttgtc gtcatcg      27

<210> SEQ ID NO 270
<211> LENGTH: 18
<212> TYPE: DNA
<213> ORGANISM: Artificial Sequence
<220> FEATURE:
<223> OTHER INFORMATION: primer SNAP19_F

<400> SEQUENCE: 270
aaaccctgct gcgtctaa      18

<210> SEQ ID NO 271
<211> LENGTH: 19
<212> TYPE: DNA
<213> ORGANISM: Artificial Sequence
<220> FEATURE:
<223> OTHER INFORMATION: primer SNAP19_R

<400> SEQUENCE: 271
atcatggatt gaagggcta      19

<210> SEQ ID NO 272
<211> LENGTH: 18
<212> TYPE: DNA
<213> ORGANISM: Artificial Sequence
<220> FEATURE:
<223> OTHER INFORMATION: primer Kif5C_F

<400> SEQUENCE: 272
tggtccggga caatgcag      18

<210> SEQ ID NO 273
<211> LENGTH: 19
<212> TYPE: DNA
<213> ORGANISM: Artificial Sequence
<220> FEATURE:
<223> OTHER INFORMATION: primer Kif5C_R

<400> SEQUENCE: 273
ggcctctttc agcgcactc      19

<210> SEQ ID NO 274
<211> LENGTH: 20
<212> TYPE: DNA
<213> ORGANISM: Artificial Sequence
<220> FEATURE:
<223> OTHER INFORMATION: primer kif5A_F

<400> SEQUENCE: 274
cagctggtac gtgacaatgc                                               20

<210> SEQ ID NO 275
<211> LENGTH: 20
<212> TYPE: DNA
<213> ORGANISM: Artificial Sequence
<220> FEATURE:
<223> OTHER INFORMATION: primer kif5A_R

<400> SEQUENCE: 275
cctccagggc cttaactctc                                               20

<210> SEQ ID NO 276
<211> LENGTH: 19
<212> TYPE: DNA
<213> ORGANISM: Artificial Sequence
<220> FEATURE:
<223> OTHER INFORMATION: primer Eef1d_F

<400> SEQUENCE: 276
gagaaccaga accttcgag                                                19

<210> SEQ ID NO 277
<211> LENGTH: 18
<212> TYPE: DNA
<213> ORGANISM: Artificial Sequence
<220> FEATURE:
<223> OTHER INFORMATION: primer Eef1d_R

<400> SEQUENCE: 277
tcggggagta ggtgaact                                                 18

<210> SEQ ID NO 278
<211> LENGTH: 18
<212> TYPE: DNA
<213> ORGANISM: Artificial Sequence
<220> FEATURE:
<223> OTHER INFORMATION: primer Nef3_F

<400> SEQUENCE: 278
ggaaccaagt gggaaatg                                                 18

<210> SEQ ID NO 279
<211> LENGTH: 19
<212> TYPE: DNA
<213> ORGANISM: Artificial Sequence
<220> FEATURE:
<223> OTHER INFORMATION: primer Nef3_R

<400> SEQUENCE: 279
ccctctagga gtttcctgt                                                19

<210> SEQ ID NO 280
<211> LENGTH: 20
<212> TYPE: DNA
<213> ORGANISM: Artificial Sequence
<220> FEATURE:
<223> OTHER INFORMATION: primer Jip-c3.1_F

<400> SEQUENCE: 280
agctggagaa agaggtgtca                                               20

<210> SEQ ID NO 281
<211> LENGTH: 18
<212> TYPE: DNA
<213> ORGANISM: Artificial Sequence
<220> FEATURE:
<223> OTHER INFORMATION: primer Jip-c3.1_R

<400> SEQUENCE: 281
cacaaactcc cggtgtag                                                   18

<210> SEQ ID NO 282
<211> LENGTH: 18
<212> TYPE: DNA
<213> ORGANISM: Artificial Sequence
<220> FEATURE:
<223> OTHER INFORMATION: primer Jip-c1_F

<400> SEQUENCE: 282
cctggaagac caaatcaa                                                   18

<210> SEQ ID NO 283
<211> LENGTH: 20
<212> TYPE: DNA
<213> ORGANISM: Artificial Sequence
<220> FEATURE:
<223> OTHER INFORMATION: primer Jip-c1_R

<400> SEQUENCE: 283
cattcaggat ctccactttc                                                 20

<210> SEQ ID NO 284
<211> LENGTH: 20
<212> TYPE: DNA
<213> ORGANISM: Artificial Sequence
<220> FEATURE:
<223> OTHER INFORMATION: primer EB2_F

<400> SEQUENCE: 284
ggacttgaag ctgaccgtag                                                 20

<210> SEQ ID NO 285
<211> LENGTH: 18
<212> TYPE: DNA
<213> ORGANISM: Artificial Sequence
<220> FEATURE:
<223> OTHER INFORMATION: primer EB2_R

<400> SEQUENCE: 285
caatgatgcc cgagatga                                                   18

<210> SEQ ID NO 286
<211> LENGTH: 19
<212> TYPE: DNA
<213> ORGANISM: Artificial Sequence
<220> FEATURE:
<223> OTHER INFORMATION: primer Cspg6_F

<400> SEQUENCE: 286
gctctgaatg atgaaatcc                                                  19

<210> SEQ ID NO 287
<211> LENGTH: 20
<212> TYPE: DNA
<213> ORGANISM: Artificial Sequence
<220> FEATURE:
<223> OTHER INFORMATION: primer Cspg6_R

<400> SEQUENCE: 287
tctgatgttg tggcagtaag                                                 20

<210> SEQ ID NO 288
<211> LENGTH: 18
<212> TYPE: DNA
<213> ORGANISM: Artificial Sequence
<220> FEATURE:
<223> OTHER INFORMATION: primer Mapk8ip3_F

<400> SEQUENCE: 288
cattgctaag gttgacca                                                 18

<210> SEQ ID NO 289
<211> LENGTH: 20
<212> TYPE: DNA
<213> ORGANISM: Artificial Sequence
<220> FEATURE:
<223> OTHER INFORMATION: primer Mapk8ip3_R

<400> SEQUENCE: 289
gttactgcct ctgacttgac                                               20

<210> SEQ ID NO 290
<211> LENGTH: 20
<212> TYPE: DNA
<213> ORGANISM: Artificial Sequence
<220> FEATURE:
<223> OTHER INFORMATION: primer Jip-xc3.2_F

<400> SEQUENCE: 290
aggctctcat taccacagat                                               20

<210> SEQ ID NO 291
<211> LENGTH: 19
<212> TYPE: DNA
<213> ORGANISM: Artificial Sequence
<220> FEATURE:
<223> OTHER INFORMATION: primer Jip-c3.2_R

<400> SEQUENCE: 291
ctcgcgcttt cattaattc                                                19

<210> SEQ ID NO 292
<211> LENGTH: 18
<212> TYPE: DNA
<213> ORGANISM: Artificial Sequence
<220> FEATURE:
<223> OTHER INFORMATION: primer GFAP_F

<400> SEQUENCE: 292
ggagggccaa agcctcaa                                                 18

<210> SEQ ID NO 293
<211> LENGTH: 22
<212> TYPE: DNA
<213> ORGANISM: Artificial Sequence
<220> FEATURE:
<223> OTHER INFORMATION: primer GFAP_R

<400> SEQUENCE: 293
cctccagcaa tttcctgtag gt                                            22

<210> SEQ ID NO 294
<211> LENGTH: 19
<212> TYPE: DNA
<213> ORGANISM: Artificial Sequence
<220> FEATURE:
<223> OTHER INFORMATION: primer Jip-c8_F

```
<400> SEQUENCE: 294
tggtcctcaa ggcttatca                                                    19

<210> SEQ ID NO 295
<211> LENGTH: 20
<212> TYPE: DNA
<213> ORGANISM: Artificial Sequence
<220> FEATURE:
<223> OTHER INFORMATION: primer Jip-c8_R

<400> SEQUENCE: 295
atctgctcct ccatctcttt                                                   20

<210> SEQ ID NO 296
<211> LENGTH: 22
<212> TYPE: DNA
<213> ORGANISM: Artificial Sequence
<220> FEATURE:
<223> OTHER INFORMATION: primer Kif5B_F

<400> SEQUENCE: 296
cggagcagtg gaaaaagaag ta                                                22

<210> SEQ ID NO 297
<211> LENGTH: 18
<212> TYPE: DNA
<213> ORGANISM: Artificial Sequence
<220> FEATURE:
<223> OTHER INFORMATION: primer Kif5B_R

<400> SEQUENCE: 297
acgccaacgg tttagctc                                                     18

<210> SEQ ID NO 298
<211> LENGTH: 21
<212> TYPE: DNA
<213> ORGANISM: Artificial Sequence
<220> FEATURE:
<223> OTHER INFORMATION: primer 5'M13_F

<400> SEQUENCE: 298
gttttcccag tcacgacgtt g                                                 21

<210> SEQ ID NO 299
<211> LENGTH: 24
<212> TYPE: DNA
<213> ORGANISM: Artificial Sequence
<220> FEATURE:
<223> OTHER INFORMATION: primer 3'M13_R

<400> SEQUENCE: 299
gaaacagcta tgaccatgat tacg                                              24
```

PROTEIN FORMING COMPLEX WITH C-JUN PROTEIN, NUCLEIC ACID ENCODING THE SAME AND METHOD OF USING THE SAME

This application is a U.S. national stage of International Application No. PCT/JP2004/017306 filed Nov. 19, 2004.

TECHNICAL FIELD

The present invention relates to proteins that interact with c-Jun, nucleic acids encoding them and inhibitors utilizing them as well as methods for detecting an interaction and screening methods.

At present, genomic nucleotide sequences of various organisms are going to be elucidated. In researches of genomic sequences, there are expected, as post-sequencing researches of the second act, researches of analyzing meanings of the elucidated genomic information, i.e., structural and functional analyses of genes and proteins (Non-patent documents 1 and 2), analyses of protein/protein and protein/nucleic acid interactions (Non-patent documents 3 and 4) and so forth.

On the basis of analyses of networks of interactions between protein and protein, protein and nucleic acid and so forth in post-sequencing genomic functional analyses utilizing such techniques as described above, it is expected to create drugs and so forth standing on discoveries of novel functions of known proteins or important biological enzymes such as novel proteins that have been unknown so far.

As methods for detecting interactions between proteins, the immunoprecipitation (Non-patent document 5), pull-down assay based on a GST fusion protein (Non-patent document 6), TAP method (Non-patent document 7), yeast two-hybrid method (Non-patent document 8) and so forth are known so far. Further, as methods for comprehensive analysis of interactions between proteins in the post-sequencing genomic functional analyses utilizing the "assignment of gene (genotype) and protein (phenotype)" born as a tool of the evolutionary molecular engineering, there are the in vitro virus method (Non-patent documents 9 and 10, Patent documents 1 and 2), STABLE method (Non-patent document 11), phage display method (Non-patent document 12), ribosome display method (Non-patent document 13, Patent document 3), mRNA-peptide fusion method (mRNA display method, Non-patent document 14), and so forth.

Furthermore, the surface plasmon resonance method, fluorescence resonance energy transfer method, fluorescence depolarization method, evanescent-field imaging method, fluorescence correlation spectroscopy, fluorescent imaging method, enzyme linked immunosorbent assay and so forth are also known. Moreover, methods of modifying C-terminals of proteins in a translation system utilizing a nucleic acid derivatives such as puromycin have been previously proposed (Patent documents 4 and 5). These methods have advantages that functions of proteins are more unlikely to be damaged compared with the conventional chemical modification methods and the fluorescent protein fusion methods.

In the field of life science, sequence analysis of the human genome was completed, and genome researches rush into functional analyses of genes of the post-genome age. Thus, innovative drug creation based on comprehensive genomic functional analyses and so forth are expected. There is desired a technique that enables comprehensive analysis of genes and proteins, which have been independently studied so far, for example, a technique of analyzing various cofactors of transcription control factors as target proteins of drug creation at once and so forth. As a transcription control factor, the c-Fos/c-Jun proteins are known well.

The c-jun gene was isolated as a human homolog of which amino acid sequence indicates more than 80% identity or more with an oncogene, v-jun which is possessed by avian sarcoma virus 17 (the v-jun afterward became known to be derived form chicken genome and be conserved among the many species) (Non-patent document 15). The c-jun is a transcription control facter detected in many cytomas as a typical immediate early gene in connection with a proliferataion stimulus. As known falimy genes, junB and junC are known. Generation of a null-mutated mouse by gene targeting and analysis conducted by Hilberg et al. confirmed that c-Jun-lacking mice exhibit impaired hepatogenesis and embryonically lethal. This suggested that an essential involvement of the c-jun gene in hepatogenesis (Non-patent document 16).

It is known that c-Jun has a trans-activation domain controlling transcription, at its N terminal, and a bZIP domain forming a homo/hetero dimer and binding a DNA element, at its C terminal (Non-patent document 17). Recently, screening by the two-hybrid method has been revealed that BAF60a, a subunit of the SWI/SNF chromatin remodeling complex interacts with the c-Fos/c-Jun complex (Non-patent document 18), and it is becoming known that the gene expression regulation by c-Jun is a complicated mechanism through structual change of chromatin, not a simple transcription model. Because there are many factors interacting with c-Jun, there is a high possibility that c-Jun plays an important role as a hub of protein-protein interactions in the maintenance of the complicated mechanism. The regulation of chromatin is an esstial mechanism involved in development and differentiation and is associated with various diseases including cancer. Thus, comprehensive analyses of factors interacting with c-Jun will make an important impact on not only basic study but also drug creation. However, such a thorough 1:1 molecule analysis technique as the two-hybrid method takes enormous time and labor and, therefore, is not practical.

<Non-Patent Document 1>
Saegusa A., Nature, 401, 6751 (1999)<

<Non-Patent Document 2>
Dalton R, Abbott A., Nature, 402, 6763 (1999)

<Non-Patent Document 3>
Etsuko Miyamoto, Hiroshi Yanagawa, Series Genome Science of Post-sequencing 3, Proteomics, pp. 136-145 (2000)

<Non-Patent Document 4>
Etsuko Miyamoto, Hiroshi Yanagawa, PROTEIN, NUCLEIC ACID AND ENZYME, 46(2), pp. 138-147 (2001)

<Non-Patent Document 5>
Xiong et al., Nature, 366, 701-704 (1993)

<Non-Patent Document 6>
Kaelin, et al., Cell, 64, 521-532 (1991)

<Non-Patent Document 7>
Guillaume Rigaut, et al., Nature Biotechnology, 17, 1030 (1999)

<Non-Patent Document 8>
Fields S., Song O., Nature, 340, 245 (1989)

<Non-Patent Document 9>
Miyamoto-Sato E., et al., Viva Origino, 25, 35 (1997)

<Non-Patent Document 10>
Nemoto N., et al., FEBS Lett., 414, 405 (1997)

<Patent Document 1>
International Publication WO98/16636

<Patent Document 2>
International Publication WO02/46395

<Non-Patent Document 11>
Doi N., Yanagawa H., FEBS Lett., 457, 227 (1999)

<Non-Patent Document 12>
Smith G. P., Science, 228, 1315 (1985)

<Non-Patent Document 13>
Mattheakis, L. C. et al., Proc. Natl. Acad. Sci. USA, 91, 9022-9026 (1994)

<Patent Document 3>
International Publication WO95/11922

<Non-Patent Document 14>
Roberts R. W. and Szostak J. W., Proc. Natl. Acad. Sci. USA, 94, 12297 (1997)

<Patent Document 4>
U.S. Pat. No. 6,228,994

<Patent Document 5>
International Publication WO02/48347

<Non-Patent Document 15>
Bohmann, D.; Bos, T. J.; Admon, A.; Nishimura, T.; Vogt, P. K.; Tjian, R. Science 238, 1386-1392 (1987)

<Non-Patent Document 16>
Hilberg, F.; Aguzzi, A.; Howells, N.; Wagner, E. F. Nature 365, 179-181 (1993)

<Non-Patent Document 17>
Chinenov Y, Kerppola T K. Oncogene. 20, 2438-2452 (2001)

<Non-Patent Document 18>
Ito T, Yamauchi M, Nishina M, Yamamichi N, Mizutani T, Ui M, Murakami M, Iba H. J Biol. Chem. 276, 2852-2857 (2001)

DISCLOSURE OF THE INVENTION

An object of the present invention is to provide a complex that interacts with the c-Jun protein, which is well known as a transcription control factor, as a target protein.

The inventors of the present invention conducted comprehensive analysis of transcription control factor complexes in a mouse brain cDNA library with c-Jun as a bait by using two of techniques, the cotranslation screening of in vitro virus (IVV) and the C-terminal labeling method (U.S. Pat. No. 6,228,994, WO02/48347) named puromycin technologies, which have been researched on the basis of the aforementioned in vitro virus method as a method for comprehensive analysis as a one-to-multiple molecule-analysis method replacing the method, and thereby attempted to analyze proteins unknown so far, proteins known so far, but unknown to form a complex with the c-Jun protein, and so forth. The expression of "a protein that form a complex" used herein refers to a protein that directly or indirectly interacts with the c-Jun protein.

A further object of the present invention is to provide a protein that interacts with c-Jun and an inhibitor utilizing it, as well as a method for detecting an interaction and method for screening.

The inventors of the present invention found novel proteins that interact with c-Jun by the cotranslation screening using IVV, also found that certain known proteins interacted with c-Jun, and accomplished the present invention. The present invention thus provides the followings.

(1) An inhibitor for an interaction between a protein that interacts with a c-Jun protein and the c-Jun protein, which comprises a protein of the following (a) or (b) as an active ingredient:
(a) a protein comprising any one of the amino acid sequences of SEQ ID NOS: 1 to 69,
(b) a protein that comprises any one of the amino acid sequences of SEQ ID NOS: 1 to 69 including deletion, substitution or addition of one or several amino acid residues and interacts with the c-Jun protein.

(2) The inhibitor according to (1), wherein the protein as the active ingredient comprises any one of the amino acid sequences of SEQ ID NOS: 1 to 69.

(3) The inhibitor according to (2), wherein the protein is a protein translated from a nucleic acid of the following (a) or (b):
(a) a nucleic acid comprising any one of the nucleotide sequences of SEQ ID NOS: 126 to 199,
(b) a nucleic acid that hybridizes with a nucleic acid comprising any one of the nucleotide sequences of SEQ ID NOS: 126 to 199 under a stringent condition and encodes a protein that interacts with the c-Jun protein.

(4) The inhibitor according to (3), wherein the nucleic acid comprises any one of the nucleotide sequences of SEQ ID NOS: 126 to 199.

(5) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising any one of the amino acid sequences of SEQ ID NOS: 1 to 69,
(b) a protein that comprises any one of the amino acid sequences of SEQ ID NOS: 1 to 69 including deletion, substitution or addition of one or several amino acid residues and interacts with a c-Jun protein,
(a') a nucleic acid comprising any one of the nucleotide sequences of SEQ ID NOS: 126 to 199,
(b') a nucleic acid that hybridizes with a nucleic acid comprising any one of the nucleotide sequences of SEQ ID NOS: 126 to 199 under a stringent condition and encodes a protein that interacts with a c-Jun protein.

(6) The method according to (5), wherein the protein comprises any one of the amino acid sequences of SEQ ID NOS: 1 to 69.

(7) The method according to (5), wherein the nucleic acid comprises any one of the nucleotide sequences of SEQ ID NOS: 126 to 199.

(8) A method for screening for a prey that interacts with a bait, which comprises the step of detecting an interaction between the bait and a prey by the method according to any one of (5) to (7) and the step of selecting a prey for which an interaction is detected.

(9) An inhibitor for an interaction between a protein that interacts with a c-Jun protein and the c-Jun protein, which comprises a protein of the following (a) or (b) as an active ingredient:
(a) a protein comprising any one of the amino acid sequences of SEQ ID NOS: 70 to 87,
(b) a protein that comprises any one of the amino acid sequences of SEQ ID NOS: 70 to 87 including deletion, substitution or addition of one or several amino acid residues and interacts with the c-Jun protein.

(10) The inhibitor according to (9), wherein the protein as the active ingredient comprises any one of the amino acid sequences of SEQ ID NOS: 70 to 87.

(11) The inhibitor according to (9), wherein the protein is a protein translated from a nucleic acid of the following (a) or (b):
(a) a nucleic acid comprising any one of the nucleotide sequences of SEQ ID NOS: 200 to 217,
(b) a nucleic acid that hybridizes with a nucleic acid comprising any one of the nucleotide sequences of SEQ ID NOS: 200 to 217 under a stringent condition and encodes a protein that interacts with the c-Jun protein.

(12) The inhibitor according to (11), wherein the nucleic acid comprises any one of the nucleotide sequences of SEQ ID NOS: 200 to 217.

(13) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising any one of the amino acid sequences of SEQ ID NOS: 70 to 87,
(b) a protein that comprises any one of the amino acid sequences of SEQ ID NOS: 70 to 87 including deletion, substitution or addition of one or several amino acid residues and interacts with a c-Jun protein,
(a') a nucleic acid comprising any one of the nucleotide sequences of SEQ ID NOS: 200 to 217,
(b') a nucleic acid that hybridizes with a nucleic acid comprising any one of the nucleotide sequences of SEQ ID NOS: 200 to 217 under a stringent condition and encodes a protein that interacts with a c-Jun protein.

(14) The method according to (13), wherein the protein comprises any one of the amino acid sequences of SEQ ID NOS: 70 to 87.

(15) The method according to (13), wherein the nucleic acid comprises any one of the nucleotide sequences of SEQ ID NOS: 200 to 217.

(16) A method for screening for a prey that interacts with a bait, which comprises the step of detecting an interaction between the bait and a prey by the method according to any one of (13) to (15) and the step of selecting a prey for which an interaction is detected.

(17) An inhibitor for an interaction between a protein that interacts with a c-Jun protein and the c-Jun protein, which comprises a protein of the following (a) or (b) as an active ingredient:
(a) a protein comprising any one of the amino acid sequences of SEQ ID NOS: 88 to 94,
(b) a protein that comprises any one of the amino acid sequences of SEQ ID NOS: 88 to 94 including deletion, substitution or addition of one or several amino acid residues and interacts with the c-Jun protein.

(18) The inhibitor according to (17), wherein the protein as the active ingredient comprises any one of the amino acid sequences of SEQ ID NOS: 88 to 94.

(19) The inhibitor according to (17), wherein the protein is a protein translated from a nucleic acid of the following (a) or (b):
(a) a nucleic acid comprising any one of the nucleotide sequences of SEQ ID NOS: 218 to 224,
(b) a nucleic acid that hybridizes with a nucleic acid comprising any one of the nucleotide sequences of SEQ ID NOS: 218 to 224 under a stringent condition and encodes a protein that interacts with the c-Jun protein.

(20) The inhibitor according to (19), wherein the nucleic acid comprises any one of the nucleotide sequences of SEQ ID NOS: 218 to 224.

(21) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising any one of the amino acid sequences of SEQ ID NOS: 88 to 94,
(b) a protein that comprises any one of the amino acid sequences of SEQ ID NOS: 88 to 94 including deletion, substitution or addition of one or several amino acid residues and interacts with a c-Jun protein,
(a') a nucleic acid comprising any one of the nucleotide sequences of SEQ ID NOS: 218 to 224,
(b') a nucleic acid that hybridizes with a nucleic acid comprising any one of the nucleotide sequences of SEQ ID NOS: 218 to 224 under a stringent condition and encodes a protein that interacts with a c-Jun protein.

(22) The method according to (21), wherein the protein comprises any one of the amino acid sequences of SEQ ID NOS: 88 to 94.

(23) The method according to (21), wherein the nucleic acid comprises any one of the nucleotide sequences of SEQ ID NOS: 218 to 224.

(24) A method for screening for a prey that interacts with a bait, which comprises the step of detecting an interaction between the bait and a prey by the method according to any one of (21) to (23) and the step of selecting a prey for which an interaction is detected.

(25) An inhibitor for an interaction between a protein that interacts with a c-Jun protein and the c-Jun protein, which comprises a protein of the following (a) or (b) as an active ingredient:
(a) a protein comprising any one of the amino acid sequences of SEQ ID NOS: 95 to 99,
(b) a protein that comprises any one of the amino acid sequences of SEQ ID NOS: 95 to 99 including deletion, substitution or addition of one or several amino acid residues and interacts with the c-Jun protein.

(26) The inhibitor according to (25), wherein the protein as the active ingredient comprises any one of the amino acid sequences of SEQ ID NOS: 95 to 99.

(27) The inhibitor according to (25), wherein the protein is a protein translated from a nucleic acid of the following (a) or (b):
(a) a nucleic acid comprising any one of the nucleotide sequences of SEQ ID NOS: 225 to 229,
(b) a nucleic acid that hybridizes with a nucleic acid comprising any one of the nucleotide sequences of SEQ ID NOS: 225 to 229 under a stringent condition and encodes a protein that interacts with the c-Jun protein.

(28) The inhibitor according to (27), wherein the nucleic acid comprises any one of the nucleotide sequences of SEQ ID NOS: 225 to 229.

(29) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising any one of the amino acid sequences of SEQ ID NOS: 95 to 99,
(b) a protein that comprises any one of the amino acid sequences of SEQ ID NOS: 95 to 99 including deletion, substitution or addition of one or several amino acid residues and interacts with a c-Jun protein, (a') a nucleic acid comprising any one of the nucleotide sequences of SEQ ID NOS: 225 to 229, (b') a nucleic acid that hybridizes with a nucleic acid comprising any one of the nucleotide sequences of SEQ ID NOS: 225 to 229 under a stringent condition and encodes a protein that interacts with a c-Jun protein.

(30) The method according to (29), wherein the protein comprises any one of the amino acid sequences of SEQ ID NOS: 95 to 99.

(31) The method according to (29), wherein the nucleic acid comprises any one of the nucleotide sequences of SEQ ID NOS: 225 to 229.

(32) A method for screening for a prey that interacts with a bait, which comprises the step of detecting an interaction between the bait and a prey by the method according to any one of (29) to (31) and the step of selecting a prey for which an interaction is detected.

(33) An inhibitor for an interaction between a protein that interacts with a c-Jun protein and the c-Jun protein, which comprises a protein of the following (a) or (b) as an active ingredient:

(a) a protein comprising any one of the amino acid sequences of SEQ ID NOS: 100 to 104, (b) a protein that comprises any one of the amino acid sequences of SEQ ID NOS: 100 to 104 including deletion, substitution or addition of one or several amino acid residues and interacts with the c-Jun protein.

(34) The inhibitor according to (33), wherein the protein as the active ingredient comprises any one of the amino acid sequences of SEQ ID NOS: 100 to 104.

(35) The inhibitor according to (33), wherein the protein is a protein translated from a nucleic acid of the following (a) or (b):

(a) a nucleic acid comprising any one of the nucleotide sequences of SEQ ID NOS: 230 to 234, (b) a nucleic acid that hybridizes with a nucleic acid comprising any one of the nucleotide sequences of SEQ ID NOS: 230 to 234 under a stringent condition and encodes a protein that interacts with the c-Jun protein.

(36) The inhibitor according to (3), wherein the nucleic acid comprises any one of the nucleotide sequences of SEQ ID NOS: 230 to 234.

(37) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):

(a) a protein comprising any one of the amino acid sequences of SEQ ID NOS: 100 to 104, (b) a protein that comprises any one of the amino acid sequences of SEQ ID NOS: 100 to 104 including deletion, substitution or addition of one or several amino acid residues and interacts with a c-Jun protein, (a') a nucleic acid comprising any one of the nucleotide sequences of SEQ ID NOS: 230 to 234, (b') a nucleic acid that hybridizes with a nucleic acid comprising any one of the nucleotide sequences of SEQ ID NOS: 230 to 234 under a stringent condition and encodes a protein that interacts with a c-Jun protein.

(38) The method according to (37), wherein the protein comprises any one of the amino acid sequences of SEQ ID NOS: 100 to 104.

(39) The method according to (37), wherein the nucleic acid comprises any one of the nucleotide sequences of SEQ ID NOS: 230 to 234.

(40) A method for screening for a prey that interacts with a bait, which comprises the step of detecting an interaction between the bait and a prey by the method according to any one of (37) to (39) and the step of selecting a prey for which an interaction is detected.

(41) An inhibitor for an interaction between a protein that interacts with a c-Jun protein and the c-Jun protein, which comprises a protein of the following (a) or (b) as an active ingredient:

(a) a protein comprising any one of the amino acid sequences of SEQ ID NOS: 105 to 108, (b) a protein that comprises any one of the amino acid sequences of SEQ ID NOS: 105 to 108 including deletion, substitution or addition of one or several amino acid residues and interacts with the c-Jun protein.

(42) The inhibitor according to (41), wherein the protein as the active ingredient comprises any one of the amino acid sequences of SEQ ID NOS: 105 to 108.

(43) The inhibitor according to (41), wherein the protein is a protein translated from a nucleic acid of the following (a) or (b):

(a) a nucleic acid comprising any one of the nucleotide sequences of SEQ ID NOS: 235 to 238, (b) a nucleic acid that hybridizes with a nucleic acid comprising any one of the nucleotide sequences of SEQ ID NOS: 235 to 238 under a stringent condition and encodes a protein that interacts with the c-Jun protein.

(44) The inhibitor according to (43), wherein the nucleic acid comprises any one of the nucleotide sequences of SEQ ID NOS: 235 to 238.

(45) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):

(a) a protein comprising any one of the amino acid sequences of SEQ ID NOS: 105 to 108, (b) a protein that comprises any one of the amino acid sequences of SEQ ID NOS: 105 to 108 including deletion, substitution or addition of one or several amino acid residues and interacts with a c-Jun protein, (a') a nucleic acid comprising any one of the nucleotide sequences of SEQ ID NOS: 235 to 238, (b') a nucleic acid that hybridizes with a nucleic acid comprising any one of the nucleotide sequences of SEQ ID NOS: 235 to 238 under a stringent condition and encodes a protein that interacts with a c-Jun protein.

(46) The method according to (45), wherein the protein comprises any one of the amino acid sequences of SEQ ID NOS: 105 to 108.

(47) The method according to (45), wherein the nucleic acid comprises any one of the nucleotide sequences of SEQ ID NOS: 235 to 238.

(48) A method for screening for a prey that interacts with a bait, which comprises the step of detecting an interaction between the bait and a prey by the method according to any one of (45) to (47) and the step of selecting a prey for which an interaction is detected.

(49) An inhibitor for an interaction between a protein that interacts with a c-Jun protein and the c-Jun protein, which comprises a protein of the following (a) or (b) as an active ingredient:
(a) a protein comprising any one of the amino acid sequences of SEQ ID NOS: 109 to 111,
(b) a protein that comprises any one of the amino acid sequences of SEQ ID NOS: 109 to 111 including deletion, substitution or addition of one or several amino acid residues and interacts with the c-Jun protein.

(50) The inhibitor according to (49), wherein the protein as the active ingredient comprises any one of the amino acid sequences of SEQ ID NOS: 109 to 111.

(51) The inhibitor according to (49), wherein the protein is a protein translated from a nucleic acid of the following (a) or (b):
(a) a nucleic acid comprising any one of the nucleotide sequences of SEQ ID NOS: 239 to 241,
(b) a nucleic acid that hybridizes with a nucleic acid comprising any one of the nucleotide sequences of SEQ ID NOS: 239 to 241 under a stringent condition and encodes a protein that interacts with the c-Jun protein.

(52) The inhibitor according to (51), wherein the nucleic acid comprises any one of the nucleotide sequences of SEQ ID NOS: 239 to 241.

(53) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising any one of the amino acid sequences of SEQ ID NOS: 109 to 111,
(b) a protein that comprises any one of the amino acid sequences of SEQ ID NOS: 109 to 111 including deletion, substitution or addition of one or several amino acid residues and interacts with a c-Jun protein,
(a') a nucleic acid comprising any one of the nucleotide sequences of SEQ ID NOS: 239 to 241,
(b') a nucleic acid that hybridizes with a nucleic acid comprising any one of the nucleotide sequences of SEQ ID NOS: 239 to 241 under a stringent condition and encodes a protein that interacts with a c-Jun protein.

(54) The method according to (53), wherein the protein comprises any one of the amino acid sequences of SEQ ID NOS: 109 to 111.

(55) The method according to (53), wherein the nucleic acid comprises any one of the nucleotide sequences of SEQ ID NOS: 239 to 241.

(56) A method for screening for a prey that interacts with a bait, which comprises the step of detecting an interaction between the bait and a prey by the method according to any one of (53) to (55) and the step of selecting a prey for which an interaction is detected.

(57) An inhibitor for an interaction between a protein that interacts with a c-Jun protein and the c-Jun protein, which comprises a protein of the following (a) or (b) as an active ingredient:
(a) a protein comprising the amino acid sequence of SEQ ID NO: 112 or 113,
(b) a protein that comprises the amino acid sequence of SEQ ID NO: 112 or 113 including deletion, substitution or addition of one or several amino acid residues and interacts with the c-Jun protein.

(58) The inhibitor according to (57), wherein the protein as the active ingredient comprises the amino acid sequence of SEQ ID NO: 112 or 113.

(59) The inhibitor according to (57), wherein the protein is a protein translated from a nucleic acid of the following (a) or (b):
(a) a nucleic acid comprising the nucleotide sequence of SEQ ID NO: 242 ro 243,
(b) a nucleic acid that hybridizes with a nucleic acid comprising the nucleotide sequence of SEQ ID NO: 242 or 243 under a stringent condition and encodes a protein that interacts with the c-Jun protein.

(60) The inhibitor according to (59), wherein the nucleic acid comprises the nucleotide sequence of SEQ ID NO: 242 or 243.

(61) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising the amino acid sequence of SEQ ID NO: 112 or 113,
(b) a protein that comprises the amino acid sequence of SEQ ID NO: 112 or 113 including deletion, substitution or addition of one or several amino acid residues and interacts with a c-Jun protein,
(a') a nucleic acid comprising the nucleotide sequence of SEQ ID NO: 242 or 243,
(b') a nucleic acid that hybridizes with a nucleic acid comprising the nucleotide sequence of SEQ ID NO: 242 or 243 under a stringent condition and encodes a protein that interacts with a c-Jun protein.

(62) The method according to (61), wherein the protein comprises the amino acid sequence of SEQ ID NO: 112 or 113.

(63) The method according to (61), wherein the nucleic acid comprises the nucleotide sequence of SEQ ID NO: 242 or 243.

(64) A method for screening for a prey that interacts with a bait, which comprises the step of detecting an interaction between the bait and a prey by the method according to any one of (61) to (63) and the step of selecting a prey for which an interaction is detected.

(65) An inhibitor for an interaction between a protein that interacts with a c-Jun protein and the c-Jun protein, which comprises a protein of the following (a) or (b) as an active ingredient:
(a) a protein comprising the amino acid sequence of SEQ ID NO: 114 or 115,
(b) a protein that comprises the amino acid sequence of SEQ ID NO: 114 or 115 including deletion, substitution or addition of one or several amino acid residues and interacts with the c-Jun protein.

(66) The inhibitor according to (65), wherein the protein as the active ingredient comprises the amino acid sequence of SEQ ID NO: 114 or 115.

(67) The inhibitor according to (65), wherein the protein is a protein translated from a nucleic acid of the following (a) or (b):
(a) a nucleic acid comprising the nucleotide sequence of SEQ ID NO: 244 or 245,
(b) a nucleic acid that hybridizes with a nucleic acid comprising the nucleotide sequence of SEQ ID NO: 244 or 245 under a stringent condition and encodes a protein that interacts with the c-Jun protein.

(68) The inhibitor according to (67), wherein the nucleic acid comprises the nucleotide sequence of SEQ ID NO: 244 or 245.

(69) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):

(a) a protein comprising the amino acid sequence of SEQ ID NO: 114 or 115, (b) a protein that comprises the amino acid sequence of SEQ ID NO: 114 or 115 including deletion, substitution or addition of one or several amino acid residues and interacts with a c-Jun protein, (a') a nucleic acid comprising the nucleotide sequence of SEQ ID NO: 244 or 245, (b') a nucleic acid that hybridizes with a nucleic acid comprising the nucleotide sequence of SEQ ID NO: 244 or 245 under a stringent condition and encodes a protein that interacts with a c-Jun protein.

(70) The method according to (69), wherein the protein comprises the amino acid sequence of SEQ ID NO: 114 or 115.

(71) The method according to (69), wherein the nucleic acid comprises the nucleotide sequence of SEQ ID NO: 244 or 245.

(72) A method for screening for a prey that interacts with a bait, which comprises the step of detecting an interaction between the bait and a prey by the method according to any one of (69) to (71) and the step of selecting a prey for which an interaction is detected.

(73) An inhibitor for an interaction between a protein that interacts with a c-Jun protein and the c-Jun protein, which comprises a protein of the following (a) or (b) as an active ingredient:

(a) a protein comprising the amino acid sequence of SEQ ID NO: 116 or 117, (b) a protein that comprises the amino acid sequence of SEQ ID NO: 116 or 117 including deletion, substitution or addition of one or several amino acid residues and interacts with the c-Jun protein.

(74) The inhibitor according to (73), wherein the protein as the active ingredient comprises the amino acid sequence of SEQ ID NO: 116 or 117.

(75) The inhibitor according to (73), wherein the protein is a protein translated from a nucleic acid of the following (a) or (b):

(a) a nucleic acid comprising the nucleotide sequence of SEQ ID NO: 246 or 247, (b) a nucleic acid that hybridizes with a nucleic acid comprising the nucleotide sequence of SEQ ID NO: 246 or 247 under a stringent condition and encodes a protein that interacts with the c-Jun protein.

(76) The inhibitor according to (75), wherein the nucleic acid comprises the nucleotide sequence of SEQ ID NO: 246 or 247.

(77) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):

(a) a protein comprising the amino acid sequence of SEQ ID NO: 116 or 117, (b) a protein that comprises the amino acid sequence of SEQ ID NO: 116 or 117 including deletion, substitution or addition of one or several amino acid residues and interacts with a c-Jun protein, (a') a nucleic acid comprising the nucleotide sequence of SEQ ID NO: 246 or 247, (b') a nucleic acid that hybridizes with a nucleic acid comprising the nucleotide sequence of SEQ ID NO: 246 or 247 under a stringent condition and encodes a protein that interacts with a c-Jun protein.

(78) The method according to (77), wherein the protein comprises the amino acid sequence of SEQ ID NO: 116 or 117.

(79) The method according to (77), wherein the nucleic acid comprises the nucleotide sequence of SEQ ID NO: 246 or 247.

(80) A method for screening for a prey that interacts with a bait, which comprises the step of detecting an interaction between the bait and a prey by the method according to any one of (77) to (79) and the step of selecting a prey for which an interaction is detected.

(81) An inhibitor for an interaction between a protein that interacts with a c-Jun protein and the c-Jun protein, which comprises a protein of the following (a) or (b) as an active ingredient:

(a) a protein comprising the amino acid sequence of SEQ ID NO: 118 or 119, (b) a protein that comprises the amino acid sequence of SEQ ID NO: 118 or 119 including deletion, substitution or addition of one or several amino acid residues and interacts with the c-Jun protein.

(82) The inhibitor according to (81), wherein the protein as the active ingredient comprises the amino acid sequence of SEQ ID NO: 118 or 119.

(83) The inhibitor according to (81), wherein the protein is a protein translated from a nucleic acid of the following (a) or (b):

(a) a nucleic acid comprising the nucleotide sequence of SEQ ID NO: 248 or 249, (b) a nucleic acid that hybridizes with a nucleic acid comprising the nucleotide sequence of SEQ ID NO: 248 or 249 under a stringent condition and encodes a protein that interacts with the c-Jun protein.

(84) The inhibitor according to (83), wherein the nucleic acid comprises the nucleotide sequence of SEQ ID NO: 248 or 249.

(85) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):

(a) a protein comprising the amino acid sequence of SEQ ID NO: 118 or 119, (b) a protein that comprises the amino acid sequence of SEQ ID NO: 118 or 119 including deletion, substitution or addition of one or several amino acid residues and interacts with a c-Jun protein, (a') a nucleic acid comprising the nucleotide sequence of SEQ ID NO: 248 or 249, (b') a nucleic acid that hybridizes with a nucleic acid comprising the nucleotide sequence of SEQ ID NO: 248 or 249 under a stringent condition and encodes a protein that interacts with a c-Jun protein.

(86) The method according to (85), wherein the protein comprises the amino acid sequence of SEQ ID NO: 118 or 119.

(87) The method according to (85), wherein the nucleic acid comprises the nucleotide sequence of SEQ ID NO: 248 or 249.

(88) A method for screening for a prey that interacts with a bait, which comprises the step of detecting an interaction between the bait and a prey by the method according to any one of (85) to (88) and the step of selecting a prey for which an interaction is detected.

(89) An inhibitor for an interaction between a protein that interacts with a c-Jun protein and the c-Jun protein, which comprises a protein of the following (a) or (b) as an active ingredient:
(a) a protein comprising the amino acid sequence of SEQ ID NO: 120 or 121,
(b) a protein that comprises the amino acid sequence of SEQ ID NO: 120 or 121 including deletion, substitution or addition of one or several amino acid residues and interacts with the c-Jun protein.

(90) The inhibitor according to (89), wherein the protein as the active ingredient comprises the amino acid sequence of SEQ ID NO: 120 or 121.

(91) The inhibitor according to (89), wherein the protein is a protein translated from a nucleic acid of the following (a) or (b):
(a) a nucleic acid comprising the nucleotide sequence of SEQ ID NO: 250 or 251,
(b) a nucleic acid that hybridizes with a nucleic acid comprising the nucleotide sequence of SEQ ID NO: 250 or 251 under a stringent condition and encodes a protein that interacts with the c-Jun protein.

(92) The inhibitor according to (91), wherein the nucleic acid comprises the nucleotide sequence of SEQ ID NO: 250 or 251.

(93) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising the amino acid sequence of SEQ ID NO: 120 or 121,
(b) a protein that comprises the amino acid sequence of SEQ ID NO: 120 or 121 including deletion, substitution or addition of one or several amino acid residues and interacts with a c-Jun protein,
(a') a nucleic acid comprising the nucleotide sequence of SEQ ID NO: 250 or 251,
(b') a nucleic acid that hybridizes with a nucleic acid comprising the nucleotide sequence of SEQ ID NO: 250 or 251 under a stringent condition and encodes a protein that interacts with a c-Jun protein.

(94) The method according to (93), wherein the protein comprises the amino acid sequence of SEQ ID NO: 120 or 121.

(95) The method according to (93), wherein the nucleic acid comprises the nucleotide sequence of SEQ ID NO: 250 or 251.

(96) A method for screening for a prey that interacts with a bait, which comprises the step of detecting an interaction between the bait and a prey by the method according to any one of (93) to (95) and the step of selecting a prey for which an interaction is detected.

(97) An inhibitor for an interaction between a protein that interacts with a c-Jun protein and the c-Jun protein, which comprises a protein of the following (a) or (b) as an active ingredient:
(a) a protein comprising the amino acid sequence of SEQ ID NO: 122 or 123,
(b) a protein that comprises the amino acid sequence of SEQ ID NO: 122 or 123 including deletion, substitution or addition of one or several amino acid residues and interacts with the c-Jun protein.

(98) The inhibitor according to (97), wherein the protein as the active ingredient comprises the amino acid sequence of SEQ ID NO: 122 or 123.

(99) The inhibitor according to (97), wherein the protein is a protein translated from a nucleic acid of the following (a) or (b):
(a) a nucleic acid comprising the nucleotide sequence of SEQ ID NO: 252 or 253,
(b) a nucleic acid that hybridizes with a nucleic acid comprising the nucleotide sequence of SEQ ID NO: 252 or 253 under a stringent condition and encodes a protein that interacts with the c-Jun protein.

(100) The inhibitor according to (99), wherein the nucleic acid comprises the nucleotide sequence of SEQ ID NO: 252 or 253.

(101) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising the amino acid sequence of SEQ ID NO: 122 or 123,
(b) a protein that comprises the amino acid sequence of SEQ ID NO: 122 or 123 including deletion, substitution or addition of one or several amino acid residues and interacts with a c-Jun protein,
(a') a nucleic acid comprising the nucleotide sequence of SEQ ID NO: 252 or 253,
(b') a nucleic acid that hybridizes with a nucleic acid comprising the nucleotide sequence of SEQ ID NO: 252 or 253 under a stringent condition and encodes a protein that interacts with a c-Jun protein.

(102) The method according to (101), wherein the protein comprises the amino acid sequence of SEQ ID NO: 122 or 123.

(103) The method according to (101), wherein the nucleic acid comprises the nucleotide sequence of SEQ ID NO: 252 or 253.

(104) A method for screening for a prey that interacts with a bait, which comprises the step of detecting an interaction between the bait and a prey by the method according to any one of (101) to (103) and the step of selecting a prey for which an interaction is detected.

(105) An inhibitor for an interaction between a protein that interacts with a c-Jun protein and the c-Jun protein, which comprises a protein of the following (a) or (b) as an active ingredient:
(a) a protein comprising the amino acid sequence of SEQ ID NO: 124 or 125,
(b) a protein that comprises the amino acid sequence of SEQ ID NO: 124 or 125 including deletion, substitution or addition of one or several amino acid residues and interacts with the c-Jun protein.

(106) The inhibitor according to (105), wherein the protein as the active ingredient comprises the amino acid sequence of SEQ ID NO: 124 or 125.

(107) The inhibitor according to (105), wherein the protein is a protein translated from a nucleic acid of the following (a) or (b):
(a) a nucleic acid comprising the nucleotide sequence of SEQ ID NO: 254 or 255, (b) a nucleic acid that hybridizes with a nucleic acid comprising the nucleotide sequence of SEQ ID NO: 254 or 255 under a stringent condition and encodes a protein that interacts with the c-Jun protein.

(108) The inhibitor according to (107), wherein the nucleic acid comprises the nucleotide sequence of SEQ ID NO: 254 or 255.

(109) A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising the amino acid sequence of SEQ ID NO: 124 or 125,
(b) a protein that comprises the amino acid sequence of SEQ ID NO: 124 or 125 including deletion, substitution or addition of one or several amino acid residues and interacts with a c-Jun protein,
(a') a nucleic acid comprising the nucleotide sequence of SEQ ID NO: 254 or 255,
(b') a nucleic acid that hybridizes with a nucleic acid comprising the nucleotide sequence of SEQ ID NO: 254 or 255 under a stringent condition and encodes a protein that interacts with a c-Jun protein.

(110) The method according to (109), wherein the protein comprises the amino acid sequence of SEQ ID NO: 124 or 125.

(111) The method according to (109), wherein the nucleic acid comprises the nucleotide sequence of SEQ ID NO: 254 or 255.

(112) A method for screening for a prey that interacts with a bait, which comprises the step of detecting an interaction between a bait and a prey by the method according to any one of (109) to (111) and the step of selecting a prey for which an interaction is detected.

BRIEF EXPLANATION OF THE DRAWINGS

[FIG. 1] It collectively shows information of amino acid sequence, gene sequence and so forth of the protein of the present invention. Each of numerals within the parentheses after the DNA sequence numbers indicates the number of amino acid sequence encoded by it. A number having a sub-number means that the DNA encodes the same amino acid sequence, but has a different nucleotide sequence.

[FIG. 4] It shows the result of the verification of the interactions of the proteins and genes of the present invention (electrophoretic photographs) and the nucleotide sequences thereof.

A: It was confirmed by the C-terminal labeling method in a wheat cell-free translation system that the proteins of SEQ ID NOS: 18 (SNAP19), 76 (KINN), 93 (Kif5a), 99 (Eef1d), 102 (Nef3), 106 (Jip-c3.1), 110 (Jip-c1), 113 (EB2), 115 (Cspg6), 117 (Mapk8ip3), 119 (Jip-c3.2), 121 (GFAP), 123 (Jip-c8) and 125 (Kif5b) (FIG. 1) were expressed form the nucleic acid sequences of SEQ ID NOS: 143, 206, 223, 229, 232, 236, 240, 243, 245, 247, 249 and 253. Lanes 1 to 14: proteins of SEQ ID NOS: 18 (SNAP19), 76 (KINN), 93 (Kif5a), 99 (Eef1d), 102 (Nef3), 106 (Jip-c3.1), 110 (Jip-c1), 113 (EB2), 115 (Cspg6), 117 (Mapk8ip3), 119 (Jip-c3.2), 121 (GFAP), 123 (Jip-c8) and 125 (Kif5b).

B: As a verification experiment of the interactions of the obtained proteins and c-Jun, direct interactions with c-Jun were confirmed by pull-down using C-terminal labeled proteins having the amino acid sequences of the proteins of SEQ ID NOS: 18 (SNAP19), 76 (KINN), 93 (Kif5a), 106 (Jip-c3.1), 110 (Jip-c1), 113 (EB2), 115 (Cspg6), 117 (Mapk8ip3), 119 (Jip-c3.2) and 123 (Jip-c8) based on the nucleic acid sequences of SEQ ID NOS: 143, 206, 223, 236, 240, 243, 245 and 249. Group 1: SEQ ID NO: 18 (SNAP19), Group 2: 76 (KINN), Group 3: 93 (Kif5a), Group 6: 106 (Jip-c3.1), Group 7: 110 (Jip-c1), Group 8: 113 (EB2), Group 9: 115 (Cspg6), Group 10: 117 (Mapk8ip3), Group 11: 119 (Jip-c3.2) and Group 13: 123 (Jip-c8); a and b: with and without bait c-Jun (Lanes 1, 2 and 3: translation product, supernatant fraction and eluted fraction).

Figure 5:
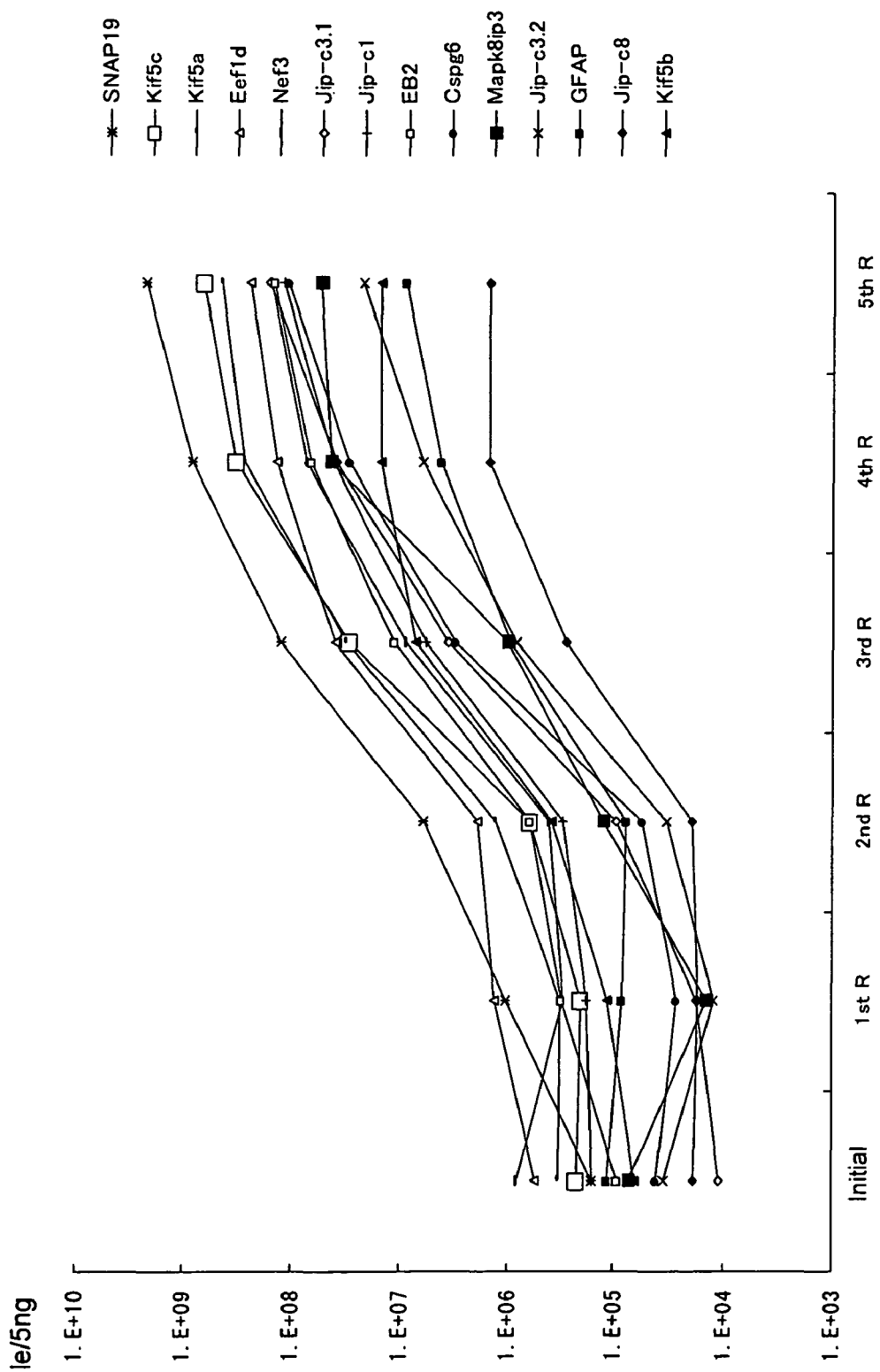

[FIG. 5] It shows the result of verification of the concentration rate and indirect interaction of the genes of the present invention. In order to confirm concentrations of 14 kinds of proteins of SEQ ID NOS: 18 (SNAP19), 76 (KINN), 93 (Kif5a), 99 (Eef1d), 102 (Nef3), 106 (Jip-c3.1), 110 (Jip-c1), 113 (EB2), 115 (Cspg6), 117 (Mapk8ip3), 119 (Jip-c3.2), 121 (GFAP), 123 (Jip-c8) and 125 (Kif5b), real-time PCR was performed by using the nucleic acid sequences of SEQ ID NO: 143, 206, 223, 229, 232, 236, 240, 243, 245, 247, 249 and 253.

Figure 6:
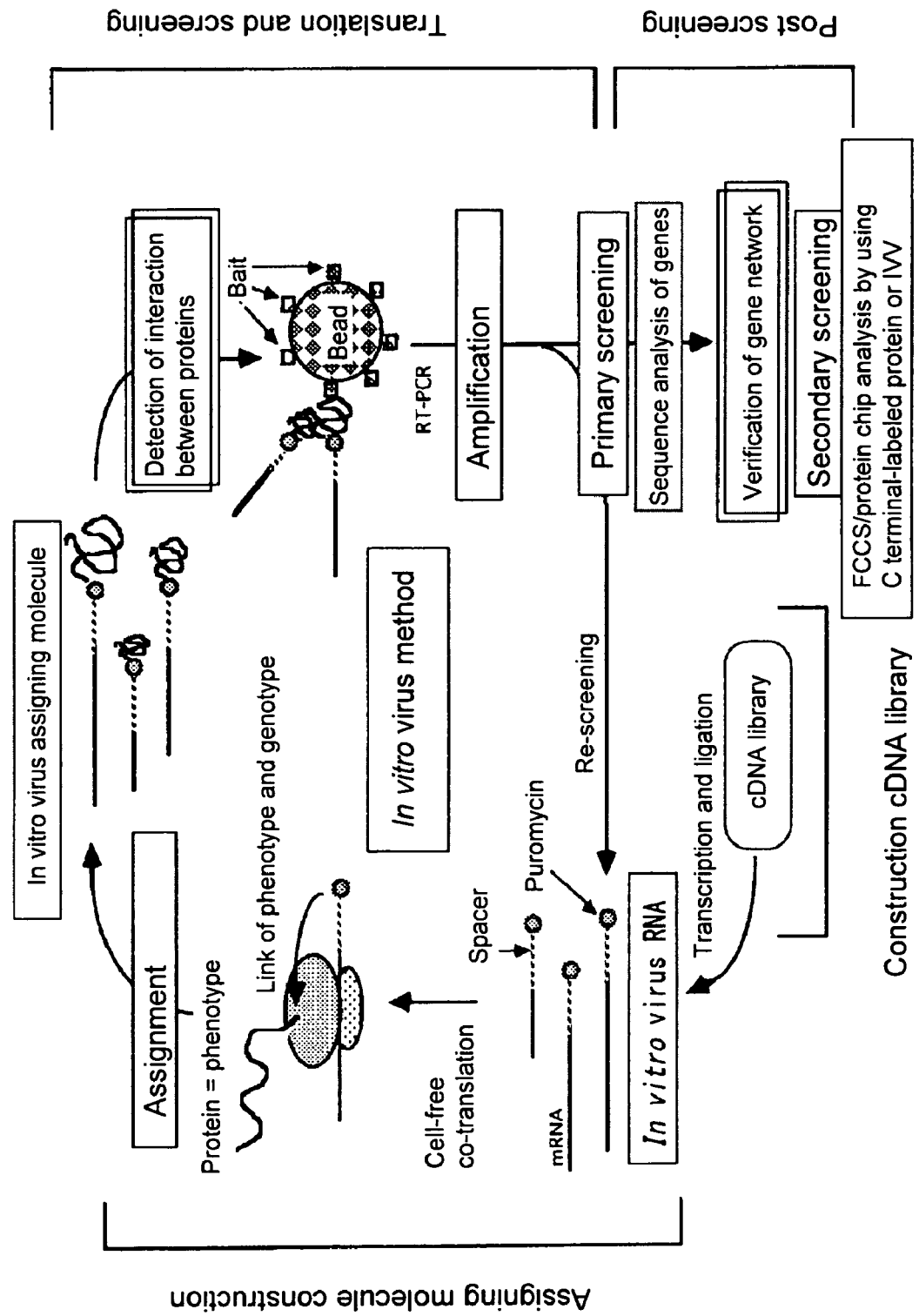

[FIG. 6] It shows outlines of the primary screening and secondary screening in the analysis of interaction of IVV with substances or proteins using the proteins and nucleic acid sequences of the present invention. It is possible to detect interactions with the substances and proteins in the primary screening using the proteins and nucleic acid sequences of the present invention, and further analyze the details of the interaction in the secondary screening using FCCS, microarray or the like. Further, the proteins and nucleic acid sequences of the present invention can also be independently used for analysis of interaction with the substances or proteins using FCCS, microarray, or the like as IVV or C-terminal labeled proteins. Furthermore, it is also possible to apply them to the evolutionary molecular engineering using IVV of the proteins or nucleic acid sequences of the present invention, and utilize them to create functional proteins in the primary screening. In such a case, it is also possible to analyze details of interactions of the created functional proteins with a combination of the primary screening and secondary screening.

[FIG. 7] It shows configurations of a translation template (A) as well as a coding molecule (B) and spacer molecule (C), which are constituents of the template. The translation template consists of a coding portion derived from the coding molecule and a spacer portion derived from the spacer molecule. F1 and F2 represent a fluorescent dye.

[FIG. 8] shows configurations of a protein modified at the C-terminal (C-terminal labeled protein) (A), translation template of the present invention (B) and modification agent (C).

[FIG. 9] It shows outline of formation of a complex by cell-free cotranslation.

A: Both of bait and prey are translated in a cell-free translation system to interact with each other to form a complex in the cell-free translation system. The prey may exist in a single number (I) or multiple number (II), and it may be a polypeptide itself obtainable by the translation in the cell-free translation system, or an assigning molecule (bound substance).

B: In the presence of the bait, the prey is translated in a cell-free translation system to interact with the bait and thereby form a complex in the cell-free translation system. The prey may exist in a single number (I) or multiple number (II), and it may be a polypeptide itself obtainable by the translation in the cell-free translation system, or an assigning molecule (bound substance).

Figure 10:
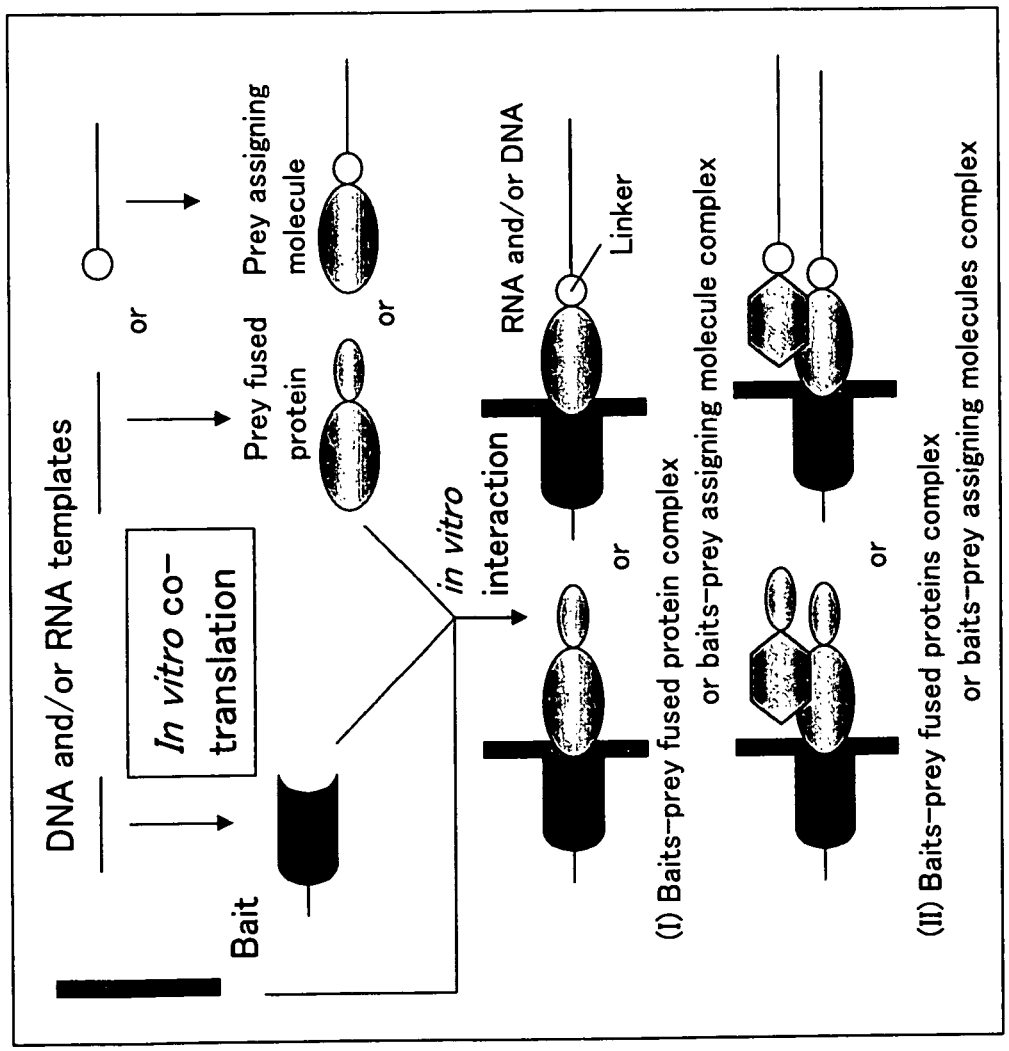

[FIG. 10] It shows outline of formation of a complex by cell-free cotranslation using a complexed bait.

Both of bait as a part constituting the complexed bait and prey are translated in a cell-free translation system and interact to form a complex in the cell-free translation system. The prey may exist in a single number (I) or multiple number (II), and it may be a polypeptide itself obtainable by the translation in the cell-free translation system, or an assigning molecule (bound substance). Further, the complexed bait is not limited to the combination of a polypeptide translated in a cell-free translation system and DNA bait shown in the drawing, and it may be, for example, a combination of multiple or single polypeptide translated in a cell-free translation system and multiple or single bait coexisting in the cell-free translation system (e.g., DNA bait etc.), or the like.

Figure 11:
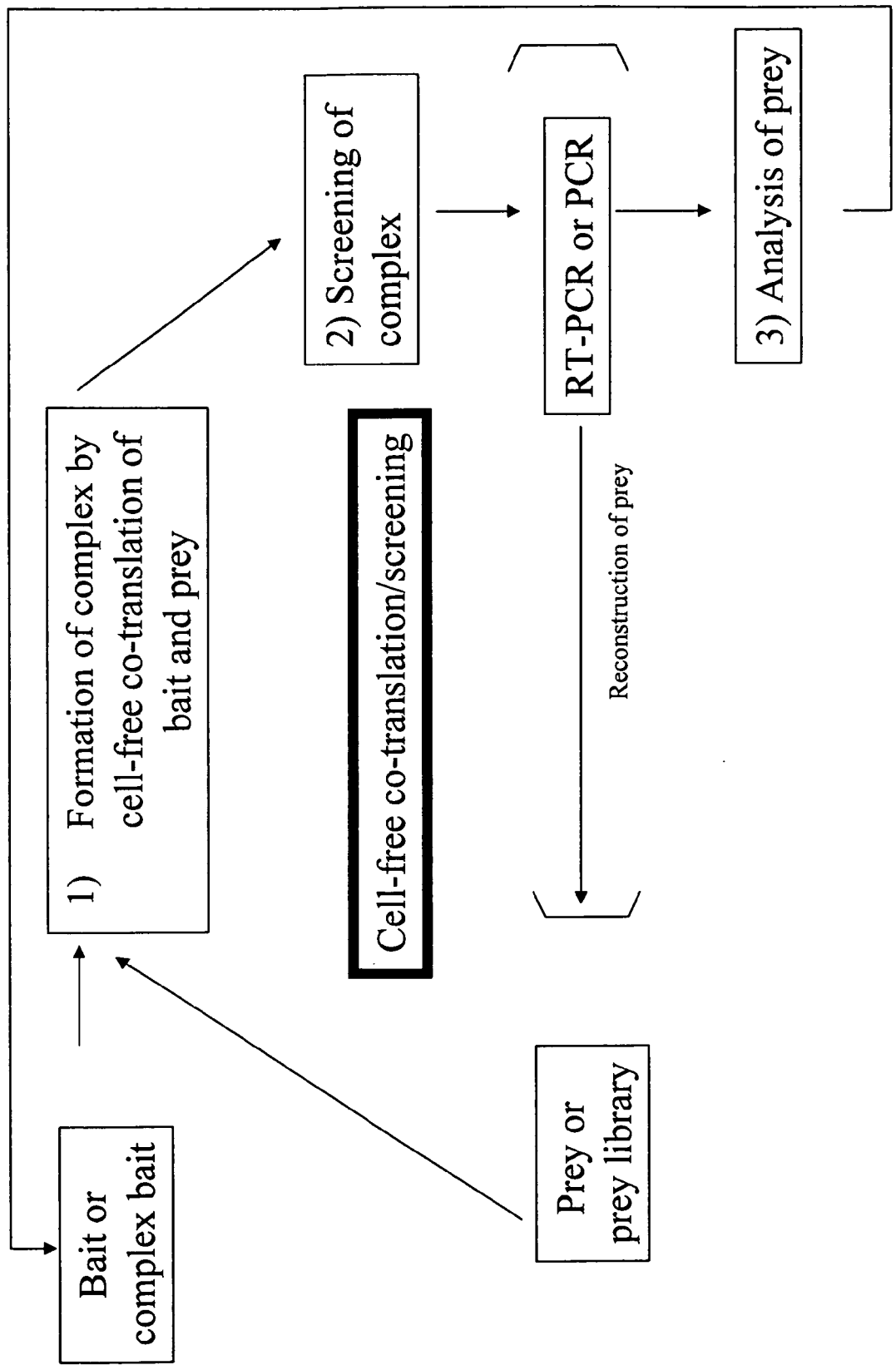

[FIG. 11] It shows outline of the method of screening for a complex based on cell-free cotranslation.

By the step (1) of forming a complex on the basis of cell-free cotranslation as shown in FIGS. 9 and 10, the step (2) of screening the prey of the complex, and the step (3) of analyzing the prey, the cell-free cotranslation and screening can be realized totally in vitro. If the prey is an assigning molecule, and it exists in a multiple number, the screening can be repeated again from the step (1) by reconstructing mRNA or DNA encoding the prey by RT-PCR or PCR. Further, after analyzing the obtained prey, screening can be newly repeated from the step of (1) using the prey as a bait.

BEST MODE FOR CARRYING OUT THE INVENTION

<1> Proteins of the Present Invention

In this specification, proteins found to interact with c-Jun, including novel proteins, are called "the proteins of the present invention" for convenience of explanation.

The first group of the proteins of the present invention consisting of proteins of which function is known but of which function of interacting with c-Jun is novel. These proteins are not any of proteins known to form a complex with c-Jun so far (Yurii Chinenovl and Tom K Kerppola, Oncogene (2001) 20, 2438-2452). Specifically, as shown in FIG. 1, SNAP19(SNAPc5) corresponding to the amino acid sequence SEQ ID NOS: 1 to 69 is one of subunits of the SNAP complex binding to PSE, a promoter of snRNA transcribed by polII and pol III, thereby regulating transcription (Henry, R. W.; Mittal, V.; Ma, B.; Kobayashi, R.; Hernandez, N. Genes Dev. 12: 2664-2672, 1998. (PubMed ID: 9732265)). Kif5c corresponding to the amino acid sequence SEQ ID NOS: 70 to 87 is one molecule of the kinesin superfamily, which is a motor protein involved in substance transportation along with microtubule. It is known to be highly expressed in brain (Nagase, T.; Ishikawa, K.; Miyajima, N.; Tanaka, A.; Kotani, H.; Nomura, N.; Ohara, O. DNA Res. 5: 31-39, 1998. (PubMed ID: 9628581)). Kif5a corresponding to the amino acid sequence SEQ ID NOS: 88 to 94 is one molecule of the kinesin superfamily, which is a motor protein involved in substance transportation along with microtubule. It is known that its mutation results in hereditary spastic paraplesia (Niclas, J.; Navone, F.; Hom-Booher, N.; Vale, R. D. Neuron 12: 1059-1072, 1994. (PubMed ID: 7514426)). Eef1d corresponding to the amino acid sequence SEQ ID NOS: 95 to 99 is known as a protein regulating elongation of translation and recently revealed that it is also a product of a gene associated with cancer and tumor (Joseph, P.; Lei, Y. X.; Whong, W. Z.; Ong, T. M. J. Biol. Chem. 277: 6131-6136, 2002. (PubMed ID: 11711542)). Nef3 corresponding to the amino acid sequence SEQ ID NOS: 100 to 104 is one of three molecules constituting neuron-specific intermediate filaments and is a protein with a molecular weight of 125 kD (Levy, E.; Liem, R. K. H.; D'Eustachio, P.; Cowan, N. J. Europ. J. Biochem. 166: 71-77, 1987. (PubMed ID: 3036526)). EB2 corresponding to the amino acid sequence SEQ ID NOS: 112 to 113 is APC-binding protein EB2(Mapre3) and is one of the EB1 family known to interact with APC to cooperatively promote aggregation of microtubule (Su, L.-K.; Qi, Y.: Characterization of human MAPRE genes and their proteins. Genomics 71: 143-149, 2001). Cspg6 corresponding to the amino acid sequence SEQ ID NOS: 114 to 115 is one of subunits of cohesin complexes which play an important role in sister chromatid partition and a protein composed of a globular portion having ATPase activity and a rod portion (Sumara, I.; Vorlaufer, E.; Gieffers, C.; Peters, B. H.; Peters, J.-M. J. Cell Biol. 151: 749-761, 2000. (PubMed ID: 11076961)). Mapk8ip3 corresponding to the amino acid sequence SEQ ID NOS: 116 to 117 is one of scaffold proteins binding to JNK and considered to play an important role in the MAP kinase signaling cascade mediated by JNK (Dickens, M.; Davis, R. J. Molec. Cell. Biol. 20: 1030-1043, 2000. (PubMed ID: 10629060)). GFAP corresponding to the amino acid sequende SEQ ID NOS: 120 to 121 is one of constituents of intermediate filaments highly expressed in glial cells of the astrocyte lineage. It has a specific sequence at its N terminal and is considered to play a cell-specific role. It is a causal gene for a strange disease, Alexander disease (Bongcam-Rudloff, E.; Nister, M.; Betsholtz, C.; Wang, J.-L.; Stenman, G.; Huebner, K.; Croce, C. M.; Westermark, B. Cancer Res. 51: 1553-1560, 1991. (PubMed ID: 1847665). Kif5b corresponding to the amino acid sequence SEQ ID NOS: 124 to 125 is one of the kinesin superfalimy, which is a motor protein involved in substance transportation along with microtubule. It is involved in organella transportation and abnormal distribution of mitochodria occurs in its KO mouse (Tanaka, Y.; Kanai, Y.; Okada, Y.; Nonaka, S.; Takeda, S.; Harada, A.; Hirokawa, N. Cell 93: 1147-1158, 1998. PubMed ID: 9657148), Kamal, A.; Almenar-Queralt, A.; LeBlanc, J. F.; Roberts, E. A.; Goldstein, L. S. B. Nature 414: 643-648, 2001. (PubMed ID 11740561)).

Among these proteins, those having no leucine zipper are Nef3, EB2, GFAP and Kif5b. Those indirectly interacting with c-Jun are Nef3 and GFAP. All the others, SNAP19, Kif5c, Kif5a, Eef1d, Cspg6 and Mapk8ip3 have the leucine zipper and form a complex with c-Jun.

The second group of the proteins of the present invention consisting of proteins of which function is unknown and of which function of interacting with c-Jun is newly found. Specifically, these are Jip-c3.1 corresponding to the amino acid sequence SEQ ID NOS: 105 to 108, Jip-c1 corresponding to the amino acid sequence SEQ ID NOS: 109 to 111, Jip-c3.2 corresponding to the amino acid sequence SEQ ID NOS: 118 to 119 and Jip-c8 corresponding to the amino acid sequence SEQ ID NOS: 122 to 123 (FIG. 1). All these proteins have the leucine zipper and directly interact with c-Jun.

Hereafter, the proteins of the present invention will be further explained.

Among the proteins of the present invention, the proteins having any one of the amino acid sequences of SEQ ID NOS: 1 to 125 are proteins for which it has been found that they interact with the c-Jun protein, i.e., form a complex, as described in the examples mentioned below. For proteins, existence of a mutant having the same function is generally expected. Further, by suitably modifying an amino acid sequence of a protein, a mutant having the same function can be obtained. Therefore, proteins that have any one of the amino acid sequences of SEQ ID NOS: 1 to 125 including deletion, substitution or addition of one or several amino acid residues and interact with the c-Jun protein also fall within the scope of the proteins of the present invention. The term "several" used herein means preferably within 5, more preferably within 2. Further, proteins that show a homology of usually 15% or more, preferably 90% or more, more preferably 95% or more to any one of the amino acid sequences of SEQ ID NOS: 1 to 125 and interact with the c-Jun protein also fall within the scope of the protein of the present invention.

An amino acid sequence of a protein can be modified by modifying a nucleotide sequence of DNA encoding the protein using a well-known means such as site-directed mutagenesis and expressing DNA of which nucleotide sequence is modified. Among such modified proteins, those that interact with the c-Jun protein fall within the scope of the protein of the present invention. The interaction with the c-Jun protein can be measured by a known method for measuring an interaction, and examples include the method of detecting formation of a complex mentioned in the examples described later.

The proteins of the present invention may be fused with another protein and thus provided as a fusion protein.

The nucleic acids of the present invention are nucleic acids encoding the proteins of the present invention. The nucleic acids are usually RNA or DNA. Examples of the nucleic acids of the present invention include nucleic acids having any one of the nucleotide sequences of SEQ ID NOS: 126 to 255. These nucleic acids are nucleic acids of which nucleotide sequences were determined in the examples mentioned below. For a gene, existence of a gene encoding the same product, but having a different nucleotide sequence, or a gene encoding a mutant having the same function is expected. Further, by suitably modifying a nucleotide sequence, a gene encoding the same product or a mutant having the same function can be obtained. Therefore, nucleic acids having a nucleotide sequence similar to any one of the nucleotide sequences of SEQ ID NOS: 126 to 255 and encoding a protein that interacts with the c-Jun protein also fall within the scope of the nucleic acids of the present invention. Examples of such nucleic acids having a similar nucleotide sequence include nucleic acids that hybridize with a nucleic acid having a nucleotide sequence complementary to any one of the nucleotide sequences of SEQ ID NOS: 126 to 255 under a stringent condition, and nucleic acids having a nucleotide sequence showing a homology of usually 16% or more, preferably 90% or more, more preferably 95% or more to any one of the nucleotide sequences of SEQ ID NOS: 126 to 255.

The stringent condition referred to here corresponds to, for example, that of hybridization using DIG Easy Hyb (Roch Diagnostics) at 42° C. followed by washing in 0.1×SSC/0.1% SDS for 15 minutes at 60° C. Homology of nucleotide sequences is obtained as a rate of number of nucleotides matching in alignment of the nucleotide sequences to be compared to the nucleotide number of the chain length of the nucleotide sequences. Further, homology of amino acid sequences is obtained as a rate of number of amino acid residues matching in alignment of the amino acid sequences to be compared to the amino acid number of the chain length of the amino acid sequences.

Whether a DNA encodes a protein that interacts with the c-Jun protein can be easily confirmed by expressing a protein from that DNA and confirming whether the expressed protein interacts with the c-Jun protein using the aforementioned method.

The nucleic acids of the present invention can be obtained by a conventional method on the basis of the elucidated nucleotide sequences. For example, it may be synthesized by a chemical synthesis method, or it may be obtained by RT-PCR using suitably designed primers from a mRNA prepared from cells or tissue expressing a protein that interacts with the c-Jun protein.

<2> Use of the Proteins of the Present Inventions and Others.

The proteins and genes of the present invention can be applied as an inhibitor that blocks transcription function, gene replication function and so forth as for c-Jun in gene therapy etc. by utilizing the novel function obtained by the nucleic acid sequences (function enabling binding with c-Jun in this case). The basis for this originates in the fact that the genes of the proteins of the present invention are detected after undergoing competitive process of screening repeated multiple times. Genes detected by this method exhibit a certain number distribution, and a gene having higher competitive power will be detected in a larger number. This means that a gene of which clones are detected by this method in a larger number should have a higher competitive power, and it more effectively functions as a blocking agent or inhibitor.

As for use of the proteins of the present invention and genes encoding them, as in vitro applications, they can be applied in, for example, evolutionary molecular engineering using a cell-free protein synthesis system or genomic function analysis by utilizing the novel function provided by the proteins, genes or nucleic acid sequences according to the present invention. In this case, analysis utilizing cotranslation screening and selection of assigning molecules is extremely effective. This is because the cotranslation screening/selection method makes it possible to comprehensively detect proteins that directly or indirectly interact with a bait protein. Furthermore, in analysis of interactions between IVVs, IVV and C-terminal labeled protein etc., they can also be use as a "target molecule (bait protein)". Examples of general methods for analyzing an interaction include, for example, microarray method, fluorescence correlation spectroscopy (FCS/FCCS), fluorescence imaging analysis, fluorescence resonance energy transfer method, evanescent-field molecular imaging method, fluorescence depolarization method, surface plasmon resonance method, enzyme linked immunosorbent assay and so forth. Specific examples of the cell-free protein synthesis system include wheat germ extract, rabbit reticulocyte lysate, Escherichia coli S30 extract and so forth. By adding a protein, gene or nucleic acid sequence as a translation template according to the present invention to any of these cell-free protein synthesis systems, simultaneously adding 1 to 100 µM of modification agent in the case of C-terminal labeling, and maintaining the system at 25 to 37° C. for 1 to several hours, a C-terminal modified protein is synthesized. In the case of assigning, only by adding a protein, gene or nucleic acid sequence as a translation template according to the present invention to the cell-free protein synthesis system and maintaining the system at 25 to 37° C. for 1 to several hours, an assigning molecule is synthesized.

Further, as for in vivo applications, by utilizing the novel function provided by the proteins, genes or nucleic acid sequences according to the present invention, for example, a protein modified for separation and labeled for detection (double modified protein) synthesized in a cell-free protein synthesis system can be used as it is for a subsequent purification process, detection process, or direct introduction into cells. Specific examples of cell expression system include any kind of cells of from bacteria such as Escherichia coli, Bacillus subtilis and thermophilic bacteria, yeast to cultured cells of insects, mammals and so forth, cells of threadworm, drosophila, zebra fish, mouse and so forth. By directly introducing the aforementioned C-terminal labeled or assigned double modified protein into these cells, an objective protein can be blocked. Alternatively, it is also possible to introduce the aforementioned gene or nucleic acid of the present invention and utilize the gene or nucleic acid as it is as an antisense sequence or RNAi sequence to block expression of an objective nucleic acid, or they can be expressed in a cell and utilized as a protein or assigning molecule to block a protein having an interacting action. When a protein is used in the C-terminal labeling method, by simultaneously introducing 1 to 100 µM modification agent for C-terminal labeling into cells using electroporation, microinjection or the like and maintaining the cells at the optimum growth temperature of the cells for several hours, a modified protein is synthesized. In the case of assigning, by introducing a template of an assigning molecule having the aforementioned gene or nucleic acid sequence of the protein of the present invention into cells and maintaining the cells at the optimum growth temperature of the cells for several hours, an assigning molecule is synthesized. The synthesized double modified protein can be collected by disrupting the cells and used for the subsequent purification process or detection process. Further, it can be used as it is in the cells for the detection process.

Hereafter, the use of the proteins of the present invention and others will be further explained.

The detection method of the present invention is a method of utilizing the proteins of the present invention as a bait in detection of interaction between the bait and a prey.

Preferably, the method is mainly characterized in that the bait and prey are modified for separation and labeled for detection in a specific manner, and the prey is produced by translation in a cell-free translation system in the presence of the bait to contact the bait and prey. In this specification, contacting a bait and a prey by producing the prey by translation in a cell-free translation system in the presence of the bait is also referred to as "cell-free cotranslation".

In this specification, the terms of "bait" and "prey" have the meanings usually used in the technical field of analysis of interaction between substances. That is, a protein, nucleic acid or the like as a known substance is called "bait", and a protein, nucleic acid or the like as a substance that interacts with the bait is called "prey". In the present invention, the prey is preferably a protein.

The bait used herein may be the protein of the present invention, or a complex constituted by arbitrary components including protein (including peptide), nucleic acid, or ligand such as antibody and hormone, metal and so forth, so long as it contains the protein of the present invention, and it may be a natural substance or artificial substance. The bait is not particularly limited as for the molecular weight and so forth. Examples include, for example, in the case of protein, a functional domain, a full-length protein containing a functional domain and so forth. If a prey library is used, use of full-length proteins enables comprehensive detection.

Further, as the prey, a protein is preferably used. The prey is not particularly limited as for the molecular weight and so forth.

Preferably, the detection method of the present invention is mainly characterized in that, in the detection of an interaction of the bait and prey, the bait and prey are modified for separation and labeled for detection in a specific manner, and cell-free cotranslation is performed as described above. Therefore, a preferred configuration of the detection method of the present invention may be the same as that of a usual method for detecting an interaction between a bait and a prey comprising contacting the bait and prey and detecting a complex formed by the contact, except that the bait and prey are modified for separation and labeled for detection in a specific manner, and cell-free cotranslation is performed.

Although the modification for separation and labeling for detection of the bait and prey are arbitrarily performed so that they are suitable for the detection of the complex, they should be performed so that both of the bait and prey should not be labeled with a label for detection or modified for separation. Therefore, the prey is used as a fusion protein with a protein that can be used as a label for detection or an assigning molecule, and the bait correspondingly has a modification for separation.

When the prey is used as a fusion protein, the bait should have a modification for separation. When the bait is a protein, the bait is preferably produced in a cell-free translation system by translation of mRNA encoding a fusion protein containing the bait as a fusion protein with a protein that can be used as a modification for separation in the cell-free translation system.

Examples of the modification for separation in the case where the bait is a protein include formation of a fusion protein with the GST protein, CBP used for the TAP method etc. (this can be separated by using affinity with calmodulin beads), protein A (this can be separated by using IgG-protein A affinity) as a protein, or any of various antibody tags etc. as an affinity tag. When the bait itself has a property that it can be used as a modification for separation, the bait can be used as it is as a bait having a modification for separation. Examples of the modification for detection of the prey include formation of a fusion protein with a fluorescent protein such as GFP (green fluorescent protein).

Preparation of mRNA encoding such a fusion protein mentioned above and translation of this mRNA in a cell-free translation system can be performed by usual methods. The mRNA may be mRNA produced by transcription of DNA in a cell-free transcription and translation system.

When the prey is an assigning molecule, arbitrary modification for separation can be added to the bait. When the bait is a protein, the aforementioned examples of the modification for separation can be used. In addition, when the bait is a nucleic acid, drug or the like, examples of the modification for separation include use of biotin etc. that interact with streptavidin or avidin. When the bait itself has a property that it can be used as modification for separation, the bait can be used it is as a bait having modification for separation.

An assigning molecule means a molecule assigning a phenotype and a genotype. The assigning molecule is usually a molecule comprising a genotype molecule containing a nucleic acid having a nucleotide sequence reflecting a genotype and a phenotype molecule containing a protein relating to expression of phenotype, which are bound to each other. By using a prey as this protein, the prey can be used as an assigning molecule. Such an assigning molecule can be formed by performing translation of mRNA encoding a prey in a cell-free translation system so that the translated prey should associate with the mRNA, or performing transcription and translation of DNA encoding a prey in a cell-free transcription and translation system so that the translated prey should associate with the DNA. Therefore, by allowing a bait to exist during the production, cell-free cotranslation can be attained. That is, the cell-free cotranslation can be perfomed by the following scheme (1) or (2).

(1) By performing translation of mRNA encoding the prey in the presence of the bait in a cell-free translation system so that the translated prey should associate with the mRNA, the prey is produced in the cell-free translation system, and thereby the bait and prey are brought into contact with each other.

(2) By performing transcription and translation of DNA encoding the prey in the presence of the bait in a cell-free transcription and translation system so that the translated prey should associate with the DNA, the prey is produced in the cell-free translation system, and thereby the bait and prey are brought into contact with each other.

Hereafter, the embodiments of (1) and (2) mentioned above will be explained.

In the embodiment of (1), the translated prey preferably associates with the mRNA, because the mRNA has a spacer region bound to the 3' end and a peptide acceptor region bound to the spacer region and containing a group that can bind to a peptide by transpeptidation reaction. Examples of the method for detecting an interaction using such an assigning molecule include the in vitro virus method.

The mRNA is preferably a nucleic acid containing a 5' untranslation region including a transcription promoter and a translation enhancer, an ORF region encoding a prey and binding to the 3' end side of the 5' untranslation region, and a 3' end region including a poly-A sequence and binding to 3' end side of the ORF region. Preferably, an expression amplification sequence containing an SNNS (S is G or C) sequence on the 5' end side of the poly-A sequence (for example, a sequence recognizable by the restriction enzyme XhoI) is further included. The mRNA may or may not have a Cap structure at the 5' end.

The poly-A sequence is a poly-A continuous chain of at least 2 or more residues comprising dA and/or rA as single kind of residues or mixture of two kinds, and the poly-A chain consists of, preferably 3 or more residues, more preferably 6 or more residues, still more preferably 8 or more residues.

One of the factors affecting the translation efficiency is a combination of the 5' UTR comprising a transcription promoter and a translation enhancer and the 3' end region including a poly-A sequence. The effect of the poly-A sequence of the 3' end region is usually exerted with a length of ten or less residues. As the transcription promoter of the 5' UTR, T7/T3, SP6, and so forth can be used, and no particular limitation is imposed. SP6 is preferred, and it is particularly preferable to use SP6, especially when a sequence containing an omega sequence or a part of omega sequence is used as the translation enhancer sequence. The translation enhancer is preferably a part of the omega sequence, and as the part of the omega sequence, one containing a part of the omega sequence of TMV (O29, refer to Gallie D. R., Walbot V., Nucleic Acids Res., vol. 20, 4631-4638 (1992), and WO02/48347, FIG. 3) is preferred.

Further, for the translation efficiency, the combination of the XhoI sequence and a poly-A sequence is preferred in the 3' end region. Furthermore, a combination of the downstream portion of the ORF region, i.e., the upstream region of the XhoI sequence having an affinity tag, and a poly-A sequence is preferred. The affinity tag sequence may be any sequence for utilizing a means that can detect a protein such as an antigen-antibody reaction, and no limitation is imposed. The affinity tag is preferably the Flag-tag sequence or His-tag sequence, which is a tag for affinity separation analysis based on an antigen-antibody reaction. As for the effect of the poly-A sequence, an affinity tag such as the Flag-tag attached with the XhoI sequence and further attached with a poly-A sequence increases the translation efficiency. As for the His-tag, even a His-tag having a configuration not containing the XhoI sequence also exhibits sufficient translation efficiency, and thus is effective.

Such a configuration effective for improvement of translation efficiency is also effective for assignment efficiency.

If SP6+O29 and Flag+XhoI+$A_n$ (n=8) or His+$A_n$ (n=8), for example, are used as the 5' UTR and the 3' end region, respectively, the 5' UTR and the 3' end region would have lengths of about 49 bp and about 38 or 26 bp, respectively, and thus they have such a length that they can be incorporated into primers for PCR as an adaptor region. Therefore, a coding region having such a 5' UTR and 3' end region can be easily produced by PCR from any of vectors, plasmids and cDNA libraries. In the coding region, translation may occur beyond the ORF region. That is, there may not be a stop codon at the end of the ORF region.

The peptide acceptor region is not particularly limited, so long as it can bind to the C-terminal of a peptide. For example, puromycin and 3'-N-aminoacylpuromycin aminonucleosides (PANS-amino acids) including PANS-amino acids corresponding to all amino acids such as PANS-Gly in which the amino acid portion is glycine, PANS-Val in which the amino acid portion is valine, and PANS-Ala in which the amino acid portion is alanine can be utilized. Further, 3'-N-aminoacyladenosine aminonucleosides (AANS-amino acids), in which a 3'-aminoacyladenosine and an amino acid are bonded via an amide bond as a chemical bond formed as a result of dehydration condensation of the amino group of the 3'-aminoacyladenosine and the carboxyl group of the amino acid, corresponding to all amino acids, for example, AANS-Gly in which the amino acid portion is glycine, AANS-Val in which the amino acid portion is valine, AANS-Ala in which the amino acid portion is alanine, and so forth can also be used. Furthermore, nucleosides and nucleosides bound with an amino acid via an ester bond can also be used. In addition, any of substances formed with a bonding scheme that can chemically bond a nucleoside or a substance having a chemical structure similar to that of nucleoside and an amino acid or a substance having a chemical structure similar to amino acid can be used.

The peptide acceptor region preferably comprises puromycin or a derivative thereof, or puromycin or a derivative thereof and one or two residues of deoxyribonucleotides or ribonucleotides. The term "derivative" used in this case means a derivative that can bind to the C-terminal of peptide in a protein translation system. The puromycin derivative is not limited to those having the total puromycin structure, and includes those having the puromycin structure a part of which is eliminated. Specific examples of the puromycin derivative include PANS-amino acids, AANS-amino acids and so forth.

Although the peptide acceptor region may have a structure consisting only of puromycin, it preferably has a nucleotide sequence comprising DNA and/or RNA of one or more residues at the 5' end side. As such a sequence, dC-puromycin, rC-puromycin, and so forth, more preferably, a CCA sequence comprising dCdC-puromycin, rCrC-puromycin, rCdC-puromycin, dCrC-puromycin or the like and imitating the 3' end of aminoacyl-tRNA (Philipps, G. R., Nature 223, 374-377 (1969)), is suitable. As for the type of nucleotide, preference is higher in the order of C>(U or T)>G>A.

The spacer region is preferably a PEG region containing polyethylene glycol as a main component. The spacer region usually contains, in addition to the PEG region, a donor region that can bind to the 3' end of a nucleic acid.

The donor region that can bind to the 3' end of nucleic acid usually consists of one or more nucleotides. The number of nucleotides is usually 1 to 15, preferably 1 to 2. The nucleotides may be a ribonucleotide or a deoxyribonucleotide. The donor region may have a modification substance.

The sequence of the 5' end of the donor region affects the ligation efficiency with the coding region encoding the prey. In order to attain ligation of the coding region and the spacer region, it is required to include at least one or more residues, and at least one residue of dC (deoxycytidylic acid) or two residues of dCdC (dideoxycytidylic acid) is preferred for an acceptor having a poly-A sequence. As for the type of nucleotide, preference is higher in the order of C>(U or T)>G>A.

The PEG region contains polyethylene glycol as a main component. The expression "contains polyethylene glycol as a main component" used herein means that the total number of nucleotides contained in the PEG region is 20 or less, or the average molecular weight of the polyethylene glycol is 400 or more. It preferably means that the total number of nucleotides is 10 or less, or the average molecular weight of the polyethylene glycol is 1000 or more.

The average molecular weight of the polyethylene glycol in the PEG region is usually 400 to 30,000, preferably 1,000 to 10,000, more preferably 2,000 to 8,000. If the molecular weight of the polyethylene glycol is lower than about 400, a posttreatment for assignment translation may be required for assignment translation of a genotype molecule containing the spacer region (Liu, R., Barrick, E., Szostak, J. W., Roberts, R. W., Methods in Enzymology, vol. 318, 268-293 (2000)). However, if PEG having a molecular weight if 1000 or more, preferably 2000 or more, is used, highly efficient assignment can be attained only by assignment translation, and therefore the posttreatment for the translation becomes unnecessary. Further, when the molecular weight of the polyethylene glycol increases, stability of the genotype molecule tends to increase, and in particular, the stability becomes favorable with a molecular weight of 1000 or more. If the molecular weight is 400 or less, properties thereof are not different so much from those of a DNA spacer, and it may become unstable.

By having a spacer region containing polyethylene glycol as a main component, it becomes possible to form an assigning molecule not only in a cell-free translation system of rabbit reticulocytes, but also in a cell-free translation system of wheat germ, the stability of the genotype molecule in both translation systems is markedly improved, and it becomes unnecessary to perform any treatment after the translation.

In the embodiment of (2), it is preferred that DNA encodes a fusion protein of a protein and streptavidin or avidin, DNA is labeled with biotin, and a translated prey associates with the DNA because transcription and translation is carried out in a state that one DNA molecule is contained in one compartment of emulsion. Examples of the method for detecting an interaction using such an assigning molecule include the STABLE method.

The emulsion is usually a W/O type emulsion formed by mixing two kinds of surface active agents, mineral oil and a reaction mixture of cell-free transcription and translation system. In order to form a W/O type emulsion, it is usually necessary for the surface active agents to have an HLB (hydrophile-lipophile balance) value of 3.5 to 6. The HLB value of mixed two kinds of surface active agents is calculated from the HLB values of the individual surface active agents by using a simple equation. For example, if Span 85 (HLB=1.8) and Tween 80 (HLB=15.0) are mixed in volumes of 40.2 μl and 9.8 μl, respectively, the mixture has an HLB value of 4.4. The ratio of the surface active agents and mineral oil is usually 1:18 (volume ratio). Further, the ratio of the reaction mixture is 1 to: 50% (volume ratio) with respect to the whole emulsion, and it is usually 5%. The emulsion can be formed by adding the reaction mixture as several divided portions to a mixture of the surface active agents and mineral oil at a low temperature with stirring and mixing them. The reactions of transcription and translation can be started by raising the temperature of the emulsion.

The preparation of DNA encoding a prey, and transcription and translation of such a DNA in a cell-free transcription and translation system can be performed in a usual manner.

As described above, by labeling the bait and prey for detection and modifying them for separation in particular schemes, a complex formed by cell-free cotranslation can be specifically detected.

As for the cell-free cotranslation of a bait and a prey, the cell-free translation system (including cell-free transcription and translation system) in which the cell-free cotranslation is performed may be any of systems of E. coli, rabbit reticulocytes, wheat germs and so forth. Although formation of assigning molecules is quite unstable with E. coli in the in vitro virus method, it has been confirmed that it is stable in a system of rabbit reticulocytes (Nemoto N., Miyamoto-Sato E., and Yanagawa H., FEBS Lett. 414, 405 (1997); Roberts R. W., Szostak J. W., Proc. Natl. Acad. Sci. USA, 94, 12297 (1997)), and it has been further confirmed that it is still more stable in a system of wheat germ (Japanese Patent Laid-open No. 2002-176987). For the STABLE method, the system may be any of systems of E. coli, rabbit reticulocyte, wheat germ and so forth.

The conditions for the translation and transcription in the cell-free cotranslation are suitably selected depending on a cell-free translation system to be used.

The templates of the bait and prey added to the cell-free translation system may be either RNA or DNA, so long as the cell-free translation system is a cell-free transcription and translation also causing transcription.

Hereafter, an example of a translation template preferred for use as a bait will be explained.

As a bait used in the cotranslation screening of this embodiment, used is a translation template characterized by comprising a coding portion having information for translation into a protein and a PEG spacer portion as shown in FIG. 7. The coding portion has information for translation into a protein, and it may be any sequence. However, it is preferably characterized by having an acceptor (A sequence) in a 3' end region of the coding portion, or having an acceptor (A sequence) in a 3' end region of the coding portion and a translation amplification sequence (X sequence) 5'-upstream from the A sequence. It contains a short poly-A sequence as the A sequence of the coding portion. The short poly-A sequence is usually a sequence comprising 2 to 10 nucleotides of A. It is characterized by having a sequence having (C or G) NN (C or G) sequence, for example, a XhoI sequence, as the X sequence. The PEG spacer portion has a PEG region containing polyethylene glycol as a main component, a donor region for ligation with the coding portion, and a CCA region at the 3' end. Although the PEG spacer portion may consist only of the donor region or CCA region, it is preferably has a configuration comprising the PEG region containing polyethylene glycol as a main component. The CCA region is characterized by not having a function of binding by a transpeptidation reaction to a protein translated from the translation template. The PEG region is characterized by having a molecular weight of the polyethylene glycol of 500 or more. Further, it is characterized by containing at least one function-imparting unit (F) in the donor region and/or the CCA region. It is characterized in that the function-imparting unit (F1 and/or F2) immobilizes or labels with fluorescence the translation template and/or a protein translated from the translation template. As the immobilization substance, biotin and so forth are contemplated, and as the fluorescent substance, fluorescein, Cy5, rhodamine green (RhG) and so forth can be contemplated. The present invention relates to these coding portion, translation template, and libraries thereof, as well as a protein translated on a ribosome and library thereof.

The translation template of a bait (FIG. 7, A) comprises a coding portion derived from a coding molecule (FIG. 7, B) and a PEG spacer portion derived from a PEG spacer molecule (FIG. 7, C). In this embodiment, a PEG spacer portion can be ligated to the coding portion to improve stability thereof, and thus translation efficiency can be improved, basically regardless of the sequence of the coding portion. However, it is further possible to further improve the translation efficiency depending on the configuration of the coding portion or the type of the PEG spacer portion. The details thereof are described below.

The coding portion of this embodiment (FIG. 7, B) comprises a 5' end region, an ORF region, and a 3' end region, and it may or may not have a Cap structure at the 5' end. Further, the sequence of the coding portion is not particularly limited, and use thereof as one incorporated into any vector or plasmid can be contemplated. The 3' end region of the coding portion includes one having a poly-A×8 sequence as the A sequence or one having, as the X sequence, the XhoI sequence or a sequence of SNNS(S is G or C) as a sequence of 4 or more nucleotides, and XA as a combination of the A sequence and X sequence. A configuration that a Flag-tag sequence is included as an affinity tag sequence upstream from the A sequence, X sequence, or XA sequence is contemplated. The affinity tag sequence used here may be a sequence for using any means that enables detection or purification of a protein, for example, those utilizing an antigen-antibody reaction such as HA-tag and protein A of IgG (z domain), His-tag, and so forth. As for factors affecting the translation efficiency, the combination of the XA sequence is important. The first four nucleotides of the X sequence are important, and one having a sequence of SNNS is preferred. Further, the 5' end region comprises a transcription promoter and a translation enhancer. As the transcription promoter, T7/T3, SP6, and so forth can be used, and no particular limitation is imposed. However, for a cell-free translation system of wheat, a sequence containing an omega sequence or a part of omega sequence is preferably used as the translation enhancer sequence, and SP6 is preferably used as the promoter. The part of the omega sequence is one containing a part of the omega sequence of TMV (O29, refer to Gallie D. R., Walbot V., Nucleic Acids Res., vol. 20, 4631-4638 (1992) and WO02/48347, FIG. 3). The ORF region of the coding portion may be any sequence comprising DNA and/or RNA. It may be a gene sequence, exon sequence, intron sequence, random sequence, or any natural sequence or artificial sequence, and the sequence is not limited.

The PEG spacer molecule of this embodiment (FIG. 8, C) comprises a CCA region, a PEG region, and a donor region. The minimum essential component is the donor region. As for the factors affecting the translation efficiency, one having not only the donor region but also the PEG region is preferred, and it preferably has puromycin which does not have an ability to bind with an amino acid. The molecular weight of the polyethylene glycol in the PEG region is 400 to 30,000, preferably 1,000 to 10,000, more preferably 2,000 to 6,000. Further, the CCA region may have a configuration including puromycin or a configuration not including puromycin. As puromycin, puromycin and 3'-N-aminoacylpuromycin aminonucleosides (PANS-amino acids) including PANS-amino acids corresponding to all amino acids such as PANS-Gly in which the amino acid portion is glycine, PANS-Val in which the amino acid portion is valine, and PANS-Ala in which the amino acid portion is alanine can be utilized. Further, 3'-N-aminoacyladenosine aminonucleosides (AANS-amino acids), in which a 3'-aminoacyladenosine and an amino acid is bonded-via an amide bond as a chemical bond formed as a result of dehydration condensation of the amino group of the 3'-aminoacyladenosine and the carboxyl group of the amino acid, corresponding to all amino acids, for example, AANS-Gly in which the amino acid portion is glycine, AANS-Val in which the amino acid portion is valine, AANS-Ala in which the amino acid portion is alanine, and so forth can also be used. Furthermore, nucleosides and nucleosides bound with an amino acid via an ester bond can also be used. In addition, any of substances formed with a bonding scheme that can chemically bond a nucleoside or a substance having a chemical structure similar to that of nucleoside and an amino acid or a substance having a chemical structure similar to amino acid can be used. For this translation template, any substances corresponding to the aforementioned puromycin derivatives of which amino group lacks the ability to bind to an amino acid, and a CCA region lacking puromycin are also contemplated. However, by incorporating puromycin that cannot bind with a protein on a ribosome, the translation efficiency can be further enhanced. Although the reason for this is not certain, it may possible that puromycin that cannot bind with a protein stimulates a ribosome to enhance the turnover. A nucleotide sequence comprising DNA and/or RNA of one or more residues is preferably contained on the 5' end side of the CCA region (CCA). As for the type of nucleotide, preference is higher in the order of C>(U or T)>G>A. As such a sequence, dC-puromycin, rC-puromycin, and so forth, more preferably, a CCA sequence comprising dCdC-puromycin, rCrC-puromycin, rCdC-puromycin, dCrC-puromycin or the like and imitating the 3' end of aminoacyl-tRNA (Philipps, G. R., Nature 223, 374-377 (1969)) is suitable. In one embodiment of the present invention, these puromycins are made incapable of binding with an amino acid in a certain manner.

The PEG spacer portion of this embodiment may have a configuration containing a modification substance (F1 and/or F2). With this characteristic, it can be used as a tag for collection, reuse by purification, or immobilization of translation template. Those comprising at least one residue of nucleotide of DNA and/or RNA incorporated with any of various separation tags such as fluorescent substance, biotin, and His-tag may be possible. Further, if SP6+O29 and Flag+XhoI+An (n=8) are used as the 5' end region and the 3' end region of the coding portion, respectively, for example, the lengths of the 5' end region and the 3' end region are about 60 bp and about 40 bp, respectively, and thus they have such a length that they can be designed in primers for PCR as an adaptor region. This provides a novel advantage. That is, it becomes possible to easily prepare a coding portion having a 5' end region and 3' end region according to this embodiment by PCR from any vector, plasmid, and cDNA library, and by ligating the PEG spacer portion, instead of a 3' UTR, to this coding portion, a translation template showing a high translation efficiency can be obtained.

The ligation of the PEG spacer molecule and the coding molecule according to this embodiment may be attained any method such as usual methods utilizing a DNA ligase or those based on a photoreaction, and the method is not particularly limited. In the ligation using an RNA ligase, as factors in the coding portion affecting the ligation efficiency, the A sequence of the 3' end region is important. It is a poly-A continuous chain consisting of at least two, preferably 3 or more, more preferably 6 to 8, of single kind or mixed kinds of residues selected from dA and/or rA. The DNA and/or RNA sequence of the 5' end of the donor region of the PEG spacer portion affects the ligation efficiency. In order to ligate the coding portion and PEG spacer portion with an RNA ligase, it is required to contain at least one or more residues, and for an acceptor having a poly-A sequence, at least 1 residue of dC (deoxycytidylic acid) or two residues of dCdC (dideoxycytidylic acid) is preferred. As for the type of nucleotide, preference is higher in the order of C>(U or T)>G>A. Furthermore, it is preferable to add polyethylene glycol of the same molecular weight as the PEG region during the ligation reaction.

Hereafter, an example of a translation template preferably used as a prey will be explained.

As a prey in cotranslation screening according to this embodiment, a protein of which C-terminal is modified with a translation template as represented in FIG. 9 (i.e., assigning molecule) is used. The translation template comprises a coding portion having information for translation into a protein and a PEG spacer portion. The coding portion has an A sequence at the 3' end, and the A sequence comprises a short poly-A sequence. The PEG spacer portion is characterized in that polyethylene glycol in the PEG region containing polyethylene glycol as a main component has a molecular weight of 400 or more, and the donor region and/or the CCA region contains at least one modification substance (F1 and/or F2). Further, the CCA region is characterized by having a function of binding by transpeptidation to a protein translated from the translation template, and the CCA region typically has puromycin. Further, it is characterized in that the modification substance (F1 and/or F2) immobilizes or labels with fluorescence the translation template and/or a protein translated from the translation template. As the immobilization substance, biotin and so forth are contemplated, and as the fluorescent substance, fluorescein, Cy5, rhodamine green (RhG) and so forth can be contemplated. The present invention relates to these coding portion, translation template, and libraries thereof, as well as a protein synthesized by translation on a ribosome (i.e., assigning molecule) and a library of such proteins (i.e., assigning molecules).

The prey is a protein synthesized by translation utilizing the translation template, of which C-terminal is modified with the translation template (FIG. 8, A, assigning molecule), and has characteristics in the translation template (FIG. 8, B) and the configuration of a protein of which C-terminal is modified with PEG (FIG. 8, C). It will be described in detail below.

The PEG spacer portion of the translation template (FIG. 8, B) is the same as that of the aforementioned translation template preferred for use as an bait except that it is characterized in that puromycin can bind with an amino acid. Further, the coding portion is also the same as that of the aforementioned translation template preferred for use as a bait. However, as for a configuration suitable for assignment, in particular, it is important to use an A sequence as the 3' end region, and this markedly increase the assignment efficiency of the total proteins and markedly decrease the amount of free proteins. Also in this case, if SP6+O29 and Flag+XhoI+An (n=8) are used as the 5' end region and the 3' end region of the coding portion, respectively, for example, the lengths of the 5' end region and the 3' end region are about 60 bp and about 40 bp, respectively, and thus they have such a length that they can be designed in primers for PCR as an adaptor region. This makes it possible to easily prepare a coding portion having a 5' end region and 3' end region according to this embodiment by PCR from any vector, plasmid, and cDNA library, and by ligating the PEG spacer portion, a translation template showing a high assignment efficiency can be obtained.

When the cording portion of the protein of which C-terminal is modified with PEG according to this embodiment (FIG. 8, C) is not used in detection of an interaction of proteins, i.e., when the protein is use for, for example, FCCS measurement, fluorescence reader, protein chip, and so forth, it may be intentionally cleaved with an RNase A or the like. By the cleavage, difficulty of detection of an interaction between proteins due to inhibition by the coding portion can be eliminated. Further, it is also possible to immobilize such a simple assigning molecule on a plate, bead, or slide glass.

The cell-free cotranslation will be explained with reference to FIG. 9. As shown in FIG. 9, a prey is translated in vitro in the presence of a bait. As shown in FIG. 9, A and B, there are a case where the bait is a protein, and it is translated simultaneously with the prey in a cell-free translation system, and a case where the bait is a nucleic acid, hormone or the like, and it is added to a cell-free translation system. As shown in FIG. 9, the prey is made into a fusion protein or assigning molecule.

The complex may be formed by binding of a bait and one prey (I), or by binding of another prey to a prey binding to a bait (II).

Because the detection method of the present invention enables in vitro formation of the complex, interactions between proteins, nucleic acid and protein, and so forth can be consistently detected in vitro.

When the bait is a protein, examples of the bait include a protein consisting only of a functional domain for an interaction with an objective protein, a protein including a functional domain, a protein of full length, and so forth. If a protein of full length is used, it is expected that it has multiple functional domains, and therefore it favorably becomes possible to more comprehensively detect preys. The protein of full length may be a single protein having a full length, or an assembly of two or more baits from which a protein of full length can be reconstructed.

The bait may be a complex as shown in FIG. 10, and this is called "complexed bait". By using such a complex, nonspecific adsorption can be further reduced, and it becomes possible to more comprehensively detect preys as the same effect as that of the full length protein.

As described above, as a complex contemplated for the cell-free cotranslation, a complex of a single bait and a single prey, a complex of a complexed bait and a prey, a complex of a bait and multiple preys, and a complex of a complexed bait and multiple preys are possible. Therefore, an interaction detectable by the detection method of the present invention includes not only a direct interaction between a bait and a prey, but also an indirect interaction for forming a complex.

It is considered that the most important factor in the cell-free cotranslation according to the present invention is that a protein is folded in a native state and in an undenatured state immediately after translation, a bait and a prey, a bait and another bait, or a prey and another prey, which should interact with each other, should coexist in a cell-free translation system, and thus they can promptly interact with each other. This is supported by the fact that a more superior result could be obtained by cotranslation compared with separate translation followed by coexistence by mixing. That is, it is considered that this is because a protein translated in vitro in a native folding state can encounter a protein, nucleic acid or the like, and therefore prompt formation of a complex by an interaction becomes possible.

The conventional methods of detecting an interaction require expression in *E. coli* and purification of a bait in a large amount. For example, when an interaction of a bait and a prey is expressed in a cell by the TAP method or the like, at least one month of preparation is needed. Further, the mRNA displaying method employing the pull-down method based on a GST fusion protein has problems that it takes at least 2 or 3 weeks because of the large amount expression in *E. coli* and purification of the bait, a substance that cannot be expressed in *E. coli* cannot be used as the bait, and so forth, and it further requires addition of bait in an amount 50 to 100 times the amount of prey to cause interaction with the prey. In the cell-free cotranslation, it becomes that only addition of almost equal weight of mRNA or DNA template to a cell-free translation system is sufficient, and it becomes completely unnecessary to express the bait in cells. Thus, the operation time can be markedly shortened. Furthermore, with a complexed bait or full length protein, an interaction of a bait and a prey can be further enhanced and made specific, and thus detection of nonspecific bonds can be avoided. Further, by using a complexed bait, a larger number of preys that interact with the second bait thereof can be comprehensively analyzed.

Although no system realizing complex formation by an interaction and screening consistently in vitro has existed so far, by performing translation and screening including those for a bait completely in vitro according to the detection method of the present invention described above, a system that can comprehensively detect interactions between proteins or between a protein and a nucleic acid with avoiding nonspecific detection can be constructed. Therefore, the present invention also provides a screening method utilizing the detection method of the present invention.

The screening method of the present invention is characterized by forming complexes by interactions of a bait and preys during cell-free cotranslation, and analyzing a prey that interacts with the bait by screening of the complexes. Therefore, the screening method of the present invention may be the same as an ordinary screening method for a prey that interacts with a bait comprising the detection step of detecting an interaction between a bait and prey and the selection step of selecting a prey for which an interaction is detected, except that the method comprises the detection step of detecting an interaction between a bait and a prey by the detection method of the present invention.

The screening method of the present invention further comprises the preparation step of preparing a prey selected in the selection step, and it is preferable to repeat the detection step, selection step and preparation step by using the prepared prey instead of or together with the bait used in the detection step. In this embodiment, the method is constituted by, for example, 1) the step of cell-free cotranslation in a cell-free translation system in which a prey and a bait cause an interaction, 2) the step of screening for detecting a prey interacting with the bait, 3) the step of examining and analyzing the prey, and 4) the step of repeating the steps from 1) by using the prey examined and analyzed in 3), as shown in FIG. 11. The steps of 1) and 2) correspond to the detection step and selection step, and the step of 3) corresponds to the preparation step. That is, the step of contacting a prey to the bait in the detection step corresponds to the step of the cell-free cotranslation, and the steps of detecting and selecting a complex in the detection step correspond to the step of screening.

In the screening method of the present invention, the prey selected in the selection step may be used again in the detection step.

In the screening method of the present invention, the cell-free cotranslation may be performed with a bait and a prey library, which is a group of multiple preys, so that two or more preys may be detected in the step of screening.

As shown in FIG. 9, a complexed bait and a prey may coexist, and a complex of the complexed bait and the prey may be formed by an interaction. By using a prey library in this cell-free cotranslation so that multiple kinds of preys of the prey library should coexist with the bait, and multiple complexes of the preys with the bait should be formed by interactions, multiple kinds of preys that interacts with the bait can be simultaneously and comprehensively detected in the screening. Further, if a full length protein is used as the bait, it becomes possible to comprehensively detect a larger number of preys, because a full length protein generally contains multiple functional domains for interactions.

Furthermore, as shown in FIG. 10, by forming multiple complexes of preys that interact with a complexed bait, multiple preys that interact with the complexed bait can be detected, and the second bait serves as a reinforcer of the interaction of a bait and a prey to realize a more specific interaction, which makes it possible to avoid nonspecific detection in the comprehensive detection. In evolutionary molecular engineering techniques such as the vitro virus method and the STABLE method, the prey is an assigning molecule (fusion). In the formation of complexes using a prey library or multiple kinds of preys, the preys may or may not directly interact with the bait.

When the complex obtained by the screening of complexes is an assigning molecule, a prey forming the complex may be detected by RT-PCR or PCR, and the screening may be performed again by using the PCR product as a prey (reconstruction of prey) or by using a prey analyzed from the PCR product as a new succeeding bait, as shown in FIG. 11. The method of performing the screening again by using the PCR product or performing screening by using a prey analyzed from the PCR product as a new succeeding bait can be performed only in the evolutionry molecular engineering techniques such as the in vitro virus method and the STABLE method, and cannot be carried out in a method of directly analyzing a protein such as the pull-down method and the TAP method.

When an assigning molecule is used, gene sequence of a proteinic prey can be known by RT-PCR or PCR after the screening. As shown in FIGS. 9 and 10, the proteinic prey referred to above is a prey interacting with a bait, a prey interacting that prey or the like, and all multiple kinds of preys interacting a bait can be comprehensively analyzed. When rescreening of a prey is further necessary, a DNA template, which is a product of RT-PCR or PCR, is transcribed, and the same cycles are repeated. Further, when a prey is determined by RT-PCR or PCR and the following sequence, it becomes possible to use that proteinic prey as a bait. If two or more kinds of preys that interact with the first bait are found, it becomes possible to form a complexed bait, and thus it becomes possible to detect a further larger number of preys.

If the cell-free cotranslation is used, it becomes possible to detect an interaction between proteins consistently in vitro even in the pull-down method or the TAP method. However, the assigning molecule is not formed in the TAP method, and therefore proteins must be directly analyzed in the analysis of preys. Then, if the pull-down method or the TAP method is used as the screening method in the in vitro virus method or the STABLE method, an assigning molecule is formed, and therefore gene sequence of a prey that causes interaction can be easily detected by RT-PCR or PCR in the analysis of the prey. Furthermore, if the cell-free cotranslation is used, it becomes possible to detect interactions between proteins consistently in vitro in the in vitro virus method or the STABLE method. Further, the number of preys is extremely large, the range of candidate preys can be narrowed down by rescreening performed by repeating the cycles. Further, the analyzed prey can be used as a bait in the next analysis, and if the number of preys increases, complexing of the bait advances, which results in detection of further preys. As described above, use of a prey as a bait in the subsequent cycle can be easily realized only in the in vitro virus method, STABLE method and so forth, which use an assigning molecule. However, the mRNA display method and the like requires synthesis in E. coli and purification of a large amount of GST fusion protein as a new bait, and thus preparation of the bait takes time, which makes the method difficult. If the cell-free cotranslation is used, such procedures are unnecessary, and the cycles can be easily repeated.

In the screening of complexes after the cell-free cotranslation, it is preferred that preys can be screened comprehensively without breaking the complexes produced by the cell-free cotranslation. For this purpose, a device for immobilization may be imparted to the bait with an affinity tag or the like so as to detect a prey that interacts with the bait. Any kind of such a device for immobilization may be used. Examples include, for example, a method of performing two-stage screening using IgG-protein A affinity or calmodulin beads as in the conventional TAP method, and a method of performing one- or two-stage screening using streptavidin or avidin/biotin affinity, GST-tag, Flag-tag, T7-tag, His-tag or the like as in the pull-down method.

Examples of the prey library include a cDNA library (random priming library, dT priming library), random library, peptide library, hormone library, antibody library, ligand library, pharmaceutical compound library, and so forth, and any kind of library may be used. For example, if a random priming cDNA library is used as the prey library, although a full length prey cannot be expected for this library, a prey containing a functional domain can be expected. If such a library is used especially for screening using combinations with a complexed bait or full length protein, it becomes effective for comprehensive detection of preys.

Examples of the random priming library include cDNAs obtained by random priming and incorporated into multicloning sites (MCS) of vectors having a 5' untranslation region (UTR) containing the promoter of the RNA polymerase of SP6 (SP6) as a transcription promoter and a part of TMV omega sequence (O29) of the tobacco mosaic virus as a translation enhancer on the 5' end side of MCS, and containing a sequence for the Flag-tag, which is a tag for affinity separation analysis based on an antigen-antibody reaction, as an affinity tag sequence on the 3' end side of MCS, so that the Flag-tag should be added to the C-terminal of a protein expressed from an insert sequence incorporated into MCS.

The aforementioned detection method of the present invention includes the step of contacting a bait and a prey to form a complex. Therefore, a method of forming a complex of a bait and a prey that interacts with the bait is provided according to this step.

The formation method of the present invention is characterized by using the protein of the present invention as a bait in the formation of a complex of a bait and a prey, which is a protein that interacts with the bait, and preferably further labeling the bait and prey for detection and modifying them for separation in particular schemes, to perform cell-free cotranslation. Therefore, a preferred configuration of the formation method of the present invention may be the same as that of an ordinary method of forming a complex of a bait and a prey comprising contacting a bait and a prey that interacts with the bait, except that the bait and prey are labeled for detection and modified for separation in particular schemes, and the cell-free cotranslation is performed. The labeling for detection and modification for separation of the bait and prey in particular schemes as well as the cell-free cotranslation may be the same as those explained for the detection method of the present invention.

In the formation method of the present invention, not only a complex of a bait and a prey, for which interaction is known, but also a complex comprising elements for which interaction is unknown can be formed by performing the step of contacting the bait with a prey that interacts with the bait by contacting a bait with a prey library consisting of multiple kinds of preys.

Other methods for utilizing the protein of the present invention include the followings:

a method for analyzing an interaction between a protein and a substance, which is performed by fluorescence correlation spectroscopy, fluorescent imaging analysis method, fluorescence resonance energy transfer method, evanescent field molecular imaging method, fluorescence depolarization method, surface plasmon resonance method or enzyme linked immunosorbent assay using the protein of the present invention, a method for detecting an interaction between a protein and a substance, which uses the protein of the present invention and detects the interaction by amplification of a nucleotide sequence of a coding portion bound to the C-terminal of the protein of the present invention, a method for detecting an interaction between a protein and a substance, which uses the protein of the present invention and uses the cell-free cotranslation method or the cell-free cotranslation screening method, a method for detecting an interaction between a protein and a substance, which uses the protein of the present invention and labels the protein with fluorescence and/or immobilizes the protein, a method for analyzing an interaction of a protein or substance in vitro by using the protein of the present invention, a method for analyzing an interaction of a protein or substance, which uses the protein of the present invention, and utilizes the cotranslation method in vitro, a method for analyzing an interaction of a protein or substance in vivo by using the protein of the present invention, and the aforementioned methods for analyzing an interaction, which uses a nucleic acid encoding the protein of the present invention.

Further, the followings are also mentioned:

a method for analyzing an interaction between a protein and a target molecule, which uses a C-terminal modified protein comprising the protein and a modification agent binding to the C-terminal of the protein. The analysis of the interaction can be carried out by fluorescence correlation spectroscopy, fluorescent imaging analysis method, fluorescence resonance energy transfer method, evanescent field molecular imaging method, fluorescence depolarization method, surface plasmon resonance method or enzyme linked immunosorbent assay. The C-terminal modified protein may be immobilized. The C-terminal modified protein may be added on an array on which the target molecule is immobilized, and then the C-terminal modified protein specifically binding to the target molecule may be detected.

In the analysis method of this embodiment, the interaction is usually analyzed by contacting the modified protein of the present invention obtained above and the target molecule in a suitable combination selected depending on the type of the modification substance or reaction system and measuring change of a signal generated by the interaction between the modified protein and the target molecule among signals generated by the modified protein or the target molecule. The analysis of the interaction is carried out by, for example, fluorescence correlation spectroscopy, fluorescent imaging analysis method, fluorescence resonance energy transfer method, evanescent field molecular imaging method, fluorescence depolarization method, surface plasmon resonance method or enzyme linked immunosorbent assay. The details of these methods are explained below.

The "target molecule" means a molecule that interacts with the modified protein of the present invention, and it may be specifically a protein, nucleic acid, sugar chain, low molecular weight compound or the like, preferably a protein or DNA.

The protein is not particularly limited so long as it has an ability to interact with the modified protein of the present invention, and it may be a protein of full length or a partial peptide containing an active site for binding. Further, it may be a protein of which amino acid sequence or function is known or unknown. It may be a synthesized peptide chain, a protein purified from an organism, a protein obtained by translation from a cDNA library using a suitable translation system and purification, or the like, and they can be used as the target molecule. The synthesized peptide chain may be a glycoprotein consisting of a synthesized peptide chain attached with a sugar chain. Among these, a purified protein of which amino acid sequence is known or a protein obtained by translation from a cDNA library and purification using suitable methods can be preferably used.

The nucleic acid is not particularly limited so long as it has an ability to interact with the modified protein of the present invention, and either DNA or RNA may be used. Further, it may be a nucleic acid of which nucleotide sequence or function is known or unknown. Preferably, a nucleic acid of which function as a nucleic acid having an ability to bind to a protein or nucleotide sequence is known or a nucleic acid obtained by cleavage with a restriction enzyme or the like and isolation from a genomic library or the like can be used.

The sugar chain is not particularly limited so long as it has an ability to interact with the modified protein of the present invention, and it may be a sugar chain of which saccharide sequence or function is known or unknown. Preferably, an already isolated and analyzed sugar chain of which saccharide sequence or function is known is used.

The low molecular weight compound is not particularly limited so long as it has an ability to interact with the modified protein of the present invention. A compound of which function is unknown or a compound of which ability to bind to a protein is already known may also be used.

The "interaction" caused by these targets molecules with the modified protein of the present invention usually means an action caused by an intermolecular force generated by at least one of covalent bond, hydrophobic bond, hydrogen bond, van der Waals binding and binding caused by electrostatic force between a protein and a target molecule. However, this term should be construed in its broadest sense, and it should not be construed in any limitative way. The covalent bond includes a coordinate bond and dipole bond. The binding caused by electrostatic force includes, besides electrostatic bond, electric repulsion. Further, a bonding reaction, synthetic reaction and decomposition reaction caused as a result of the aforementioned action are also included in the interaction.

Specific examples of the interaction include association and dissociation of an antigen and an antibody, association and dissociation of a protein receptor and a ligand, association and dissociation of an adhesion molecule and a partner molecule, association and dissociation of an enzyme and a substrate, association and dissociation of a nucleic acid and a protein binding to it, association and dissociation of proteins in an information transmission system, association and dissociation of a glycoprotein and a protein and association and dissociation of a sugar chain and a protein.

The target molecule to be used may be modified with a modification substance and used depending on embodiments. The modification substance is usually selected from nonradioactive modification substances such as fluorescent substances. The fluorescent substances may be any of various fluorescent dyes of, for example, fluorescein type, rhodamine type, Cy3, Cy5, eosine type, NBD type and so forth, which have a free functional group (e.g., carboxyl group, hydroxyl group, amino group etc.) and can bind to the aforementioned target substance such as proteins and nucleic acids. In addition, other compounds such as dyes may be used, and type and size of the compounds are not critical so long as they enable the modification.

Among these modification substances, a substance suitable for the method of measurement or analysis of change of signal generated due to an interaction between the target molecule and the modified protein of the present invention is used.

The aforementioned modification substance can be bound to the target molecule by a suitable method known per se. Specifically, when the target molecule is a protein, the method of modifying the C-terminal described in WO02/48347 or the like may be used. Further, when the target molecule is a nucleic acid, it can by easily modified by a method of performing PCR using an oligo DNA primer bound with a modification substance beforehand via a covalent bond or the like.

Further, the modified protein of the present invention or the target molecule used for present invention may be bound to a solid phase (i.e., immobilized) depending on the embodiment. As the method for binding to a solid phase, there are a method of binding it via the modification substance and a method of binding it via another portion.

The modification substance used in binding via the modification substance is usually a molecule specifically binding to a particular polypeptide (henceforth also referred to as a "ligand"), and a particular polypeptide binding to the ligand (henceforth also referred to as an "adaptor protein") is bound to the solid phase. The adaptor protein also includes binding proteins, receptor proteins constituting receptors, antibodies and so forth.

Examples of combinations of the adaptor protein and the ligand include any of various receptor proteins and a ligand thereof, for example, a biotin or iminobiotin binding protein such as avidin and streptavidin and biotin or iminobiotin, maltose binding protein and maltose, G protein and guanine nucleotide, polyhistidine peptide and metal ion such as nickel or cobalt ion, glutathione-S-transferase and glutathione, DNA binding protein and DNA, antibody and antigen molecule (epitope), calmodulin and calmodulin binding peptide, ATP binding protein and ATP, estradiol receptor protein and estradiol and so forth.

Among these, preferred combinations of the adaptor protein and the ligand are biotin or iminobiotin binding protein such as avidin and streptavidin and biotin or iminobiotin, maltose binding protein and maltose, polyhistidine peptide and metal ion such as nickel or cobalt ion, glutathione-5-transferase and glutathione, antibody and antigen molecule (epitope) and so forth, and a combination of streptavidin and biotin or iminobiotin is the most preferred. These binding proteins per se are known, and DNAs coding these proteins have already been cloned.

The adaptor protein can be bound to a solid phase surface by using a method known per se. Specifically, for example, there can be used a method of utilizing tannic acid, formalin, glutaraldehyde, pyruvic aldehyde, bis-diazotized benzizone, toluene-2,4-diisocyanate, amino group, carboxyl group that can be converted into an active ester group, hydroxyl group or amino group that can be converted into phosphoramidite group, or the like.

When the binding is attained via a portion other than the modification substance, there can be used a known method usually used for binding a protein, nucleic acid, sugar chain or low molecular weight compound to a solid phase. Specifically, there can be used, for example, a method of utilizing tannic acid, formalin, glutaraldehyde, pyruvic aldehyde, bis-diazotized benzizone, toluene-2,4-diisocyanate, amino group, carboxyl group that can be converted into an active ester group, hydroxyl group or amino group that can be converted into phosphoramidite group, or the like.

The solid phase may be one usually used for immobilizing a protein, nucleic acid or the like, and material and shape thereof are not particularly limited. For example, glass plates, nitrocellulose membranes, nylon membranes, polyvinylidene fluoride membranes, microplates made of plastics and so forth can be used.

The "measurement" is a means for collecting changes of signals used for analysis, and it should not be construed in any limitative way. As the measurement method used, any of methods that can detect an intermolecular interaction can be used, including fluorescence correlation spectroscopy, fluorescence resonance energy transfer method, evanescent field molecular imaging method, fluorescence depolarization method, fluorescence imaging analysis method, surface plasmon resonance method, enzyme linked immunosorbent assay and so forth.

The measurement method includes a method comprising adding the modified protein of the present invention onto an array on which a target molecule is immobilized and detecting the modified protein of the present invention specifically binding to the target molecule. The array on which the target molecule is immobilized means a solid phase on which the target molecule is immobilized in an arrangement enabling identification thereof. The method for detecting the modified protein of the present invention specifically binding to the target molecule is not particularly limited, so long as the method enables detection of the modified protein of the present invention specifically binding to the target molecule. However, there is usually used, for example, a method of removing the modified protein of the present invention not binding to the target molecule by washing from the array to which the modified protein of the present invention is added and detecting the remaining modified protein of the present invention.

Hereafter, examples of the measurement method will be explained.

(1) Fluorescence Correlation Spectroscopy

The fluorescence correlation spectroscopy (FCS, Eigen, M., et al., Proc. Natl. Acad. Sci., USA, 91, 5740-5747 (1994)) is a method of measuring flow rate, diffusion coefficient, volume shrinkage or the like of particles under a confocal laser microscope or the like. In the present invention, interacting molecules can be measured by measuring change of translational Brownian movement of one original modified molecule of the present invention (C-terminal modified protein) caused by an interaction between the modified protein and a target molecule.

Specifically, fluorescence emitted from sample particles in a partial volume of a sample solution due to excitation of the sample particles by an excitation light is measured to obtain a photon ratio. This value changes with the number of the particles existing in a space volume observed during a specific period of time. The aforementioned various parameters can be calculated from the change of signals using an autocorrelation function. Apparatuses for carrying out FCS are also marketed from Carl Zeiss and so forth, and analysis can be performed by using these apparatuses also in the present invention.

When a protein-target molecule interaction is measured or analyzed by using this method, it is required to provide both of the C-terminal modified protein and the target molecule as solutions (liquid phase method). The target molecule does not need to be labeled. Further, a molecule having a molecular weight extremely smaller than that of the C-terminal modified protein of which interaction should be investigated is not suitable for this method, since such a molecule does not affect the Brownian movement of the C-terminal modified protein.

However, fluorescence cross-correlation spectroscopy (FCCS) using two kinds of fluorescent dyes can detect even an interaction between proteins having molecular weights of similar order, of which detection is difficult by FCS using one kind of fluorescent dye. Although the fluorescence resonance energy transfer (FRET) method is known as another method of using two kinds of fluorescent dyes, two kinds of fluorescent dyes need to approach each other at a distance within 40 to 50 Å in order to cause FRET, and there is a risk in this method that FRET may not be observed depending on sizes of proteins, locations at which the fluorescent dyes are attached or the like, even an interaction occurs. On the other hand, since the detection of cross-correlation does not depend on the distance between the fluorescent dyes in the FCCS method, it does not suffer from such a problem. Further, comparing with the fluorescence depolarization method as another detection system, the FCCS method has advantages of a smaller amount of required sample, shorter detection time, easier automatization for HTS and so forth. Further, since the FCCS method provides extremely fundamental information such as size and number of fluorescence-labeled molecules, it may be used for general purpose like the surface plasmon resonance method. The difference between the both is that, in the surface plasmon resonance method, an interaction is detected in the state that proteins are immobilized, whereas the FCCS method enables observation of interaction in a solution, which is closer to a natural state. In the FCCS method, although proteins do not need to be immobilized, the proteins must be labeled with fluorescent dyes instead. However, it has been made possible by the present invention to overcome this problem.

Further, the FCCS method enables investigation of a protein-protein interaction or protein-nucleic acid interaction in a state of solution, which is close to the intracellular environment, and enables convenient calculation of dissociation constant (binding constant) by one measurement.

The method for bringing a target molecule into contact with the C-terminal modified protein in this method may be any method that allows the contact in a sufficient degree such that they can interact with each other. However, it is preferably attained by a method of introducing a solution dissolving the C-terminal modified protein in a buffer usually used for biochemical purpose or the like at an appropriate concentration into a well for measurement in a commercially available FCS apparatus and further introducing a solution dissolving the target molecule in the same buffer at an appropriate concentration into the well.

In this method, as a method of performing multiple analyses, for example, there is used a method of introducing multiple kinds of different C-terminal modified proteins into wells for measurement in the aforementioned FCS apparatus, respectively, and further introducing a solution of a particular target molecule into the wells, or introducing a particular C-terminal modified protein into wells, and further introducing solutions of multiple kinds of different target molecules into the wells, respectively.

(2) Fluorescence Imaging Analysis Method

The fluorescence imaging analysis method is a method of bringing a modifying molecule into contact with an immobilized molecule and measuring or analyzing fluorescence emitted by the immobilized modifying molecule remained on the immobilized molecule due to an interaction between the both molecules using a commercially available fluorescence imaging analyzer.

When a protein-target molecule interaction is measured or analyzed by using this method, one of the C-terminal modified protein or the target molecule must be immobilized by the aforementioned method. When an immobilized target molecule is used, either a modified or unmodified target molecule can be used. Further, when it is used without immobilization, it must be modified with the aforementioned modification substance. Either a C-terminal modified protein immobilized at the modified portion or a C-terminal modified protein immobilized at a portion other than the modified portion may be used.

As a substrate for immobilizing a C-terminal modified protein or target molecule (solid phase), there can be used glass plates, nitrocellulose membranes, nylon membranes, microplates made of plastics and so forth, which are usually used for immobilizing a protein, nucleic acid or the like. Further, such substrates as mentioned above of which surfaces are bound with various functional groups (amino group, carboxyl group, thiol group, hydroxyl group etc.) or various ligands (biotin, iminobiotin, metal ions such as nickel or cobalt ion, glutathione, saccharides, nucleotides, DNA, RNA, antibody, calmodulin, receptor protein etc.) can also be used.

The method for bringing a modified target molecule or a C-terminal modified protein into contact with an immobilized molecule in this method may be any method that allows the contact in a sufficient degree such that the both molecules can interact with each other. However, it is preferably attained by a method of preparing a solution dissolving the modified target molecule or the C-terminal modified protein in a buffer usually used for biochemical purpose at an appropriate concentration and bringing the solution into contact with the solid phase surface.

After bringing the both molecules into contact with each other, a step of washing off excessively existing modified target molecule or C-terminal modified protein with the same buffer or the like is preferably performed, and fluorescence signal emitted from the modification substance of the target molecule or C-terminal modified protein which remained on the solid phase, or a mixed signal of fluorescence emitted from the immobilized modified molecule and fluorescence emitted from the modified molecule remained on the solid phase can be measured or analyzed by using a commercially available imaging analyzer to identify the molecule that interacts with the immobilized molecule.

In this method, as a method of simultaneously performing multiple analyses, for example, there is used a method of immobilizing multiple kinds of C-terminal modified proteins or modified or unmodified target molecules on the aforementioned solid phase surface with positioning addresses, a method of bringing multiple kinds of non-immobilized C-terminal modified proteins or modified target molecules into contact with one kind of C-terminal modified protein or modified or unmodified target molecule, or the like. When multiple kinds of C-terminal modified proteins or modified target molecules are brought into contact, the molecules remained on the solid phase can be obtained by dissociating them using difference of buffer concentration or the like and analyzed by a known method to identify them.

(3) Fluorescence Resonance Energy Transfer Method

As another intermolecular interaction detection method using two kinds of fluorescent dyes, the fluorescence resonance energy transfer (FRET) method is well known. FRET means a phenomenon that, if a fluorescence spectrum of one of two kinds of fluorescent dyes (energy donor) and an absorption spectrum of the other (energy receptor) overlap, and the distance between two of the fluorescent dyes is sufficiently small, it becomes more likely that excitation energy of the donor excites the receptor before the donor emits fluorescence. Therefore, two kinds of proteins of which interaction is desired to be detected are labeled with fluorescent dyes serving as the donor and the receptor, respectively, and the donor is excited. When the two kinds of proteins do not interact with each other, FRET is not caused because the distance between the fluorescence dyes is large, and thus fluorescence spectrum of the donor is observed. However, if the two kinds of proteins interact with each other, and hence the distance between the fluorescent dyes becomes smaller, fluorescence spectrum of the receptor is observed due to FRET. Therefore, presence or absence of an interaction between the proteins can be determined on the basis of difference in wavelengths of fluorescence spectra. As for the fluorescent dyes, a combination of fluorescein as the donor and rhodamine as the receptor is frequently used. Further, it is recently attempted to observe FRET in a cell to detect an interaction by using combination of mutant green fluorescence proteins (GFP) emitting fluorescence of different wavelengths. As a drawback of this method, it is mentioned that since two kinds of fluorescent dyes need to approach to each other at a distance within 40 to 50 Å in order to cause FRET, there is a risk that FRET may not be observed depending on sizes of proteins, locations at which the fluorescent dyes are attached or the like, even if an interaction occurs.

(4) Evanescent Field Molecular Imaging Method

The evanescent field molecular imaging method is a method described in Funatsu, T., et al., Nature, 374, 555-559 (1995) or the like, and it is a method of bringing a second molecule as a solution into contact with a molecule immobilized on a transparent material such as glass, irradiating them with a laser light or the like from a light source at such an angle that an evanescent field should be generated, and measuring or analyzing the generated evanescent light using a detector. These operations can be performed by using an evanescent field fluorescence microscope known per se.

When a protein-target molecule interaction is measured or analyzed by using this method, one of the C-terminal modified protein or the target molecule must be immobilized by the aforementioned method. When an immobilized target molecule is used, it does not need to be modified. However, when it is used without immobilization, it must be modified with the aforementioned modification substance.

As the substrate for immobilizing the C-terminal modified protein or target molecule, a substrate made of a material of glass or the like is used, and quartz glass is preferably used. Further, a substrate of which surface is cleaned by ultrasonication is preferred in order to prevent scatter of laser light or the like.

The method for bringing a non-immobilized C-terminal modified protein or target molecule into contact with an immobilized molecule in this method may be any method that allows the contact in a sufficient degree such that the both molecules can interact with each other. However, a method of preparing a solution dissolving the non-immobilized C-terminal modified protein or modified target molecule in a buffer usually used for biochemical purpose at an appropriate concentration and adding the solution dropwise to the solid phase surface is preferred.

After bringing the both molecules into contact with each other, fluorescence generated through excitation by the evanescent field illumination can be measured by using a detector such as a CCD camera to identify the molecule that interacts with the immobilized molecule.

In this method, as a method of simultaneously performing multiple analyses, for example, there is used a method of immobilizing multiple kinds of C-terminal modified proteins or modified target molecules on the aforementioned substrate with positioning addresses, or the like.

(5) Fluorescence Depolarization Method

The fluorescence polarization method (Perran, J., et al., J. Phys. Rad., 1, 390-401 (1926)) is a method utilizing the fact that a fluorescent molecule excited with a polarized fluorescent light emits fluorescence in the same plane of polarization during the excited state while it maintains a stationary state, whereas the emitted fluorescence has a plane different from that of the excitation light when the excited molecule undergoes rotational Brownian movement or the like during the excited state. The movement of molecule is affected by the size thereof, and when the fluorescent molecule is a macromolecule, the molecule scarcely shows movement during the excited state, and emitted light is maintained to be a polarized light. However, in the case of a low molecular weight fluorescent molecule, since it shows high moving velocity, the emitted light is depolarized. Therefore, if intensity of the fluorescence emitted from a fluorescent molecule excited by a plane polarized light is measured along the original plane and a plane perpendicular thereto, information of motility and existing state of the molecule can be obtained from a ratio of the fluorescence intensities for the both planes. According to this method, behavior of a target molecule that interacts with a fluorescence-modified molecule can be traced without being affected by contaminants, if any. This is because shift of polarization degree is measured only when the fluorescence-modified molecule and the target molecule interact with each other.

As apparatuses for carrying out this method, BECON (produced by Panyera) and so forth are marketed, and this method can be carried out by using these apparatuses.

When a protein-target molecule interaction is measured or analyzed by using this method, it is required to provide both of the C-terminal modified protein and the target molecule as solutions. The target molecule does not need to be modified. Further, a molecule having a molecular weight extremely smaller than that of the C-terminal modified protein of which interaction should be investigated is not suitable for this method, since such a molecule does not affect the Brownian movement of the C-terminal modified protein.

The method for bringing a target molecule into contact with the C-terminal modified protein in this method may be any method that allows the contact in sufficient degree such that they should interact with each other. However, it is preferably attained by a method of introducing a solution dissolving the C-terminal modified protein in a buffer usually used for biochemical purpose at an appropriate concentration into a well for measurement in a commercially available fluorescence depolarization apparatus and further introducing a solution dissolving the target molecule in the same buffer at an appropriate concentration into the well.

It is expected that specificity of interaction between the C-terminal modified protein and the target molecules to be measured in this method is not necessarily so high as that of an antigen-antibody reaction. Therefore, in order to identify an optimum combination, it is effective that degree of interaction should be numerically defined. As an index representing degree of interaction, for example, a value of the minimum target substance concentration providing the maximum fluorescence polarization degree for a C-terminal modified protein of a fixed concentration or the like can be used.

In this method, as a method of simultaneously performing multiple analyses, for example, there is used a method of introducing multiple kinds of different C-terminal modified proteins into wells for measurement in the aforementioned fluorescence depolarization apparatus, respectively, and further introducing a solution of a particular target molecule into the wells, or introducing a particular C-terminal modified protein into wells and further introducing solutions of multiple kinds of different target molecules into the wells, respectively.

(6) Surface Plasmon Resonance Method

The surface plasmon resonance method is a method of measuring surface plasmon excited by a molecule interacting at a metal/liquid interface as change of intensity of reflected light (Cullen, D. C., et al., Biosensors, 3 (4), 211-225 (1987-88)). When a protein-target molecule interaction is measured or analyzed by using this method, the C-terminal modified protein must be immobilized by the aforementioned method, but the target molecule does not need to be modified.

As a substrate for immobilizing the C-terminal modified protein, a transparent substrate made of glass or the like on which a thin film of metal such as gold, silver or platinum is formed is used. The transparent substrate may be any of those usually used for surface plasmon resonance apparatuses. It generally consists of glass as a substrate consisting of a material transparent to a laser light, and such a substrate having a thickness of about 0.1 to 5 mm is generally used. Further, thickness of the metal thin film is suitably about 100 to 2000 Å. Those marketed as such immobilization substrates for surface plasmon resonance apparatuses can also be used. The C-terminal modified protein can be immobilized on the substrate by the method described above.

The method for bringing a target molecule into contact with the C-terminal modified protein in this method may be any method that allows the contact in a sufficient degree such that the both molecules can interact with each other. However, a method of bringing the immobilized C-terminal modified protein into contact with a solution dissolving the target molecule in a buffer usually used for biochemical purpose at an appropriate concentration can be preferably used.

These steps may also be performed by using a commercially available surface plasmon resonance apparatus, for example, BIAcore 2000 (produced by Pharmacia Biosensor). After bringing the both molecules into contact with each other, change with time of relative intensity of each reflected light can be measured by using a surface plasmon resonance apparatus known per se to analyze or measure an interaction of the immobilized C-terminal modified protein and the target molecule.

In this method, as a method of simultaneously performing multiple analyses, for example, there is used a method of immobilizing multiple kinds of C-terminal modified proteins on a substrate used for the surface plasmon resonance apparatus with positioning addresses, a method of bringing multiple kinds of target molecules into contact with one kind of immobilized C-terminal modified protein, or the like.

(7) Enzyme Linked Immunosorbent Assay

The enzyme linked immunosorbent assay (ELISA, Crowther, J. R., Methods in Molecular Biology, 42 (1995)) is a method of bringing a solution containing an antibody into contact with an antigen immobilized on a solid phase and measuring or analyzing the antibody remaining on the immobilized antigen due to the interaction between the both molecules (antigen-antibody reaction) on the basis of fluorescence emitted from a modification molecule (IgG etc.) specifically binding to the antibody or a signal emitted by a dye formed from the modification molecule as a substrate using a commercially available detector (ELISA reader).

When a protein-target molecule interaction is measured or analyzed by using this method, the C-terminal modified protein serving as the antigen must be immobilized by the aforementioned method. Further, the target molecule serving as the antibody must be modified with the aforementioned modification substance.

As a substrate for immobilizing the C-terminal modified protein serving as the antigen, microplates made of plastics usually used for ELISA and so forth can also be used.

The method for bringing the modified target molecule serving as the antibody into contact with an immobilized molecule in this method may be any method that allows the contact in a sufficient degree such that the both molecules can interact with each other. However, a method of preparing a solution dissolving the modified target molecule in a buffer usually used for biochemical purpose at an appropriate concentration and introducing the solution into a microplate is preferred.

After bringing the both molecules into contact with each other, a step of washing off excessively existing modified molecule not binding to the immobilized molecule is preferably performed, and fluorescence emitted from the modified molecule remained on the solid phase can be measured or analyzed by using a commercially available ELISA reader or the like to identify the molecule that interacts with the immobilized antigen molecule.

In this method, as a method of simultaneously performing multiple analyses, for example, there is used a method of immobilizing multiple kinds of different modified target molecules in each well of the aforementioned microplate.

Further, the protein of the present invention can also be used for identification of a molecule that causes an interaction.

When primary structure of a target molecule for which an interaction with a C-terminal modified protein is recognized on the basis of measurement according to any one of the methods described above is unknown, the primary structure can be analyzed by a suitable method known per se. Specifically, when the target molecule for which an interaction is recognized is a protein, its amino acid sequence can be analyzed by using an amino acid analyzer etc. to identify the primary structure. Further, when the target molecule is a nucleic acid, nucleotide sequence can be determined by a nucleotide sequence determination method using an automatic DNA sequencer or the like.

Furthermore, the protein of the present invention can also be used for analysis of an interaction with a protein library.

The present invention provides a gene or nucleic acid sequence encoding a novel protein that can form a complex with the c-Jun protein, which was obtained by performing cotranslation selection/screening of IVV using the c-Jun protein as the bait and a mouse brain cDNA library as the prey, and methods for utilizing them. The present invention also provides a method for utilizing a gene or nucleic acid sequence encoding a known protein, which is not known to form a complex with the c-Jun protein.

The present invention not only enables screening of known gene sequences and known nucleic acid sequences, but also can provide a novel protein having a novel amino acid sequence formed by unexpected frame shift, a novel protein having a nucleic acid sequence for which only the nucleic acid sequence is published on the basis of genome information, or a novel protein having a completely novel nucleic acid sequence, further, a protein that forms a complex by an unexpected indirect interaction in addition to a direct interaction, a gene or nucleic acid sequence encoding the protein, and methods for utilizing them.

Hereafter, the amino acid sequences of the proteins of the present invention and the sequences of the nucleic acids encoding them will be specifically described. However, the following examples should be construed as a mere aid for specifically understanding the present invention, and the scope of the present invention is no way limited by the following examples.

EXAMPLE 1

Figure 2:
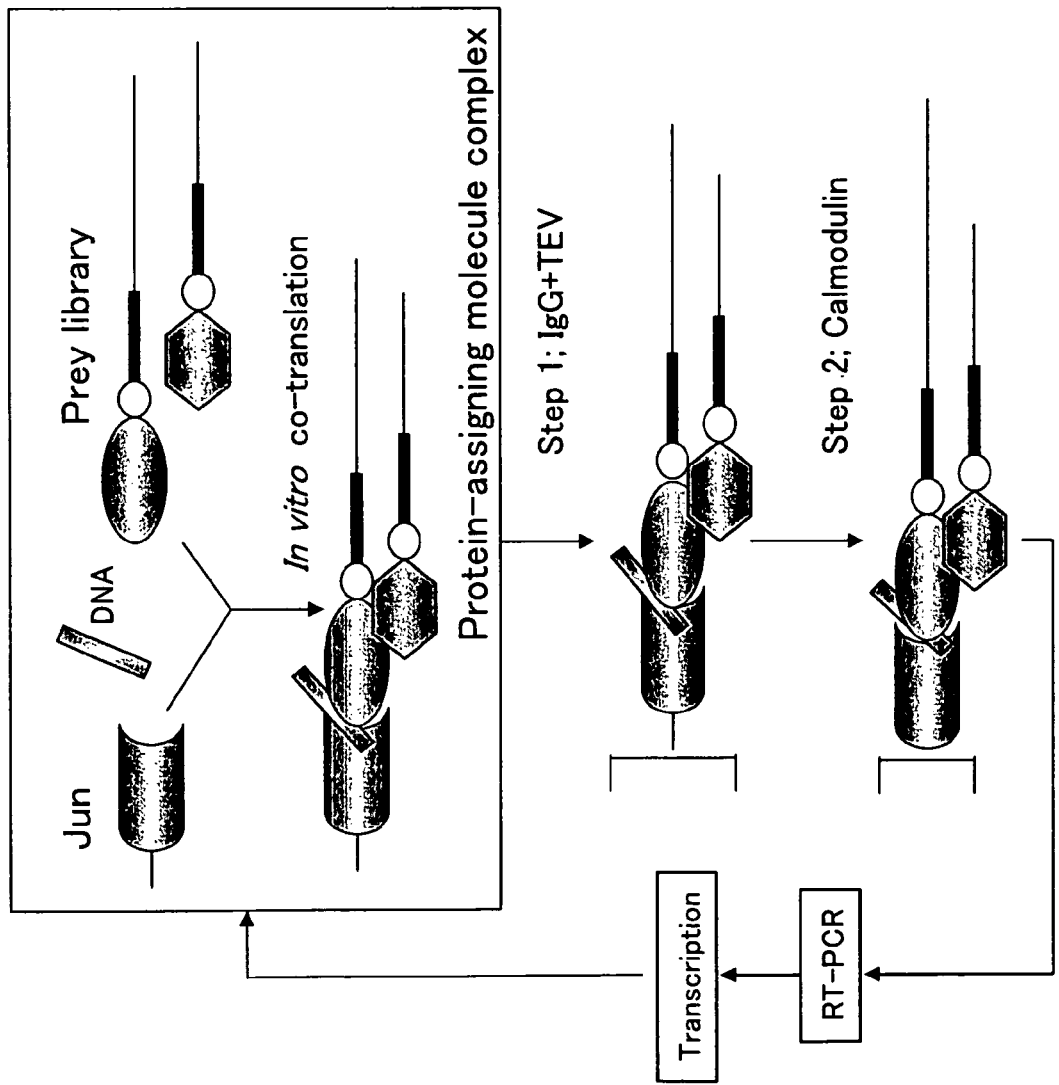
[FIG. 2] It shows the outline of the cotranslation screening method using an IVV random library, which is a method for detecting the proteins and genes of the present invention and the nucleotide sequences thereof. An IVV random library of mouse brain and c-Jun as a bait were used to carry out cell-free cotranslation screening, and the library after the screening was amplified by RT-PCR and then subjected to the cell-free cotranslation screening again with the bait. This procedure was repeated 3 times to detect the proteins and genes of the present invention and the nucleotide sequences thereof.

Cotranslation selection/screening of IVV was carried out by using the c-Jun protein as a bait and a mouse brain cDNA library as a prey (FIG. 2), and as a result, genes or nucleic acid sequences encoding novel proteins that can form a complex with the c-Jun protein were obtained.

The preparation method of the bait, c-Jun protein, was as follows. A DNA template was prepared from a pCMV-cJun (502-957)CBPzz vector (SEQ ID NO: 256) by PCR (primers 5'SP6(O29)T7 (SEQ ID NO: 257) and 3'FosCBPzz (SEQ ID NO: 258), and PCR program CYCB1 (refer to Table 1)) using TaKaRa Ex Taq (Takara Shuzo). The DNA template was transcribed (37° C., 2 hours) by using RiboMAX™ Large Scale RNA Production Systems (Promega) to prepare a mRNA template of the bait c-Jun protein. A bait DNA made to coexist was prepared by PCR (primers 5' DNA (SEQ ID NO: 260) and 3' DNA (SEQ ID NO: 161)) using DNA-Fos/Jun (SEQ ID NO: 259) containing the Fos/Jun binding sequence as a template according to the PCR program V-2 (refer to Table 1).

Figure 3:
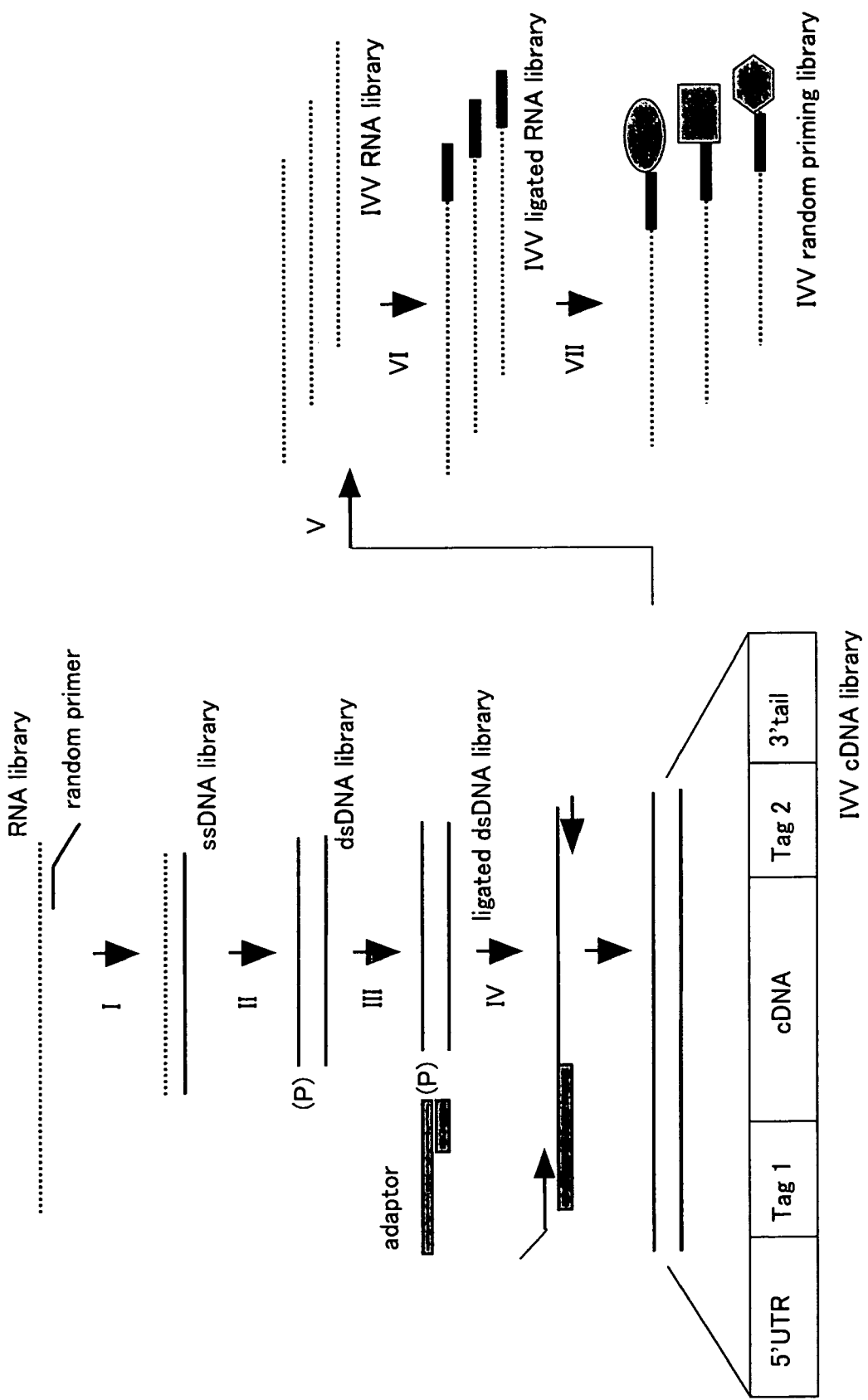
[FIG. 3] It shows the random priming library of IVV used for detection of the proteins and genes of the present invention and the nucleotide sequences thereof, and the outline of the method for producing it. Using an RNA library as a template and a random primer including a random sequence consisting of nine nucleotides and a specific sequence (tag2 sequence) in the random priming method, a library of single strand cDNAs (ssDNA) complementary to mRNAs is synthesized by reverse transcription (I). Only RNAs are decomposed in the double strands of cDNA and RNA with RNaseH, at the same time, DNAs complementary to cDNAs are synthesized with DNA-polymerase I, and further a nick existing between the DNAs synthesized with DNA polymerase I is modified by using a DNA ligase to synthesized a double strand (dsDNA) library (II). The synthesized double-stranded cDNAs have a phosphate group at the 5' end only on the side synthesized with the DNA polymerase I, and therefore this is utilized to ligate an adaptor having a specific sequence (5' UTR=promoter+enhancer) using a DNA ligase to synthesize a ligated dsDNA library (III). PCR is carried out by utilizing the adaptor and the specific sequence of the random primer to prepare a cDNA library of assigning molecules having the sequences of a promoter and an enhancer on the 5' end side and an A tail on the 3' end side (IVV cDNA library) (IV). Then, the IVV cDNA library is transcribed to form an IVV RNA library (V), a spacer for preparing IVV is ligated (VI), and further it is translated in a cell-free translation system or the like to form a library of assigning molecules (VII).

The preparation method of the mouse brain cDNA library as the prey was as follows. An IVV random library was prepared as shown in FIG. 3. As an RNA library, a commercially available mouse brain (polyA+) RNA library (obtained by purifying a tissue extracted RNA library in an oligo dT column, Clontech) was purchased. As for design of an adaptor, it was designed so as to add a 5' UTR sequence suitable for the production of assigning molecules (promoter SP6+enhancer O29 or O') to the library as a sequence required for IVV formation. For the mouse brain (polyA+) RNA library, an adaptor having the enhancer O29 was used. The main chain (SEQ ID NO: 262 or 263) and the subchain (gaattcgc) of the adaptor for the enhancer O29 were each dissolved in the TE buffer (10 mM Tris-Cl, pH8.0, 1 mM EDTA) at a concentration of 100 μM, and 10 μl each of the solutions of the main chain and subchain were mixed so that the main chain and the subchain were mixed in equimolar amounts. The mixture was heated at 90° C. for 2 minutes and at 70° C. for 5 minutes, set on a water bath of 60° C., and then slowly cooled from 60° C. to room temperature by turning off the heater of the bath. The mixture was divided into 5 μl aliquots, and stored at −20° C. Then, the mouse brain (polyA+) RNA library was reverse-transcribed into single stranded DNAs (FIG. 3, I). 0.5 μg of the mouse brain (polyA+) RNA library (1.4 pmole/0.5 μg), 2 pmol of 3' random primer (SEQ ID NO: 264) and DEPC water were added to obtain a volume of 12.0 μl, and the mixture was heated at 70° C. for 10 minutes, and cooled for 1 minute on ice. A reverse transcription reaction was performed at 45° C. for 1 hour by using this mixture and SuperScriptII RT (SuperScript Double-stranded cDNA Synthesis Kit, Invitrogen). Then, the total amount of the single stranded DNAs synthesized by the reverse transcription reaction was used for a reaction with an E. coli DNA ligase, E. coli Polymerase I and E. coli RNase H (SuperScript Double-stranded cDNA Synthesis Kit, Invitrogen) at 16° C. for 2 hours, and the product was blunt-ended with T4 DNA polymerase at 16° C. for 5 minutes to synthesize double-stranded DNAs (FIG. 3, II). Then, the adaptor previously prepared was ligated by taking advantage of the fact that the 5' ends of the double-stranded DNAs were phosphorylated (FIG. 3, III). The synthesized double-stranded DNA library was subjected to ethanol precipitation, and dissolved in 4 μl of DEPC water. 100 μM of the prepared adaptor in a volume of 1.0 μl and 50 μl of Ligation High (TOYOBO) were added thereto, reacted overnight at 16° C., purified (DNA purification kit, QIAGEN), and then adjusted to a volume of 50 μl. Thereafter, PCR (EX Taq Hot Start Version, TaKaRa) was performed (FIG. 3, IV). Out of 50 μl of the ligated double-stranded DNA library, 2 μl was used as a template together with 5' PCR primer (SEQ ID NO: 260) having a specific sequence required for IVV (O29) and 3' PCR primer (SEQ ID NO: 261) to prepare an IVV cDNA library. As for the PCR conditions, the total volume was 100 μl, and 22 cycles of the reactions (each cycle consists of reactions at 94° C. for 30 seconds, at 60° C. for 30 seconds, and at 72° C. for 90 seconds, and the final extension reaction was performed at 72° C. for 180 seconds).

Cotranslation (26° C., 60 minutes) of the mRNA template of the bait c-Jun protein, the mouse brain cDNA library as the prey, and the bait DNA made to coexist was carried out in a cell-free translation system of wheat (Wheat Germ Extract, Promega) in a volume of 50 μl. To 50 μl of the sample, 50 μl of IgG binding buffer (10 mM Tris-Cl, pH 8.0, 150 mM NaCl, 0.1% NP40) was added to obtain the total volume of 100 μl (cotranslation sample). Then, IgG agarose (Sigma) was washed twice with the IgG binding buffer, and the cotranslation sample (100 μl) was added thereto, and the mixture was stirred by rotation at 4° C. for 2 hours. The IgG agarose was washed 3 times with the binding buffer and once with a TEV cleaving buffer (10 mM Tris-Cl, pH 8.0, 150 mM NaCl, 0.1% NP40, 0.5 mM EDTA, 1 mM DTT), and the bait/prey complex binding to the IgG agarose was cleaved with TEV protease (GIBCO-BRL, 16° C., 2 hours). By using 1 μl of the collected 100 μl solution as a template, RT-PCR (One step RT-PCR kit (QIAGEN), primers: SEQ ID NOS: 265 and 266, program: RT-QH3090 (refer to Table 1)) was carried out in a volume of 50 μl. After this procedure (Step 1 in FIG. 2) was repeated for 5 rounds, the library was cloned and sequenced to obtain the amino acid and nucleotide sequences of the genes shown in FIG. 1. The DNA sequence SEQ ID NOS. corresponding to the amino acid SEQ ID NOS.: 1 to 69 are shown in List 1 below. The same results were obtained for both of the library prepared by using the sequence of SEQ ID NO: 262 as the main chain of the adaptor for enhancer O29 and the library prepared by using the sequence of SEQ ID NO: 263 as the same.

<List 1>

126(1), 127(2), 128(3), 129(4), 130(5), 131(6), 132(7), 133 (8), 134(9), 135(10), 136(11), 137(12), 138(13), 139(14), 140(15), 141(16), 142(17), 143(18), 144(19), 145(20), 146 (21-1), 147(21-2), 148(22), 149(23), 150(24), 151(25), 152 (26), 153(27), 154(28), 155(29), 156(30), 157(31), 158(32), 159(33), 160(34-1), 161(34-2), 162(35), 163(36), 164(37), 165(38), 166(39), 167(40), 168(41), 169(42), 170(43-1), 171 (43-2), 172(44), 173(45), 174(46), 175(47), 176(48), 177 (49), 178(50), 179(51), 180(52), 181(53), 182(54), 183(55), 184(56), 185(57), 186(58), 187(59), 188(60), 189(61-1), 190 (61-2), 191(62), 192(63), 193(64-1), 194(64-2), 195(65), 196 (66), 197(67), 198(68), 199(69)

All the proteins are proteins found by the present invention for the first time to form a complex with c-Jun.

As a verification experiment of the interactions of the obtained proteins and c-Fos, expression of the proteins of SEQ ID NOS: 18 (SNAP19), 76 (KINN), 93 (Kif5a), 99 (Eef1d), 102 (Nef3), 106 (Jip-c3.1), 110 (Jip-c1), 113 (EB2), 115 (Cspg6), 117 (Mapk8ip3), 119 (Jip-c3.2), 121 (GFAP), 123 (Jip-c8) and 125 (Kif5b) (FIG. 1) in a cell-free translation system was experimentally confirmed by using the DNA sequences of SEQ ID NOS: 143, 206, 223, 229, 232, 236, 240, 243, 245, 247, 249 and 253 according to the descriptions of WO02/46395, Example 1, (2) Preparation of coding molecule and (3) Translation of coding molecule, i.e., it was confirmed by the C-terminal labeling method that the proteins were expressed in a wheat cell-free translation system (FIG. 4, A). Further, the C-terminal labeled proteins for which expression was confirmed, were used as a prey protein to confirm interactions thereof with the bait c-Jun by pull-down. As for the preparation method of the prey protein, specifically, PCR cloning kit (QIAGEN) was used to extract a sequence cloned in the pDrive vector (SEQ ID NO: 267, QIAGEN) from cells, and a DNA template was prepared by PCR (primers 5'F3 (SEQ ID NO: 268) and 3'R3 (SEQ ID NO: 269), PCR program: ISHI1562 (refer to Table 1), 100 μl scale)

using TaKaRa Ex Taq (Takara Shuzo). The DNA template was transcribed (37° C., 2 hours, 50 μl scale) by using RiboMAXT™ Large Scale RNA Production Systems (Promega) to prepare a mRNA template of the prey protein.

The preparation method of the bait c-Jun protein is the same as that used for the screening.

Cell-free translation of the prey template (10 μl scale) was performed for 1 hour by using the C-terminal labeling method to prepare a prey protein in a C-terminal labeled state. At the same time, the translation reaction of the bait c-jun template was performed for 1 hour by the cell-free translation (50 μl scale) to produce the bait protein. After the translation, the both and the binding buffer were mixed (prey: 8 μl, bait: 10 μl, IgG binding buffer: 82 μl), and incubated with 50 μl of IgG agarose beads for 2 hours, and the beads were washed, then added with 20 μl of a buffer containing SDS, boiled at 100° C. for 5 minutes, and eluted. This sample was developed by 17.5% SDS-PAGE, and the FITC fluorochrome was observed by means of a fluorescence imager (FIG. 4, B). In addition, a reaction was also performed without adding the bait c-Jun protein as a control.

As a result, it could be confirmed that the proteins of SEQ ID NOS: 18 (SNAP19), 76 (KINN), 93 (Kif5a), 99 (Eef1d), 102 (Nef3), 106 (Jip-c3.1), 110 (Jip-c1), 113 (EB2), 115 (Cspg6), 117 (Mapk8ip3), 119(Jip-c3.2) and 123 (Jip-c8) directly interacted with c-Jun.

Furthermore, concentration of genes directly or indirectly interacting with c-Jun was confirmed by real time PCR using the nucleic acid sequences of SEQ ID NOS: 143, 206, 223, 229, 232, 236, 240, 243, 245, 247, 249, 253 and 255 (FIG. 5). Because SEQ ID NOS: 251 (GFAP) and 255 (Kif5b) were also concentrated similarly to other genes of direct interaction, it could be confirmed that there were indirect interaction with c-Jun. As for the specific method of the real time PCR, primers (SEQ ID NOS: 270 to 297) were designed for fourteen kinds of genes (SEQ ID NOS: 143, 206, 223, 229, 232, 236, 240, 243, 245, 247, 249, 253 and 255) so that the amplification should be attained in the ranges of sequences obtained by the screening. For preparation of calibration curves, a gene comprising a DNA fragment of positive control incorporated into the pDrive vector was amplified by PCR (5'M13_F primer (SEQ ID NO: 298) and 3'M13_R primer (SEQ ID NO: 299) were used, and the PCR program lightcycler of Table 1 was used), which was controlled so that 1E03, 1E05, 1E07 or 1E09 clones/reaction should be obtained. The measurement was controlled so that each of the library DNA before screening, library DNA in each cycle of screening, and Mock library DNA not added with the bait c-jun should be in an amount of 5 ng/reaction. The PCR measurement reaction was performed in a scale of 20 μl according to the programs shown in Table 1 by using LightCycler Instrument or LightCycler FastStart DNA Master SYBR Green I (both are produced by Roche Diagnostics).

Further, the proteins and genes or nucleic acid sequences of the present invention can be used as an inhibitor for blocking transcription, gene duplication and so forth as functions of c-Jun by utilizing the novel function thereof (function of enabling binding with c-Jun in this case). The basis of the above is originates in the fact that the genes detected by the IVV method have been detected through a competitive process constituted by screening repeated multiple times. Therefore, the genes detected by the IVV method show a certain number distribution, and a gene having a stronger competitive power should be detected in a larger number. This suggests that a larger number of clones corresponds to stronger competitive power, and thus such a gene acts more effectively as a blocking agent or inhibitor. In the IVV selection performed in this example, three (/132) of c-Fos well known as a prey, one (/132) of c-Jun, one (/132) of ATF4 and five (/132) of Jpp2 were detected for the bait c-Jun. Thus, the numbers of clones (FIG. 1) detected in the selection indicate that SNAP19, KINN and so forth have extremely stronger competitive power compared with known proteins; Kif5a, Eef1d, Nef3, Jip-c3.1, Jip-c1 and so forth can sufficiently compete with c-Fos; and EB2, Cspg6, Mapk8ip3, Jip-c3.2, Jip-c8 and so forth can sufficiently compete with c-Jun or ATF4, and thus the proteins can be utilized as an inhibitor for blocking functions of transcription of a complex, gene duplication and so forth by the interaction of c-Jun and a known protein.

TABLE 1

PCR programs

Program name: CYCB1
Reaction conditions:

95° C.  1 minute
98° C.  20 seconds
55° C.  1 minute          15 cycles
72° C.  4 minutes
4° C.  Pause Program name: V-2
Reaction conditions:

98° C.  20 seconds
55° C.  1 minute          35 cycles
72° C.  3 minutes
4° C.  Pause Program name: RT-QH3090
Reaction conditions:

50° C.  30 minutes
95° C.  15 minutes
94° C.  30 seconds        (30 cycles for 1st round,
60° C.  30 seconds        26 cycles for 2rd to 4th rounds
72° C.  90 seconds        28 cycles for 5th round)
72° C.  10 minutes Program name: ISHI1562
Reaction conditions:

94° C.  2 minutes
94° C.  30 seconds
62° C.  30 seconds        15 cycles
73° C.  2 minutes
73° C.  15 minutes Program name: lightcycler
Reaction condition:

95° C.  10 minutes
95° C.  15 seconds
X° C.  10 seconds         40 cycles
72° C.  5 seconds X: Annealing temperature was 62 to 51° C. depending on the Tm values of primers.

INDUSTRIAL APPLICABILITY

Because proteins that interact with c-Jun have been provided, it becomes possible to provide proteins forming a complex with c-Jun by not only a direct interaction, but also an unexpected indirect interaction, and nucleic acids encoding these proteins as well as methods for utilizing them.

What is claimed is:

1. A method for detecting an interaction between a bait and a prey, which comprises bringing the bait and the prey into contact and detecting a complex formed by the contact, wherein the prey is a c-Jun protein, and wherein the bait is a protein comprising any one of the amino acid sequences of SEQ ID NOS: 120 and 121.

2. The method according to claim 1, wherein the bait protein is translated from a nucleic acid comprising any one of the nucleotide sequences of SEQ ID NOS: 250 and 251.

* * * * *